United States Patent
DeRosa et al.

(10) Patent No.: US 11,964,051 B2
(45) Date of Patent: Apr. 23, 2024

(54) RIBOSE CATIONIC LIPIDS

(71) Applicant: Translate Bio, Inc., Lexington, MA (US)

(72) Inventors: Frank DeRosa, Lexington, MA (US); Shrirang Karve, Lexington, MA (US); Yi Zhang, Lexington, MA (US); Michael Heartlein, Lexington, MA (US)

(73) Assignee: TRANSLATE BIO, INC., Lexington, MA (US)

( * ) Notice: Subject to any disclaimer, the term of this patent is extended or adjusted under 35 U.S.C. 154(b) by 486 days.

(21) Appl. No.: 17/054,886

(22) PCT Filed: May 15, 2019

(86) PCT No.: PCT/US2019/032522
§ 371 (c)(1),
(2) Date: Nov. 12, 2020

(87) PCT Pub. No.: WO2019/222424
PCT Pub. Date: Nov. 21, 2019

(65) Prior Publication Data
US 2022/0323355 A1 Oct. 13, 2022

Related U.S. Application Data

(60) Provisional application No. 62/749,442, filed on Oct. 23, 2018, provisional application No. 62/740,095, (Continued)

(51) Int. Cl.
*A61K 9/127* (2006.01)
*A61K 9/00* (2006.01)
(Continued)

(52) U.S. Cl.
CPC .......... *A61K 9/1272* (2013.01); *A61K 9/0019* (2013.01); *A61K 9/0078* (2013.01); *A61K 38/1816* (2013.01); *C07H 13/06* (2013.01)

(58) Field of Classification Search
None
See application file for complete search history.

(56) References Cited

U.S. PATENT DOCUMENTS

2002/0035082 A1* 3/2002 Grinstaff ................ A61K 47/26
548/413
2003/0175966 A1 9/2003 Wang et al.
(Continued)

FOREIGN PATENT DOCUMENTS

EP 2 003 140 A2 12/2008
JP 2004 231622 A 8/2004
(Continued)

OTHER PUBLICATIONS

Google Patents. English Translation of WO1998055490A1. Obtained from https://patents.google.com/patent/WO1998055490A1/en?oq=WO+9855490++++++++++++ on Apr. 18, 2023, originally published in French on Dec. 10, 1998, 17 printed pages. (Year: 1998).*
(Continued)

*Primary Examiner* — Isaac Shomer
(74) *Attorney, Agent, or Firm* — LATHROP GPM LLP; James H. Velema, Esq.

(57) ABSTRACT

Disclosed are cationic lipids which are compounds of Formula (I'). Cationic lipids provided herein can be useful for delivery and expression of mRNA and encoded protein, e.g., as a component of liposomal delivery vehicle, and accordingly can be useful for treating various diseases, disorders and conditions, such as those associated with deficiency of one or more proteins.

(Continued)

LNP formulations

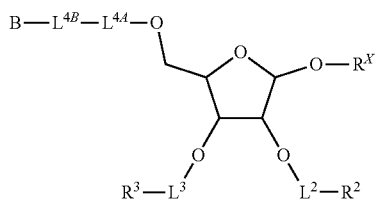 (I′)

17 Claims, 1 Drawing Sheet

Related U.S. Application Data filed on Oct. 2, 2018, provisional application No. 62/672,194, filed on May 16, 2018.

(51) Int. Cl.
*A61K 38/18* (2006.01)
*C07H 13/06* (2006.01)

(56) References Cited

U.S. PATENT DOCUMENTS

| 2013/0123485 | A1  | 5/2013  | Park et al. |
| 2015/0166462 | A1* | 6/2015  | DeRosa ............... A61P 43/00 564/509 |
| 2016/0317647 | A1* | 11/2016 | Ciaramella ........... A61K 48/00 |
| 2017/0326255 | A1  | 11/2017 | Zhang et al. |

FOREIGN PATENT DOCUMENTS

| WO | WO-9855490 A1 * | 12/1998 | ............ A61K 48/00 |
| WO | WO 99/12945 A2  | 3/1999  | |
| WO | WO 2019/207060 A1 | 10/2019 | |

OTHER PUBLICATIONS

Rosa Larralde, Michael P. Robertson, and Stanley L. Miller. "Rates of decomposition of ribose and other sugars: Implications for chemical evolution." Proceedings of the National Academy of Sciences, vol. 92, Aug. 1995, pp. 8158-8160. (Year: 1995).*

Alton et al., "A randomised, double-blind, placebo-controlled trial of repeated nebulisation of non-viral cystic fibrosis transmembrane conductance regulator (CFTR) gene therapy in patients with cystic fibrosis", National Institute for Health Research, 3(5), (2016).

International Preliminary Report on Patentability for PCT/US19/32522, dated Nov. 17, 2020 (8 pages).

International Search Report and Written Opinion for PCT/US19/32522, dated Sep. 6, 2019 (17 pages).

Kochetkov et al., "Glycopeptides Communication 9. Synthesis of o-(amino-acyl) derivatives of some monosaccharides", Bulletin of the Academy of Sciences of the USSR, Division of chemical science, Jun. 1, 1965 (Jun. 1, 1965), 1045-1051.

Negm et al., "Synthesis, Characterization and Biological Activity of Sugar-Based Gemini Cationic Amphiphiles", Journal of Surfactants and Detergents, vol. 11, No. 3, Sep. 1, 2008 (Sep. 1, 2008), 215-221.

Zhi et al., "Transfection Efficiency of Cationic Lipids with Different Hydrophobic Domains in Gene Delivery", Bioconjugate Chemistry, vol. 21, No. 4, Apr. 21, 2010 (Apr. 21, 2010), 563-577.

* cited by examiner

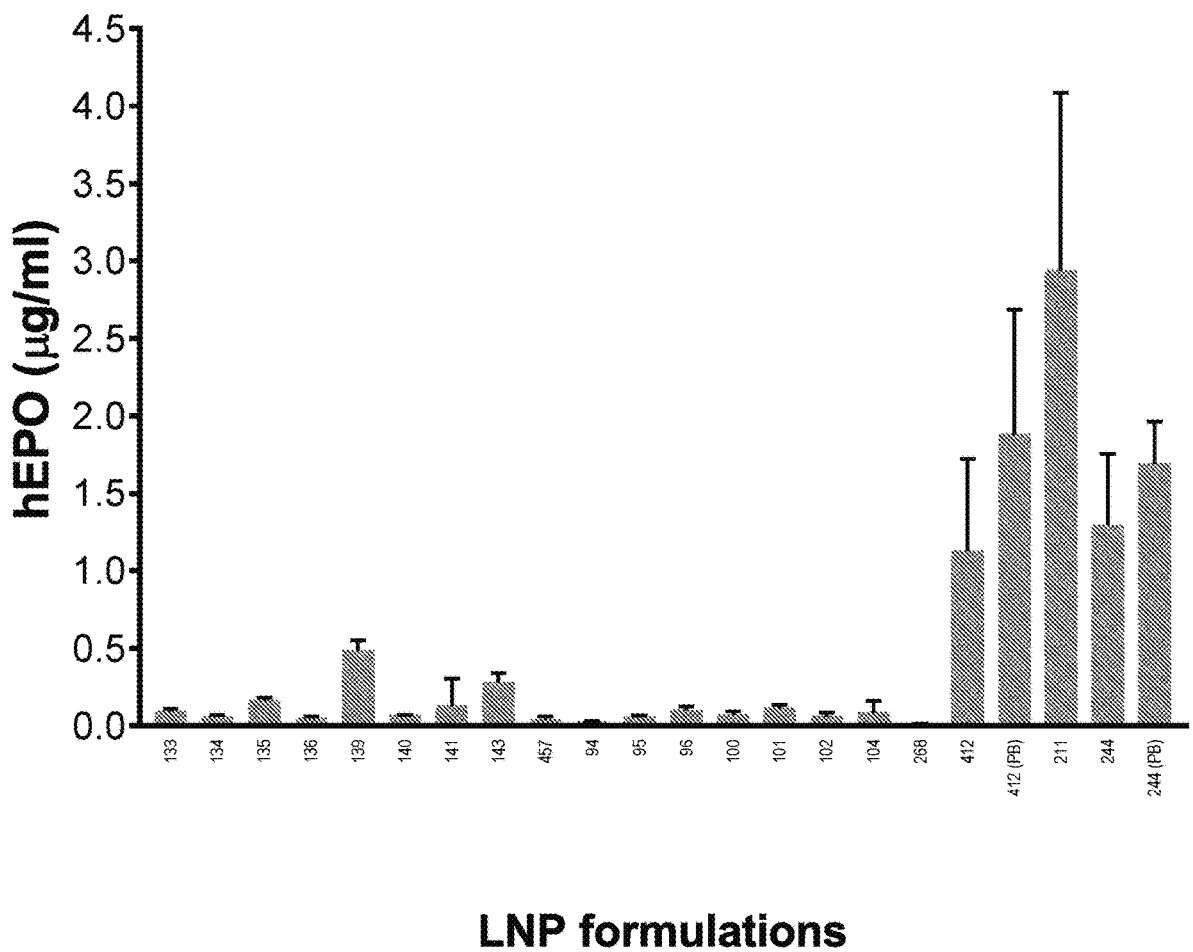

RIBOSE CATIONIC LIPIDS

CROSS-REFERENCE TO RELATED APPLICATIONS

The present application is a 35 U.S.C. § 371 National Stage Application of International Application No. PCT/US19/32522, filed on May 15, 2019, which claims benefit of U.S. Patent Application No. 62/672,194, filed May 16, 2018; U.S. Patent Application No. 62/740,095, filed Oct. 2, 2018; and U.S. Patent Application No. 62/749,442, filed Oct. 23, 2018, each of which is incorporated by reference in its entirety.

BACKGROUND

Delivery of nucleic acids has been explored extensively as a potential therapeutic option for certain disease states. In particular, messenger RNA (mRNA) therapy has become an increasingly important option for treatment of various diseases, including for those associated with deficiency of one or more proteins.

SUMMARY

The present invention provides, among other things, cationic lipids useful in for delivery of mRNA. Delivery of mRNA provided by cationic lipids described herein can result in targeted delivery, reduce administration frequency, improve patient tolerability, and provide more potent and less toxic mRNA therapy for the treatment of a variety of diseases, including but not limited to cancer, cardiovascular, cystic fibrosis, infectious, and neurological diseases.

In one aspect, the present invention provides a cationic lipid of Formula (I'):

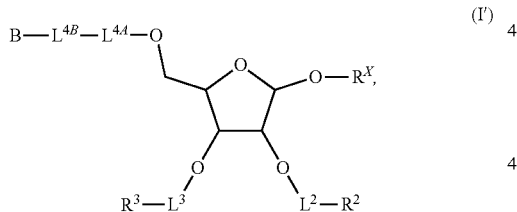

(I')

wherein:
  $R^X$ is independently —H, -$L^1$-$R^1$, or -$L^{5A}$-$L^{5B}$-B';
  each of $L^1$, $L^2$, and $L^3$ is independently a covalent bond, —C(O)—, —C(O)O—, —C(O)S—, or —C(O)$NR^L$—;
  each $L^{4A}$ and $L^{5A}$ is independently —C(O)—, —C(O)O—, or —C(O)$NR^L$—;
  each $L^{4B}$ and $L^{5B}$ is independently $C_1$-$C_{20}$ alkylene; $C_2$-$C_{20}$ alkenylene; or $C_2$-$C_{20}$ alkynylene;
  each B and B' is $NR^4R^5$, a 5- to 10-membered nitrogen-containing heterocyclyl, or a 5- to 10-membered nitrogen-containing heteroaryl;
  each $R^1$, $R^2$, and $R^3$ is independently $C_6$-$C_{30}$ alkyl, $C_6$-$C_{30}$ alkenyl, or $C_6$-$C_{30}$ alkynyl;
  each $R^4$ and $R^5$ is independently hydrogen, $C_1$-$C_{10}$ alkyl; $C_2$-$C_{10}$ alkenyl; or $C_2$-$C_{10}$ alkynyl; or $R^4$ and $R^5$ combine to form a 5- to 10-membered heterocyclyl or a 5- to 10-membered heteroaryl; and
  each $R^L$ is independently hydrogen, $C_1$-$C_{20}$ alkyl, $C_2$-$C_{20}$ alkenyl, or $C_2$-$C_{20}$ alkynyl.

In embodiments, the present invention provides a cationic lipid of Formula (I):

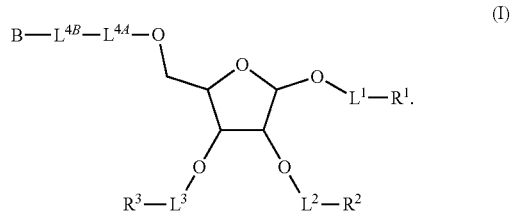

(I)

In embodiments, the present invention provides a cationic lipid of Formula (Ia):

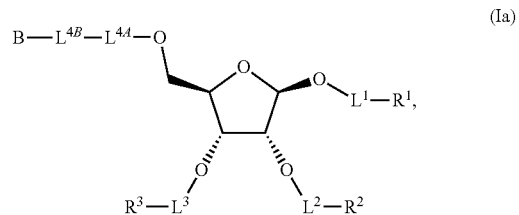

(Ia)

wherein each of $L^1$, $L^2$, $L^3$, $R^1$, $R^2$, $R^3$, B, $L^{4A}$ and $L^{4B}$ is independently as defined herein.

In embodiments, the present invention provides a cationic lipid of Formula (Ib):

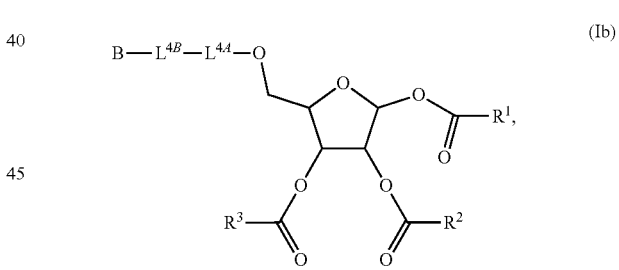

(Ib)

wherein: each of $R^1$, $R^2$, $R^3$, B, $L^{4A}$ and $L^{4B}$ is independently as defined herein.

In embodiments, the present invention provides a cationic lipid of Formula (Ic):

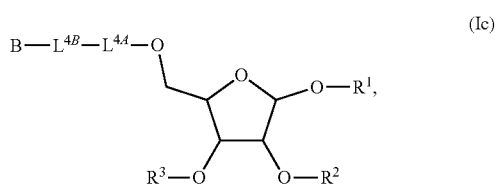

(Ic)

wherein each of $R^1$, $R^2$, $R^3$, B, $L^{4A}$ and $L^{4B}$ is independently as defined herein.

In embodiments, the present invention provides a cationic lipid of Formula (Id):

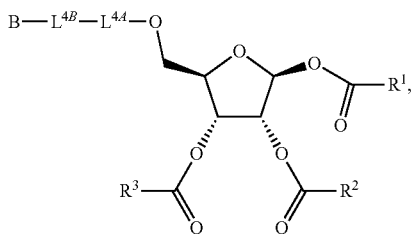

wherein each of $R^1$, $R^2$, $R^3$, B, $L^{4A}$ and $L^{4B}$ is independently as defined herein.

In embodiments, the present invention provides a cationic lipid of Formula (Ie):

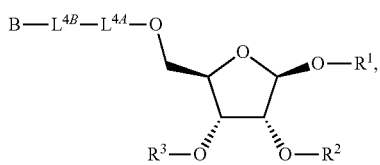

wherein each of $R^1$, $R^2$, $R^3$, B, $L^{4A}$ and $L^{4B}$ is independently as defined herein.

In embodiments, each $L^3$ is independently —C(O)— or a covalent bond.

In embodiments, $L^{4A}$ is —C(O)—.

In embodiments, $L^{4B}$ is unsubstituted $C_1$-$C_6$ alkylene; $C_2$-$C_6$ alkenylene; or $C_2$-$C_6$ alkynylene. In embodiments, $L^{4B}$ is —$CH_2$—. In embodiments, $L^{4B}$ is —$CH_2CH_2$—. In embodiments, $L^{4B}$ is —$CH_2CH_2CH_2$—. In embodiments, $L^{4B}$ is —$CH_2CH_2CH_2CH_2$—

In embodiments, B is $NR^4R^5$, and each $R^4$ and $R^5$ is independently hydrogen or unsubstituted $C_1$-$C_6$ alkyl. In embodiments, B is $N(CH_3)_2$.

In embodiments, B is $NR^4R^5$, and $R^4$ and $R^5$ combine to form a 5- to 10-membered heterocyclyl or a 5- to 10-membered heteroaryl. In embodiments, B is piperdinyl or piperazinyl. In embodiments, B is 4-methylpiperazinyl.

In another aspect, the present invention provides a cationic lipid of Formula (II):

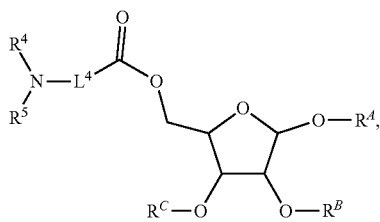

wherein:
$R^A$ is hydrogen or -L-$R^1$;
$R^B$ is hydrogen or -$L^2$-$R^2$;
$R^C$ is hydrogen or -$L^3$-$R^3$;
each of $L^1$, $L^2$, and $L^3$ is independently a covalent bond, —C(O)—, —C(O)O—, —C(O)S—, or —C(O)$NR^L$—;
$L^4$ is independently $C_1$-$C_{10}$ alkylene;

each $R^1$, $R^2$, and $R^3$ is independently $C_6$-$C_{30}$ alkyl, $C_6$-$C_{30}$ alkenyl, or $C_6$-$C_{30}$ alkynyl;

each $R^4$ and $R^5$ is independently hydrogen, $C_1$-$C_{10}$ alkyl; $C_2$-$C_{10}$ alkenyl; or $C_2$-$C_{10}$ alkynyl; or $R^4$ and $R^5$ combine to form a 5- to 10-membered heterocyclyl or a 5- to 10-membered heteroaryl; and each $R^L$ is independently hydrogen, $C_1$-$C_{20}$ alkyl, $C_2$-$C_{20}$ alkenyl, or $C_2$-$C_{20}$ alkynyl.

In embodiments, $R^A$ is -L-$R^1$; $R^B$ is -$L^2$-$R^2$; and $R^C$-$L^3$-$R^3$.

In embodiments, the present invention provides a cationic lipid of Formula (IIa):

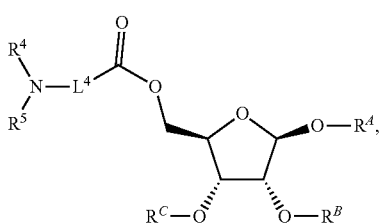

wherein each $R^A$, $R^B$, $R^C$, $L^4$, $R^4$ and $R^5$ is as independently as defined herein.

In embodiments, the present invention provides a cationic lipid of Formula (IIb):

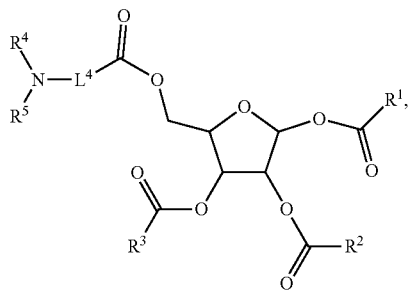

wherein each $R^A$, $R^B$, $R^C$, $L^4$, $R^4$ and $R^5$ independently as defined herein.

In embodiments, the present invention provides a cationic lipid of Formula (IIc):

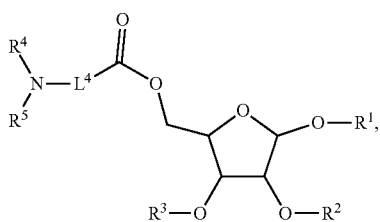

wherein each $R^A$, $R^B$, $R^C$, $L^4$, $R^4$ and $R^5$ is independently as defined herein.

In embodiments, the present invention provides a cationic lipid of Formula (IId):

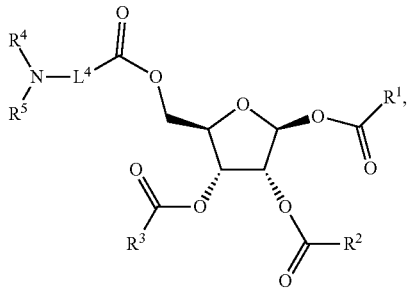

(IId)

wherein each $R^A$, $R^B$, $R^C$, $L^4$, $R^4$ and $R^5$ is independently as defined herein.

In embodiments, the present invention provides a cationic lipid of Formula (IIe):

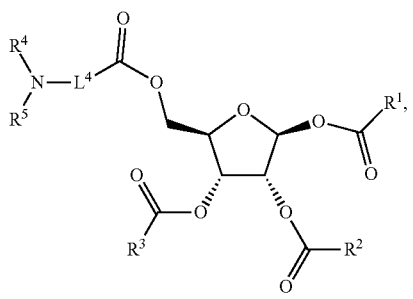

(IIe)

wherein each $R^A$, $R^B$, $R^C$, $L^4$, $R^4$ and $R^5$ is independently as defined herein.

In embodiments, $L^4$ is unsubstituted $C_1$-$C_6$ alkylene. In embodiments, $L^{4B}$ is —$CH_2$—. In embodiments, $L^{4B}$ is —$CH_2CH_2$—. In embodiments, $L^{4B}$ is —$CH_2CH_2CH_2$—.

In embodiments, each $R^4$ and $R^5$ is independently hydrogen or unsubstituted $C_1$-$C_6$ alkyl, or $R^4$ and $R^5$ combine to form a 5- to 6-membered heterocyclyl comprising one or two ring nitrogens. In embodiments, each $R^4$ and $R^5$ is $CH_3$.

In embodiments, $R^4$ and $R^5$ combine to form a 5- to 10-membered heterocyclyl. In embodiments, $R^4$ and $R^5$ combine to form a piperdinyl or piperazinyl. In embodiments, $R^4$ and $R^5$ combine to form 4-methylpiperazinyl.

In embodiments, each $R^1$, $R^2$, and $R^3$ is independently $C_6$-$C_{22}$ alkyl, $C_6$-$C_{22}$ alkenyl, or $C_6$-$C_{22}$ alkynyl. In embodiments, each $R^1$, $R^2$, and $R^3$ is unsubstituted linear $C_6$-$C_{22}$ alkyl, unsubstituted linear $C_6$-$C_{22}$ alkenyl, unsubstituted linear $C_6$-$C_{22}$ alkynyl, unsubstituted branched $C_6$-$C_{22}$ alkyl, unsubstituted branched $C_6$-$C_{22}$ alkenyl, or unsubstituted branched $C_6$-$C_{22}$ alkynyl. In embodiments, each $R^1$, $R^2$, and $R^3$ is unsubstituted linear $C_6$-$C_{22}$ alkyl. In embodiments, each $R^1$, $R^2$ and $R^3$ is unsubstituted linear $C_6$-$C_{22}$ alkenyl. In embodiments, each $R^1$, $R^2$, and $R^3$ is unsubstituted linear $C_6$-$C_{22}$ alkynyl. In embodiments, each $R^1$, $R^2$, and $R^3$ is unsubstituted branched $C_6$-$C_{22}$ alkyl. In embodiments, each $R^1$, $R^2$, and $R^3$ is unsubstituted branched $C_6$-$C_{22}$ alkenyl. In embodiments, each $R^1$, $R^2$, and $R^3$ is unsubstituted branched $C_6$-$C_{22}$ alkynyl.

In embodiments, each $R^1$, $R^2$, and $R^3$ is unsubstituted $C_6$-$C_{22}$ alkyl. In embodiments, $R^6$ is unsubstituted linear $C_6$-$C_{14}$ alkyl. In embodiments, $R^6$ is unsubstituted branched $C_6$-$C_{14}$ alkyl. In embodiments, each $R^1$, $R^2$, and $R^3$ is $(CH_2)_7CH_3$, $(CH_2)_9CH_3$, $(CH_2)_{11}CH_3$, $(CH_2)_{13}CH_3$, $(CH_2)_{15}CH_3$, or $(CH_2)_{17}CH_3$. In embodiments, each $R^1$, $R^2$, and $R^3$ is $(CH_2)_6CH_3$, $(CH_2)_8CH_3$, $(CH_2)_{10}CH_3$, $(CH_2)_{12}CH_3$, $(CH_2)_{14}CH_3$, or $(CH_2)_{16}CH_3$.

In embodiments, each $R^1$, $R^2$, and $R^3$ is $C_6$-$C_{12}$ alkyl substituted by —O(CO)$R^6$ or —C(O)O$R^6$, wherein $R^6$ is unsubstituted $C_6$-$C_{14}$ alkyl. In embodiments, each $R^1$, $R^2$, and $R^3$ is $(CH_2)_8OC(O)(CH_2)_6CH_3$, $(CH_2)_9OC(O)(CH_2)_6CH_3$, $(CH_2)_7C(O)O(CH_2)_2CH(C_5H_{11})_2$, or $(CH_2)_8C(O)O(CH_2)_2CH(C_5H_{11})_2$.

In embodiments, each $R^1$, $R^2$, and $R^3$ is unsubstituted $C_6$-$C_{22}$ alkenyl (e.g., a monoalkenyl, a dienyl, or a trienyl).

In embodiments, each $R^1$, $R^2$, and $R^3$ is:

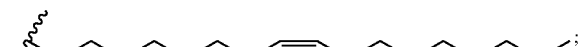

;


; or

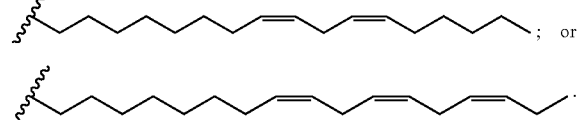

.

In embodiments, each $R^1$, $R^2$, and $R^3$ is:

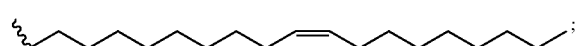

;

; or

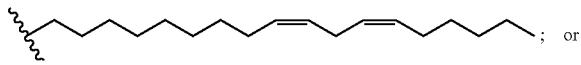

.

In embodiments, each $R^1$, $R^2$, and $R^3$ is

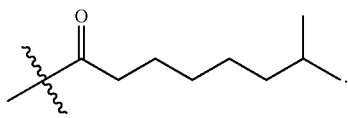 [SMILES: *C(=O)CCCCCC(C)C]

.

In another aspect, the invention provides a cationic lipid selected from the group consisting of:

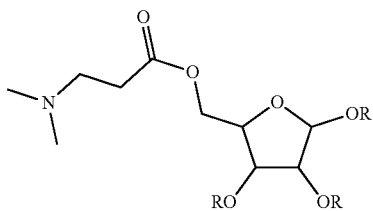

R =
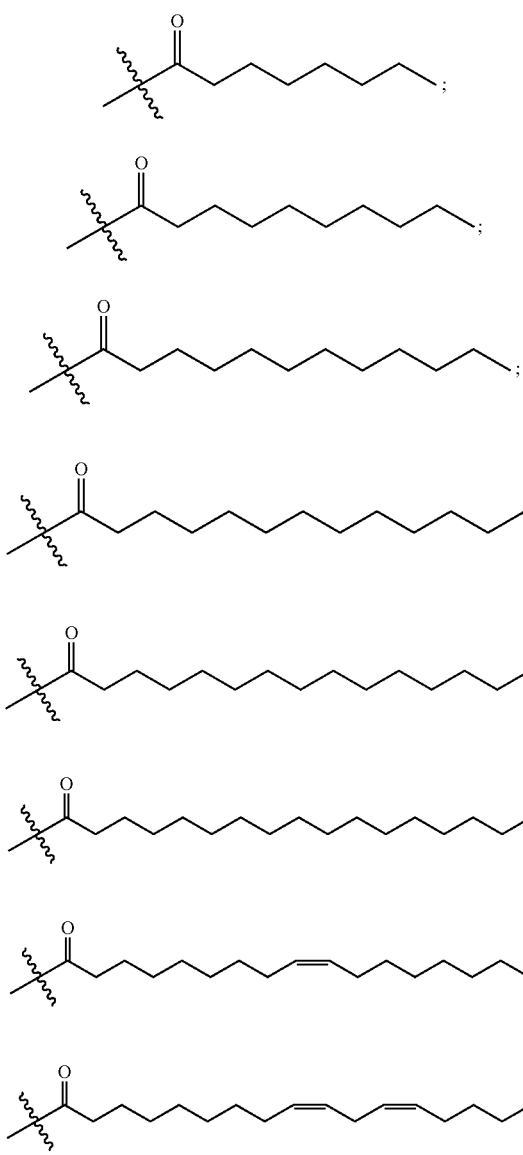
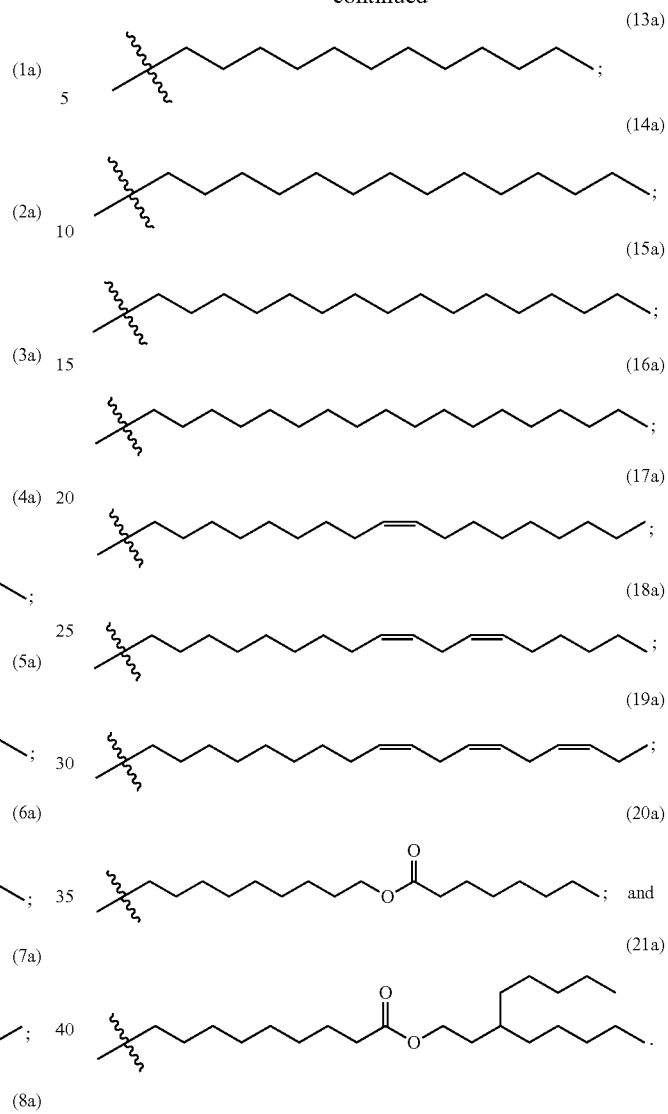
In another aspect, the invention provides a cationic lipid selected from the group consisting of:
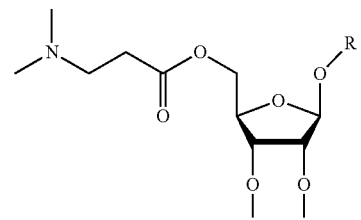
R =
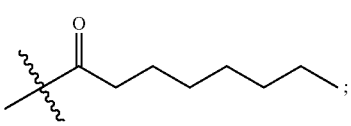

(2b)
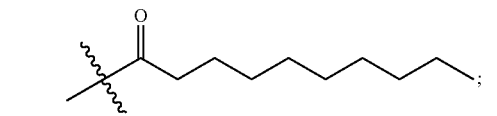
(3b)
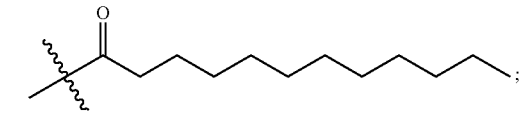
(4b)
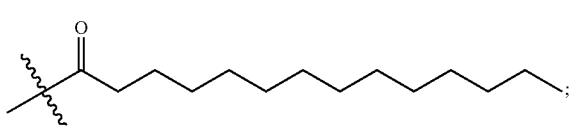
(5b)
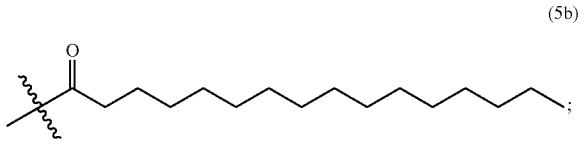
(6b)
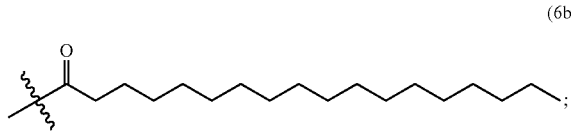
(7b)
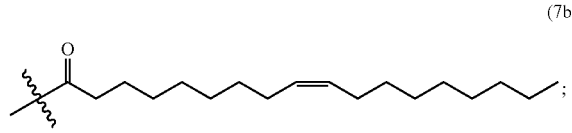
(8b)
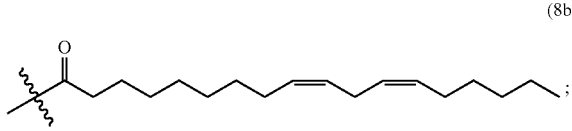
(9b)
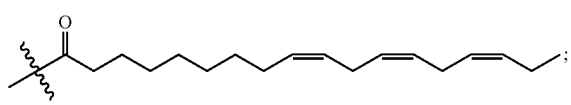
(10b)
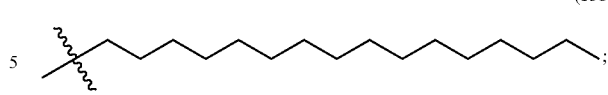
(11b)
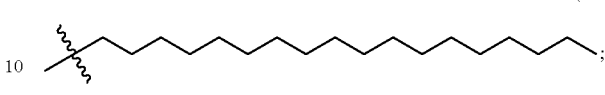
(12b)
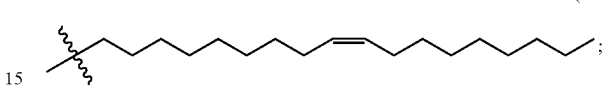
(13b)
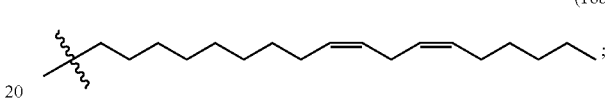
(14b)
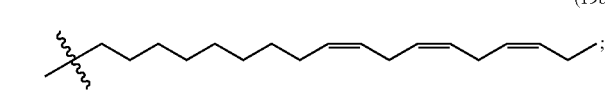
(15b)
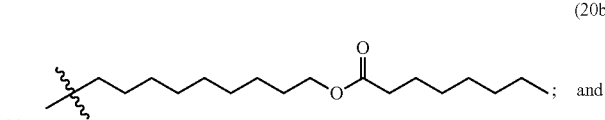
(16b)
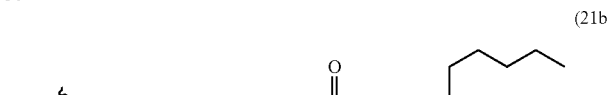
(17b)
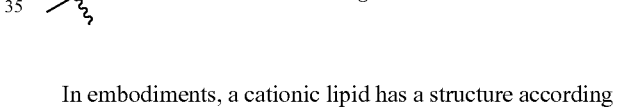
(18b)
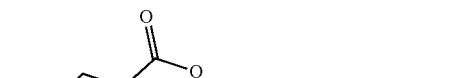
(19b)
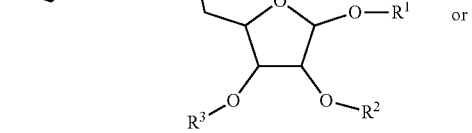
(20b)
; and
(21b)
.
In embodiments, a cationic lipid has a structure according to one of the following formulas,
(IIIn)
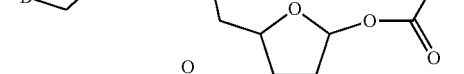
or
(IIIq)
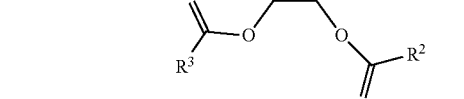

In embodiments, a cationic lipid has a structure according to one of the following formulas,
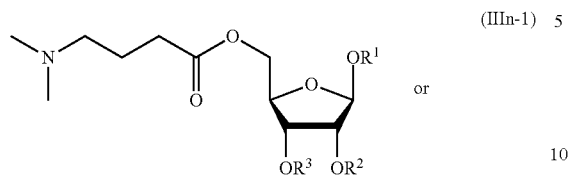
(IIIn-1)
or
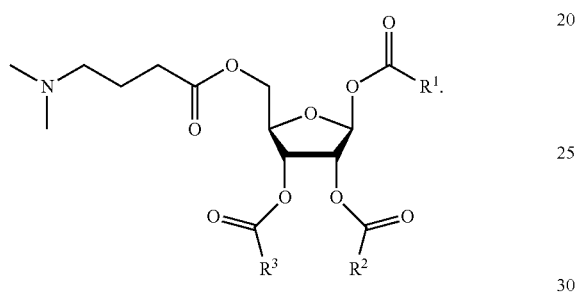
(IIIq-1)
In embodiments, a cationic lipid is selected from the group consisting of:
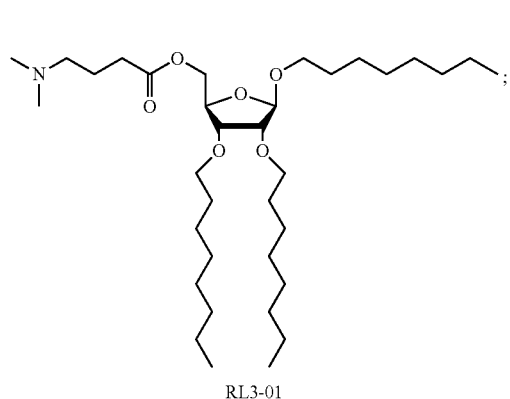
RL3-01
(166)
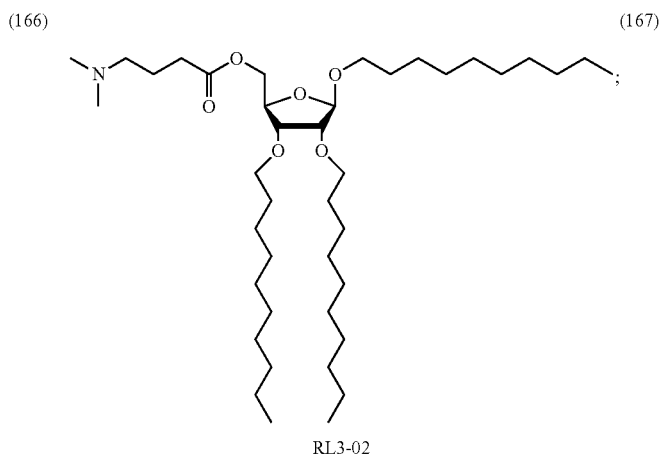
RL3-02
(167)

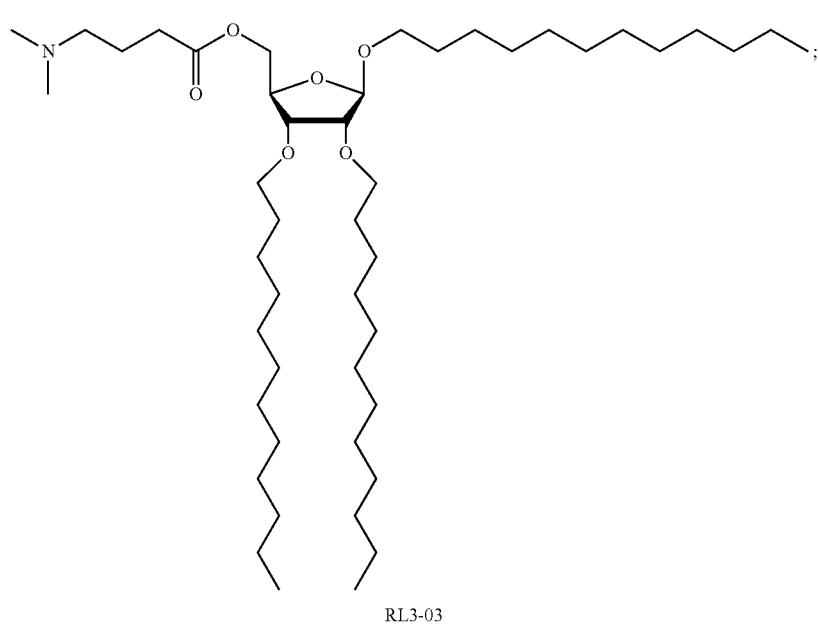
(168)
RL3-03
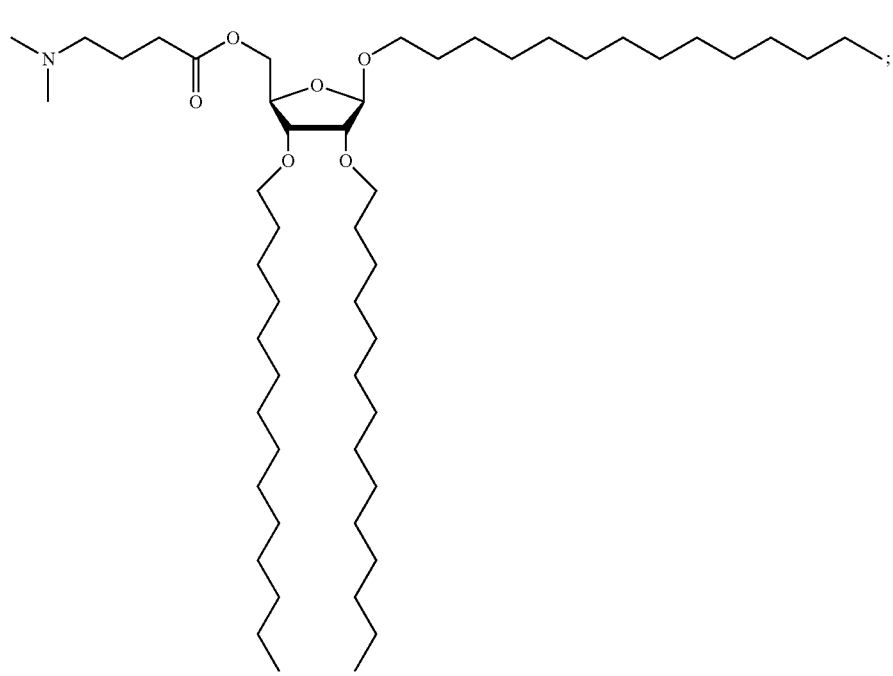
(169)
RL3-04

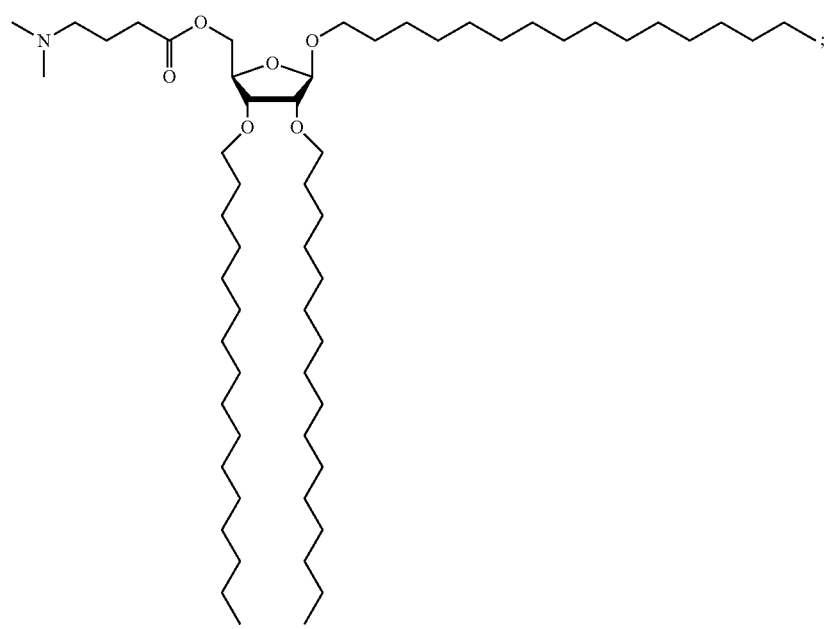
(170)
RL3-05
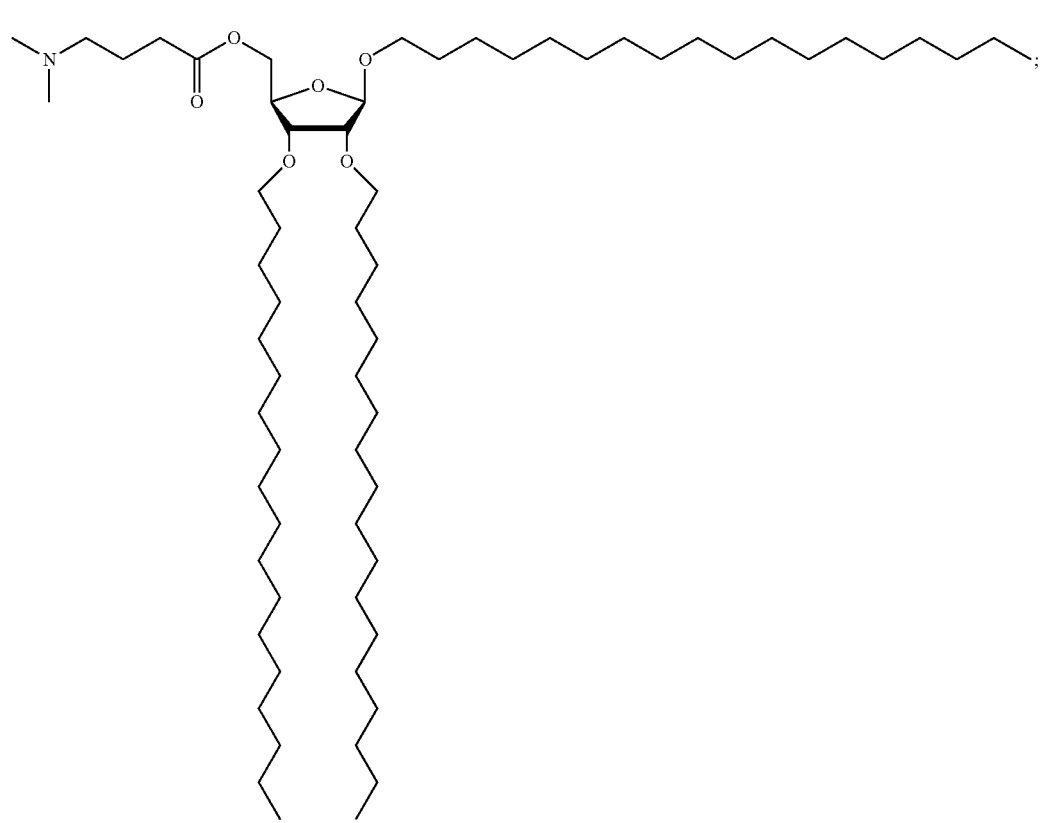
(171)
RL3-06

(172)
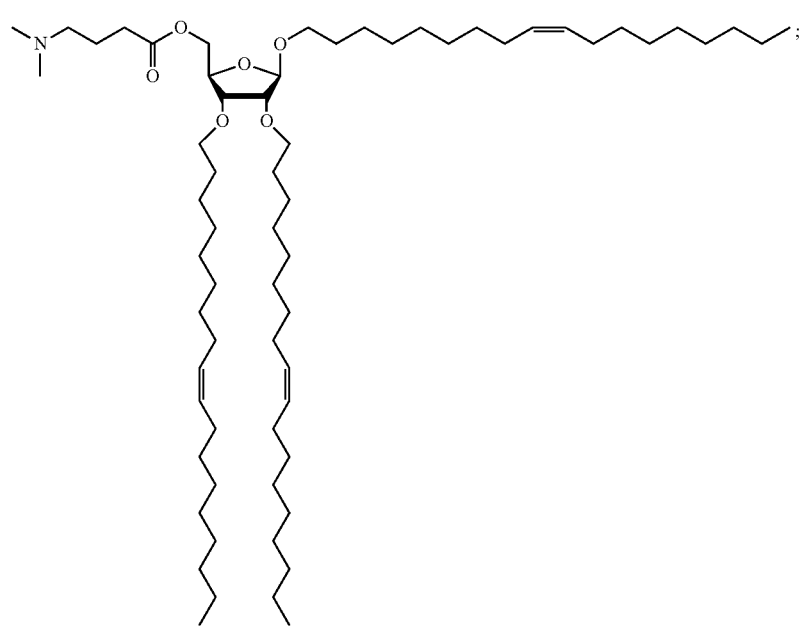
RL3-07
(173)
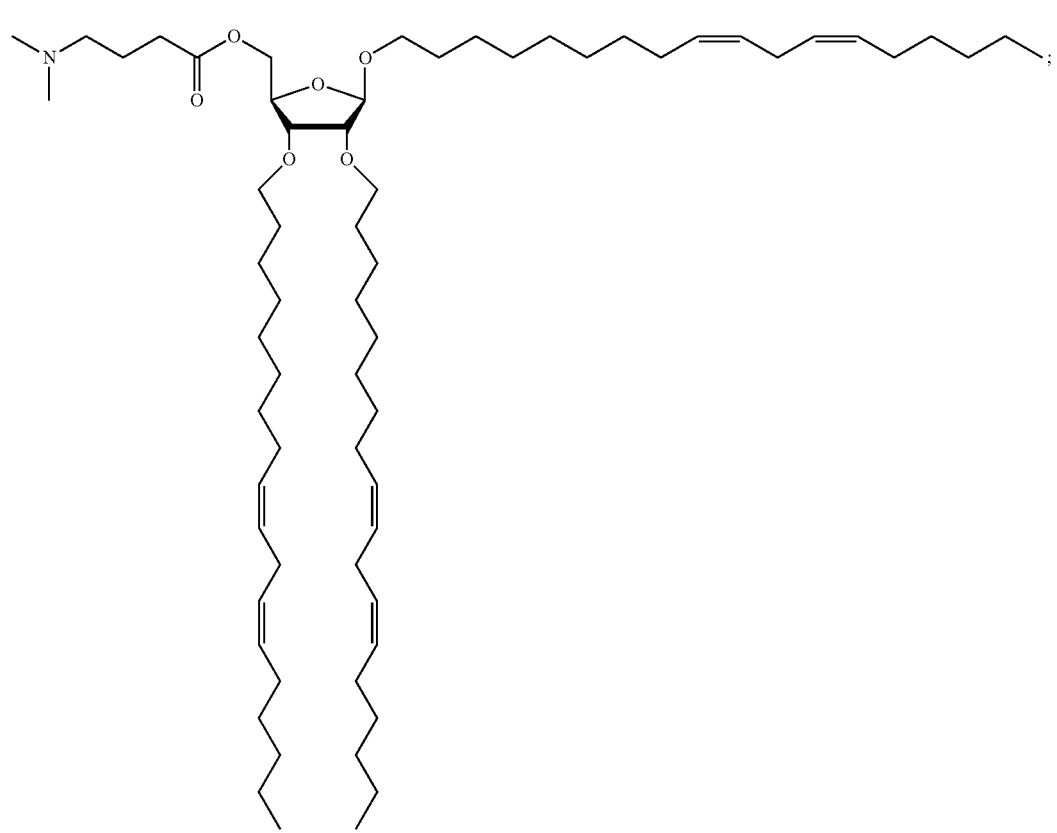
RL3-08

-continued
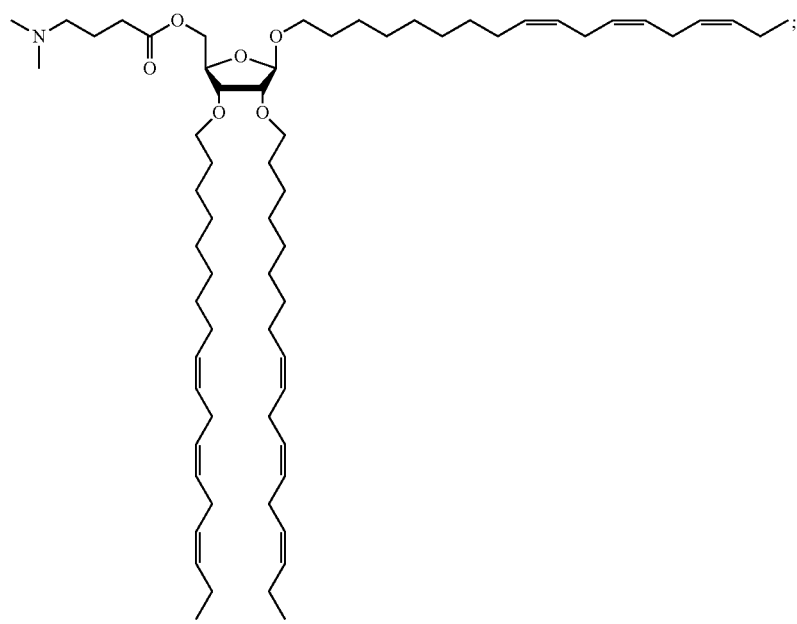
(174)
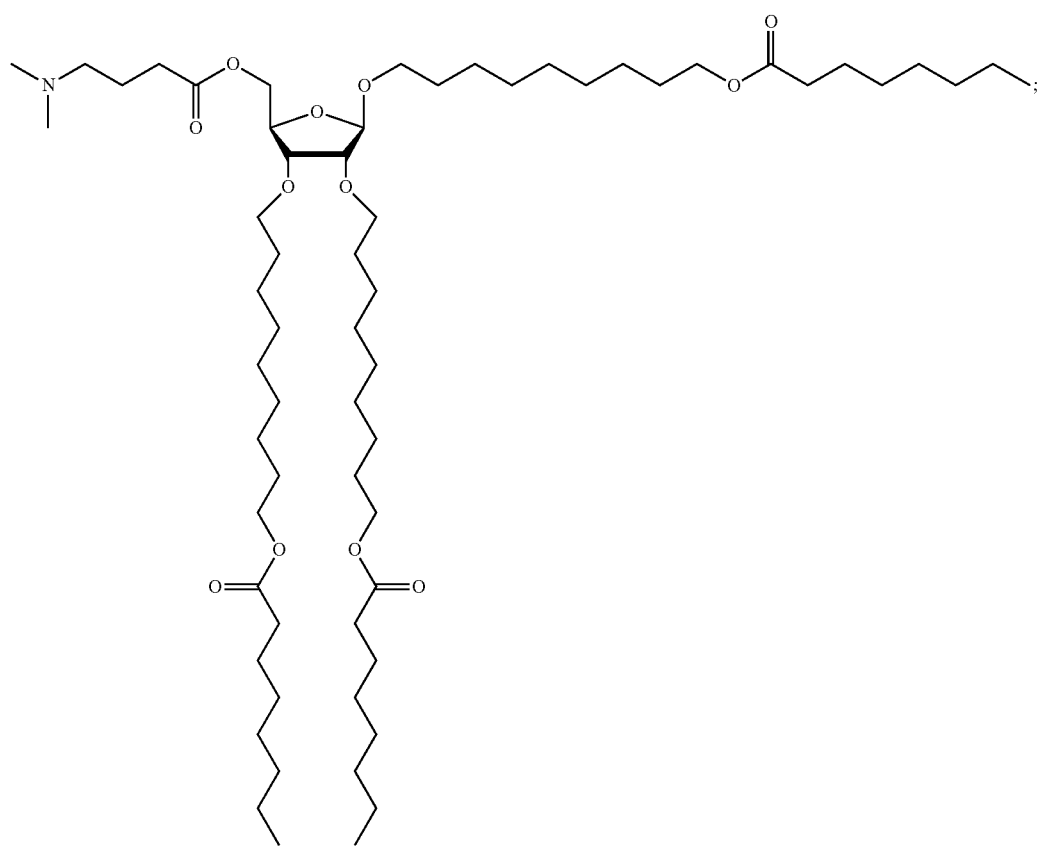
(175)

(176)
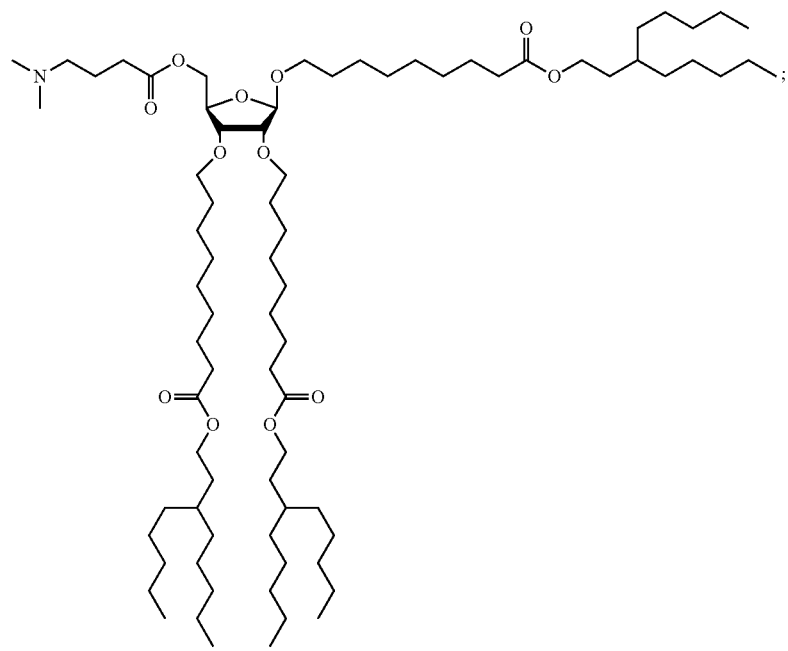
RL3-11
(177)
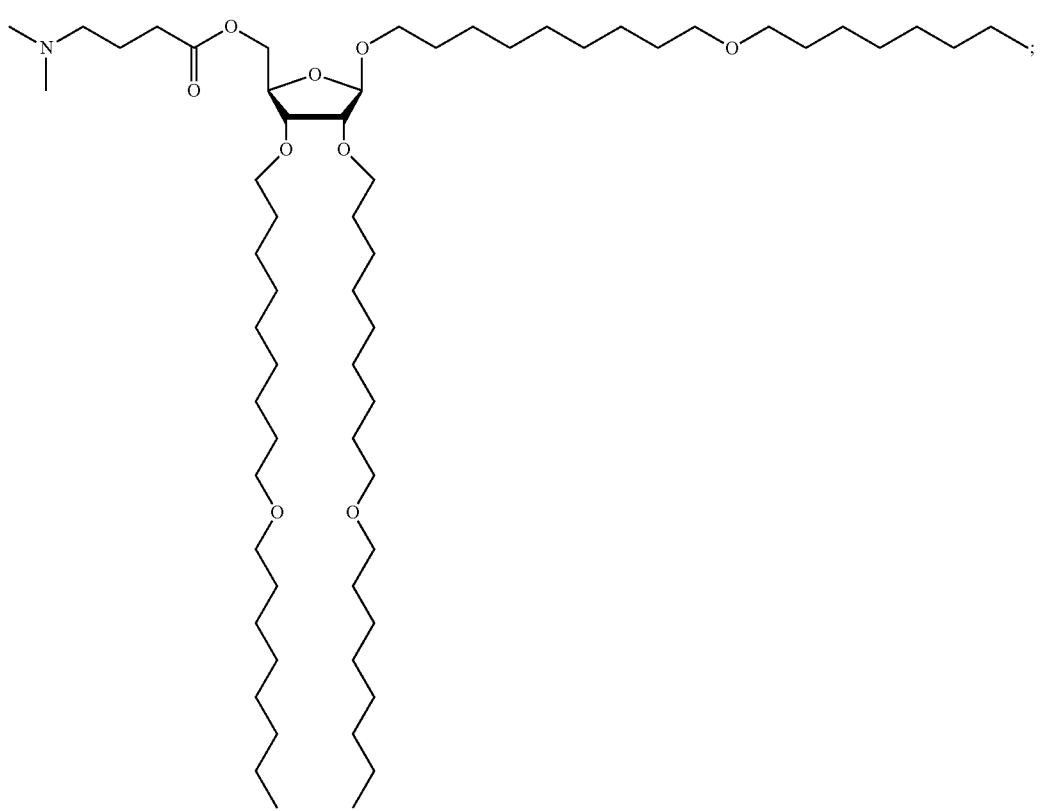
RL3-12

-continued
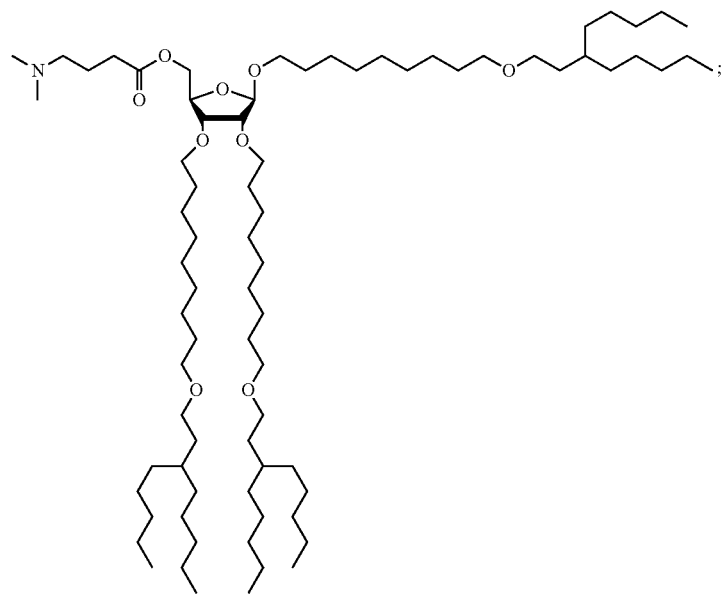
(178)
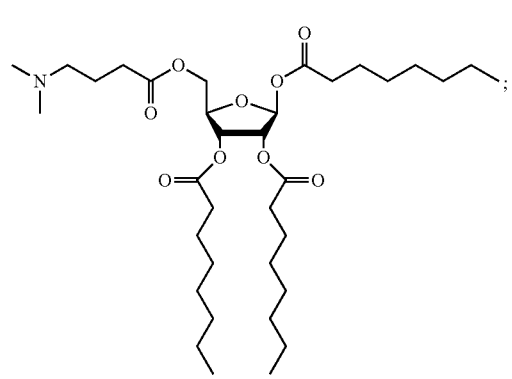
(205)
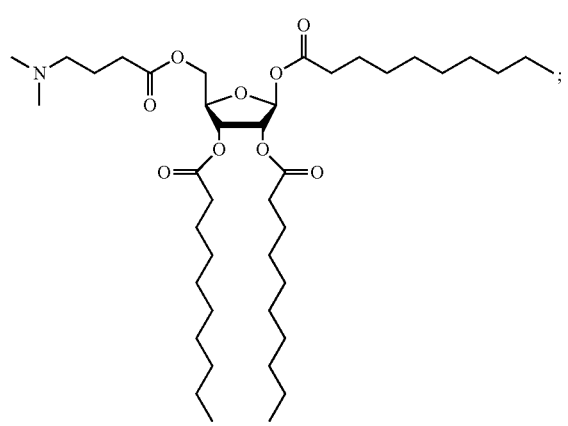
(206)

(207)
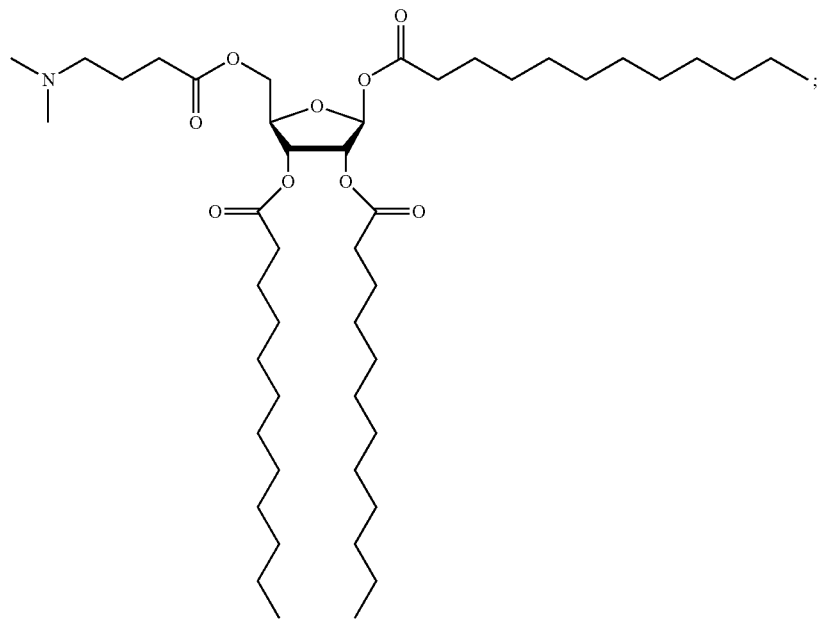
RL3-03D
(208)
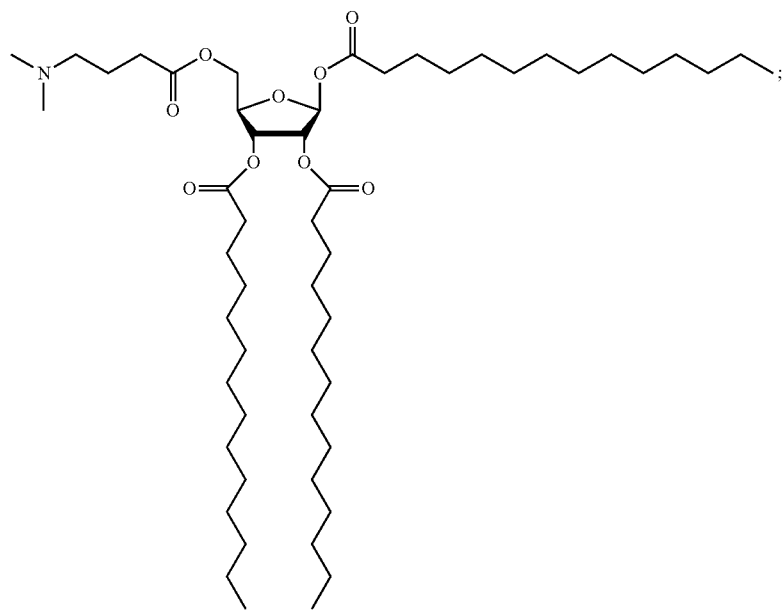
RL3-04D

-continued
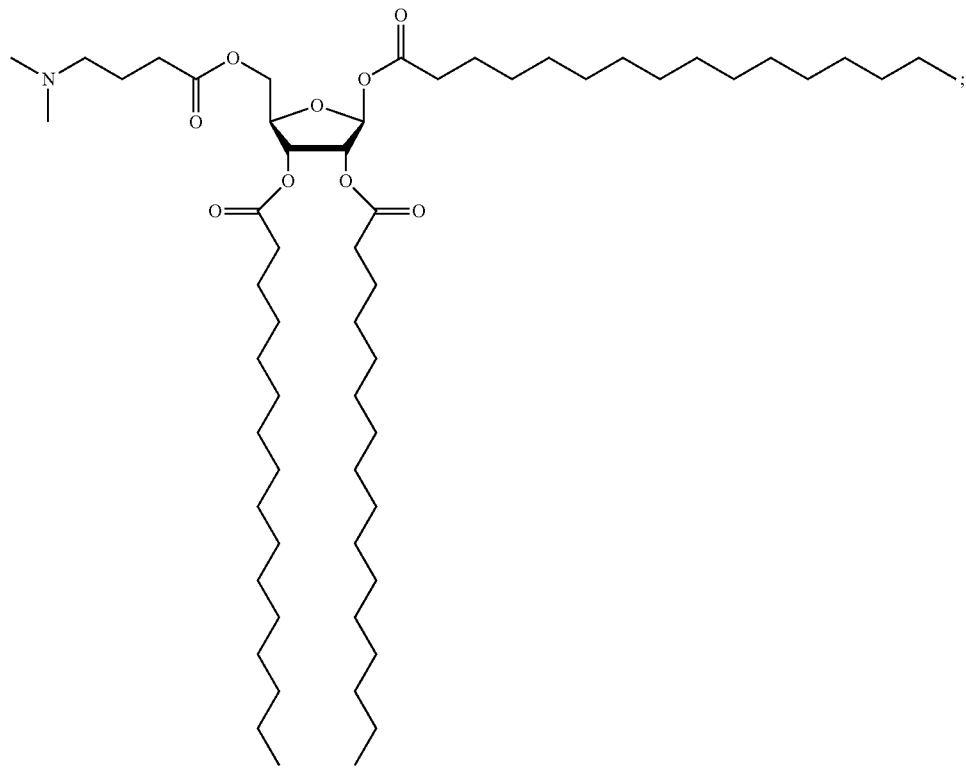
RL3-05D
(209)
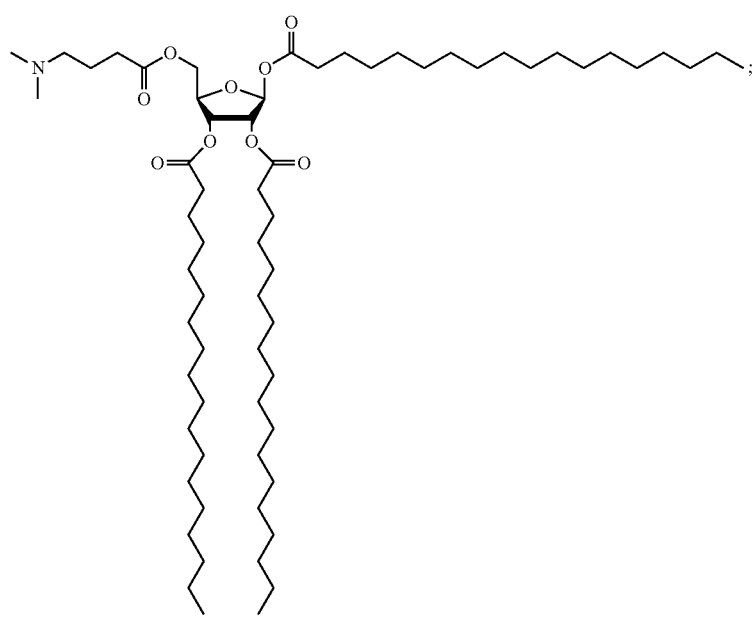
RL3-06D
(210)

(211)
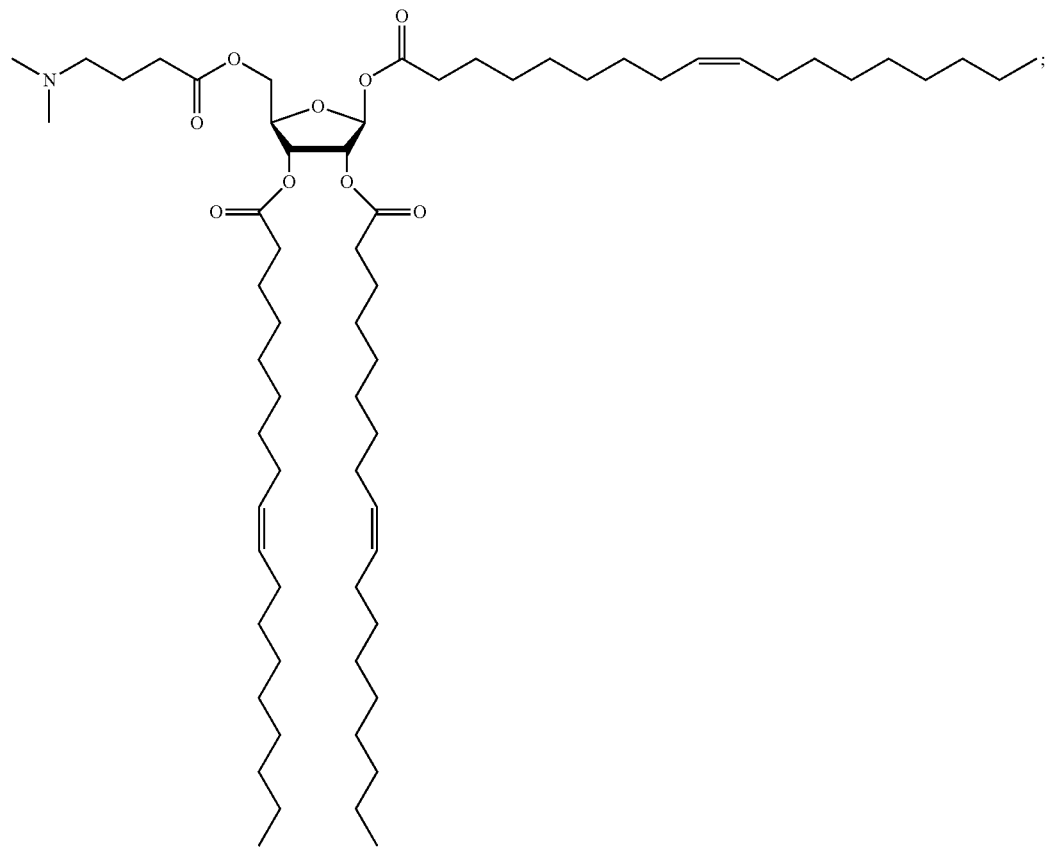
RL3-07D
(212)
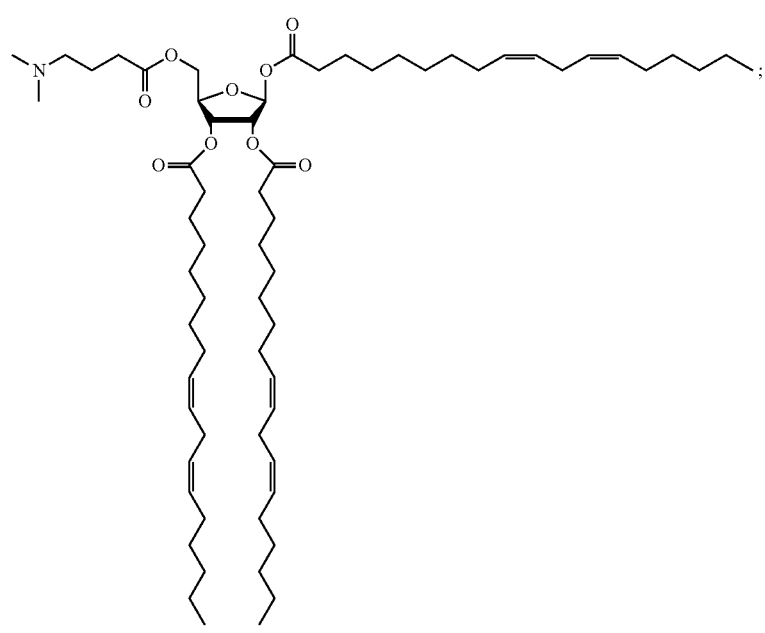
RL3-08D (213)
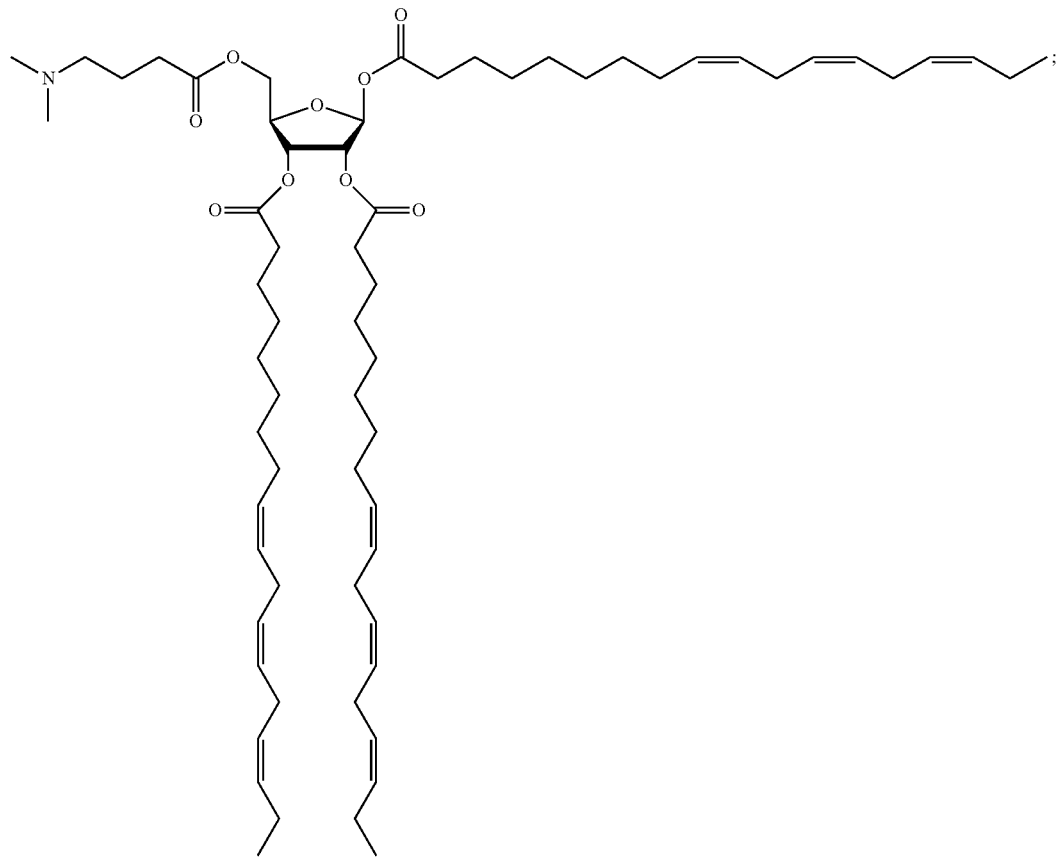
RL3-09D
(214)
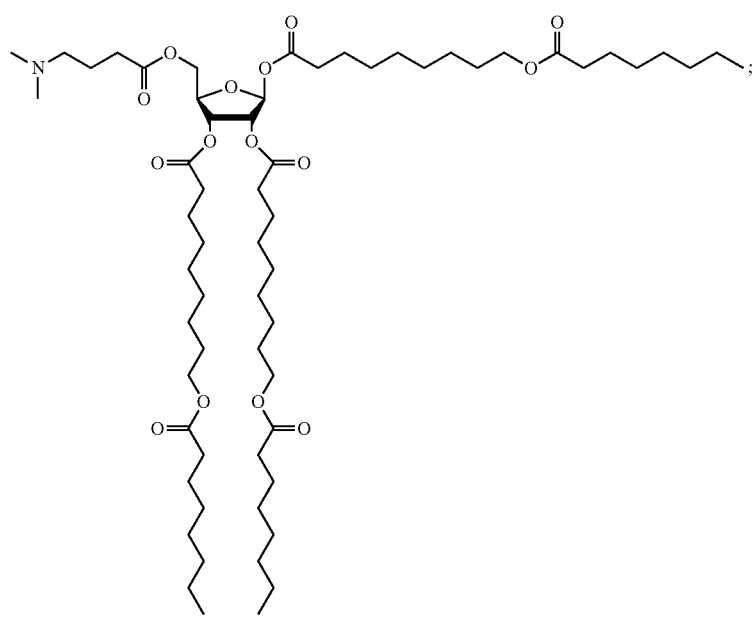
RL3-10D

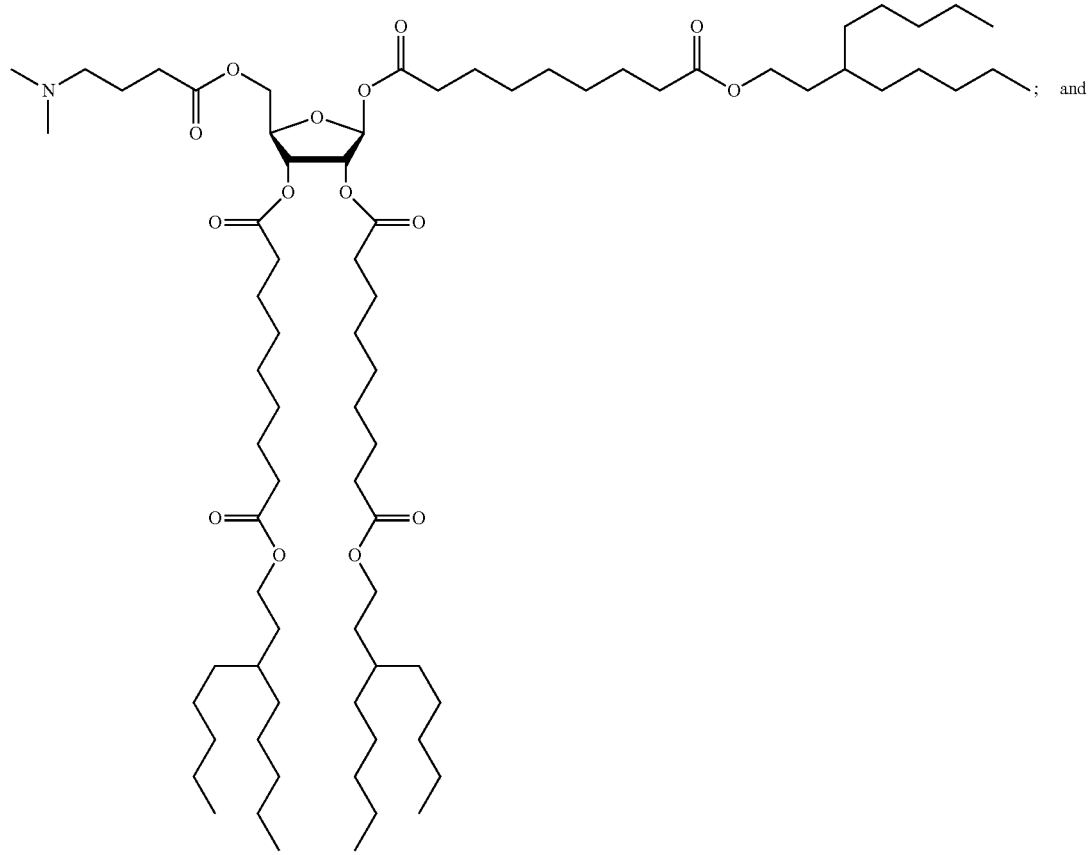
RL3-11D
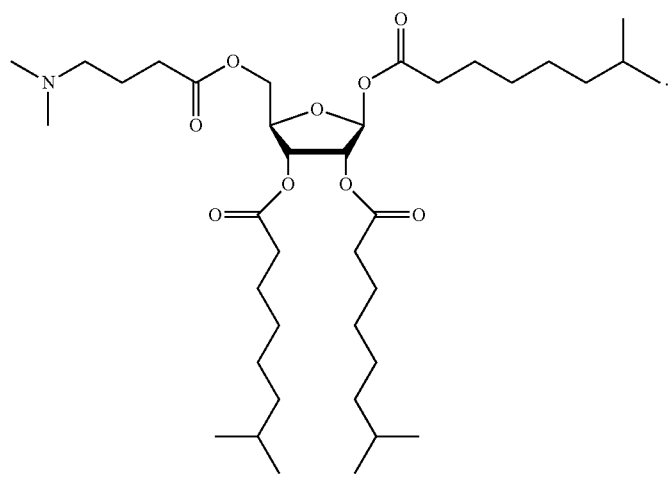

In embodiments, a cationic lipid is selected from the group consisting of:
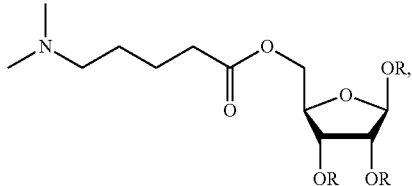
(IIIt)
| R = | Compound |
|---|---|
| (acyl C8) | (238); |
| (acyl C10) | (239); |
| (acyl C12) | (240); |
| (acyl C14) | (241); |
| (acyl C16) | (242); |
| (acyl C18) | (243); |
| (acyl C18:1) | (244); |
| (acyl C18:2) | (245); |
| (acyl C18:3) | (246); |

| R = | Compound |
|---|---|
| 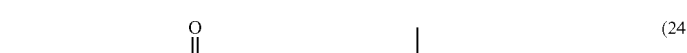 | (247); |
| 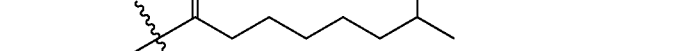 | (248); |
| 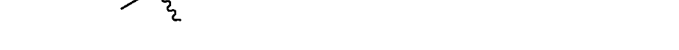 | (249); |
|  | (250); |
|  | (251); |
| 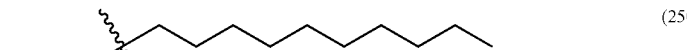 | (252); |
|  | (253); |
|  | (254); |
|  | (255); |
| 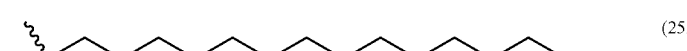 | (256); |
| 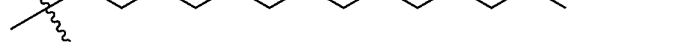 | (257); |
|  | (258); |
| 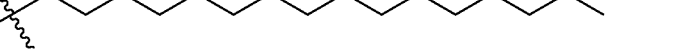 | (259); |
|  | (260); and |

-continued

| R = | Compound |
|---|---|
| 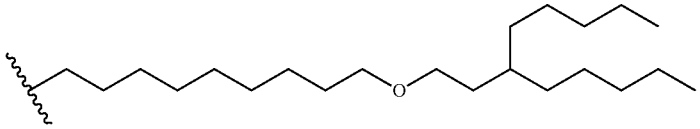 [SMILES: *CCCCCCCCCOCCC(CCCCC)CCCCC] | (261). |

In embodiments, a cationic lipid has a structure according to the following formula, (If)

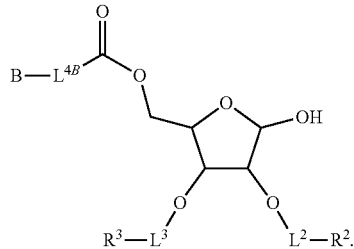

In embodiments, a cationic lipid has a structure according to the following formula, (Ig)

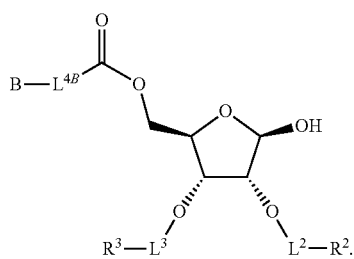

In embodiments, a cationic lipid has a structure according to the following formula, (Ih)

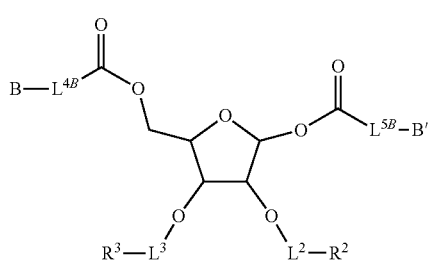

In embodiments, a cationic lipid has a structure according to the following formula, (Ij)

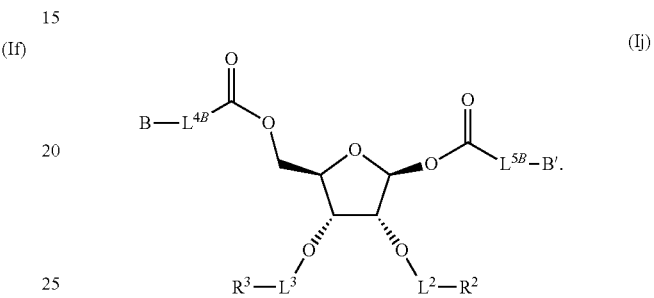

In embodiments, $L^{5B}$ is —$CH_2$—, —$CH_2CH_2$—, —$CH_2CH_2CH_2$—, or —$CH_2CH_2CH_2CH_2$—.

In embodiments, B' is $NR^4R^5$, and each $R^4$ and $R^5$ is independently hydrogen or unsubstituted $C_1$-$C_6$ alkyl, or $R^4$ and $R^5$ combine to form a 5- to 6-membered heterocyclyl comprising one or two ring nitrogens. In embodiments, B' is $N(CH_3)_2$.

In embodiments, $L^{4B}$ is —$CH_2$—. In embodiments, $L^{4B}$ is —$CH_2CH_2$—. In embodiments, $L^{4B}$ is —$CH_2CH_2CH_2$—. In embodiments, $L^{4B}$ is —$CH_2CH_2CH_2CH_2$—.

In embodiments, B' is $NR^4R^5$, and each $R^4$ and $R^5$ is independently hydrogen or unsubstituted $C_1$-$C_6$ alkyl, or $R^4$ and $R^5$ combine to form a 5- to 6-membered heterocyclyl comprising one or two ring nitrogens. In embodiments, B' is $N(CH_3)_2$.

In embodiments, each of $L^2$ and $L^3$ is a covalent bond.

In embodiments, each of $L^2$ and $L^3$ is —C(O)—.

In embodiments, each of $R^2$ and $R^3$ is independently $C_6$-$C_{22}$ alkyl, $C_6$-$C_{22}$ alkenyl, or $C_6$-$C_{22}$ alkynyl.

In embodiments, each $R^2$ and $R^3$ is unsubstituted linear $C_6$-$C_{22}$ alkyl, unsubstituted linear $C_6$-$C_{22}$ alkenyl, unsubstituted linear $C_6$-$C_{22}$ alkynyl, unsubstituted branched $C_6$-$C_{22}$ alkyl, unsubstituted branched $C_6$-$C_{22}$ alkenyl, or unsubstituted branched $C_6$-$C_{22}$ alkynyl. In embodiments, each $R^2$ and $R^3$ is unsubstituted linear $C_6$-$C_{22}$ alkyl. In embodiments, each $R^2$ and $R^3$ is unsubstituted linear $C_6$-$C_{22}$ alkenyl. In embodiments, each $R^2$ and $R^3$ is unsubstituted linear $C_6$-$C_{22}$ alkynyl. In embodiments, each $R^2$ and $R^3$ is unsubstituted branched $C_6$-$C_{22}$ alkyl. In embodiments, each $R^2$ and $R^3$ is unsubstituted branched $C_6$-$C_{22}$ alkenyl. In embodiments, each $R^2$ and $R^3$ is unsubstituted branched $C_6$-$C_{22}$ alkynyl.

In embodiments, each of $R^2$ and $R^3$ is unsubstituted $C_6$-$C_{22}$ alkyl. In embodiments, each of $R^2$ and $R^3$ is $(CH_2)_7CH_3$, $(CH_2)_9CH_3$, $(CH_2)_{11}CH_3$, $(CH_2)_{13}CH_3$, $(CH_2)_{15}CH_3$, or $(CH_2)_{17}CH_3$. In embodiments, each of $R^2$ and $R^3$ is $(CH_2)_6CH_3$, $(CH_2)_8CH_3$, $(CH_2)_{10}CH_3$, $(CH_2)_{12}CH_3$, $(CH_2)_{14}CH_3$, or $(CH_2)_{16}CH_3$. In embodiments, each of $R^2$ and $R^3$ is $C_6$-$C_{12}$ alkyl substituted by —O(CO)$R^6$ or —C(O)O$R^6$, wherein $R^6$ is unsubstituted $C_6$-$C_{14}$ alkyl. In embodiments, $R^6$ is unsubstituted linear $C_6$-$C_{14}$ alkyl. In embodiments, $R^6$ is unsubstituted branched $C_6$-$C_{14}$ alkyl. In embodiments, each of $R^2$ and $R^3$ is $(CH_2)_8OC(O)(CH_2)CH_3$, $(CH_2)_9OC(O)(CH_2)_6CH_3$, $(CH_2)_7C(O)O(CH_2)_2CH(C_5H_{11})_2$, or $(CH_2)_8C(O)O(CH_2)_2CH(C_5H_{11})_2$.

In embodiments, each of $R^2$ and $R^3$ is unsubstituted $C_6$-$C_{22}$ alkenyl. In embodiments, a $C_6$-$C_{22}$ alkenyl is a monoalkenyl, a dienyl, or a trienyl.

In embodiments, each of $R^2$ and $R^3$ is

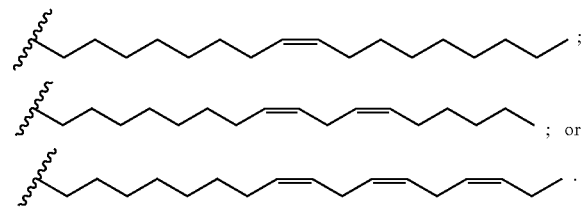

In embodiments, each of $R^2$ and $R^3$ is

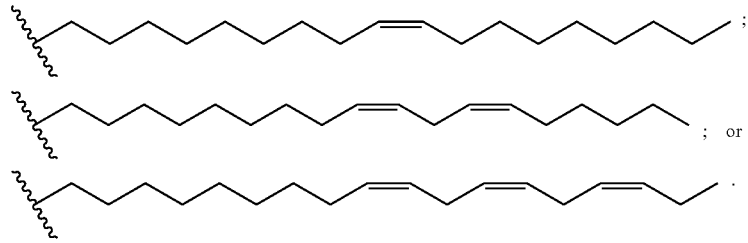

In embodiments, a cationic lipid selected from the group consisting of cationic lipids (22)-(462).

In another aspect, the invention features a compound having the following structure,

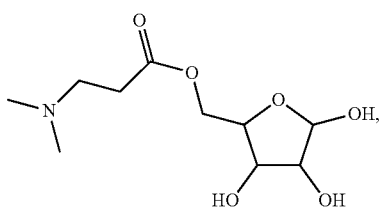 (C)

or a salt thereof.

In another aspect, the invention features a compound having the following structure,

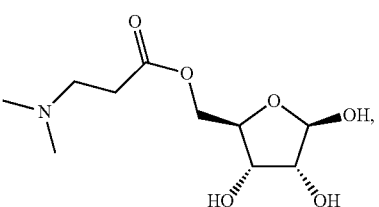 (C1)

or a salt thereof.

In some aspects, the present invention provides methods of preparing cationic lipids described herein (e.g., a cationic lipid of Formula (I'), (I), (II), or (IIIa)-(IIIab) such as cationic lipids (1a)-(21a), (1b)-(21b), and (22)-(462)).

In some aspects, the present invention provides a composition such as a pharmaceutical composition comprising a cationic lipid of the present invention and one or more polynucleotides.

In some embodiments, a composition (e.g., a pharmaceutical composition) comprises an mRNA encoding a protein, encapsulated within a liposome. In embodiments, the liposome comprises one or more cationic lipids described herein (e.g., a cationic lipid of Formula (I'), (I), (II), or (IIIa)-(IIIab) such as cationic lipids (1a)-(21a), (1b)-(21b), and (22)-(462)), one or more non-cationic lipids, one or more cholesterol-based lipids and/or one or more PEG-modified lipids. In embodiments, the liposome comprises one or more cationic lipids described herein (e.g., a cationic lipid of Formula (I'), (I), (II), or (IIIa)-(IIIab) such as cationic lipids (1a)-(21a), (1b)-(21b), and (22)-(462)), one or more non-cationic lipids, one or more cholesterol-based lipids and one or more PEG-modified lipids. In embodiments, an mRNA encodes for cystic fibrosis transmembrane conductance regulator (CFTR) protein. In embodiments, an mRNA encodes for ornithine transcarbamylase (OTC) protein. In embodiments, an mRNA encodes for an antigen from an infectious agent.

In embodiments, a composition (e.g., a pharmaceutical composition) comprises a nucleic acid encapsulated within a liposome, wherein the liposome comprises a cationic lipid as described herein (e.g., a cationic lipid of Formula (I'), (I), (II), or (IIIa)-(IIIab) such as cationic lipids (1a)-(21a), (1b)-(21b), and (22)-(462)). In embodiments, a composition further comprises one more lipids selected from the group consisting of one or more cationic lipids, one or more non-cationic lipids, and one or more PEG-modified lipids. In embodiments, a composition further comprises one more lipids selected from the group consisting of one or more non-cationic lipids and one or more PEG-modified lipids. In embodiments, a nucleic acid is an mRNA encoding a peptide or polypeptide. In embodiments, an mRNA encodes a peptide or polypeptide for use in the delivery to or treatment of the lung of a subject or a lung cell (e.g., an mRNA encodes cystic fibrosis transmembrane conductance regulator (CFTR) protein). In embodiments, an mRNA encodes a peptide or polypeptide for use in the delivery to or treatment of the liver of a subject or a liver cell (e.g., an mRNA encodes ornithine transcarbamylase (OTC) protein). In embodiments, an mRNA encodes for an antigen from an infectious agent.

In some aspects, the present invention provides methods of treating a disease in a subject comprising administering to the subject a composition (e.g., a pharmaceutical composition) as described herein.

In embodiments, a composition (e.g., a pharmaceutical composition) is formulated for intravenous (IV) administration.

In embodiments, a composition (e.g., a pharmaceutical composition) is formulated for intramuscular (IM) administration.

In embodiments, a composition (e.g., a pharmaceutical composition) is formulated for administration by inhalation. In embodiments, a composition (e.g., a pharmaceutical composition) is formulated for nebulization.

BRIEF DESCRIPTION OF DRAWINGS

FIG. 1 shows hEPO protein expression following intravenous (IV) administration of lipid nanoparticle formulations comprising a cationic lipid described herein and mRNA encoding hEPO. Protein expression was determined using ELISA.

DETAILED DESCRIPTION OF CERTAIN EMBODIMENTS

Definitions

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Amino acid: As used herein, the term "amino acid," in its broadest sense, refers to any compound and/or substance that can be incorporated into a polypeptide chain. In some embodiments, an amino acid has the general structure $H_2N$—$C(H)(R)$—$COOH$. In some embodiments, an amino acid is a naturally occurring amino acid. In some embodiments, an amino acid is a synthetic amino acid; in some embodiments, an amino acid is a d-amino acid; in some embodiments, an amino acid is an I-amino acid. "Standard amino acid" refers to any of the twenty standard I-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the term "biologically active" refers to a characteristic of any agent that has activity in a biological system, and particularly in an organism. For instance, an agent that, when administered to an organism, has a biological effect on that organism, is considered to be biologically active.

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery").

Expression: As used herein, "expression" of a nucleic acid sequence refers to translation of an mRNA into a polypeptide, assemble multiple polypeptides into an intact protein (e.g., enzyme) and/or post-translational modification of a polypeptide or fully assembled protein (e.g., enzyme). In this application, the terms "expression" and "production," and grammatical equivalent, are used inter-changeably.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

messenger RNA (mRNA): As used herein, the term "messenger RNA (mRNA)" or "mRNA" refers to a polynucleotide that encodes at least one polypeptide. mRNA as used herein encompasses both modified and unmodified RNA. The term "modified mRNA" related to mRNA comprising at least one chemically modified nucleotide. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. In some embodiments, "nucleic acid" encompasses ribonucleic acids (RNA), including but not limited to any one or more of interference RNAs (RNAi), small interfering RNA (siRNA), short hairpin RNA (shRNA), antisense RNA (aRNA), messenger RNA (mRNA), modified messenger RNA (mmRNA), long non-coding RNA (lncRNA), micro-RNA (miRNA) multimeric coding nucleic acid (MCNA), polymeric coding nucleic acid (PCNA), guide RNA (gRNA) and CRISPR RNA (crRNA). In some embodiments, "nucleic acid" encompasses deoxyribonucleic acid (DNA), including but not limited to any one or more of single-stranded DNA (ssDNA), double-stranded DNA (dsDNA) and complementary DNA (cDNA). In some embodiments, "nucleic acid" encompasses both RNA and DNA. In embodiments, DNA may be in the form of antisense DNA, plasmid DNA, parts of a plasmid DNA, pre-condensed DNA, a product of a polymerase chain reaction (PCR), vectors (e.g., P1, PAC, BAC, YAC, artificial chromosomes), expression cassettes, chimeric sequences, chromosomal DNA, or derivatives of these groups. In embodiments, RNA may be in the form of messenger RNA (mRNA), ribosomal RNA (rRNA), signal recognition particle RNA (7 SL RNA or SRP RNA), transfer RNA (tRNA), transfer-messenger RNA (tmRNA), small nuclear RNA (snRNA), small nucleolar RNA (snoRNA), SmY RNA, small Cajal body-specific RNA (scaRNA), guide RNA (gRNA), ribonuclease P (RNase P), Y RNA, telomerase RNA component (TERC), spliced leader RNA (SL RNA), antisense RNA (aRNA or asRNA), cis-natural antisense transcript (cis-NAT), CRISPR RNA (crRNA), long noncoding RNA (lncRNA), micro-RNA (miRNA), piwi-interacting RNA (piRNA), small interfering RNA (siRNA), transacting siRNA (tasiRNA), repeat associated siRNA (rasiRNA), 73K RNA, retrotransposons, a viral genome, a viroid, satellite RNA, or derivatives of these groups. In some embodiments, a nucleic acid is a mRNA encoding a protein such as an enzyme.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable", as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium. quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quaternization of an amine using an appropriate electrophile, e.g., an alkyl halide, to form a quarternized alkylated amino salt.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Aliphatic: As used herein, the term aliphatic refers to $C_1$-$C_{40}$ hydrocarbons and includes both saturated and unsaturated hydrocarbons. An aliphatic may be linear, branched, or cyclic. For example, $C_1$-$C_{20}$ aliphatics can include $C_1$-$C_{20}$ alkyls (e.g., linear or branched $C_1$-$C_{20}$ saturated alkyls), $C_2$-$C_{20}$ alkenyls (e.g., linear or branched $C_4$-$C_{20}$ dienyls, linear or branched $C_6$-$C_{20}$ trienyls, and the like), and $C_2$-$C_{20}$ alkynyls (e.g., linear or branched $C_2$-$C_{20}$ alkynyls). $C_1$-$C_{20}$ aliphatics can include $C_3$-$C_{20}$ cyclic aliphatics (e.g., $C_3$-$C_{20}$ cycloalkyls, $C_4$-$C_{20}$ cycloalkenyls, or $C_8$-$C_{20}$ cycloalkynyls). In certain embodiments, the aliphatic may comprise one or more cyclic aliphatic and/or one or more heteroatoms such as oxygen, nitrogen, or sulfur and may optionally be substituted with one or more substituents such as alkyl, halo, alkoxyl, hydroxy, amino, aryl, ether, ester or amide. An aliphatic group is unsubstituted or substituted with one or more substituent groups as described herein. For example, an aliphatic may be substituted with one or more (e.g., 1, 2, 3, 4, 5, or 6 independently selected substituents) of halogen, —COR', —CO$_2$H, —CO$_2$R', —CN, —OH, —OR', —OCOR', —OCO$_2$R', —NH$_2$, —NHR', —N(R')$_2$, —SR' or —SO$_2$R', wherein each instance of R' independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In embodiments, R' independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In embodiments, R' independently is unsubstituted $C_1$-$C_3$ alkyl. In embodiments, the aliphatic is unsubstituted. In embodiments, the aliphatic does not include any heteroatoms.

Alkyl: As used herein, the term "alkyl" means acyclic linear and branched hydrocarbon groups, e.g. "$C_1$-$C_{20}$ alkyl" refers to alkyl groups having 1-20 carbons. An alkyl group may be linear or branched. Examples of alkyl groups include, but are not limited to, methyl, ethyl, n-propyl, isopropyl, butyl, isobutyl, sec-butyl, tert-butyl, pentyl, isopentyl tert-pentylhexyl, Isohexyletc. Other alkyl groups will be readily apparent to those of skill in the art given the benefit of the present disclosure. An alkyl group may be unsubstituted or substituted with one or more substituent groups as described herein. For example, an alkyl group may be substituted with one or more (e.g., 1, 2, 3, 4, 5, or 6 independently selected substituents) of halogen, —COR', —CO$_2$H, —CO$_2$R', —CN, —OH, —OR', —OCOR', —OCO$_2$R', —NH$_2$, —NHR', —N(R')$_2$, —SR' or —S$_2$R', wherein each instance of R' independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In embodiments, R' independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In embodiments, R' independently is unsubstituted $C_1$-$C_3$ alkyl. In embodiments, the alkyl is substituted (e.g., with 1, 2, 3, 4, 5, or 6 substituent groups as described herein).

Alkylene: The term "alkylene," as used herein, represents a saturated divalent straight or branched chain hydrocarbon group and is exemplified by methylene, ethylene, isopropylene and the like. Likewise, the term "alkenylene" as used herein represents an unsaturated divalent straight or branched chain hydrocarbon group having one or more unsaturated carbon-carbon double bonds that may occur in any stable point along the chain, and the term "alkynylene" herein represents an unsaturated divalent straight or branched chain hydrocarbon group having one or more unsaturated carbon-carbon triple bonds that may occur in any stable point along the chain. In certain embodiments, an alkylene, alkenylene, or alkynylene group may comprise one or more cyclic aliphatic and/or one or more heteroatoms such as oxygen, nitrogen, or sulfur and may optionally be substituted with one or more substituents such as alkyl, halo, alkoxyl, hydroxy, amino, aryl, ether, ester or amide. For example, an alkylene, alkenylene, or alkynylene may be substituted with one or more (e.g., 1, 2, 3, 4, 5, or 6 independently selected substituents) of halogen, —COR', —CO$_2$H, —C$_2$R', —CN, —OH, —OR', —OCOR', —OCO$_2$R', —NH$_2$, —NHR', —N(R')$_2$, —SR' or —S$_2$R', wherein each instance of R' independently is C$_1$-C$_{20}$ aliphatic (e.g., C$_1$-C$_{20}$ alkyl, C$_1$-C$_{15}$ alkyl, C$_1$-C$_{10}$ alkyl, or C$_1$-C$_3$ alkyl). In embodiments, R' independently is an unsubstituted alkyl (e.g., unsubstituted C$_1$-C$_{20}$ alkyl, C$_1$-C$_{15}$ alkyl, C$_1$-C$_{10}$ alkyl, or C$_1$-C$_3$ alkyl). In embodiments, R' independently is unsubstituted C$_1$-C$_3$ alkyl. In certain embodiments, an alkylene, alkenylene, or alkynylene is unsubstituted. In certain embodiments, an alkylene, alkenylene, or alkynylene does not include any heteroatoms.

Alkenyl: As used herein, "alkenyl" means any linear or branched hydrocarbon chains having one or more unsaturated carbon-carbon double bonds that may occur in any stable point along the chain, e.g. "C$_2$-C$_{20}$ alkenyl" refers to an alkenyl group having 2-20 carbons. For example, an alkenyl group includes prop-2-enyl, but-2-enyl, but-3-enyl, 2-methylprop-2-enyl, hex-2-enyl, hex-5-enyl, 2,3-dimethylbut-2-enyl, and the like. In embodiments, the alkenyl comprises 1, 2, or 3 carbon-carbon double bond. In embodiments, the alkenyl comprises a single carbon-carbon double bond. In embodiments, multiple double bonds (e.g., 2 or 3) are conjugated. An alkenyl group may be unsubstituted or substituted with one or more substituent groups as described herein. For example, an alkenyl group may be substituted with one or more (e.g., 1, 2, 3, 4, 5, or 6 independently selected substituents) of halogen, —COR', —CO$_2$H, —CO$_2$R', —CN, —OH, —OR', —OCOR', —OCO$_2$R', —NH$_2$, —NHR', —N(R')$_2$, —SR' or —SO$_2$R', wherein each instance of R' independently is C$_1$-C$_{20}$ aliphatic (e.g., C$_1$-C$_{20}$ alkyl, C$_1$-C$_{15}$ alkyl, C$_1$-C$_{10}$ alkyl, or C$_1$-C$_3$ alkyl). In embodiments, R' independently is an unsubstituted alkyl (e.g., unsubstituted C$_1$-C$_{20}$ alkyl, C$_1$-C$_{15}$ alkyl, C$_1$-C$_{10}$ alkyl, or C$_1$-C$_3$ alkyl). In embodiments, R' independently is unsubstituted C$_1$-C$_3$ alkyl. In embodiments, the alkenyl is unsubstituted. In embodiments, the alkenyl is substituted (e.g., with 1, 2, 3, 4, 5, or 6 substituent groups as described herein).

Alkynyl: As used herein, "alkynyl" means any hydrocarbon chain of either linear or branched configuration, having one or more carbon-carbon triple bonds occurring in any stable point along the chain, e.g. "C$_2$-C$_{20}$ alkynyl" refers to an alkynyl group having 2-20 carbons. Examples of an alkynyl group include prop-2-ynyl, but-2-ynyl, but-3-ynyl, pent-2-ynyl, 3-methylpent-4-ynyl, hex-2-ynyl, hex-5-ynyl, etc. In embodiments, an alkynyl comprises one carbon-carbon triple bond. An alkynyl group may be unsubstituted or substituted with one or more substituent groups as described herein. For example, an alkynyl group may be substituted with one or more (e.g., 1, 2, 3, 4, 5, or 6 independently selected substituents) of halogen, —COR', —C$_2$H, —C$_2$R', —CN, —OH, —OR', —OCOR', —OCO$_2$R', —NH$_2$, —NHR', —N(R')$_2$, —SR' or —S$_2$R', wherein each instance of R' independently is C$_1$-C$_{20}$ aliphatic (e.g., C$_1$-C$_{20}$ alkyl, C$_1$-C$_{15}$ alkyl, C$_1$-C$_{10}$ alkyl, or C$_1$-C$_3$ alkyl). In embodiments, R' independently is an unsubstituted alkyl (e.g., unsubstituted C$_1$-C$_{20}$ alkyl, C$_1$-C$_{15}$ alkyl, C$_1$-C$_{10}$ alkyl, or C$_1$-C$_3$ alkyl). In embodiments, R' independently is unsubstituted C$_1$-C$_3$ alkyl. In embodiments, the alkynyl is unsubstituted. In embodiments, the alkynyl is substituted (e.g., with 1, 2, 3, 4, 5, or 6 substituent groups as described herein).

Cycloalkyl: As used herein, the term "cycloalkyl" means a nonaromatic, saturated, cyclic group, e.g. "C$_3$-C$_{10}$ cycloalkyl." In embodiments, a cycloalkyl is monocyclic. In embodiments, a cycloalkyl is polycyclic (e.g., bicyclic or tricyclic). In polycyclic cycloalkyl groups, individual rings can be fused, bridged, or spirocyclic. Examples of a cycloalkyl group include cyclopropyl, cyclobutyl, cyclopentyl, cyclohexyl, norbornanyl, bicyclo[3.2.1]octanyl, octahydropentalenyl, and spiro[4.5]decanyl, and the like. The term "cycloalkyl" may be used interchangeably with the term "carbocycle". A cycloalkyl group may be unsubstituted or substituted with one or more substituent groups as described herein. For example, a cycloalkyl group may be substituted with one or more (e.g., 1, 2, 3, 4, 5, or 6 independently selected substituents) of halogen, —COR', —CO$_2$H, —CO$_2$R', —CN, —OH, —OR', —OCOR', —OCO$_2$R', —NH$_2$, —NHR', —N(R')$_2$, —SR' or —SO$_2$R', wherein each instance of R' independently is C$_1$-C$_{20}$ aliphatic (e.g., C$_1$-C$_{20}$ alkyl, C$_1$-C$_{15}$ alkyl, C$_1$-C$_{10}$ alkyl, or C$_1$-C$_3$ alkyl). In embodiments, R' independently is an unsubstituted alkyl (e.g., unsubstituted C$_1$-C$_{20}$ alkyl, C$_1$-C$_{15}$ alkyl, C$_1$-C$_{10}$ alkyl, or C$_1$-C$_3$ alkyl). In embodiments, R' independently is unsubstituted C$_1$-C$_3$ alkyl. In embodiments, the cycloalkyl is unsubstituted. In embodiments, the cycloalkyl is substituted (e.g., with 1, 2, 3, 4, 5, or 6 substituent groups as described herein).

Heterocyclyl: As used herein, "heterocyclyl" refers to a radical of a 3- to 14-membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, and phosphorus ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, and phosphorus ("5-10 membered heterocyclyl"). In some embodiments, a heterocyclyl group is a 5-8 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, and phosphorus ("5-8 membered heterocyclyl"). In some embodiments, a heterocyclyl group is a 5-6 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, and phosphorus ("5-6 membered heterocyclyl"). In some embodiments, the 5-6 membered heterocyclyl has 1 or more (e.g., 1, 2, or 3) ring heteroatoms selected from oxygen, sulfur, nitrogen, boron, silicon, and phosphorus. In some embodiments, the 5-6 membered heterocyclyl has 1 or 2 ring heteroatoms selected from oxygen, sulfur, nitrogen, boron, silicon, and phosphorus. In some embodiments, the 5-6 membered heterocyclyl has 1 ring heteroatom selected from oxygen, sulfur, nitrogen, boron, silicon, and phosphorus.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation. tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b] pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

Halogen: As used herein, the term "halogen" means fluorine, chlorine, bromine, or iodine.

Cationic Lipids

Liposomal-based vehicles are considered an attractive carrier for therapeutic agents and remain subject to continued development efforts. While liposomal-based vehicles that comprise a cationic lipid component have shown promising results with regards to encapsulation, stability and site localization, there remains a great need for improvement of liposomal-based delivery systems. For example, a significant drawback of liposomal delivery systems relates to the construction of liposomes that have sufficient cell culture or in vivo stability to reach desired target cells and/or intracellular compartments, and the ability of such liposomal delivery systems to efficiently release their encapsulated materials to such target cells.

In particular, there remains a need for improved cationic lipids that demonstrate improved pharmacokinetic properties and which are capable of delivering macromolecules, such as nucleic acids to a wide variety cell types and tissues with enhanced efficiency. Importantly, there also remains a particular need for novel cationic lipids that are characterized as having reduced toxicity and are capable of efficiently delivering encapsulated nucleic acids and polynucleotides to targeted cells, tissues and organs.

Described herein are novel cationic lipids, compositions comprising such lipids, and related methods of their use. In embodiments, the compounds described herein are useful as liposomal compositions or as components of liposomal compositions to facilitate the delivery to, and subsequent transfection of one or more target cells.

Cationic lipids disclosed herein comprise a basic, ionizable functional group (e.g., an amine or a nitrogen-containing heteroaryl as described herein), which is present in neutral or charged form.

In embodiments, cationic lipids described herein can provide one or more desired characteristics or properties. That is, in certain embodiments, cationic lipids described herein can be characterized as having one or more properties that afford such compounds advantages relative to other similarly classified lipids. For example, cationic lipids disclosed herein can allow for the control and tailoring of the properties of liposomal compositions (e.g., lipid nanoparticles) of which they are a component. In particular, cationic lipids disclosed herein can be characterized by enhanced transfection efficiencies and their ability to provoke specific biological outcomes. Such outcomes can include, for example enhanced cellular uptake, endosomal/lysosomal disruption capabilities and/or promoting the release of encapsulated materials (e.g., polynucleotides) intracellularly.

Cationic Lipids of Formula (I'), (I), (II), and (III)

In one aspect, the present invention provides a cationic lipid of Formula (I'):

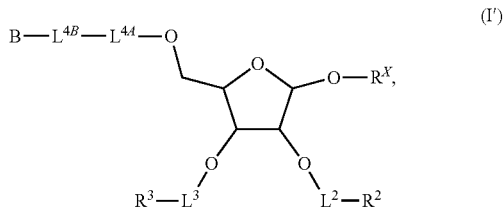

(I')

wherein:

$R^X$ is independently —H, -$L^1$-$R^1$, or -$L^{5A}$-$L^{5B}$-B';

each of $L^1$, $L^2$, and $L^3$ is independently a covalent bond, —C(O)—, —C(O)O—, —C(O)S—, or —C(O)NR$^L$—;

each $L^{4A}$ and $L^{5A}$ is independently —C(O)—, —C(O)O—, or —C(O)NR$^L$—;

each $L^{4B}$ and $L^{5B}$ is independently $C_1$-$C_{20}$ alkylene; $C_2$-$C_{20}$ alkenylene; or $C_2$-$C_{20}$ alkynylene;

each B and B' is NR$^4$R$^5$, a 5- to 10-membered nitrogen-containing heterocyclyl, or a 5- to 10-membered nitrogen-containing heteroaryl;

each $R^1$, $R^2$, and $R^3$ is independently $C_6$-$C_{30}$ alkyl, $C_6$-$C_{30}$ alkenyl, or $C_6$-$C_{30}$ alkynyl;

each $R^4$ and $R^5$ is independently hydrogen, $C_1$-$C_{10}$ alkyl; $C_2$-$C_{10}$ alkenyl; or $C_2$-$C_{10}$ alkynyl; or $R^4$ and $R^5$ combine to form a 5- to 10-membered heterocyclyl or a 5- to 10-membered heteroaryl; and each $R^L$ is independently hydrogen, $C_1$-$C_{20}$ alkyl, $C_1$-$C_{20}$ alkenyl, or $C_1$-$C_{20}$ alkynyl.

In embodiments, $R^X$ is —H. In embodiments, $R^X$ is -$L^1$-$R^1$. In embodiments, $R^X$ is -$L^{5A}$-$L^{5B}$-B'.

In some embodiments, the present invention provides a cationic lipid of Formula (I):

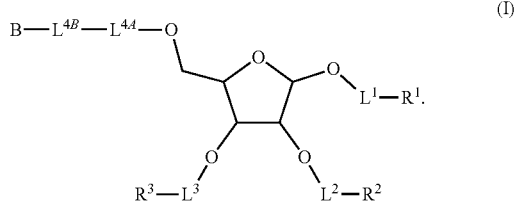

(I)

In embodiments, $L^1$ is a covalent bond. In embodiments, $L^1$ is —C(O)—. In embodiments, $L^1$ is —C(O)O—. In embodiments, $L^1$ is —C(O)S—. In embodiments, $L^1$ is —C(O)NR$^L$. In embodiments, $L^1$ is a covalent bond or —C(O)—.

In embodiments, $R^1$ is $C_6$-$C_{30}$ alkyl (e.g., $C_6$-$C_{22}$ alkyl). In embodiments, $R^1$ is unsubstituted $C_6$-$C_{30}$ alkyl (e.g., unsubstituted $C_6$-$C_{22}$ alkyl). In embodiments, $R^1$ is substituted $C_6$-$C_{30}$ alkyl (e.g., substituted $C_6$-$C_{22}$ alkyl). In embodiments, $R^1$ is $C_6$-$C_{30}$ alkenyl (e.g., $C_6$-$C_{22}$ alkenyl). In embodiments, $R^1$ is unsubstituted $C_6$-$C_{30}$ alkenyl (e.g., unsubstituted $C_6$-$C_{22}$ alkenyl). In embodiments, $R^1$ is substituted $C_6$-$C_{30}$ alkenyl (e.g., substituted $C_6$-$C_{22}$ alkenyl). In embodiments, $R^1$ is $C_6$-$C_{30}$ alkynyl (e.g., $C_6$-$C_{22}$ alkynyl). In embodiments, $R^1$ is unsubstituted $C_6$-$C_{30}$ alkynyl (e.g., unsubstituted $C_6$-$C_{22}$ alkynyl). In embodiments, $R^1$ is substituted $C_6$-$C_{30}$ alkynyl (e.g., substituted $C_6$-$C_{22}$ alkynyl). In embodiments, a $R^1$ group (e.g., as described herein) is a branched group; for example, a branched alkyl, branched alkenyl, or branched alkynyl group. In embodiments, a $R^1$ group (e.g., as described herein) is a linear group; for example, a linear alkyl, linear alkenyl, or linear alkynyl group.

In embodiments, $L^2$ is a covalent bond. In some, $L^2$ is —C(O)—. In embodiments, $L^2$ is —C(O)O—. In embodiments, $L^2$ is —C(O)S—. In some embodiments, $L^2$ is —C(O)NR$^L$. In embodiments, $L^2$ is a covalent bond or —C(O)—.

In embodiments, $R^2$ is $C_6$-$C_{30}$ alkyl (e.g., $C_6$-$C_{22}$ alkyl). In embodiments, $R^2$ is unsubstituted $C_6$-$C_{30}$ alkyl (e.g., unsubstituted $C_6$-$C_{22}$ alkyl). In embodiments, $R^2$ is substituted $C_6$-$C_{30}$ alkyl (e.g., substituted $C_6$-$C_{22}$ alkyl). In embodiments, $R^2$ is $C_6$-$C_{30}$ alkenyl (e.g., $C_6$-$C_{22}$ alkenyl). In embodiments, $R^2$ is unsubstituted $C_6$-$C_{30}$ alkenyl (e.g., unsubstituted $C_6$-$C_{22}$ alkenyl). In embodiments, $R^2$ is substituted $C_6$-$C_{30}$ alkenyl (e.g., substituted $C_6$-$C_{22}$ alkenyl). In embodiments, $R^2$ is $C_6$-$C_{30}$ alkynyl (e.g., $C_6$-$C_{22}$ alkynyl). In embodiments, $R^2$ is unsubstituted $C_6$-$C_{30}$ alkynyl (e.g., unsubstituted $C_6$-$C_{22}$ alkynyl). In embodiments, $R^2$ is substituted $C_6$-$C_{30}$ alkynyl (e.g., substituted $C_6$-$C_{22}$ alkynyl). In embodiments, a $R^2$ group (e.g., as described herein) is a branched group; for example, a branched alkyl, branched alkenyl, or branched alkynyl group. In embodiments, a $R^2$ group (e.g., as described herein) is a linear group; for example, a linear alkyl, linear alkenyl, or linear alkynyl group.

In embodiments, $L^3$ is a covalent bond. In some, $L^3$ is —C(O)—. In embodiments, $L^3$ is —C(O)O—. In embodiments, $L^3$ is —C(O)S—. In some embodiments, $L^3$ is —C(O)NR$^L$. In embodiments, $L^3$ is a covalent bond or —C(O)—.

In embodiments, -$L^{4A}$-$L^{4B}$-B is

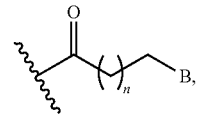

where in is an integer of 0-6.

In embodiments, -$L^{4A}$-$L^{4B}$-B is

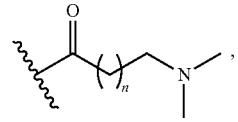

where in is an integer of 0-6.

In embodiments, -$L^{4A}$-$L^{4B}$-B is

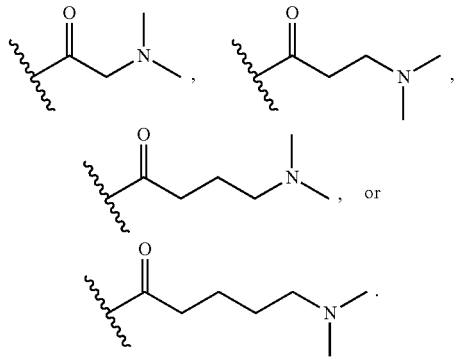

In embodiments, $R^3$ is $C_6$-$C_{30}$ alkyl (e.g., $C_6$-$C_{22}$ alkyl). In embodiments, $R^3$ is unsubstituted $C_6$-$C_{30}$ alkyl (e.g., unsubstituted $C_6$-$C_{22}$ alkyl). In embodiments, $R^3$ is substituted $C_6$-$C_{30}$ alkyl (e.g., substituted $C_6$-$C_{22}$ alkyl). In embodiments, $R^3$ is $C_6$-$C_{30}$ alkenyl (e.g., $C_6$-$C_{22}$ alkenyl). In embodiments, $R^3$ is unsubstituted $C_6$-$C_{30}$ alkenyl (e.g., unsubstituted $C_6$-$C_{22}$ alkenyl). In embodiments, $R^3$ is substituted $C_6$-$C_{30}$ alkenyl (e.g., substituted $C_6$-$C_{22}$ alkenyl). In embodiments, $R^3$ is $C_6$-$C_{30}$ alkynyl (e.g., $C_6$-$C_{22}$ alkynyl). In embodiments, $R^3$ is unsubstituted $C_6$-$C_{30}$ alkynyl (e.g., unsubstituted $C_6$-$C_{22}$ alkynyl). In embodiments, $R^3$ is substituted $C_6$-$C_{30}$ alkynyl (e.g., substituted $C_6$-$C_{22}$ alkynyl). In embodiments, a $R^3$ group (e.g., as described herein) is a branched group; for example, a branched alkyl, branched alkenyl, or branched alkynyl group. In embodiments, a $R^3$ group (e.g., as described herein) is a linear group; for example, a linear alkyl, linear alkenyl, or linear alkynyl group.

In embodiments, each of $L^1$, $L^2$, and $L^3$ is the same group. In embodiments, each of $L^1$, $L^2$, and $L^3$ is a covalent bond. In some, each of $L^1$, $L^2$, and $L^3$ is —C(O)—. In embodiments, each of $L^1$, $L^2$, and $L^3$ is —C(O)O—. In embodiments, each of $L^1$, $L^2$, and $L^3$ is —C(O)S—. In some embodiments, each of $L^1$, $L^2$, and $L^3$ is —C(O)NR$^L$—. In embodiments, each of $L^1$, $L^2$, and $L^3$ is a covalent bond or each of $L^1$, $L^2$, and $L^3$ is —C(O)—.

In embodiments, each of $R^1$, $R^2$, and $R^3$ is the same group. In embodiments, each of $R^1$, $R^2$, and $R^3$ is $C_6$-$C_{30}$ alkyl (e.g., $C_6$-$C_{22}$ alkyl). In embodiments, each of $R^1$, $R^2$, and $R^3$ is unsubstituted $C_6$-$C_{30}$ alkyl (e.g., unsubstituted $C_6$-$C_{22}$ alkyl). In embodiments, each of $R^1$, $R^2$, and $R^3$ is substituted $C_6$-$C_{30}$ alkyl (e.g., substituted $C_6$-$C_{22}$ alkyl). In embodiments, each of $R^1$, $R^2$, and $R^3$ is $C_6$-$C_{30}$ alkenyl (e.g., $C_6$-$C_{22}$ alkenyl). In embodiments, each of $R^1$, $R^2$, and $R^3$ is unsubstituted $C_6$-$C_{30}$ alkenyl (e.g., unsubstituted $C_6$-$C_{22}$ alkenyl). In embodiments, each of $R^1$, $R^2$, and $R^3$ is substituted $C_6$-$C_{30}$ alkenyl (e.g., substituted $C_6$-$C_{22}$ alkenyl). In embodiments, each of $R^1$, $R^2$, and $R^3$ is $C_6$-$C_{30}$ alkynyl (e.g., $C_6$-$C_{22}$ alkynyl). In embodiments, each of $R^1$, $R^2$, and $R^3$ is unsubstituted $C_6$-$C_{30}$ alkynyl (e.g., unsubstituted $C_6$-$C_{22}$ alkynyl). In embodiments, each of $R^1$, $R^2$, and $R^3$ is substituted $C_6$-$C_{30}$ alkynyl (e.g., substituted $C_6$-$C_{22}$ alkynyl). In embodiments, each $R^1$, $R^2$, and $R^3$ (e.g., as described herein) is a branched group; for example, a branched alkyl, branched alkenyl, or branched alkynyl group. In embodiments, each $R^1$, $R^2$, and $R^3$ (e.g., as described herein) is a linear group; for example, a linear alkyl, linear alkenyl, or linear alkynyl group.

In embodiments, $L^{4A}$ is —C(O)—. In embodiments, $L^{4A}$ is —C(O)O—. In embodiments, $L^{4A}$ is —C(O)NR$^L$—.

In embodiments, $L^{4B}$ is $C_1$-$C_{20}$ alkylene (e.g., $C_1$-$C_6$ alkylene). In embodiments, $L^{4B}$ is unsubstituted $C_1$-$C_{20}$ alkylene (e.g., unsubstituted $C_1$-$C_6$ alkylene). In embodiments, $L^{4B}$ is substituted $C_1$-$C_{20}$ alkylene (e.g., substituted $C_1$-$C_6$ alkylene). In embodiments, $L^{4B}$ is $C_2$-$C_{20}$ alkenylene (e.g., $C_2$-$C_6$ alkenylene). In embodiments, $L^{4B}$ is unsubstituted $C_2$-$C_{20}$ alkenylene (e.g., unsubstituted $C_2$-$C_6$ alkenylene). In embodiments, $L^{4B}$ is substituted $C_2$-$C_{20}$ alkenylene (e.g., substituted $C_2$-$C_6$ alkenylene). In embodiments, $L^{4B}$ is $C_2$-$C_{20}$ alkynylene (e.g., $C_2$-$C_6$ alkynylene). In embodiments, $L^{4B}$ is unsubstituted $C_2$-$C_{20}$ alkynylene (e.g., unsubstituted $C_2$-$C_6$ alkynylene). In embodiments, $L^{4B}$ is substituted $C_2$-$C_{20}$ alkynylene (e.g., substituted $C_2$-$C_6$ alkynylene). In embodiments, $L^{4B}$ is —CH$_2$—. In embodiments, $L^{4B}$ is —CH$_2$CH$_2$—. In embodiments, $L^{4B}$ is —CH$_2$CH$_2$—.

In embodiments, B is NR$^4$R$^5$. In embodiments, each $R^4$ and $R^5$ is independently hydrogen or unsubstituted $C_1$-$C_{10}$ alkyl (e.g., unsubstituted $C_1$-$C_6$ alkyl such as CH$_3$), or $R^4$ and $R^5$ combine to form a 5- to 6-membered heterocyclyl comprising one or two ring nitrogens.

In embodiments, B is NR$^4$R$^5$, and $R^4$ and $R^5$ combine to form a 5- to 10-membered heterocyclyl or a 5- to 10-membered heteroaryl. In embodiments, $R^4$ and $R^5$ combine to form a 5- to 10-membered heterocyclyl. In embodiments, $R^4$ and $R^5$ combine to form a 5- to 10-membered heterocyclyl comprising one or two nitrogens in the ring or rings. In embodiments, $R^4$ and $R^5$ combine to form a piperdinyl or piperazinyl. In embodiments, $R^4$ and $R^5$ combine to form an unsubstituted piperdinyl. In embodiments, $R^4$ and $R^5$ combine to form an unsubstituted piperazinyl. In embodiments, $R^4$ and $R^5$ combine to form a substituted piperdinyl. In embodiments, $R^4$ and $R^5$ combine to form a substituted piperazinyl. In embodiments, $R^4$ and $R^5$ combine to form 4-methylpiperazinyl.

In embodiments, $L^{5A}$ is —C(O)—. In embodiments, $L^{5A}$ is —C(O)O—. In embodiments, $L^{5A}$ is —C(O)NR$^L$—. In embodiments, $L^{5A}$ and $L^{4A}$ are the same. In embodiments, $L^{5A}$ and $L^{4A}$ are different.

In embodiments, $L^{5B}$ is $C_1$-$C_{20}$ alkylene (e.g., $C_1$-$C_6$ alkylene). In embodiments, $L^{5B}$ is unsubstituted $C_1$-$C_{20}$ alkylene (e.g., unsubstituted $C_1$-$C_6$ alkylene). In embodiments, $L^{5B}$ is substituted $C_1$-$C_{20}$ alkylene (e.g., substituted $C_1$-$C_6$ alkylene). In embodiments, $L^{5B}$ is $C_2$-$C_{20}$ alkenylene (e.g., $C_2$-$C_6$ alkenylene). In embodiments, $L^{5B}$ is unsubstituted $C_2$-$C_{20}$ alkenylene (e.g., unsubstituted $C_2$-$C_6$ alkenylene). In embodiments, $L^{5B}$ is substituted $C_2$-$C_{20}$ alkenylene (e.g., substituted $C_2$-$C_6$ alkenylene). In embodiments, $L^{5B}$ is $C_2$-$C_{20}$ alkynylene (e.g., $C_2$-$C_6$ alkynylene). In embodiments, $L^{5B}$ is unsubstituted $C_2$-$C_{20}$ alkynylene (e.g., unsubstituted $C_2$-$C_6$ alkynylene). In embodiments, $L^{5B}$ is substituted $C_2$-$C_{20}$ alkynylene (e.g., substituted $C_2$-$C_6$ alkynylene). In embodiments, $L^{5B}$ is —CH$_2$—. In embodiments, $L^{5B}$ is —CH$_2$CH$_2$—. In embodiments, $L^{5B}$ is —CH$_2$CH$_2$CH$_2$—. In embodiments, $L^{5B}$ and $L^{4B}$ are the same. In embodiments, $L^{5B}$ and $L^{4B}$ are different.

In embodiments, B' is NR$^4$R$^5$. In embodiments, each $R^4$ and $R^5$ is independently hydrogen or unsubstituted $C_1$-$C_{10}$ alkyl (e.g., unsubstituted $C_1$-$C_6$ alkyl such as CH$_3$). In embodiments, B' and B are the same. In embodiments, B' and B are different.

In embodiments, $R^4$ is hydrogen or $C_1$-$C_{10}$ alkyl (e.g., $C_1$-$C_6$ alkyl). In embodiments, $R^4$ is hydrogen. In embodiments, $R^4$ is $C_1$-$C_{10}$ alkyl (e.g., $C_1$-$C_6$ alkyl). In embodiments, $R^4$ is unsubstituted $C_1$-$C_{10}$ alkyl (e.g., unsubstituted $C_1$-$C_6$ alkyl). In embodiments, $R^4$ is substituted $C_1$-$C_{10}$ alkyl (e.g., substitute $C_1$-$C_6$ alkyl). In embodiments, $R^4$ is $C_2$-$C_{10}$ alkenyl (e.g., $C_2$-$C_6$ alkenyl). In embodiments, $R^4$ is unsubstituted $C_2$-$C_{10}$ alkenyl (e.g., unsubstituted $C_2$-$C_6$ alkenyl). In embodiments, $R^4$ is unsubstituted $C_2$-$C_{10}$ alkenyl (e.g., substituted $C_2$-$C_6$ alkenyl). In embodiments, $R^4$ is $C_2$-$C_{10}$ alkynyl (e.g., $C_2$-$C_6$ alkynyl). In embodiments, $R^4$ is unsubstituted $C_2$-$C_{10}$ alkynyl (e.g., unsubstituted $C_2$-$C_6$ alkynyl). In embodiments, $R^4$ is substituted $C_2$-$C_{10}$ alkynyl (e.g., substituted $C_2$-$C_6$ alkynyl). In embodiments, $R^4$ is CH$_3$.

In embodiments, $R^5$ is hydrogen or $C_1$-$C_{10}$ alkyl (e.g., $C_1$-$C_6$ alkyl). In embodiments, $R^5$ is hydrogen. In embodiments, $R^5$ is $C_1$-$C_{10}$ alkyl (e.g., $C_1$-$C_6$ alkyl). In embodiments, $R^5$ is unsubstituted $C_1$-$C_{10}$ alkyl (e.g., unsubstituted $C_1$-$C_6$ alkyl). In embodiments, $R^5$ is substituted $C_1$-$C_{10}$ alkyl (e.g., substitute $C_1$-$C_6$ alkyl). In embodiments, $R^5$ is $C_2$-$C_{10}$ alkenyl (e.g., $C_2$-$C_6$ alkenyl). In embodiments, $R^5$ is unsubstituted $C_2$-$C_{10}$ alkenyl (e.g., unsubstituted $C_2$-$C_6$ alkenyl). In embodiments, $R^5$ is unsubstituted $C_2$-$C_{10}$ alkenyl (e.g., substituted $C_2$-$C_6$ alkenyl). In embodiments, $R^5$ is $C_2$-$C_{10}$ alkynyl (e.g., $C_2$-$C_6$ alkynyl). In embodiments, $R^5$ is unsubstituted $C_2$-$C_{10}$ alkynyl (e.g., unsubstituted $C_2$-$C_6$ alkynyl). In embodiments, $R^5$ is substituted $C_2$-$C_{10}$ alkynyl (e.g., substituted $C_2$-$C_6$ alkynyl). In embodiments, $R^5$ is CH$_3$.

In embodiments, B is N(CH$_3$)$_2$.

In embodiments, B is 5- to 10-membered nitrogen-containing heteroaryl. In embodiments, B is pyrrolyl, imidazolyl, pyrazolyl, oxazolyl, isoxazolyl, thiazolyl, isothiazolyl, triazolyl, tetrazolyl, pyridyl, pyrazinyl, pyridazinyl, pyrimidinyl, indolyl, quinolyl, or isoquinolyl. In embodiments, B is an unsubstituted heteroaryl that is pyrrolyl, imidazolyl, pyrazolyl, oxazolyl, isoxazolyl, thiazolyl, isothiazolyl, triazolyl, tetrazolyl, pyridyl, pyrazinyl, pyridazinyl, pyrimidinyl, indolyl, quinolyl, or isoquinolyl. In embodiments, B is a substituted heteroaryl that is pyrrolyl, imidazolyl, pyrazolyl, oxazolyl, isoxazolyl, thiazolyl, isothiazolyl, triazolyl, tetrazolyl, pyridyl, pyrazinyl, pyridazinyl, pyrimidinyl, indolyl, quinolyl, or isoquinolyl. In embodiments B is imidazolyl (e.g., unsubstituted imidazolyl or substituted imidazolyl). In embodiments B is pyridyl (e.g., unsubstituted pyridyl or unsubstituted pyridyl).

In embodiments, B is 5- to 10-membered nitrogen-containing heterocyclyl. In embodiments, B is pyrrolidinyl, imidazolidinyl, pyrazolidinyl, piperidinyl, piperazinyl, hexahydro-1,3,5-triazinyl, azepanyl, diazepanyl, azocanyl, azonanyl, and the like. In embodiments, B is piperdinyl (e.g., unsubstituted piperdinyl or substituted piperdinyl). In embodiments, B is piperazinyl (e.g., unsubstituted piperazinyl or substituted piperazinyl).

In embodiments, $R^L$ is independently hydrogen. In embodiments, $R^L$ is independently $C_1$-$C_{20}$ alkyl (e.g., $C_1$-$C_6$ alkyl). In embodiments, $R^L$ is independently unsubstituted $C_1$-$C_{20}$ alkyl (e.g., unsubstituted $C_1$-$C_6$ alkyl). In embodiments, $R^L$ is independently substituted $C_1$-$C_{20}$ alkyl (e.g., substituted $C_1$-$C_6$ alkyl). In embodiments, $R^L$ is independently $C_2$-$C_{20}$ alkenyl (e.g., $C_2$-$C_6$ alkenyl). In embodiments, $R^L$ is independently unsubstituted $C_2$-$C_{20}$ alkenyl (e.g., unsubstituted $C_2$-$C_6$ alkenyl). In embodiments, $R^L$ is independently substituted $C_2$-$C_{20}$ alkenyl (e.g., substituted $C_2$-$C_6$ alkenyl). In embodiments, $R^L$ is independently $C_2$-$C_{20}$ alkynyl (e.g., $C_2$-$C_6$ alkynyl). In embodiments, $R^L$ is independently unsubstituted $C_2$-$C_{20}$ alkynyl (e.g., unsubstituted $C_2$-$C_6$ alkynyl). In embodiments, $R^L$ is independently substituted $C_2$-$C_{20}$ alkynyl (e.g., substituted $C_2$-$C_6$ alkynyl).

In embodiments, a cationic lipid of Formula (I) has a structure according to Formula (Ia):

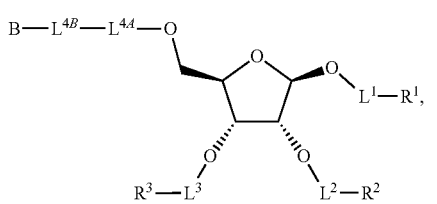

(Ia)

wherein each of $L^1$, $L^2$, $L^3$, $R^1$, $R^2$, $R^3$, B, $L^{4A}$ and $L^{4B}$ is independently as defined herein.

In embodiments, a cationic lipid of Formula (I) has a structure according to Formula (Ib):

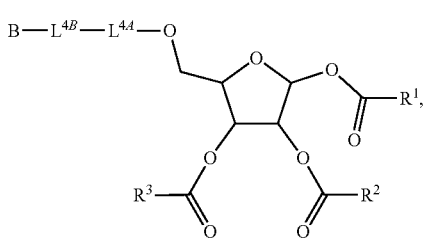

(Ib)

wherein each of $R^1$, $R^2$, $R^3$, B, $L^{4A}$ and $L^{4B}$ is independently as defined herein.

In embodiments, a cationic lipid of Formula (I) has a structure according to Formula (Ic):

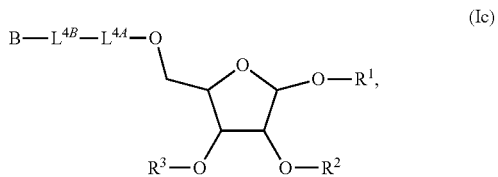

(Ic)

wherein:
each of $R^1$, $R^2$, $R^3$, B, $L^{4A}$ and $L^{4B}$ is independently as defined herein.

In embodiments, a cationic lipid of Formula (I) has a structure according to Formula (Id):

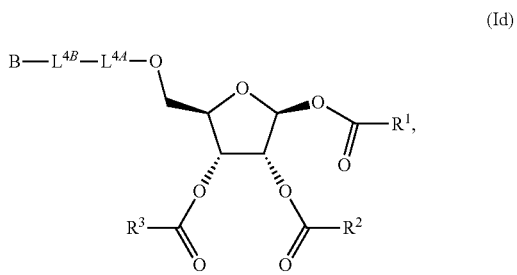

(Id)

wherein each of $R^1$, $R^2$, $R^3$, B, $L^{4A}$ and $L^{4B}$ is independently as defined herein.

In embodiments, the present invention provides a cationic lipid of Formula (Ie):

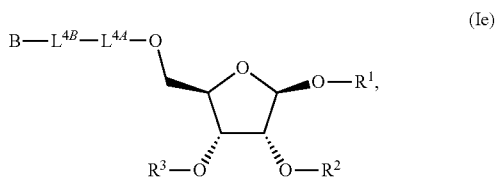

(Ie)

wherein each of $R^1$, $R^2$, $R^3$, B, $L^{4A}$ and $L^{4B}$ is independently as defined herein.

In embodiments, a cationic lipid of Formula (I) has a structure according to Formula (II):

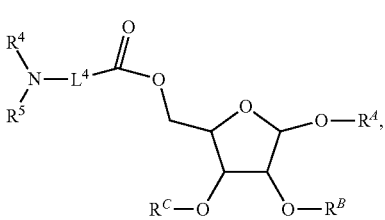

(II)

wherein:
$R^A$ is hydrogen or -$L^1$-$R^1$;
$R^B$ is hydrogen or -$L^2$-$R^2$;
$R^C$ is hydrogen or -$L^3$-$R^3$;
each of $L^1$, $L^2$, and $L^3$ is independently a covalent bond, —C(O)—, —C(O)O—, —C(O)S—, or —C(O)NR$^L$—;

$L^4$ is independently $C_1$-$C_{10}$ alkylene;

each $R^1$, $R^2$, and $R^3$ is independently $C_6$-$C_{30}$ alkyl, $C_6$-$C_{30}$ alkenyl, or $C_6$-$C_{30}$ alkynyl;

each $R^4$ and $R^5$ is independently hydrogen, $C_1$-$C_{10}$ alkyl; $C_2$-$C_{10}$ alkenyl; or $C_2$-$C_{10}$ alkynyl; or $R^4$ and $R^5$ combine to form a 5- to 10-membered heterocyclyl or a 5- to 10-membered heteroaryl;

each $R^L$ is independently hydrogen, $C_1$-$C_{20}$ alkyl, $C_2$-$C_{20}$ alkenyl, or $C_2$-$C_{20}$ alkynyl.

In embodiments, $R^A$ is -$L^1$-$R^1$; $R^B$ is -$L^2$-$R^2$; and $R^C$-$L^3$-$R^3$.

In embodiments, $R^A$ is hydrogen. In embodiments, $R^A$ is -$L^1$-$R^1$.

In embodiments, $L^1$ is a covalent bond or —C(O)—. In embodiments, $L^1$ is a covalent bond. In embodiments, $L^1$ is —C(O)—. In embodiments, $L^1$ is —C(O)O—. In embodiments, $L^1$ is —C(O)S—. In embodiments, $L^1$ is —C(O)NR$^L$—.

In embodiments, $R^1$ is $C_6$-$C_{30}$ alkyl (e.g., $C_6$-$C_{22}$ alkyl). In embodiments, $R^1$ is unsubstituted $C_6$-$C_{30}$ alkyl (e.g., unsubstituted $C_6$-$C_{22}$ alkyl). In embodiments, $R^1$ is substituted $C_6$-$C_{30}$ alkyl (e.g., substituted $C_6$-$C_{22}$ alkyl). In embodiments, $R^1$ is $C_6$-$C_{30}$ alkenyl (e.g., $C_6$-$C_{22}$ alkenyl). In embodiments, $R^1$ is unsubstituted $C_6$-$C_{30}$ alkenyl (e.g., unsubstituted $C_6$-$C_{22}$ alkenyl). In embodiments, $R^1$ is substituted $C_6$-$C_{30}$ alkenyl (e.g., substituted $C_6$-$C_{22}$ alkenyl). In embodiments, $R^1$ is $C_6$-$C_{30}$ alkynyl (e.g., $C_6$-$C_{22}$ alkynyl). In embodiments, $R^1$ is unsubstituted $C_6$-$C_{30}$ alkynyl (e.g., unsubstituted $C_6$-$C_{22}$ alkynyl). In embodiments, $R^1$ is substituted $C_6$-$C_{30}$ alkynyl (e.g., substituted $C_6$-$C_{22}$ alkynyl).

In embodiments, $R^B$ is hydrogen. In embodiments, $R^B$ is -$L^2$-$R^2$.

In embodiments, $L^2$ is a covalent bond or —C(O)—. In embodiments, $L^2$ is a covalent bond. In some, $L^2$ is —C(O)—. In embodiments, $L^2$ is —C(O)O—. In embodiments, $L^2$ is —C(O)S—. In some embodiments, $L^2$ is —C(O)NR$^L$.

In embodiments, $R^2$ is $C_6$-$C_{30}$ alkyl (e.g., $C_6$-$C_{22}$ alkyl). In embodiments, $R^2$ is unsubstituted $C_6$-$C_{30}$ alkyl (e.g., unsubstituted $C_6$-$C_{22}$ alkyl). In embodiments, $R^2$ is substituted $C_6$-$C_{30}$ alkyl (e.g., substituted $C_6$-$C_{22}$ alkyl). In embodiments, $R^2$ is $C_6$-$C_{30}$ alkenyl (e.g., $C_6$-$C_{22}$ alkenyl). In embodiments, $R^2$ is unsubstituted $C_6$-$C_{30}$ alkenyl (e.g., unsubstituted $C_6$-$C_{22}$ alkenyl). In embodiments, $R^2$ is substituted $C_6$-$C_{30}$ alkenyl (e.g., substituted $C_6$-$C_{22}$ alkenyl). In embodiments, $R^2$ is $C_6$-$C_{30}$ alkynyl (e.g., $C_6$-$C_{22}$ alkynyl). In embodiments, $R^2$ is unsubstituted $C_6$-$C_{30}$ alkynyl (e.g., unsubstituted $C_6$-$C_{22}$ alkynyl). In embodiments, $R^2$ is substituted $C_6$-$C_{30}$ alkynyl (e.g., substituted $C_6$-$C_{22}$ alkynyl).

In embodiments, $R^C$ is hydrogen. In embodiments, $R^C$ is -$L^3$-$R^3$.

In embodiments, $L^3$ is a covalent bond or —C(O)—. In embodiments, $L^3$ is a covalent bond. In some, $L^3$ is —C(O)—. In embodiments, $L^3$ is —C(O)O—. In embodiments, $L^3$ is —C(O)S—. In some embodiments, $L^3$ is —C(O)NR$^L$.

In embodiments, $R^3$ is $C_6$-$C_{30}$ alkyl (e.g., $C_6$-$C_{22}$ alkyl). In embodiments, $R^3$ is unsubstituted $C_6$-$C_{30}$ alkyl (e.g., unsubstituted $C_6$-$C_{22}$ alkyl). In embodiments, $R^3$ is substituted $C_6$-$C_{30}$ alkyl (e.g., substituted $C_6$-$C_{22}$ alkyl). In embodiments, $R^3$ is $C_6$-$C_{30}$ alkenyl (e.g., $C_6$-$C_{22}$ alkenyl). In embodiments, $R^3$ is unsubstituted $C_6$-$C_{30}$ alkenyl (e.g., unsubstituted $C_6$-$C_{22}$ alkenyl). In embodiments, $R^3$ is substituted $C_6$-$C_{30}$ alkenyl (e.g., substituted $C_6$-$C_{22}$ alkenyl). In embodiments, $R^3$ is $C_6$-$C_{30}$ alkynyl (e.g., $C_6$-$C_{22}$ alkynyl). In embodiments, $R^3$ is unsubstituted $C_6$-$C_{30}$ alkynyl (e.g., unsubstituted $C_6$-$C_{22}$ alkynyl). In embodiments, $R^3$ is substituted $C_6$-$C_{30}$ alkynyl (e.g., substituted $C_6$-$C_{22}$ alkynyl).

In embodiments, each of $L^1$, $L^2$, and $L^3$ is the same group. In embodiments, each of $L^1$, $L^2$, and $L^3$ is a covalent bond. In some, each of $L^1$, $L^2$, and $L^3$ is —C(O)—. In embodiments, each of $L^1$, $L^2$, and $L^3$ is —C(O)O—. In embodiments, each of $L^1$, $L^2$, and $L^3$ is —C(O)S—. In some embodiments, each of $L^1$, $L^2$, and $L^3$ is —C(O)NR$^L$. In embodiments, each of $L^1$, $L^2$, and $L^3$ is a covalent bond or each of $L^1$, $L^2$, and $L^3$ is —C(O)—.

In embodiments, each of $R^1$, $R^2$, and $R^3$ is the same group. In embodiments, each of $R^1$, $R^2$, and $R^3$ is $C_6$-$C_{30}$ alkyl (e.g., $C_6$-$C_{22}$ alkyl). In embodiments, each of $R^1$, $R^2$, and $R^3$ is unsubstituted $C_6$-$C_{30}$ alkyl (e.g., unsubstituted $C_6$-$C_{22}$ alkyl). In embodiments, each of $R^1$, $R^2$, and $R^3$ is substituted $C_6$-$C_{30}$ alkyl (e.g., substituted $C_6$-$C_{22}$ alkyl). In embodiments, each of $R^1$, $R^2$, and $R^3$ is $C_6$-$C_{30}$ alkenyl (e.g., $C_6$-$C_{22}$ alkenyl). In embodiments, each of $R^1$, $R^2$, and $R^3$ is unsubstituted $C_6$-$C_{30}$ alkenyl (e.g., unsubstituted $C_6$-$C_{22}$ alkenyl). In embodiments, each of $R^1$, $R^2$, and $R^3$ is substituted $C_6$-$C_{30}$ alkenyl (e.g., substituted $C_6$-$C_{22}$ alkenyl). In embodiments, each of $R^1$, $R^2$, and $R^3$ is $C_6$-$C_{30}$ alkynyl (e.g., $C_6$-$C_{22}$ alkynyl). In embodiments, each of $R^1$, $R^2$, and $R^3$ is unsubstituted $C_6$-$C_{30}$ alkynyl (e.g., unsubstituted $C_6$-$C_{22}$ alkynyl). In embodiments, each of $R^1$, $R^2$, and $R^3$ is substituted $C_6$-$C_{30}$ alkynyl (e.g., substituted $C_6$-$C_{22}$ alkynyl).

In embodiments, $L^4$ is independently $C_1$-$C_{10}$ alkylene (e.g., $C_1$-$C_6$ alkylene). In embodiments, $L^4$ is independently unsubstituted $C_1$-$C_{10}$ alkylene (e.g., unsubstituted $C_1$-$C_6$ alkylene). In embodiments, $L^4$ is independently substituted $C_1$-$C_{10}$ alkylene (e.g., substituted $C_1$-$C_6$ alkylene). In embodiments, $L^4$ is —CH$_2$CH$_2$—.

In embodiments, B is NR$^4$R$^5$. In embodiments, each $R^4$ and $R^5$ is independently hydrogen or unsubstituted $C_1$-$C_{10}$ alkyl (e.g., unsubstituted $C_1$-$C_6$ alkyl such as CH$_3$), or $R^4$ and $R^5$ combine to form a 5- to 6-membered heterocyclyl comprising one or two ring nitrogens.

In embodiments, $R^4$ is hydrogen or $C_1$-$C_{10}$ alkyl (e.g., $C_1$-$C_6$ alkyl). In embodiments, $R^4$ is hydrogen. In embodiments, $R^4$ is $C_1$-$C_{10}$ alkyl (e.g., $C_1$-$C_6$ alkyl). In embodiments, $R^4$ is unsubstituted $C_1$-$C_{10}$ alkyl (e.g., unsubstituted $C_1$-$C_6$ alkyl). In embodiments, $R^4$ is substituted $C_1$-$C_{10}$ alkyl (e.g., substitute $C_1$-$C_6$ alkyl). In embodiments, $R^4$ is $C_2$-$C_{10}$ alkenyl (e.g., $C_2$-$C_6$ alkenyl). In embodiments, $R^4$ is unsubstituted $C_2$-$C_{10}$ alkenyl (e.g., unsubstituted $C_2$-$C_6$ alkenyl). In embodiments, $R^4$ is unsubstituted $C_2$-$C_{10}$ alkenyl (e.g., substituted $C_2$-$C_6$ alkenyl). In embodiments, $R^4$ is $C_2$-$C_{10}$ alkynyl (e.g., $C_2$-$C_6$ alkynyl). In embodiments, $R^4$ is unsubstituted $C_2$-$C_{10}$ alkynyl (e.g., unsubstituted $C_2$-$C_6$ alkynyl). In embodiments, $R^4$ is substituted $C_2$-$C_{10}$ alkynyl (e.g., substituted $C_2$-$C_6$ alkynyl). In embodiments, $R^4$ is CH$_3$.

In embodiments, $R^5$ is hydrogen or $C_1$-$C_{10}$ alkyl (e.g., $C_1$-$C_6$ alkyl). In embodiments, $R^5$ is hydrogen. In embodiments, $R^5$ is $C_1$-$C_{10}$ alkyl (e.g., $C_1$-$C_6$ alkyl). In embodiments, $R^5$ is unsubstituted $C_1$-$C_{10}$ alkyl (e.g., unsubstituted $C_1$-$C_6$ alkyl). In embodiments, $R^5$ is substituted $C_1$-$C_{10}$ alkyl (e.g., substitute $C_1$-$C_6$ alkyl). In embodiments, $R^5$ is $C_2$-$C_{10}$ alkenyl (e.g., $C_2$-$C_6$ alkenyl). In embodiments, $R^5$ is unsubstituted $C_2$-$C_{10}$ alkenyl (e.g., unsubstituted $C_2$-$C_6$ alkenyl). In embodiments, $R^5$ is unsubstituted $C_2$-$C_{10}$ alkenyl (e.g., substituted $C_2$-$C_6$ alkenyl). In embodiments, $R^5$ is $C_2$-$C_{10}$ alkynyl (e.g., $C_2$-$C_6$ alkynyl). In embodiments, $R^5$ is unsubstituted $C_2$-$C_{10}$ alkynyl (e.g., unsubstituted $C_2$-$C_6$ alkynyl). In embodiments, $R^5$ is substituted $C_2$-$C_{10}$ alkynyl (e.g., substituted $C_2$-$C_6$ alkynyl). In embodiments, $R^5$ is CH$_3$.

In embodiments, $R^4$ and $R^5$ combine to form a 5- to 10-membered heterocyclyl. In embodiments, $R^4$ and $R^5$ combine to form a 5- to 10-membered heterocyclyl comprising one or two nitrogens in the ring or rings. In embodiments, $R^4$ and $R^5$ combine to form a piperdinyl or piperazinyl. In embodiments, $R^4$ and $R^5$ combine to form an unsubstituted piperdinyl. In embodiments, $R^4$ and $R^5$ combine to form an unsubstituted piperazinyl. In embodiments, $R^4$ and $R^5$ combine to form a substituted piperdinyl. In embodiments, $R^4$ and $R^5$ combine to form a substituted piperazinyl. In embodiments, $R^4$ and $R^5$ combine to form 4-methylpiperazinyl.

In embodiments, $R^L$ is independently hydrogen. In embodiments, $R^L$ is independently $C_1$-$C_{20}$ alkyl (e.g., $C_1$-$C_6$ alkyl). In embodiments, $R^L$ is independently unsubstituted $C_1$-$C_{20}$ alkyl (e.g., unsubstituted $C_1$-$C_6$ alkyl). In embodiments, $R^L$ is independently substituted $C_1$-$C_{20}$ alkyl (e.g., substituted $C_1$-$C_6$ alkyl). In embodiments, $R^L$ is independently $C_2$-$C_{20}$ alkenyl (e.g., $C_2$-$C_6$ alkenyl). In embodiments, $R^L$ is independently unsubstituted $C_2$-$C_{20}$ alkenyl (e.g., unsubstituted $C_2$-$C_6$ alkenyl). In embodiments, $R^L$ is independently substituted $C_2$-$C_{20}$ alkenyl (e.g., substituted $C_2$-$C_6$ alkenyl). In embodiments, $R^L$ is independently $C_2$-$C_{20}$ alkynyl (e.g., $C_2$-$C_6$ alkynyl). In embodiments, $R^L$ is independently unsubstituted $C_2$-$C_{20}$ alkynyl (e.g., unsubstituted $C_2$-$C_6$ alkynyl). In embodiments, $R^L$ is independently substituted $C_2$-$C_{20}$ alkynyl (e.g., substituted $C_2$-$C_6$ alkynyl).

In embodiments, a cationic lipid of Formula (II) has a structure according to Formula (IIa):

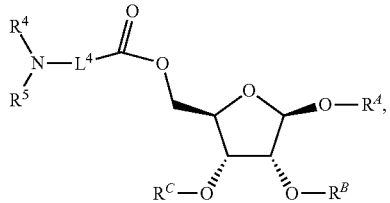

(IIa)

wherein each $R^A$, $R^B$, $R^C$, $L^4$, $R^4$ and $R^5$ is as independently as defined herein.

In embodiments, a cationic lipid of Formula (II) has a structure according to Formula (IIb):

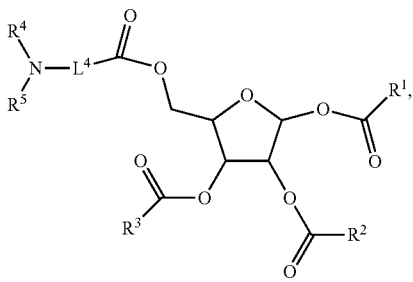

(IIb)

wherein each $R^A$, $R^B$, $R^C$, $L^4$, $R^4$ and $R^5$ independently as defined herein.

In embodiments, a cationic lipid of Formula (II) has a structure according to Formula (IIc):

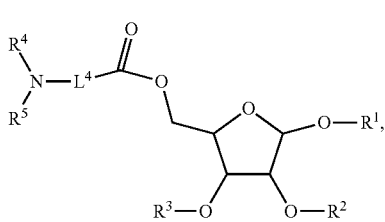

(IIc)

wherein each $R^A$, $R^B$, $R^C$, $L^4$, $R^4$ and $R^5$ is independently as defined herein.

In embodiments, a cationic lipid of Formula (II) has a structure according to Formula (IId):

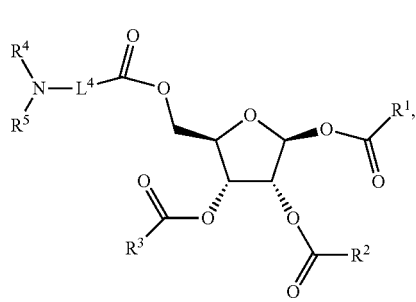

(IId)

wherein each $R^A$, $R^B$, $R^C$, $L^4$, $R^4$ and $R^5$ is independently as defined herein.

In embodiments, a cationic lipid of Formula (II) has a structure according to Formula (IIe):

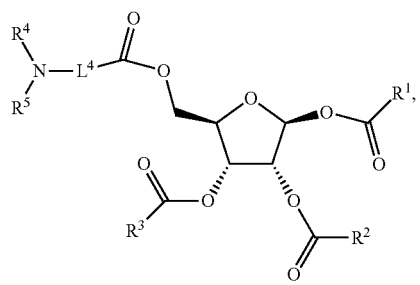

(IIe)

wherein each $R^A$, $R^B$, $R^C$, $L^4$, $R^4$ and $R^5$ is independently as defined herein.

In embodiments, a $C_6$-$C_{30}$ alkyl (e.g., $R^1$, $R^2$, and/or $R^3$) is a $C_{8-2}$ alkyl. In embodiments, a $C_6$-$C_{30}$ alkyl (e.g., $R^1$, $R^2$, and/or $R^3$) is a straight-chain $C_{8-26}$ alkyl.

In embodiments, a $C_6$-$C_{30}$ alkyl (e.g., $R^1$, $R^2$, and/or $R^3$) is $CH_3(CH_2)_6CH_2$—, $CH_3(CH_2)_7CH_2$—, $CH_3(CH_2)_8CH_2$—, $CH_3(CH_2)_9CH_2$—, $CH_3(CH_2)_{10}CH_2$—, $CH_3(CH_2)_{11}CH_2$—, $CH_3(CH_2)_{12}CH_2$—, $CH_3(CH_2)_{13}CH_2$—, $CH_3(CH_2)_{14}CH_2$—, $CH_3(CH_2)_{15}CH_2$—, $CH_3(CH_2)_{16}CH_2$—, $CH_3(CH_2)_{17}CH_2$—, $CH_3(CH_2)_{18}CH_2$—, $CH_3(CH_2)_{19}CH_2$—, $CH_3(CH_2)_{20}CH_2$—, $CH_3(CH_2)_{21}CH_2$—, $CH_3(CH_2)_{22}CH_2$—, $CH_3(CH_2)_{23}CH_2$— or $CH_3(CH_2)_{24}CH_2$—.

In embodiments, a $C_6$-$C_{30}$ alkyl (e.g., $R^1$, $R^2$, and/or $R^3$) is $CH_3(CH_2)_{13}CH_2$—, $CH_3(CH_2)_{14}CH_2$—, $CH_3(CH_2)_{15}CH_2$—, $CH_3(CH_2)_{16}CH_2$—, $CH_3(CH_2)_{17}CH_2$— or $CH_3(CH_2)_{18}CH_2$—.

In embodiments, a $C_6$-$C_{30}$ alkyl (e.g., $R^1$, $R^2$, and/or $R^3$) is $CH_3(CH_2)_{14}CH_2$—, $CH_3(CH_2)_{15}CH_2$— or $CH_3(CH_2)_{16}CH_2$—.

In embodiments, a $C_6$-$C_{30}$ alkenyl (e.g., $R^1$, $R^2$, and/or $R^3$) is a $C_{8-26}$ alkenyl having one or two carbon-carbon double bonds.

In embodiments, a $C_6$-$C_{30}$ alkenyl (e.g., $R^1$, $R^2$, and/or $R^3$) is cis-$CH_3(CH_2)_3CH$=$CH(CH_2)_7CH_2$—, cis-$CH_3(CH_2)_5CH$=$CH(CH_2)_7CH_2$—, cis-$CH_3(CH_2)_8CH$=$CH(CH_2)_4CH_2$—, cis-$CH_3(CH_2)_7CH$=$CH(CH_2)_7CH_2$—, cis-$CH_3(CH_2)_9CH$=$CH(CH_2)_7CH_2$—, cis-$CH_3(CH_2)_7CH$=$CH(CH_2)_9CH_2$—, trans-$CH_3(CH_2)_7CH$=$CH(CH_2)_7CH_2$—, trans-$CH_3(CH_2)_5CH$=$CH(CH_2)_9CH_2$—, cis-$CH_3(CH_2)_9CH$=$CH(CH_2)_7CH_2$—, cis-$CH_3(CH_2)_7CH$=$CH(CH_2)_{11}CH_2$—, cis-$CH_3(CH_2)_7CH$=$CH(CH_2)_{13}CH_2$—, cis,cis-$CH_3(CH_2)_4CH$=$CHCH_2CH$=$CH(CH_2)_7CH_2$—, cis,cis-$CH_3(CH_2)_4CH$=$CHCH_2CH$=$CH(CH_2)_9CH_2$— or cis,cis-$CH_3(CH_2)_4CH$=$CHCH_2CH$=$CH(CH_2)_{11}CH_2$—.

In embodiments, a $C_6$-$C_{30}$ alkenyl (e.g., $R^1$, $R^2$, and/or $R^3$) is cis-$CH_3(CH_2)_3CH$=$CH(CH_2)_7CH_2$—, cis-$CH_3(CH_2)_5CH$=$CH(CH_2)_7CH_2$—, cis-$CH_3(CH_2)_8CH$=$CH(CH_2)_4CH_2$—, cis-$CH_3(CH_2)_7CH$=$CH(CH_2)_7CH_2$—, cis-$CH_3(CH_2)_9CH$=$CH(CH_2)_7CH_2$—, trans-$CH_3(CH_2)_7CH$=$CH(CH_2)_7CH_2$—, cis,cis-$CH_3(CH_2)_4CH$=$CHCH_2CH$=$CH(CH_2)_7CH_2$— or cis,cis-$CH_3(CH_2)_4CH$=$CHCH_2CH$=$CH(CH_2)_9CH_2$—.

In embodiments, a $C_6$-$C_{30}$ alkenyl (e.g., $R^1$, $R^2$, and/or $R^3$) is cis-$CH_3(CH_2)_7CH$=$CH(CH_2)_7CH_2$—, cis-$CH_3(CH_2)_9CH$=$CH(CH_2)_7CH_2$—, cis,cis-$CH_3(CH_2)_4CH$=$CHCH_2CH$=$CH(CH_2)_7CH_2$— or cis,cis-$CH_3(CH_2)_4CH$=$CHCH_2CH$=$CH(CH_2)_9CH_2$—.

In embodiments, a $C_6$-$C_{30}$ alkenyl (e.g., $R^1$, $R^2$, and/or $R^3$) is cis-$CH_3(CH_2)_7CH$=$CH(CH_2)_7CH_2$— or cis,cis-$CH_3(CH_2)_4CH$=$CH$—$CH_2CH$=$CH(CH_2)_7CH_2$—.

In embodiments, a $C_6$-$C_{30}$ alkenyl (e.g., $R^1$, $R^2$, and/or $R^3$) is $C_{8-26}$ aliphatic having three, four, five or six carbon-carbon double bonds.

In embodiments, a $C_6$-$C_{30}$ alkenyl (e.g., $R^1$, $R^2$, and/or $R^3$) is cis,cis,cis-$CH_3CH_2CH$=$CHCH_2CH$=$CHCH_2CH$=$CH(CH_2)_7CH_2$—, cis,cis,cis-$CH_3(CH_2)_4CH$=$CHCH_2CH$=$CHCH_2CH$=$CH(CH_2)_4CH_2$—, cis,cis,cis-$CH_3(CH_2)_4CH$=$CHCH_2CH$=$CHCH_2CH$=$CH(CH_2)_3CH_2$—, trans,trans,trans-$CH_3(CH_2)_7CH$=$CHCH_2CH$=$CHCH_2CH$=$CH(CH_2)_3CH_2$—, cis,cis,cis-$CH_3(CH_2)_4CH$=$CHCH_2CH$=$CHCH_2CH$=$CH(CH_2)_6CH_2$—, cis,cis,cis-$CH_3CH_2CH$=$CHCH_2CH$=$CHCH_2CH$=$CH(CH_2)_9CH_2$—, cis,cis,cis-$CH_3CH_2CH$=$CHCH_2CH$=$CHCH_2CH$=$CHCH_2CH$=$CH(CH_2)_4CH_2$—, cis,cis,cis-$CH_3(CH_2)_4CH$=$CHCH_2CH$=$CHCH_2CH$=$CHCH_2CH$=$CH(CH_2)_3CH_2$-cis,cis,cis-$CH_3CH_2CH$=$CHCH_2CH$=$CHCH_2CH$=$CHCH_2CH$=$CH(CH_2)_6CH_2$—, cis,cis,trans,trans,cis-$CH_3(CH_2)_4CH$=$CHCH$=$CHCH$=$CHCH_2CH$=$CH(CH_2)_3CH_2$—, cis,cis,cis,cis-$CH_3CH_2CH$=$CHCH_2CH$=$CHCH_2CH$=$CHCH_2CH$=$CH(CH_2)_3CH_2$—, cis,cis,cis,cis-$CH_3(CH_2)_4CH$=$CHCH_2CH$=$CHCH_2CH$=$CHCH_2CH$=$CHCH_2CH$=$CH(CH_2)_2CH_2$—, cis,cis,cis,cis-$CH_3CH_2CH$=$CHCH_2CH$=$CHCH_2CH$=$CHCH_2CH$=$CH(CH_2)_5CH_2$—, cis,cis,cis,cis-$CH_3CH_2CH$=$CHCH_2CH$=$CHCH_2CH$=$CHCH_2CH$=$CH(CH_2)_7CH_2$—, cis,cis,cis,cis,cis-$CH_3CH_2CH$=$CHCH_2CH$=$CHCH_2CH$=$CHCH_2CH$=$CHCH_2CH$=$CH(CH_2)_2CH_2$—, or cis,cis,cis,cis,cis-$CH_3CH_2CH$=$CHCH_2CH$=$CHCH_2CH$=$CHCH_2CH$=$CHCH_2CH$=$CH(CH_2)_4CH_2$—.

In embodiments, a $C_6$-$C_{30}$ alkenyl (e.g., $R^1$, $R^2$, and/or $R^3$) is cis,cis,cis-$CH_3CH_2CH$=$CHCH_2CH$=$CHCH_2CH$=$CH(CH_2)_7CH_2$—, cis,cis,cis,cis-$CH_3CH_2CH$=$CHCH_2CH$=$CHCH_2CH$=$CHCH_2CH$=$CH(CH_2)_4CH_2$—, cis,cis,trans,trans,cis-$CH_3(CH_2)_4CH$=$CHCH$=$CHCH$=$CHCH_2CH$=$CH(CH_2)_3CH_2$—, cis,cis,cis,cis,cis-$CH_3CH_2CH$=$CHCH_2CH$=$CHCH_2CH$=$CHCH_2CH$=$CHCH_2CH$=$CH(CH_2)_2CH_2$—.

In embodiments, a $C_6$-$C_{30}$ alkenyl (e.g., $R^1$, $R^2$, and/or $R^3$) is cis,cis,cis-$CH_3CH_2CH$=$CHCH_2CH$=$CHCH_2CH$=$CH(CH_2)_7CH_2$— or cis,cis,cis,cis-$CH_3CH_2CH$=$CHCH_2CH$=$CHCH_2CH$=$CHCH_2CH$=$CH(CH_2)_4CH_2$—.

In some embodiments, each of $R^1$, $R^2$ and $R^3$ independently is an aliphatic chain of a saturated or unsaturated fatty acid, i.e., R'—$(CH_2)$— for a fatty acid R'—$C(O)$—. In some embodiments, each of $R^1$, $R^2$ and $R^3$ independently is the aliphatic chain of caprylic, pelargonic, capric, undecylic, lauric, tridecyclic, myristic, pentadecylic, margaric, stearic, nonadecylic, arachidic, heneicosylic, behenic, triosylic, lignoceric, oleic, linoleic, pentacosylic or cerotic acid. In some embodiments, each of R and $R^1$ is the aliphatic chain of caprylic, pelargonic, capric, undecylic, lauric, tridecyclic, myristic, pentadecylic, or margaric acid. In some embodiments, each of $R^1$, $R^2$ and $R^3$ is the aliphatic chain of lauric, tridecyclic, myristic, or pentadecylic acid. In some embodiments, each of $R^1$, $R^2$ and $R^3$ is the aliphatic chain of lauric or myristic acid. In some embodiments, each of $R^1$, $R^2$ and $R^3$ is the aliphatic chain of stearic, nonadecylic, arachidic, heneicosylic, behenic, triosylic, lignoceric, oleic, linoleic, pentacosylic or cerotic acid. In some embodiments, each of $R^1$, $R^2$ and $R^3$ is the aliphatic chain of lignoceric, oleic, linoleic, pentacosylic or cerotic acid. In some embodiments, each of $R^1$, $R^2$ and $R^3$ is the aliphatic chain of oleic, linoleic or pentacosylic acid. In some embodiments, each of $R^1$, $R^2$ and $R^3$ is the aliphatic chain of oleic or linoleic acid. In some embodiments, each of $R^1$, $R^2$ and $R^3$ is the aliphatic chain of oleic acid. In some embodiments, each of $R^1$, $R^2$ and $R^3$ is the aliphatic chain of linoleic acid.

In some embodiments (e.g., any of Formulas (I'), (I), and (II) and any of formulas (IIIa)-(IIIaa)), each of $R^1$, $R^2$ and $R^3$ independently is any of the following aliphatic chains. In some embodiments, each of $R^1$, $R^2$ and $R^3$ is the same aliphatic chain.

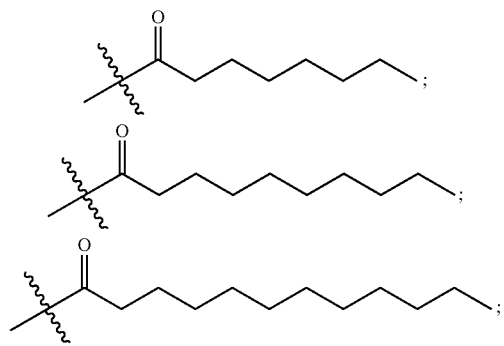

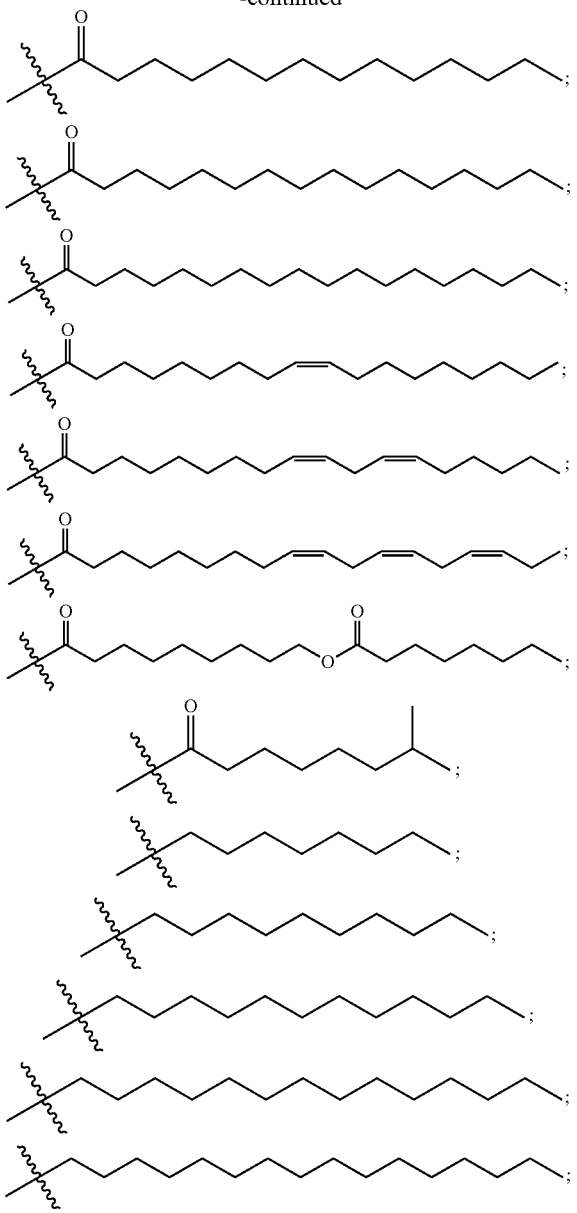
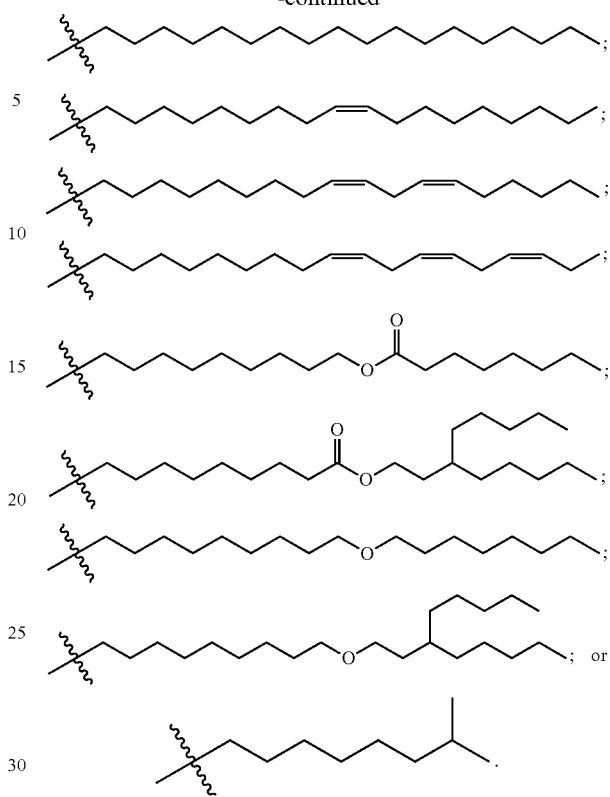
Exemplary Cationic Lipids
Exemplary cationic lipids include cationic lipids (1a)-(21a) (Table A).
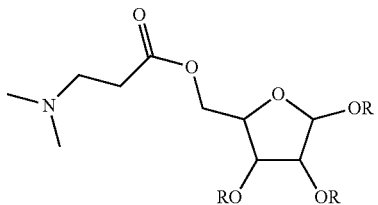
TABLE A
| Cationic Lipids (1a)-(21a) |
|---|
| R = |
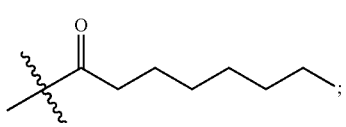 (1a)
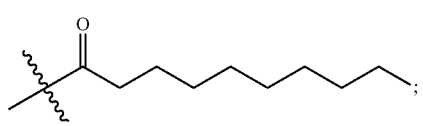 (2a)

TABLE A-continued

Cationic Lipids (1a)-(21a)

R =

(3a) [structure]

(4a) [structure]

(5a) [structure]

(6a) [structure]

(7a) [structure]

(8a) [structure]

(9a) [structure]

(10a) [structure]

(11a) [structure]

(12a) [structure]

(13a) [structure]

(14a) [structure]

(15a) [structure]

TABLE A-continued
Cationic Lipids (1a)-(21a)
R =
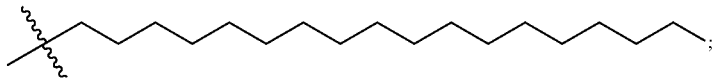 (16a)
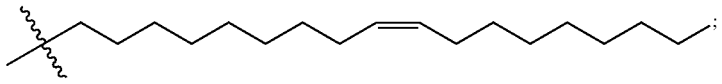 (17a)
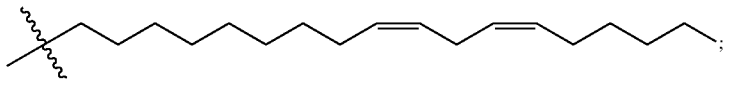 (18a)
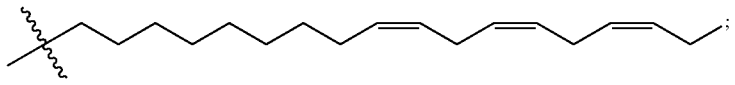 (19a)
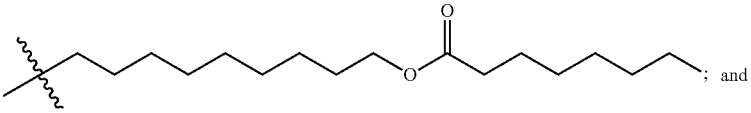 ; and (20a)
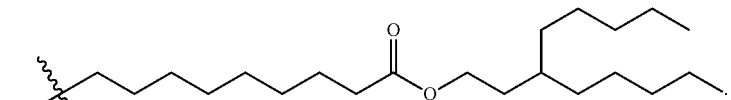 . (21a)
Exemplary cationic lipids include cationic lipids (1b)-(21b) (Table B).
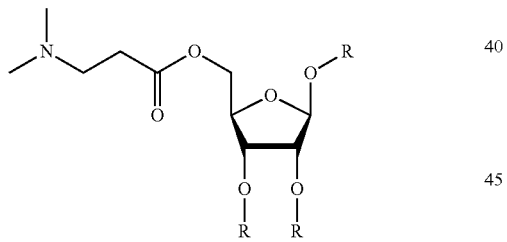
TABLE B
Cationic Lipids (1b)-(21b)
R =
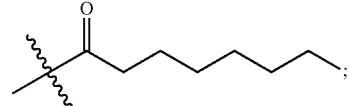 (1b)
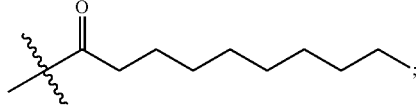 (2b)

TABLE B-continued
Cationic Lipids (1b)-(21b)
R =
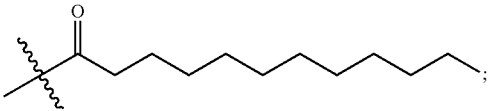 (3b)
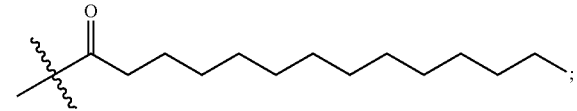 (4b)
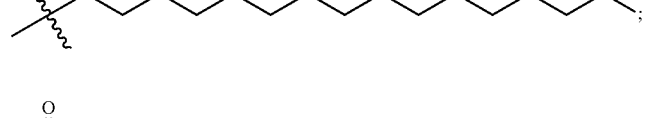 (5b)
 (6b)
 (7b)
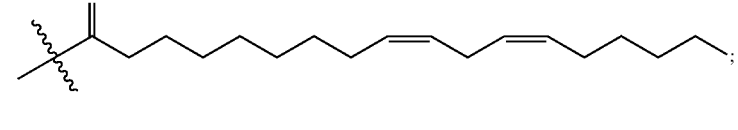 (8b)
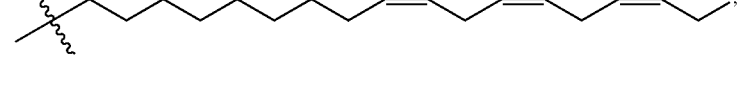 (9b)
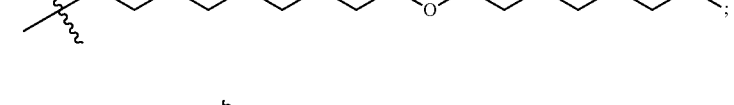 (10b)
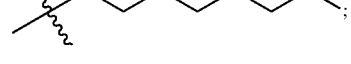 (11b)

TABLE B-continued
Cationic Lipids (1b)-(21b)
R =
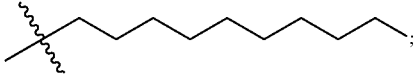 (12b)
(13b)
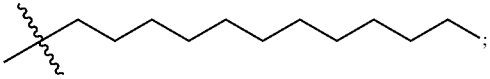 (14b)
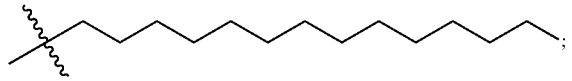 (15b)
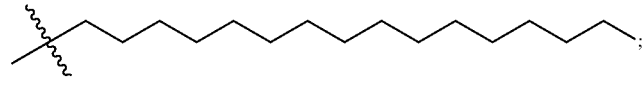
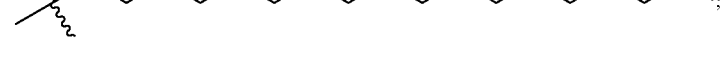 (16b)
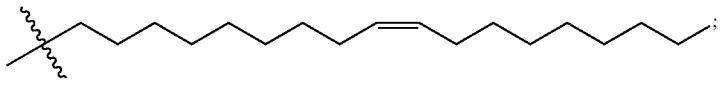 (17b)
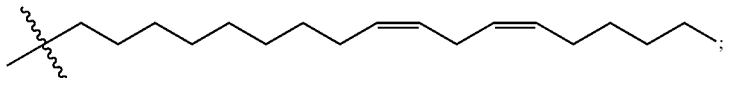 (18b)
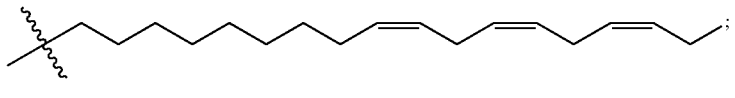 (19b)
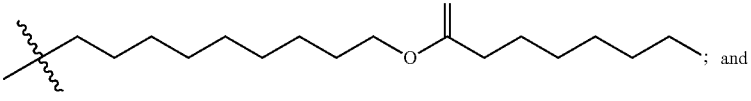 (20b)
; and
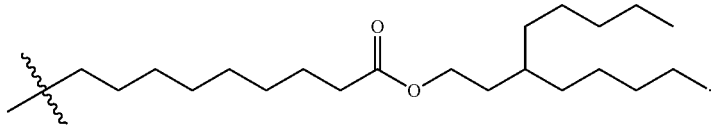 (21b)
.

Exemplary cationic lipids include cationic lipids according to formula (IIIa) such as cationic lipids (22)-(34) (Table C):
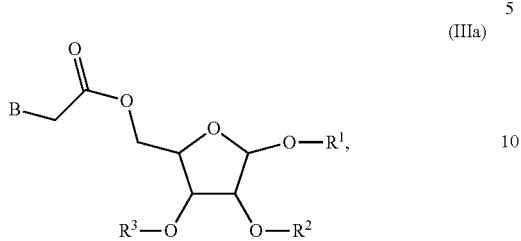
(IIIa)
where B, $R^1$, $R^2$, and $R^3$ are independently as described herein, including the exemplified groups of Table C.
TABLE C
Formula (IIIa) Cationic Lipids
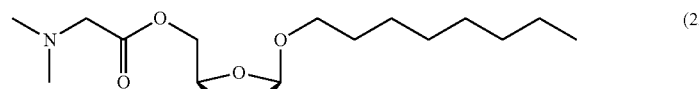
RL1-01
(22)
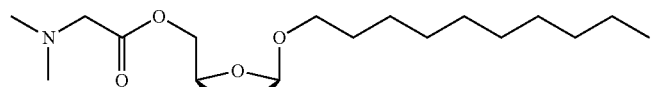
RL1-02
(23)

TABLE C-continued
Formula (IIIa) Cationic Lipids
(24)
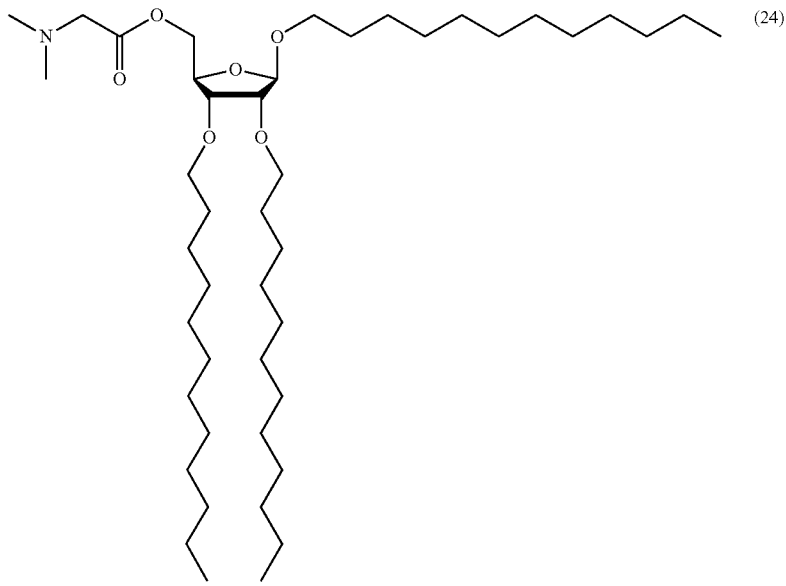
RL1-03
(25)
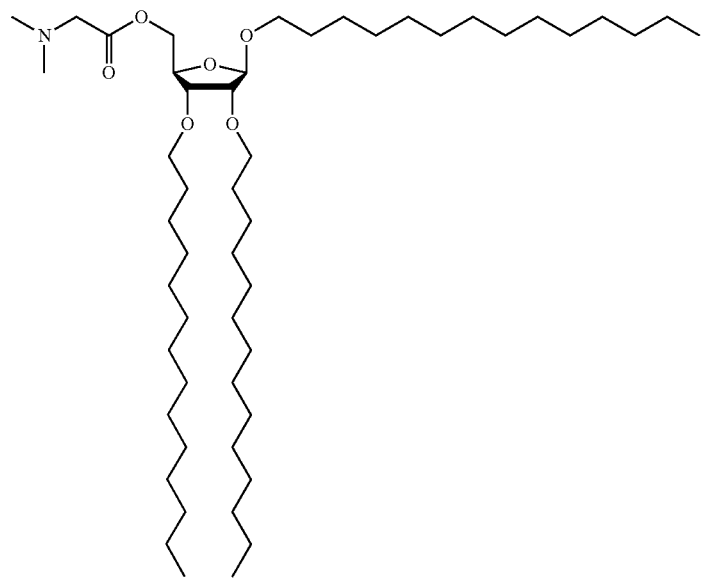
RL1-04

TABLE C-continued
Formula (IIIa) Cationic Lipids
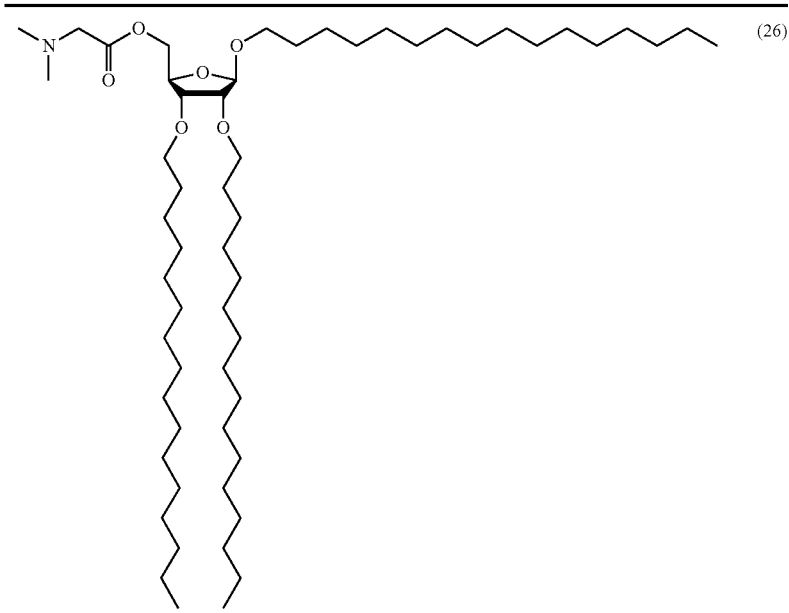
(26)
RL1-05
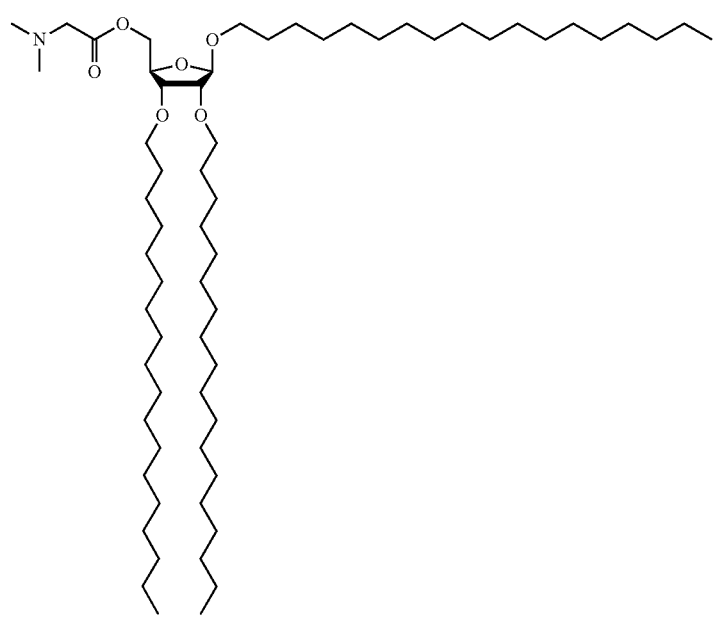
(27)
RL1-06

TABLE C-continued
Formula (IIIa) Cationic Lipids
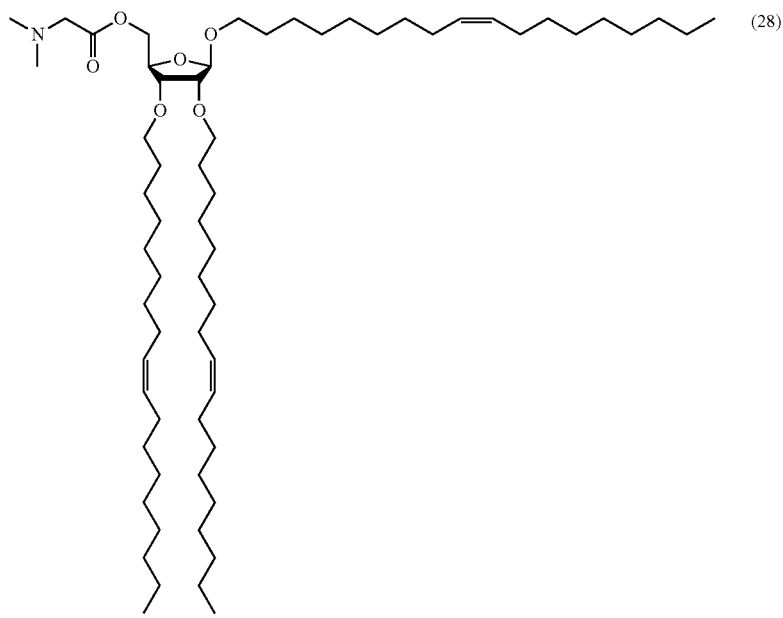
RL1-07 (28)
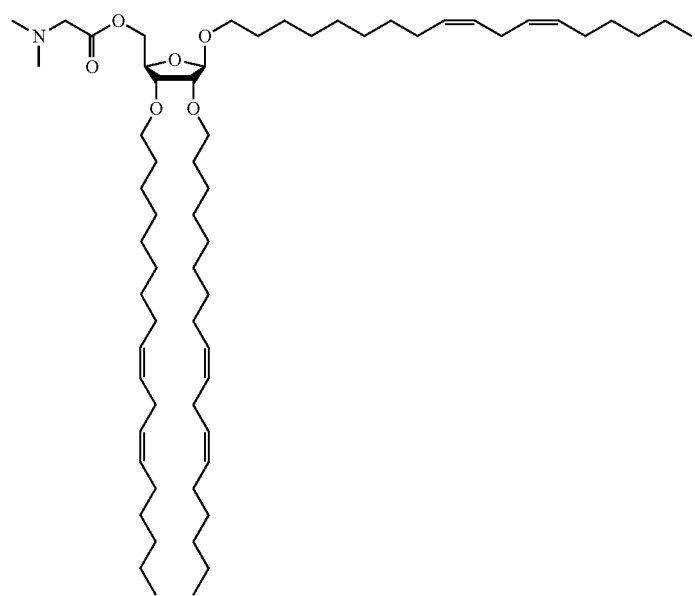
RL1-08 (29)

TABLE C-continued
Formula (IIIa) Cationic Lipids
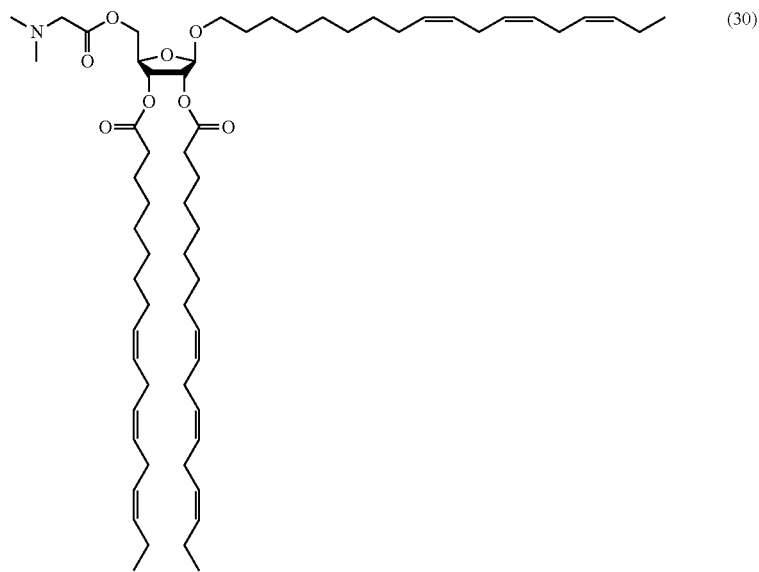
(30)
RL1-09
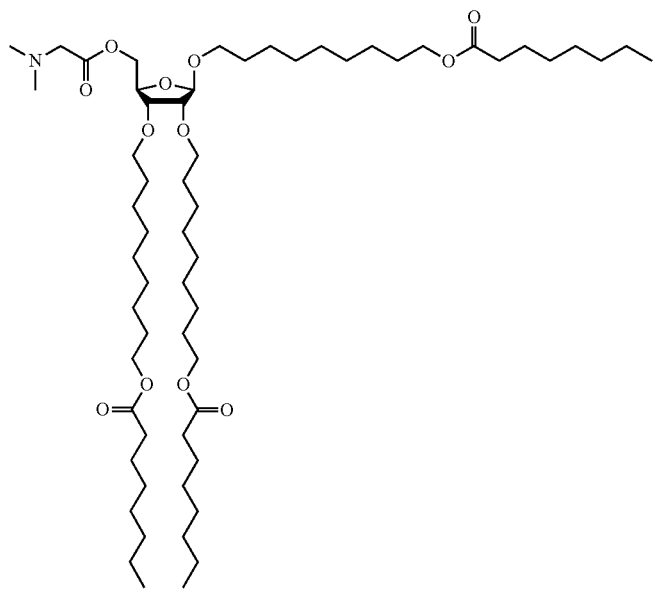
(31)
RL1-10

TABLE C-continued
Formula (IIIa) Cationic Lipids
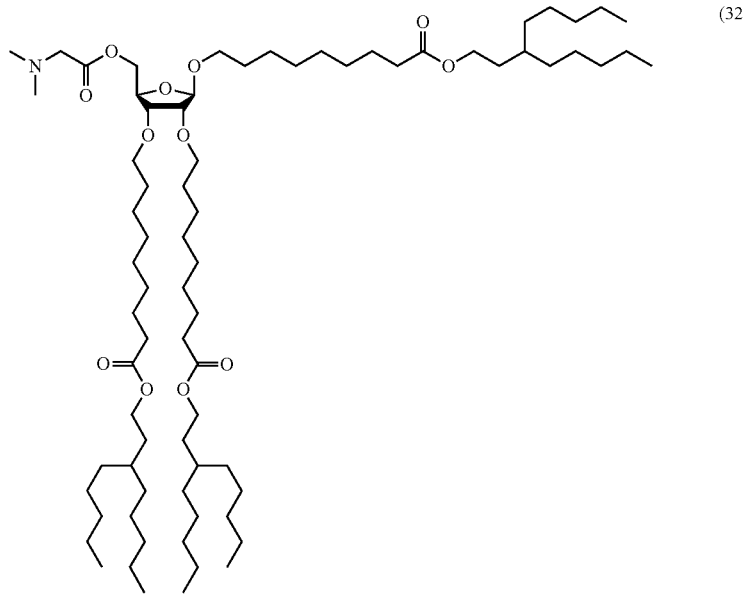
RL1-11
(32)
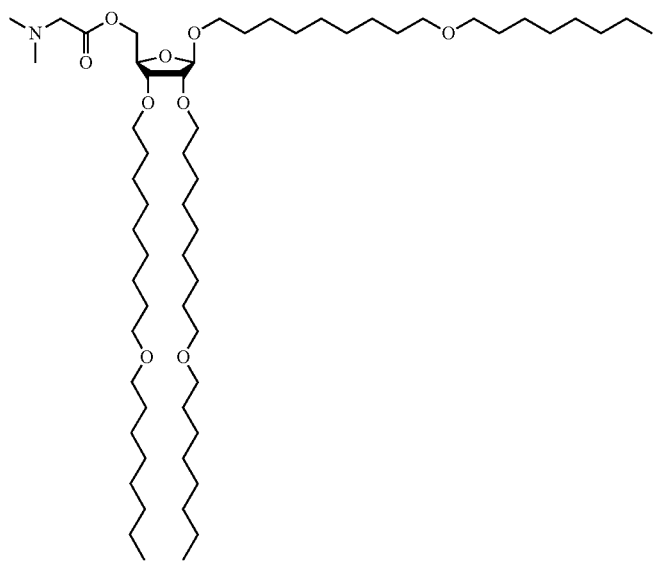
RL1-12
(33)

TABLE C-continued

Formula (IIIa) Cationic Lipids (34)

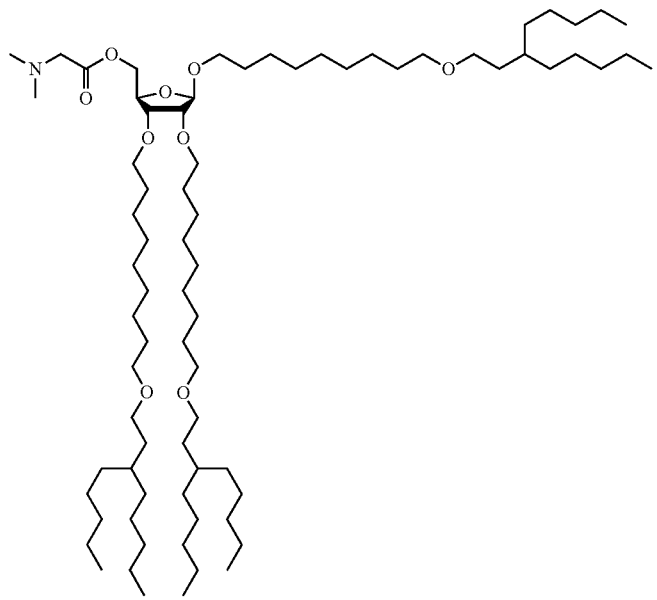

RL1-13

In embodiments, a cationic lipid is cationic lipid (22). In embodiments, a cationic lipid is cationic lipid (23). In embodiments, a cationic lipid is cationic lipid (24). In embodiments, a cationic lipid is cationic lipid (25). In embodiments, a cationic lipid is cationic lipid (26). In embodiments, a cationic lipid is cationic lipid (27). In embodiments, a cationic lipid is cationic lipid (28). In embodiments, a cationic lipid is cationic lipid (29). In embodiments, a cationic lipid is cationic lipid (30). In embodiments, a cationic lipid is cationic lipid (31). In embodiments, a cationic lipid is cationic lipid (32). In embodiments, a cationic lipid is cationic lipid (33). In embodiments, a cationic lipid is cationic lipid (34).

Exemplary cationic lipids include cationic lipids according to formula (IIIb) such as cationic lipids (35)-(47) (Table D):

(IIIb)

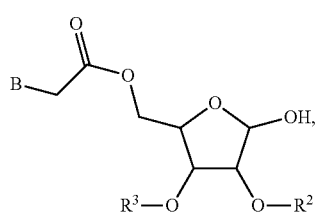

where B, $R^2$, and $R^3$ are independently as described herein, including the exemplified groups of Table D.

TABLE D

Formula (IIIb) Cationic Lipids (35)

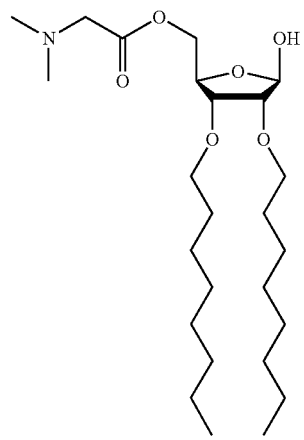

RL1-01x2

TABLE D-continued
Formula (IIIb) Cationic Lipids
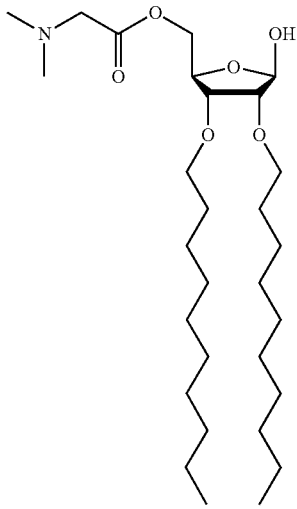
RL1-02x2 (36)
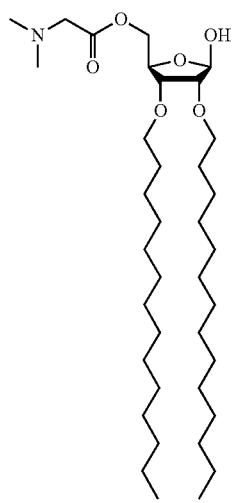
RL1-04x2 (38)
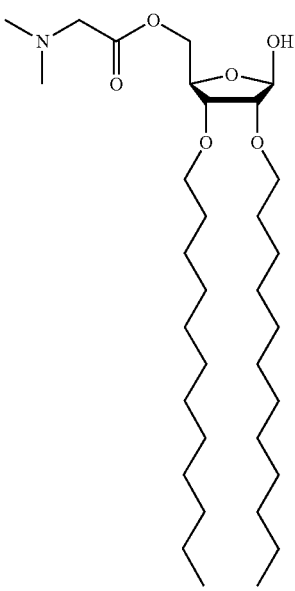
RL1-03x2 (37)
RL1-05x2 (39)

TABLE D-continued
Formula (IIIb) Cationic Lipids
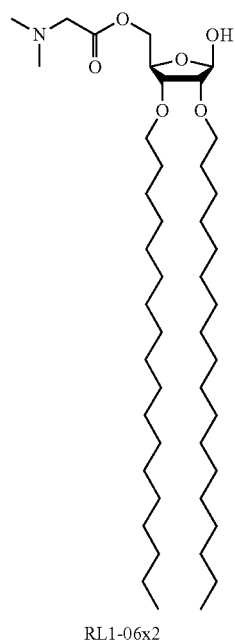
RL1-06x2 (40)
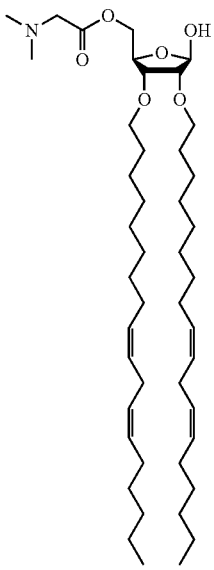
RL1-08x2 (42)
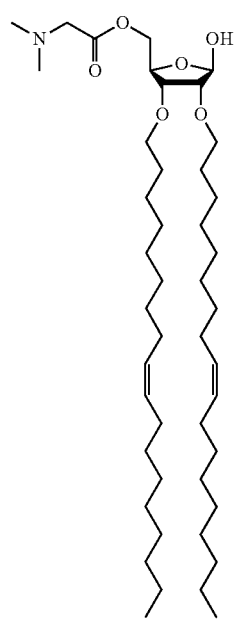
RL1-07x2 (41)
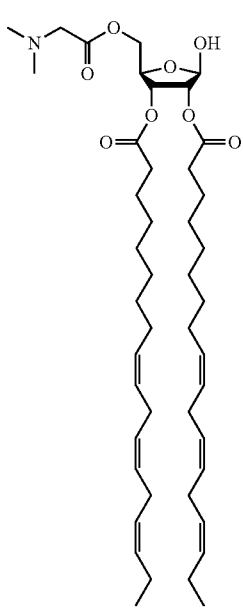
RL1-09x2 (43)

TABLE D-continued

Formula (IIIb) Cationic Lipids

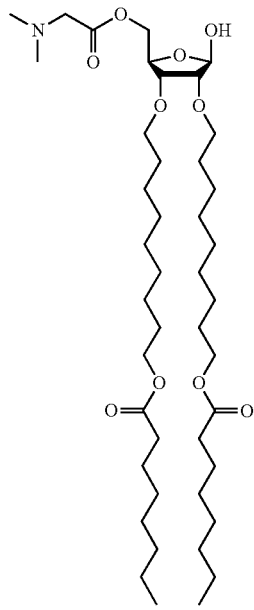

RL1-10x2 (44)

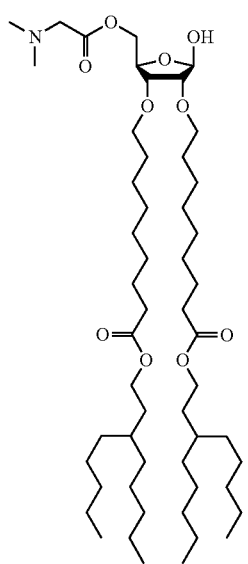

RL1-11x2 (45)

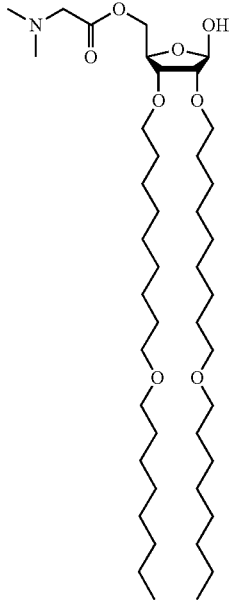

RL1-12x2 (46)

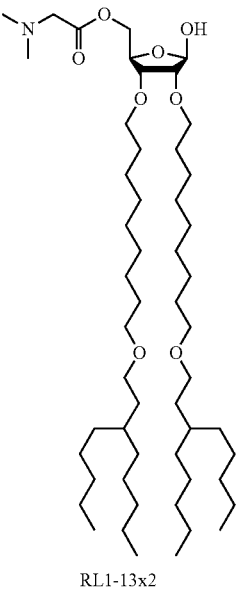

RL1-13x2 (47)

In embodiments, a cationic lipid is cationic lipid (35). In embodiments, a cationic lipid is cationic lipid (36). In embodiments, a cationic lipid is cationic lipid (37). In embodiments, a cationic lipid is cationic lipid (38). In embodiments, a cationic lipid is cationic lipid (39). In embodiments, a cationic lipid is cationic lipid (40). In embodiments, a cationic lipid is cationic lipid (41). In embodiments, a cationic lipid is cationic lipid (42). In embodiments, a cationic lipid is cationic lipid (43). In embodiments, a cationic lipid is cationic lipid (44). In embodiments, a cationic lipid is cationic lipid (45). In embodiments, a cationic lipid is cationic lipid (46). In embodiments, a cationic lipid is cationic lipid (47).

Exemplary cationic lipids include cationic lipids according to formula (IIIc) such as cationic lipids (48)-(60) (Table E):
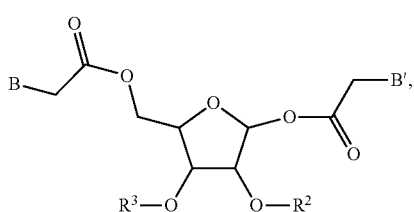
(IIIc)
where B, B', $R^2$, and $R^3$ are independently as described herein, including the exemplified groups of Table E.
TABLE E
Formula (IIIc) Cationic Lipids
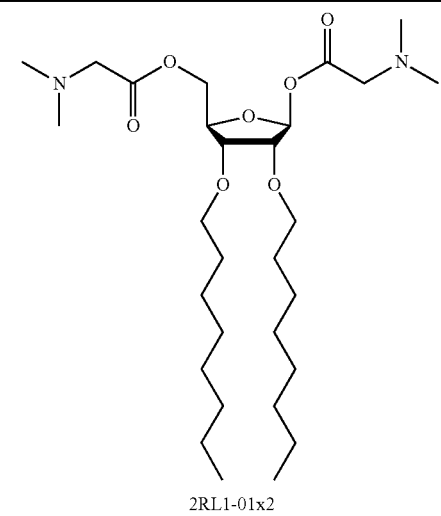
2RL1-01x2
(48)
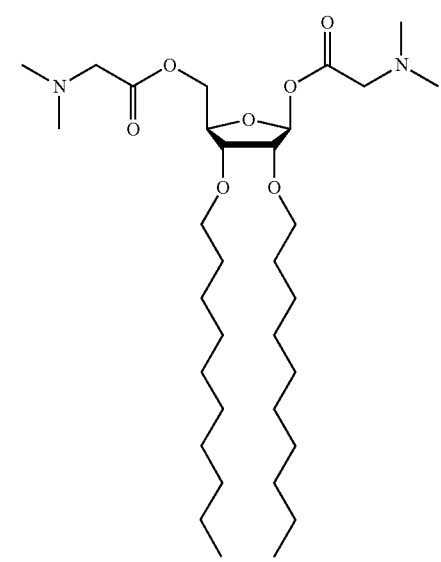
2RL1-02x2
(49)
TABLE E-continued
Formula (IIIc) Cationic Lipids
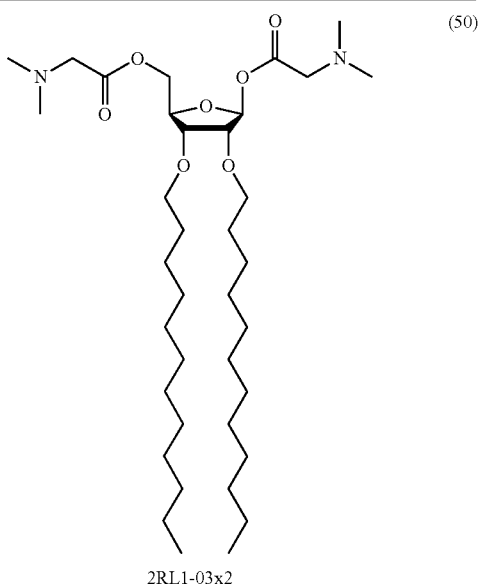
2RL1-03x2
(50)
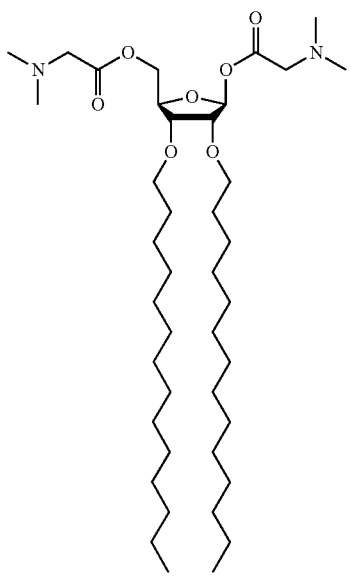
2RL1-04x2
(51)

TABLE E-continued
Formula (IIIc) Cationic Lipids
(52)
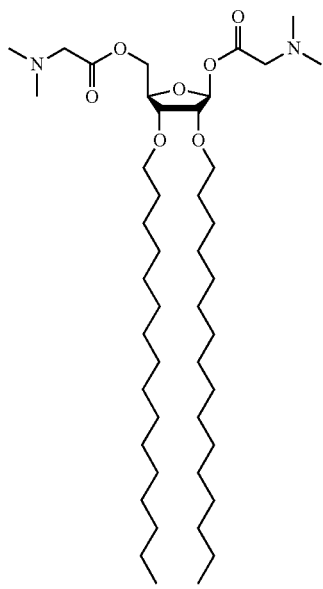
2RL1-05x2
(53)
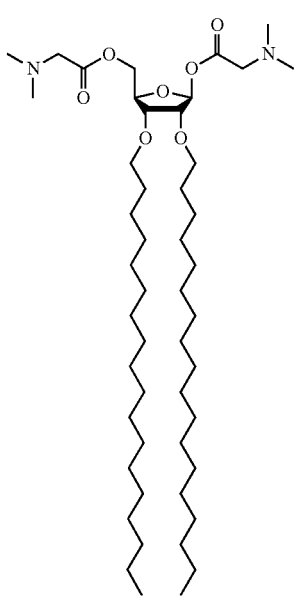
2RL1-06x2
TABLE E-continued
Formula (IIIc) Cationic Lipids
(54)
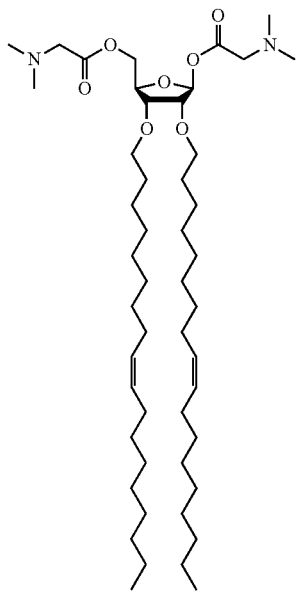
2RL1-07x2
(55)
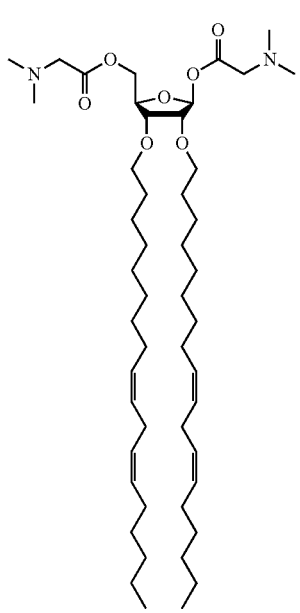
2RL1-08x2

TABLE E-continued
Formula (IIIc) Cationic Lipids
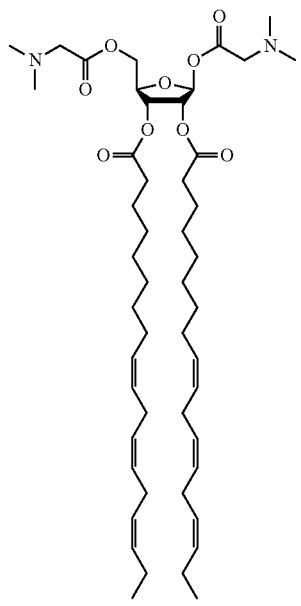
2RL1-09x2 (56)
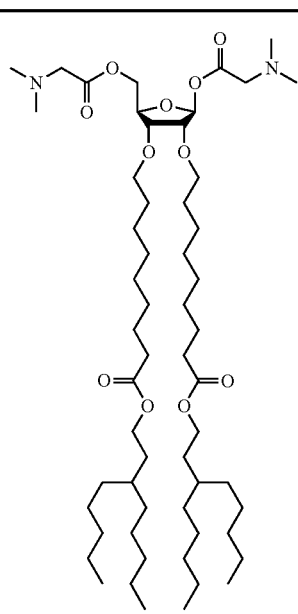
2RL1-11x2 (58)
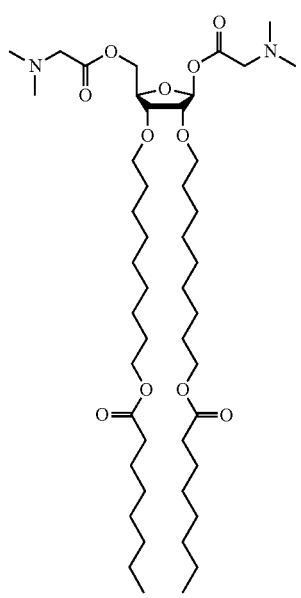
2RL1-10x2 (57)
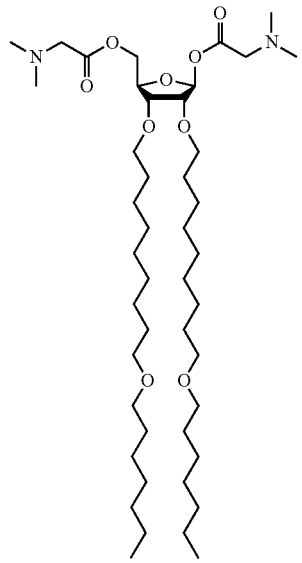
2RL1-12x2 (59)

TABLE E-continued

Formula (IIIc) Cationic Lipids

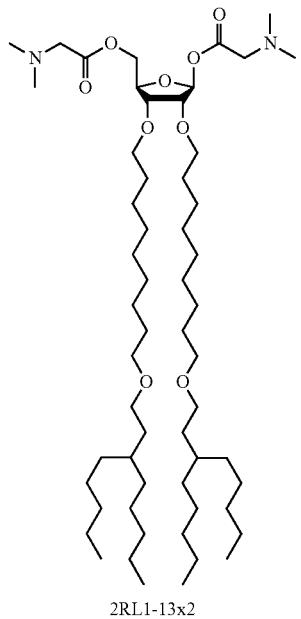

(60)

2RL1-13x2

In embodiments, a cationic lipid is cationic lipid (48). In embodiments, a cationic lipid is cationic lipid (49). In embodiments, a cationic lipid is cationic lipid (50). In embodiments, a cationic lipid is cationic lipid (51). In embodiments, a cationic lipid is cationic lipid (52). In embodiments, a cationic lipid is cationic lipid (53). In embodiments, a cationic lipid is cationic lipid (54). In embodiments, a cationic lipid is cationic lipid (55). In embodiments, a cationic lipid is cationic lipid (56). In embodiments, a cationic lipid is cationic lipid (57). In embodiments, a cationic lipid is cationic lipid (58). In embodiments, a cationic lipid is cationic lipid (59). In embodiments, a cationic lipid is cationic lipid (60).

Exemplary cationic lipids include cationic lipids according to formula (IIId) such as cationic lipids (61)-(71) (Table F):

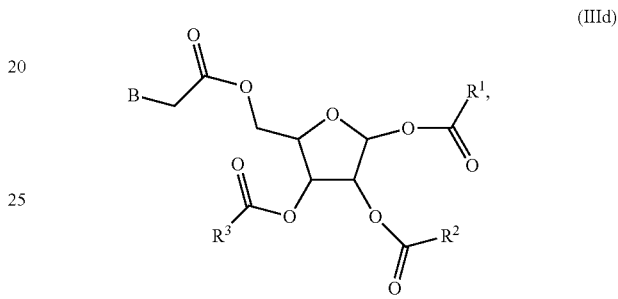

(IIId)

where B, $R^1$, $R^2$, and $R^3$ are independently as described herein, including the exemplified groups of Table F.

TABLE F

Formula (IIId) Cationic Lipids (61)

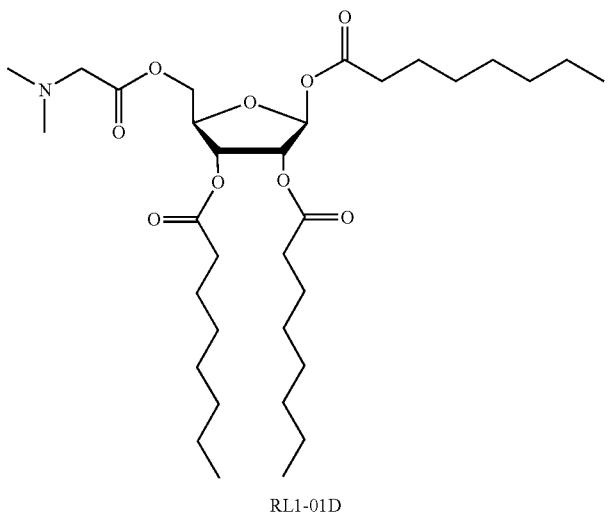

RL1-01D

TABLE F-continued
Formula (IIId) Cationic Lipids
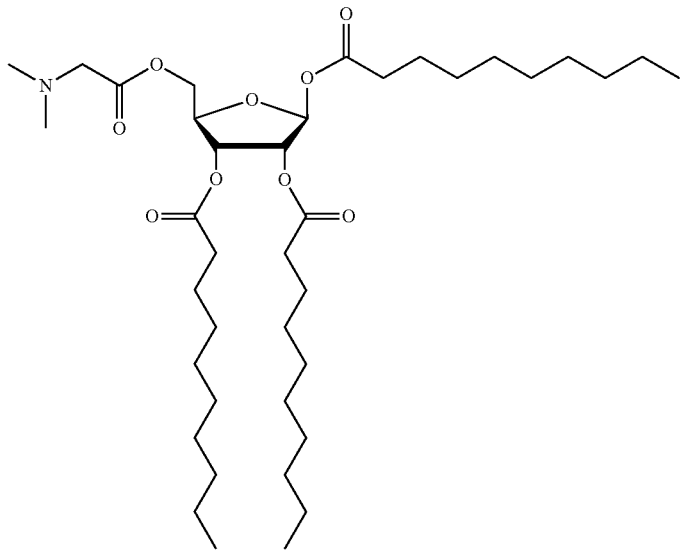
RL1-02D (62)
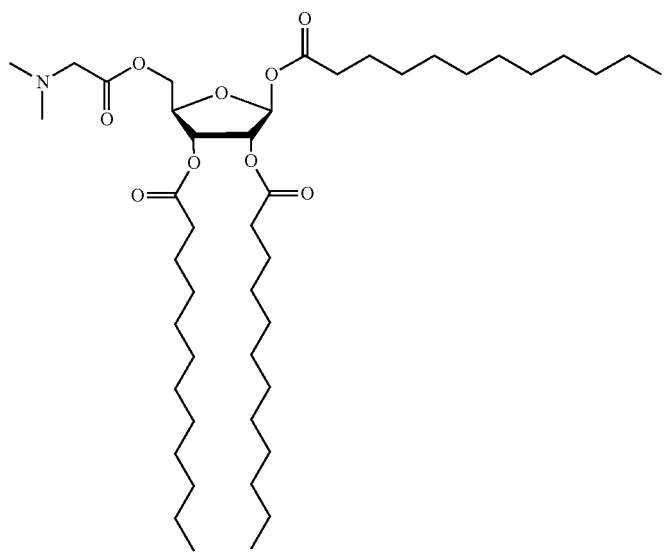
RL1-03D (63)

TABLE F-continued
Formula (IIId) Cationic Lipids
(64)
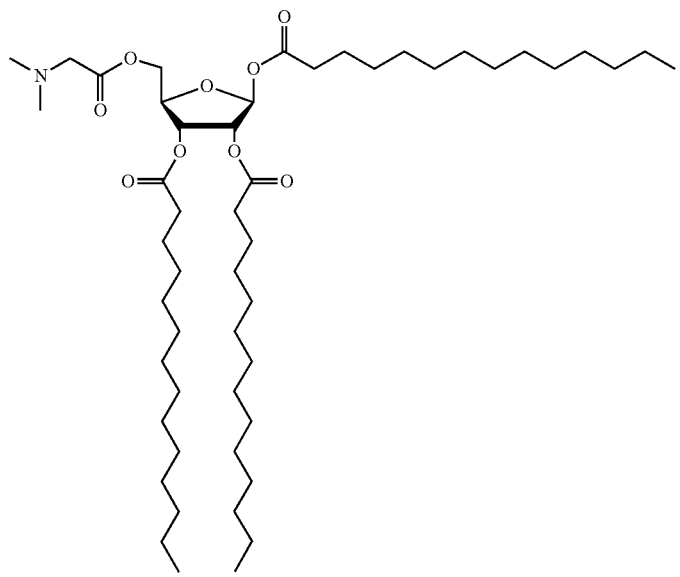
RL1-04D
(65)
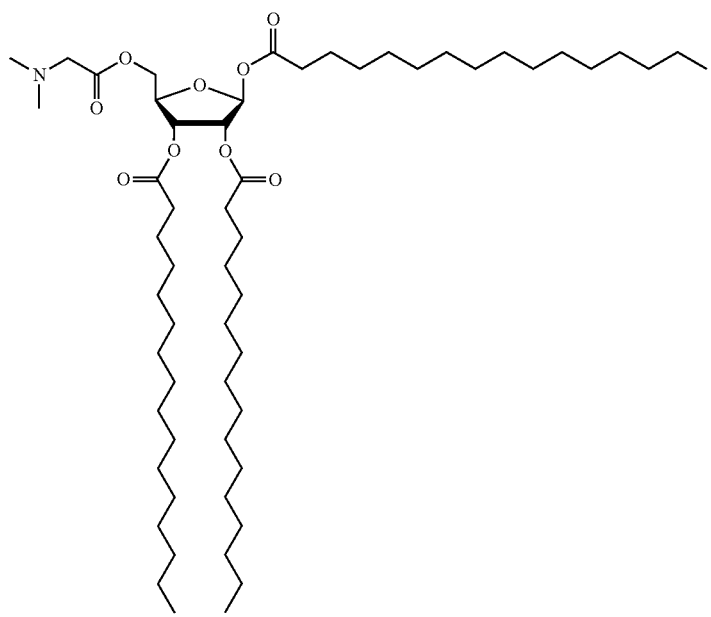
RL1-05D TABLE F-continued
Formula (IIId) Cationic Lipids
(66)
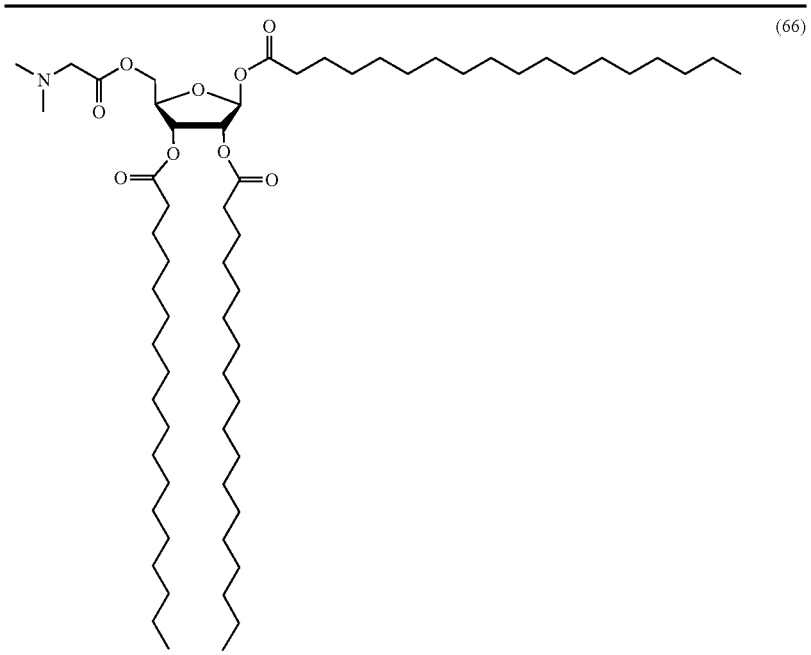
RL1-06D
(67)
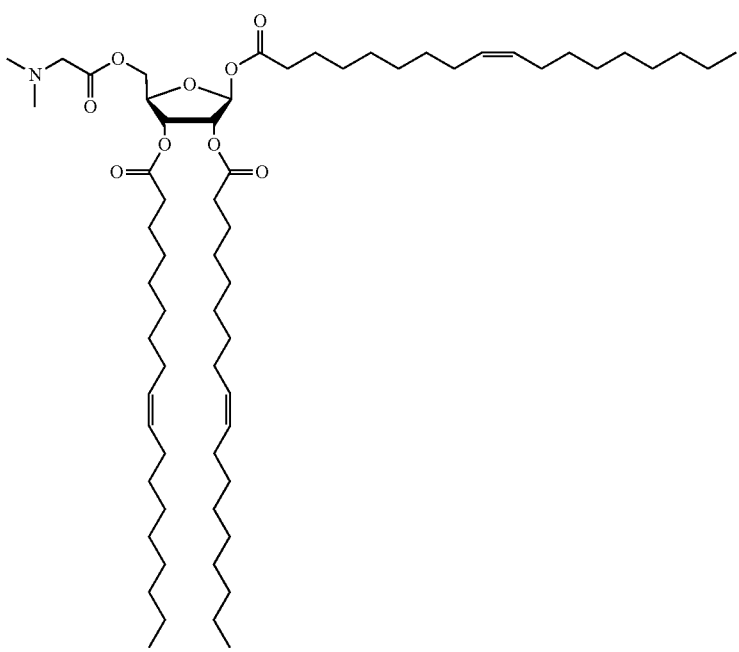
RL1-07D TABLE F-continued
Formula (IIId) Cationic Lipids
(68)
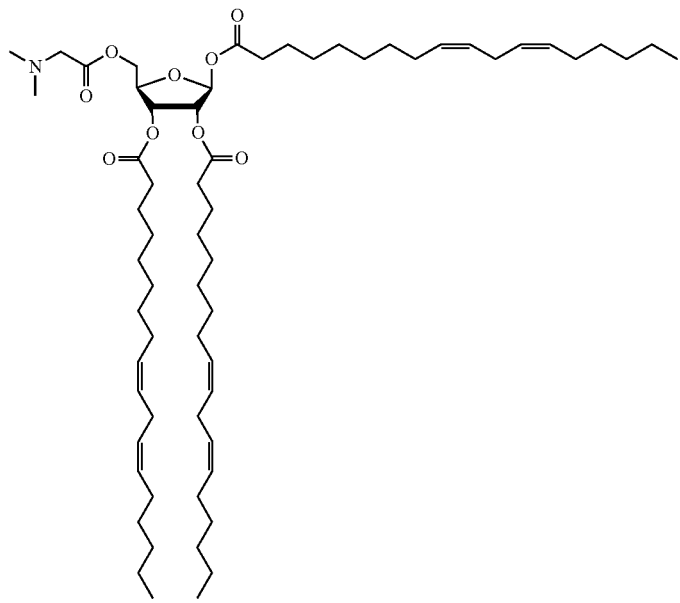
RL1-08D
(69)
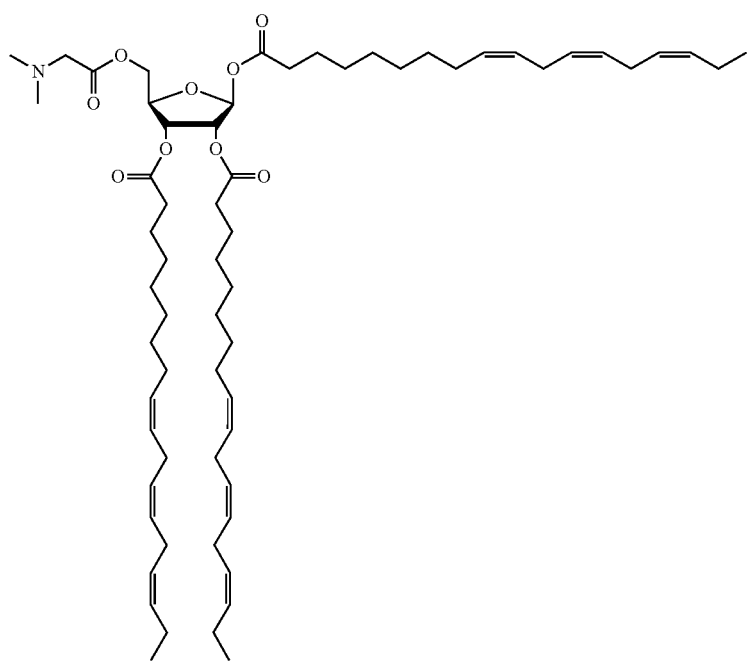
RL1-09D TABLE F-continued
Formula (IIId) Cationic Lipids
(70)
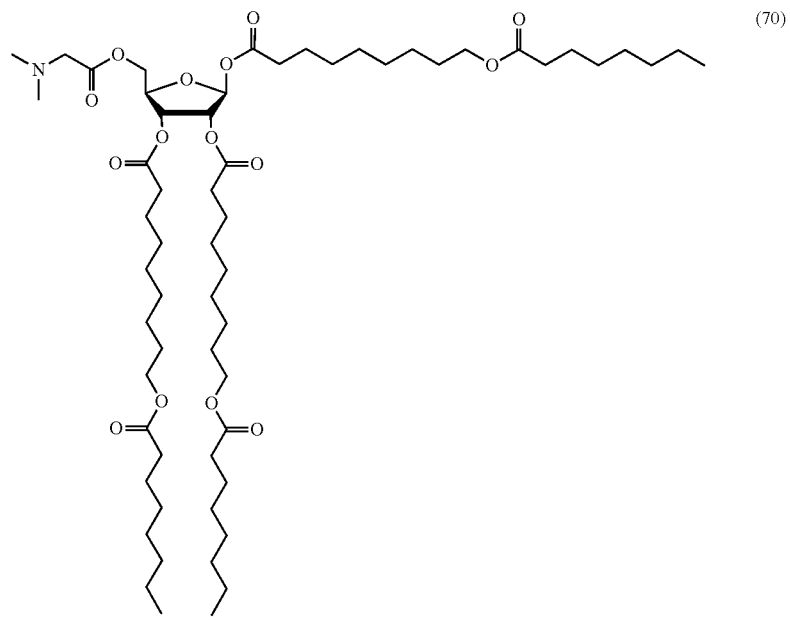
RL1-10D
(71)
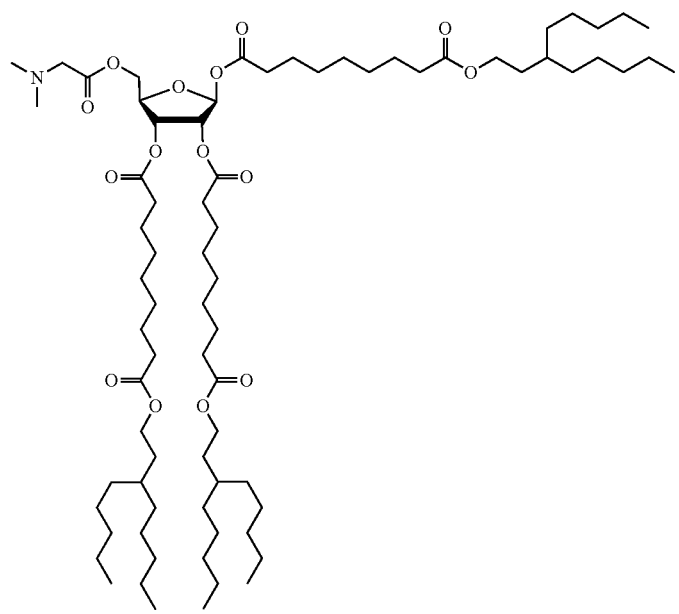
RL1-11D In embodiments, a cationic lipid is cationic lipid (61). In embodiments, a cationic lipid is cationic lipid (62). In embodiments, a cationic lipid is cationic lipid (63). In embodiments, a cationic lipid is cationic lipid (64). In embodiments, a cationic lipid is cationic lipid (65). In embodiments, a cationic lipid is cationic lipid (66). In embodiments, a cationic lipid is cationic lipid (67). In embodiments, a cationic lipid is cationic lipid (68). In embodiments, a cationic lipid is cationic lipid (69). In embodiments, a cationic lipid is cationic lipid (70). In embodiments, a cationic lipid is cationic lipid (71).

Exemplary cationic lipids include cationic lipids according to formula (IIIe) such as cationic lipids (72)-(82) (Table F):

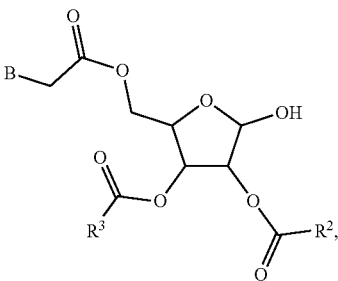

(IIIe)

where B, $R^2$, and $R^3$ are independently as described herein, including the exemplified groups of Table F.

TABLE G

Formula (IIIe) Cationic Lipids (72)

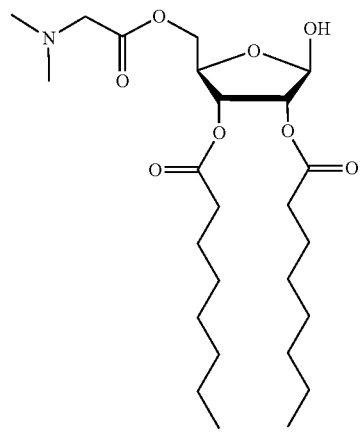

RL1-01Dx2

TABLE G-continued

Formula (IIIe) Cationic Lipids (73)

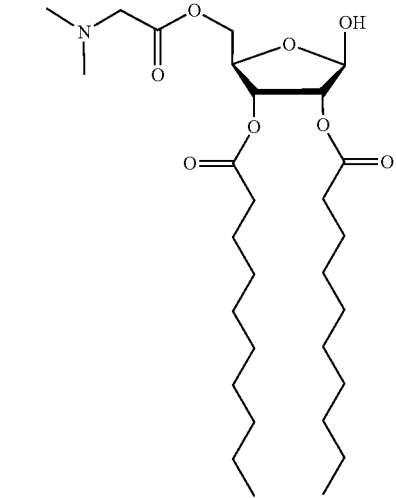

RL1-02Dx2

(74)

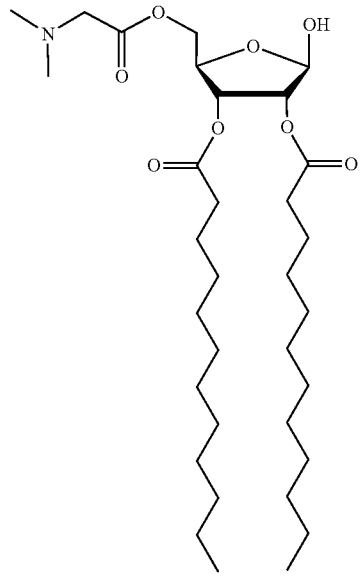

RL1-03Dx2

TABLE G-continued
Formula (IIIe) Cationic Lipids
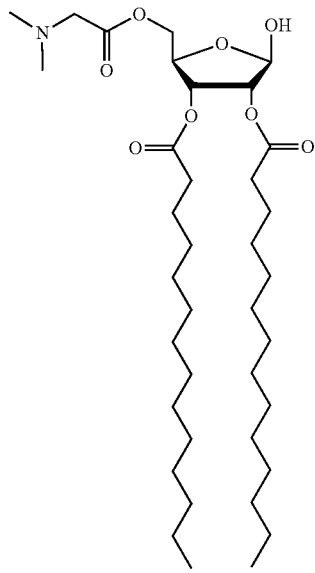
RL1-04Dx2 (75)
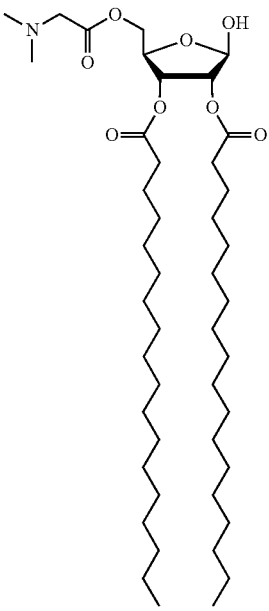
RL1-06Dx2 (77)
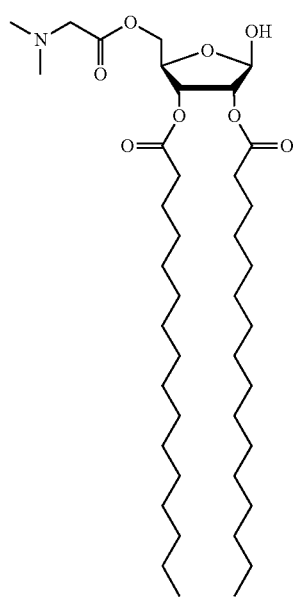
RL1-05Dx2 (76)
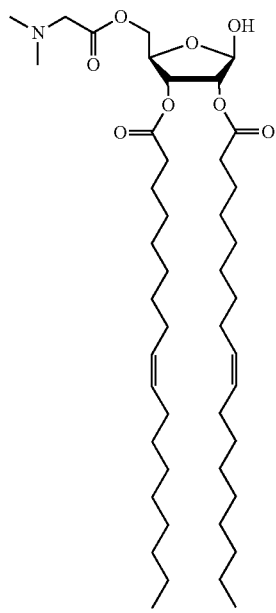
RL1-07Dx2 (78)

TABLE G-continued

Formula (IIIe) Cationic Lipids

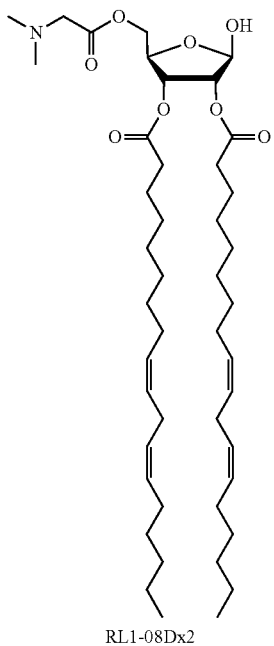

RL1-08Dx2 (79)

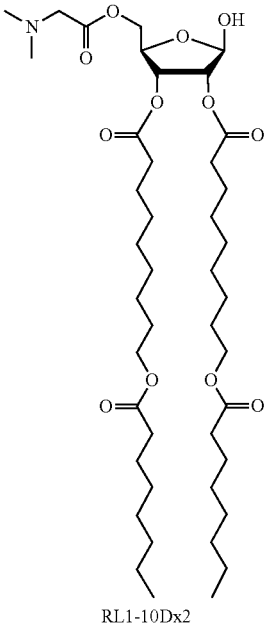

RL1-10Dx2 (81)

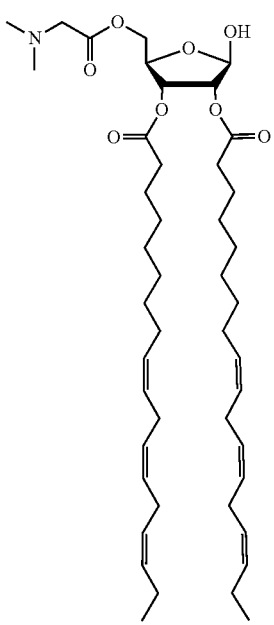

RL1-09Dx2 (80)

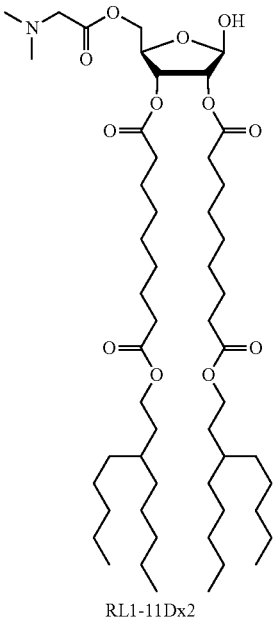

RL1-11Dx2 (82)

In embodiments, a cationic lipid is cationic lipid (72). In embodiments, a cationic lipid is cationic lipid (73). In embodiments, a cationic lipid is cationic lipid (74). In embodiments, a cationic lipid is cationic lipid (75). In embodiments, a cationic lipid is cationic lipid (76). In embodiments, a cationic lipid is cationic lipid (77). In embodiments, a cationic lipid is cationic lipid (78). In embodiments, a cationic lipid is cationic lipid (79). In embodiments, a cationic lipid is cationic lipid (80). In embodiments, a cationic lipid is cationic lipid (81). In embodiments, a cationic lipid is cationic lipid (82).

Exemplary cationic lipids include cationic lipids according to formula (IIIf) such as cationic lipids (83)-(93) (Table H):

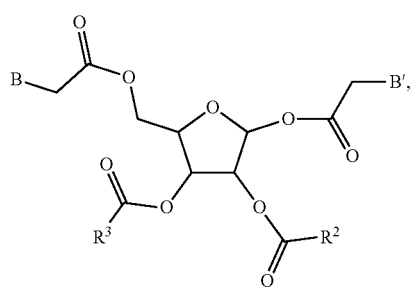
(IIIf)
where B, $R^1$, $R^2$, and $R^3$ are independently as described herein, including the exemplified groups of Table H.
TABLE H
Formula (IIIf) Cationic Lipids
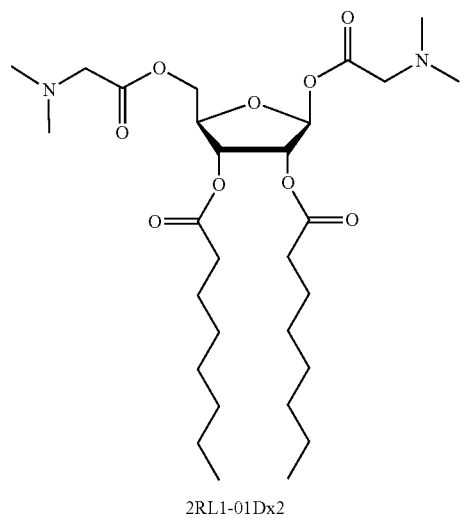
(83) 2RL1-01Dx2
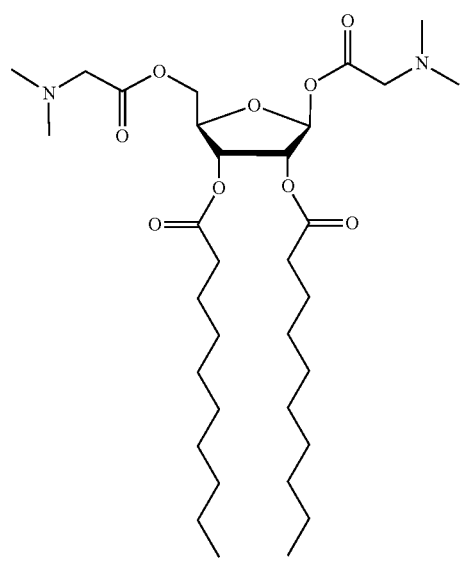
(84) 2RL1-02Dx2
TABLE H-continued
Formula (IIIf) Cationic Lipids
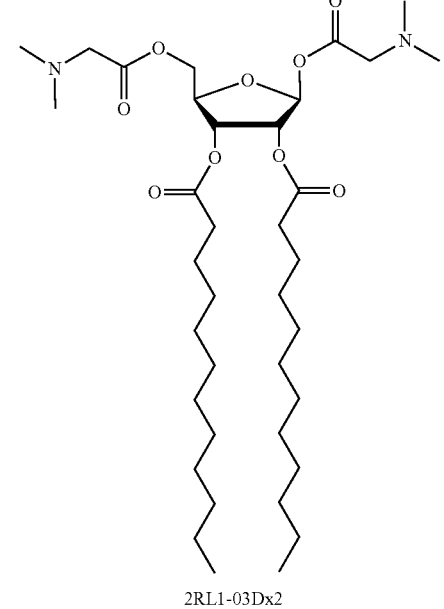
(85) 2RL1-03Dx2
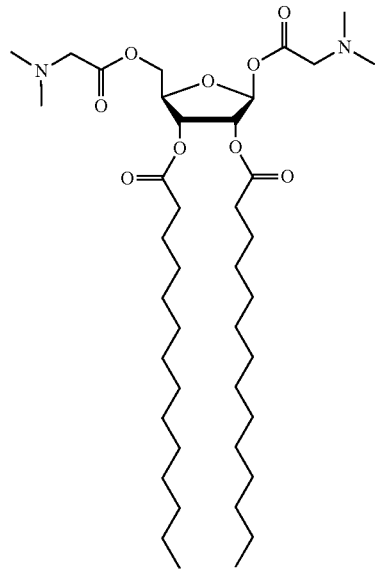
(86) 2RL1-04Dx2

TABLE H-continued
Formula (IIIf) Cationic Lipids
(87)
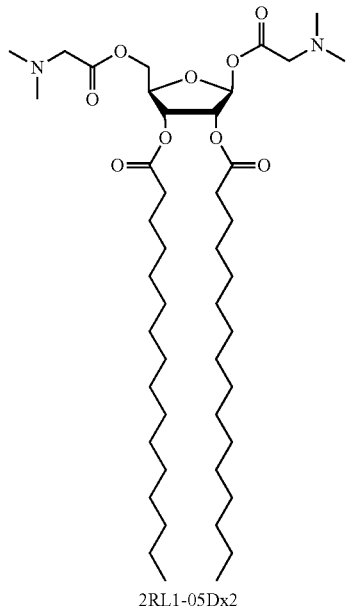
2RL1-05Dx2
(88)
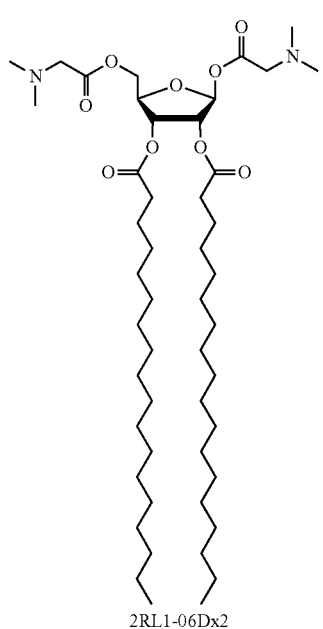
2RL1-06Dx2
(89)
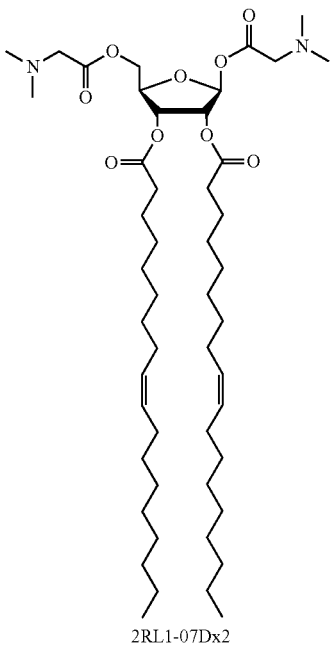
2RL1-07Dx2
(90)
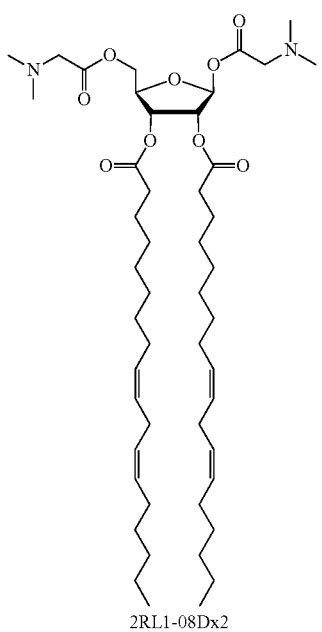
2RL1-08Dx2

TABLE H-continued

Formula (IIIf) Cationic Lipids

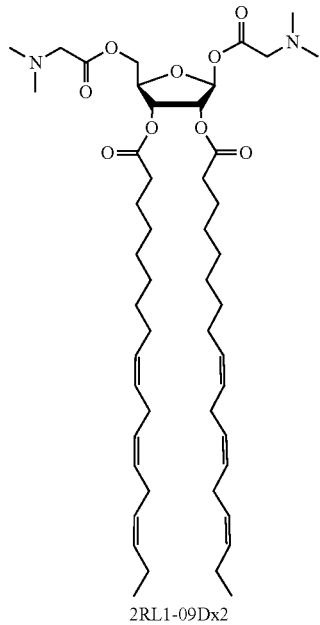

(91) 2RL1-09Dx2

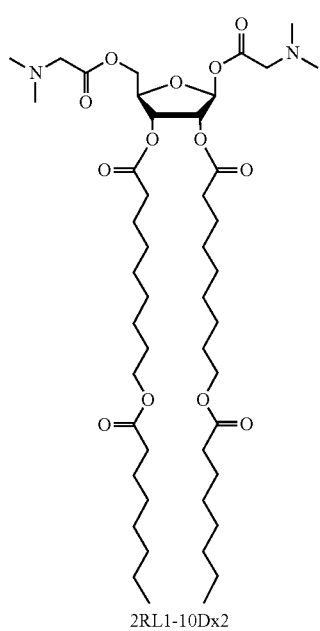

(92) 2RL1-10Dx2

TABLE H-continued

Formula (IIIf) Cationic Lipids

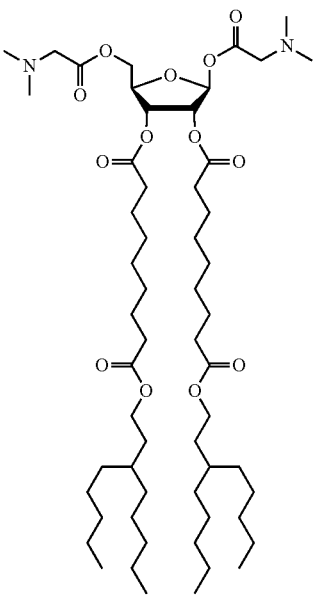

(93) 2RL1-11Dx2

In embodiments, a cationic lipid is cationic lipid (83). In embodiments, a cationic lipid is cationic lipid (84). In embodiments, a cationic lipid is cationic lipid (85). In embodiments, a cationic lipid is cationic lipid (86). In embodiments, a cationic lipid is cationic lipid (87). In embodiments, a cationic lipid is cationic lipid (88). In embodiments, a cationic lipid is cationic lipid (89). In embodiments, a cationic lipid is cationic lipid (90). In embodiments, a cationic lipid is cationic lipid (91). In embodiments, a cationic lipid is cationic lipid (92). In embodiments, a cationic lipid is cationic lipid (93).

Exemplary cationic lipids include cationic lipids according to formula (IIIg) such as cationic lipids (94)-(106) (Table I):

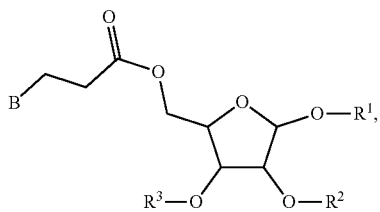

(IIIg)

where B, $R^1$, $R^2$, and $R^3$ are independently as described herein, including the exemplified groups of Table I.

TABLE 1
Formula (IIIg) Cationic Lipids
(94)
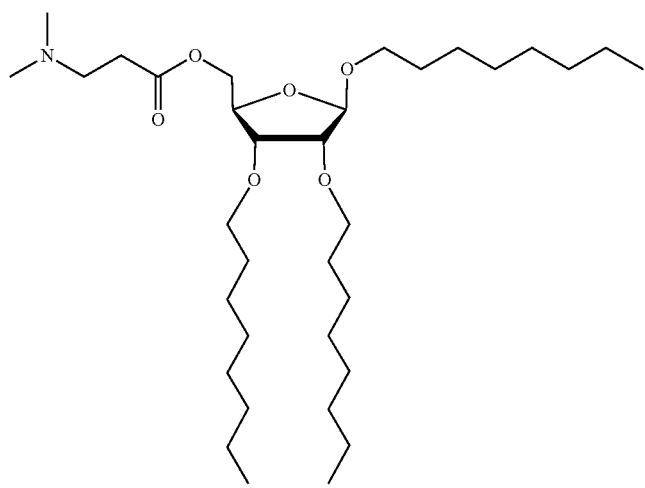
RL2-01
(95)
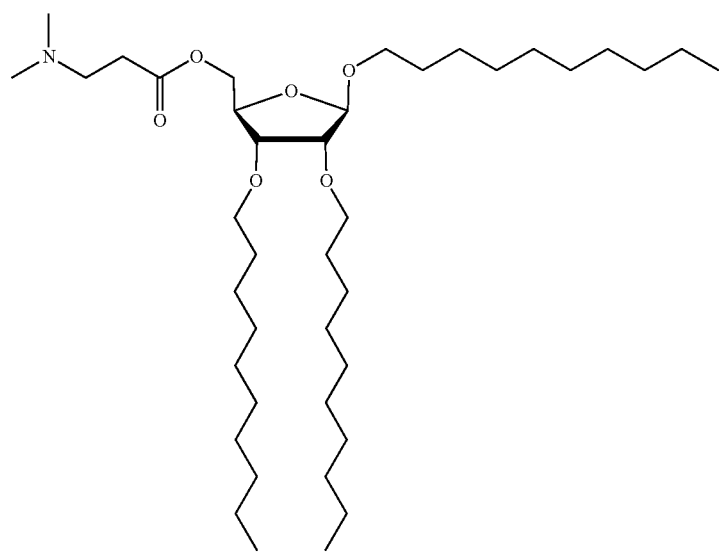
RL2-02

TABLE 1-continued
Formula (IIIg) Cationic Lipids
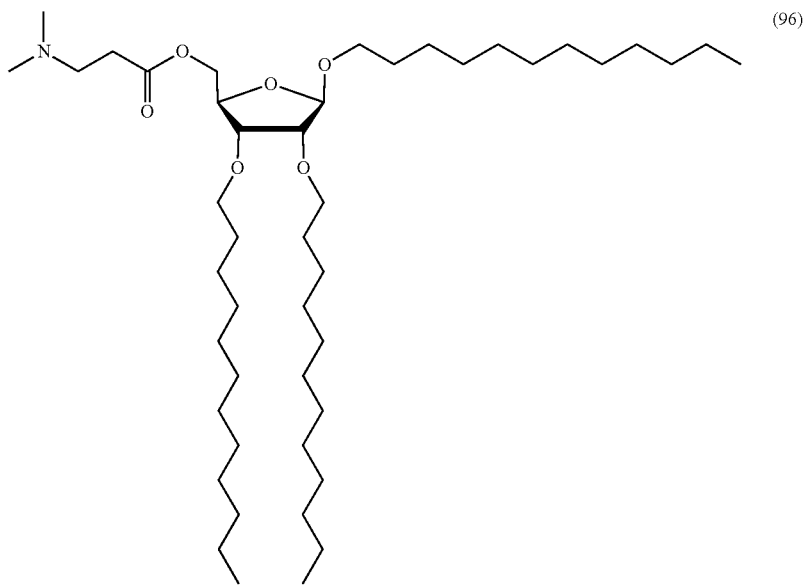
RL2-03
(96)
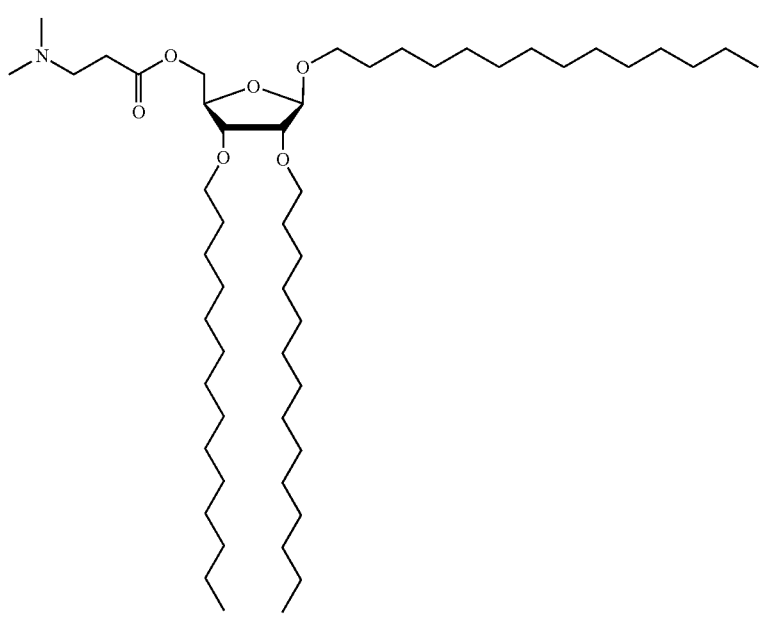
RL2-04
(97)

TABLE 1-continued
Formula (IIIg) Cationic Lipids
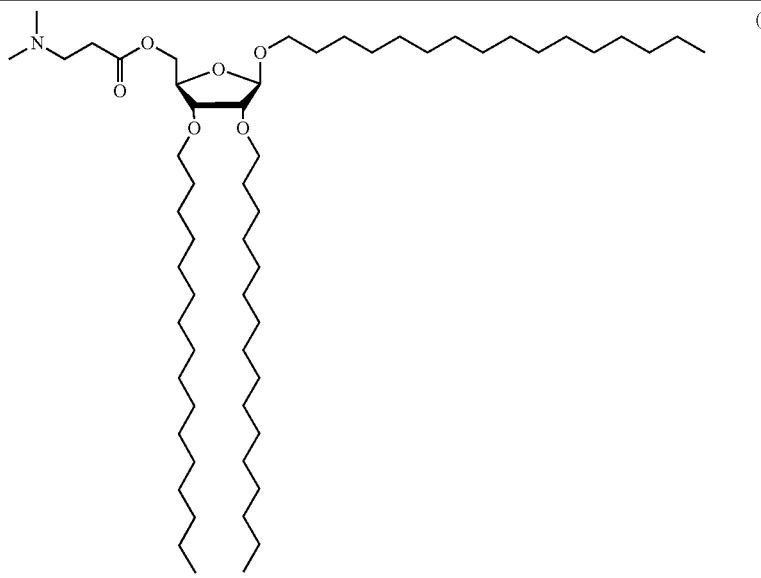
(98)
RL2-05
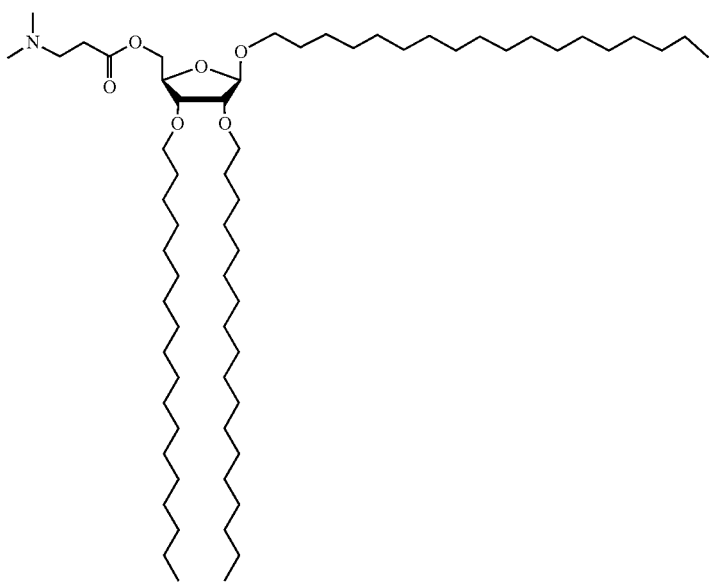
(99)
RL2-06

TABLE 1-continued
Formula (IIIg) Cationic Lipids
(100)
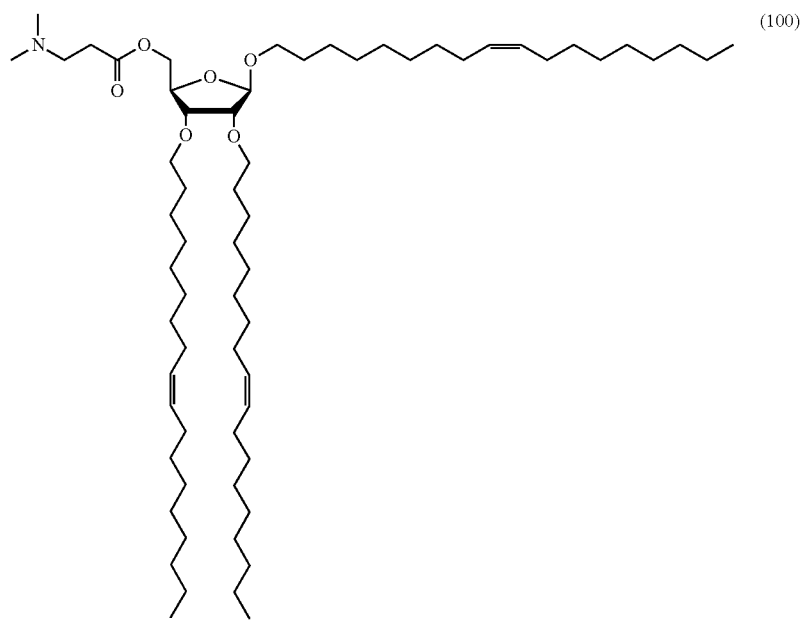
RL2-07
(101)
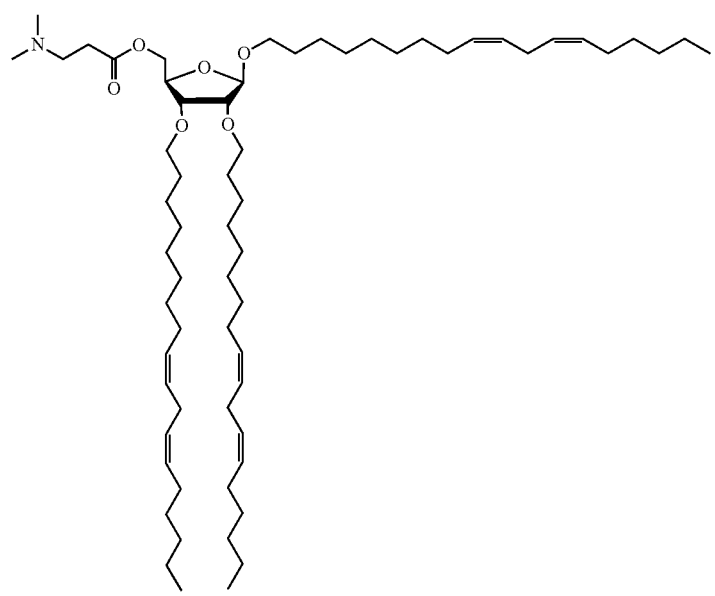
RL2-08

TABLE 1-continued
Formula (IIIg) Cationic Lipids
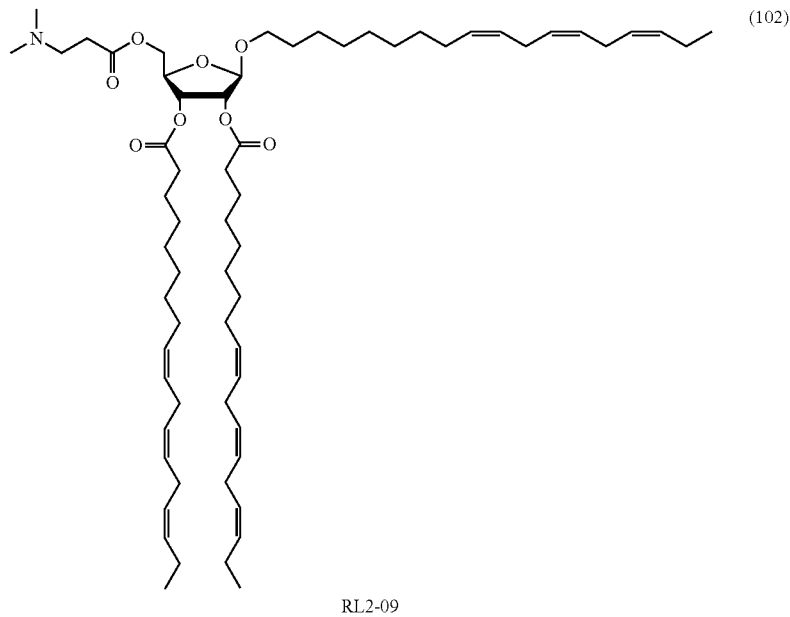
(102)
RL2-09
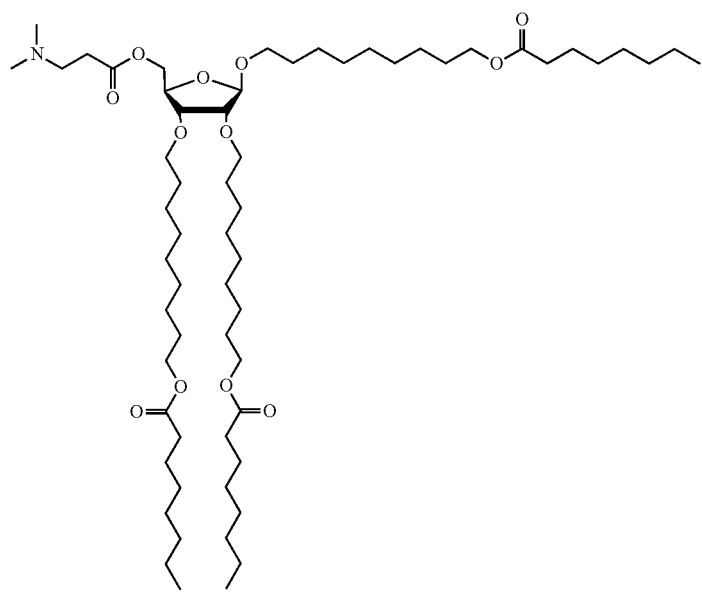
(103)
RL2-10

TABLE 1-continued
Formula (IIIg) Cationic Lipids
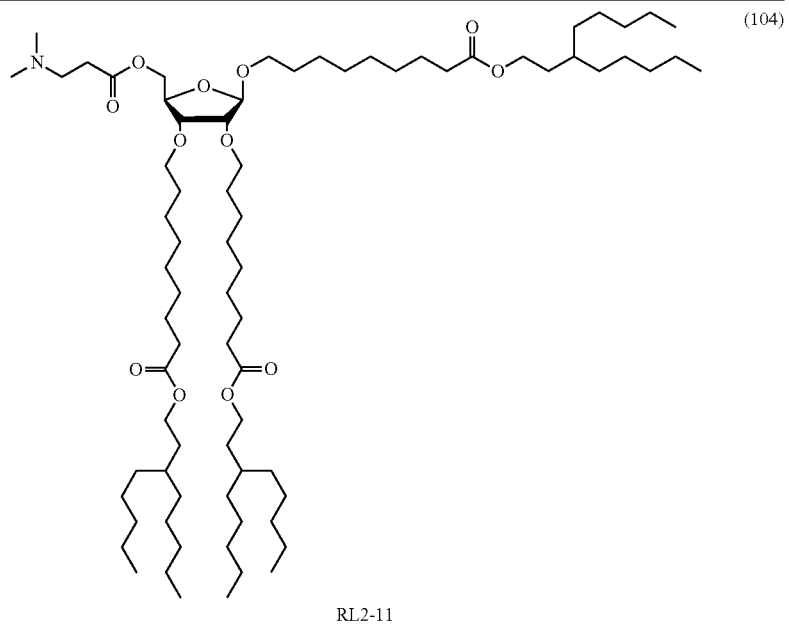
RL2-11 (104)
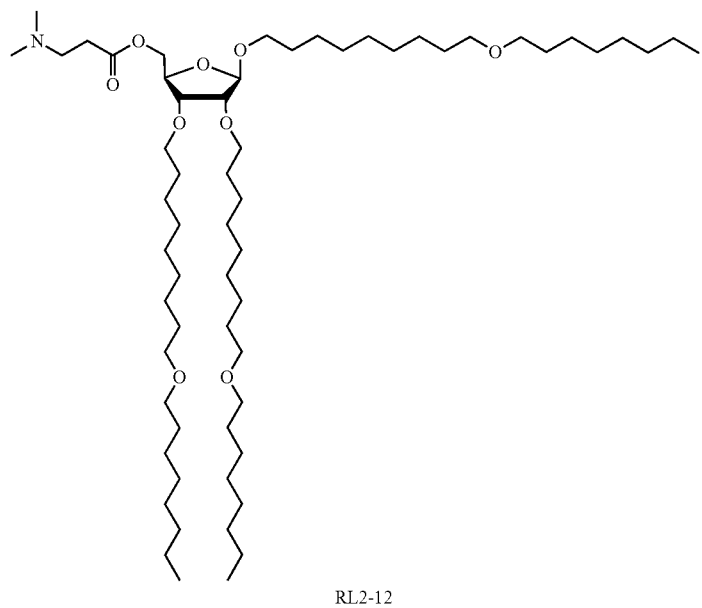
RL2-12 (105)

TABLE 1-continued

Formula (IIIg) Cationic Lipids (106)

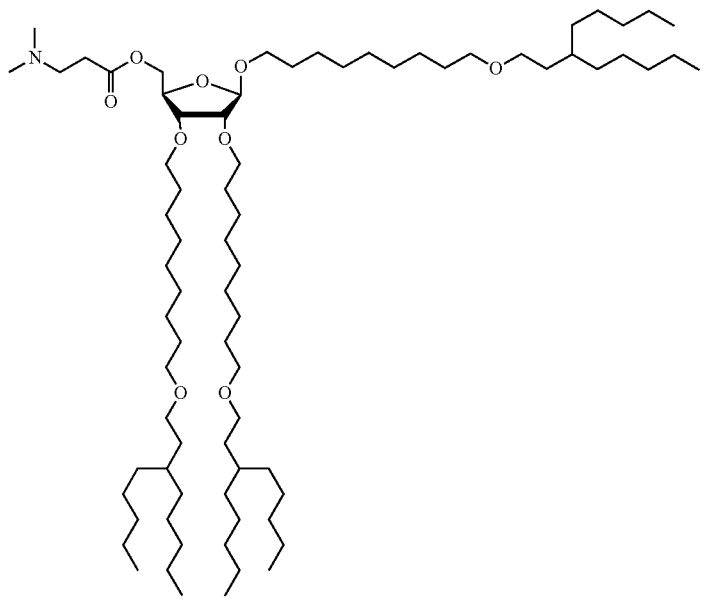

RL2-13

In embodiments, a cationic lipid is cationic lipid (94). In embodiments, a cationic lipid is cationic lipid (95). In embodiments, a cationic lipid is cationic lipid (96). In embodiments, a cationic lipid is cationic lipid (97). In embodiments, a cationic lipid is cationic lipid (98). In embodiments, a cationic lipid is cationic lipid (99). In embodiments, a cationic lipid is cationic lipid (100). In embodiments, a cationic lipid is cationic lipid (101). In embodiments, a cationic lipid is cationic lipid (102). In embodiments, a cationic lipid is cationic lipid (103). In embodiments, a cationic lipid is cationic lipid (104). In embodiments, a cationic lipid is cationic lipid (105). In embodiments, a cationic lipid is cationic lipid (106).

Exemplary cationic lipids include cationic lipids according to formula (IIIh) such as cationic lipids (107)-(119) (Table J):

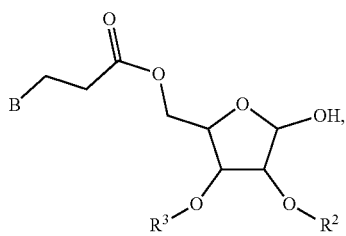

(IIIh)

where B, $R^2$, and $R^3$ are independently as described herein, including the exemplified groups of Table J.

TABLE J

Formula (IIIh) Cationic Lipids (107)

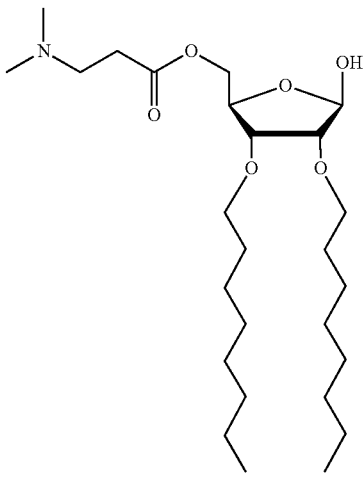

RL2-01x2

TABLE J-continued
Formula (IIIh) Cationic Lipids
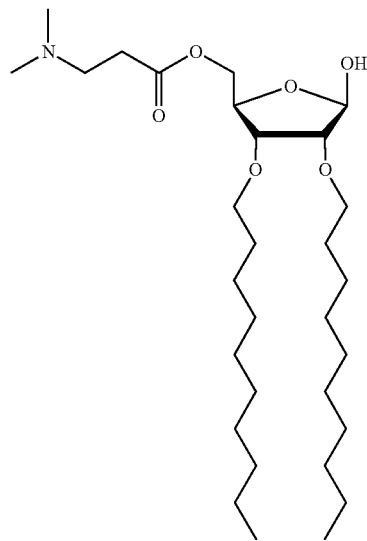
RL2-02x2 (108)
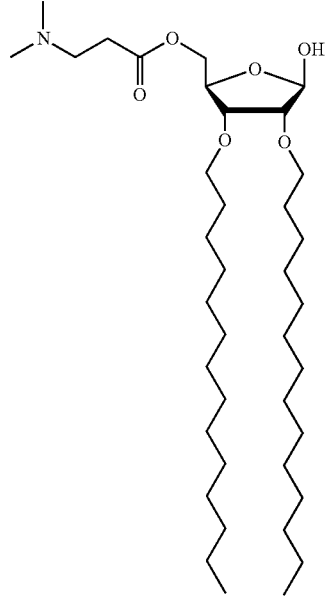
RL2-04x2 (110)
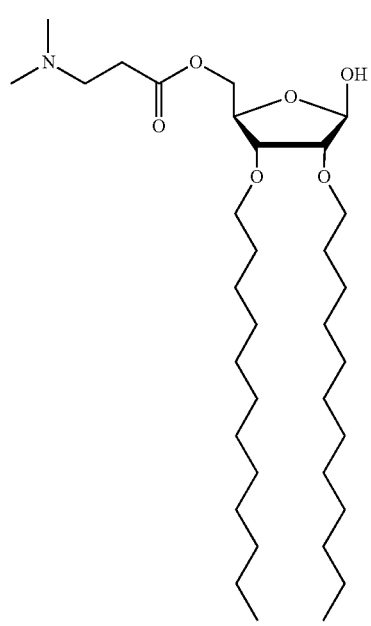
RL2-03x2 (109)
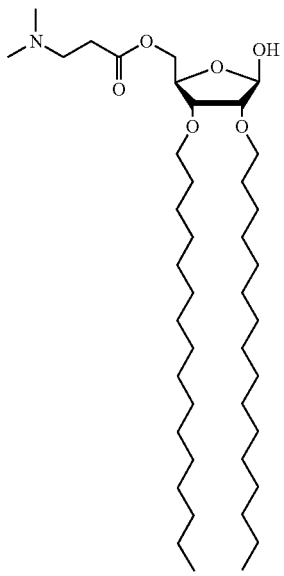
RL2-05x2 (111)

TABLE J-continued
Formula (IIIh) Cationic Lipids
(112)
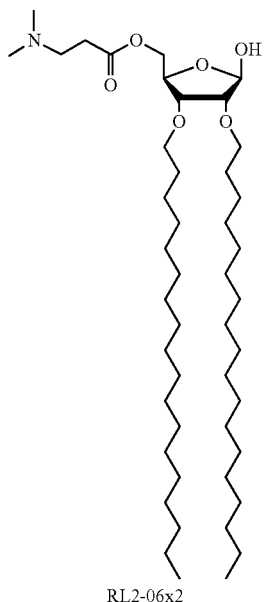
RL2-06x2
(113)
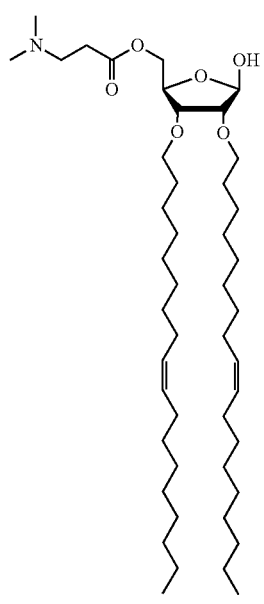
RL2-07x2
(114)
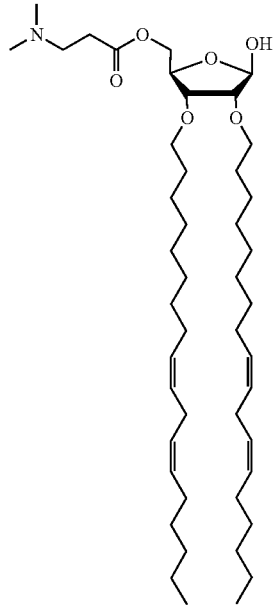
RL2-08x2
(115)
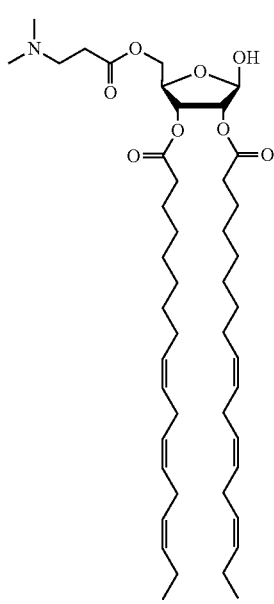
RL2-09x2

TABLE J-continued

Formula (IIIh) Cationic Lipids

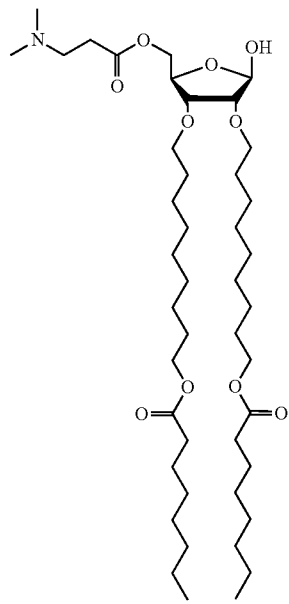

RL2-10x2 (116)

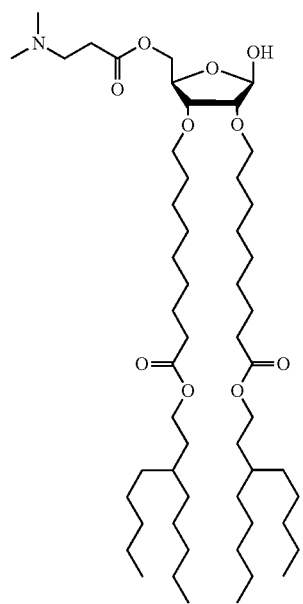

RL2-11x2 (117)

TABLE J-continued

Formula (IIIh) Cationic Lipids

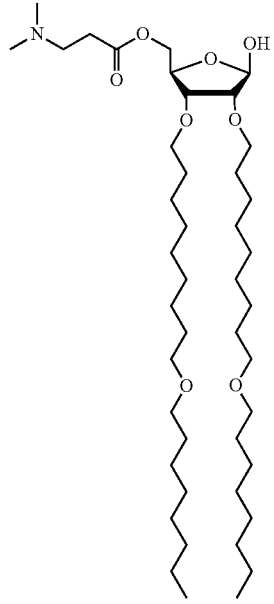

RL2-12x2 (118)

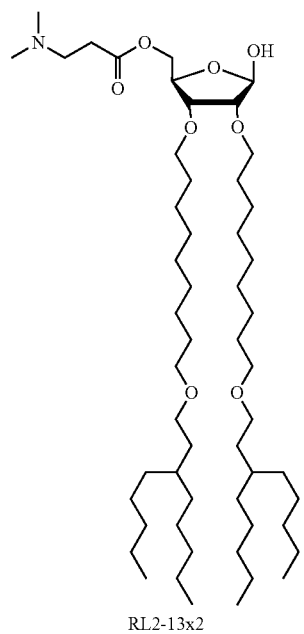

RL2-13x2 (119)

In embodiments, a cationic lipid is cationic lipid (107). In embodiments, a cationic lipid is cationic lipid (108). In embodiments, a cationic lipid is cationic lipid (109). In embodiments, a cationic lipid is cationic lipid (110). In embodiments, a cationic lipid is cationic lipid (111). In embodiments, a cationic lipid is cationic lipid (112). In embodiments, a cationic lipid is cationic lipid (113). In embodiments, a cationic lipid is cationic lipid (114). In embodiments, a cationic lipid is cationic lipid (115). In embodiments, a cationic lipid is cationic lipid (116). In embodiments, a cationic lipid is cationic lipid (117). In embodiments, a cationic lipid is cationic lipid (118). In embodiments, a cationic lipid is cationic lipid (119).

Exemplary cationic lipids include cationic lipids according to formula (IIIi) such as cationic lipids (120)-(132) (Table K):
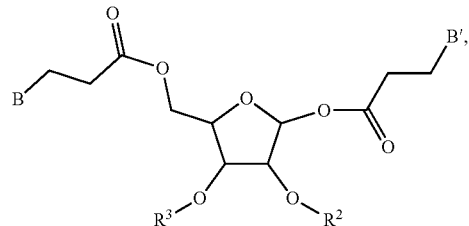
(IIIi)
where B, B', R², and R³ are independently as described herein, including the exemplified groups of Table K.
TABLE K
Formula (IIIi) Cationic Lipids
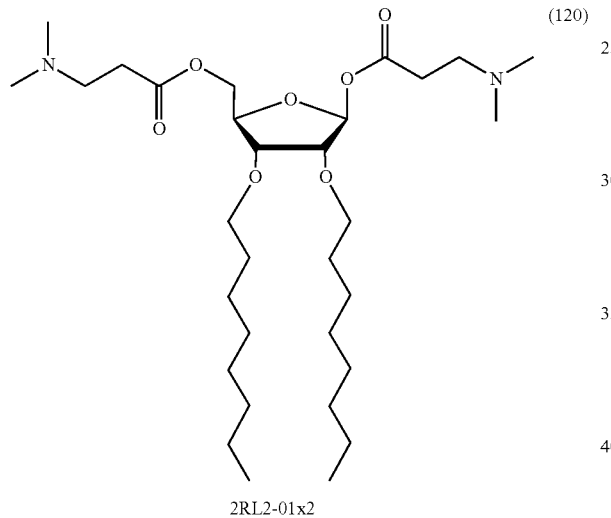
2RL2-01x2 (120)
2RL2-02x2 (121)
TABLE K-continued
Formula (IIIi) Cationic Lipids
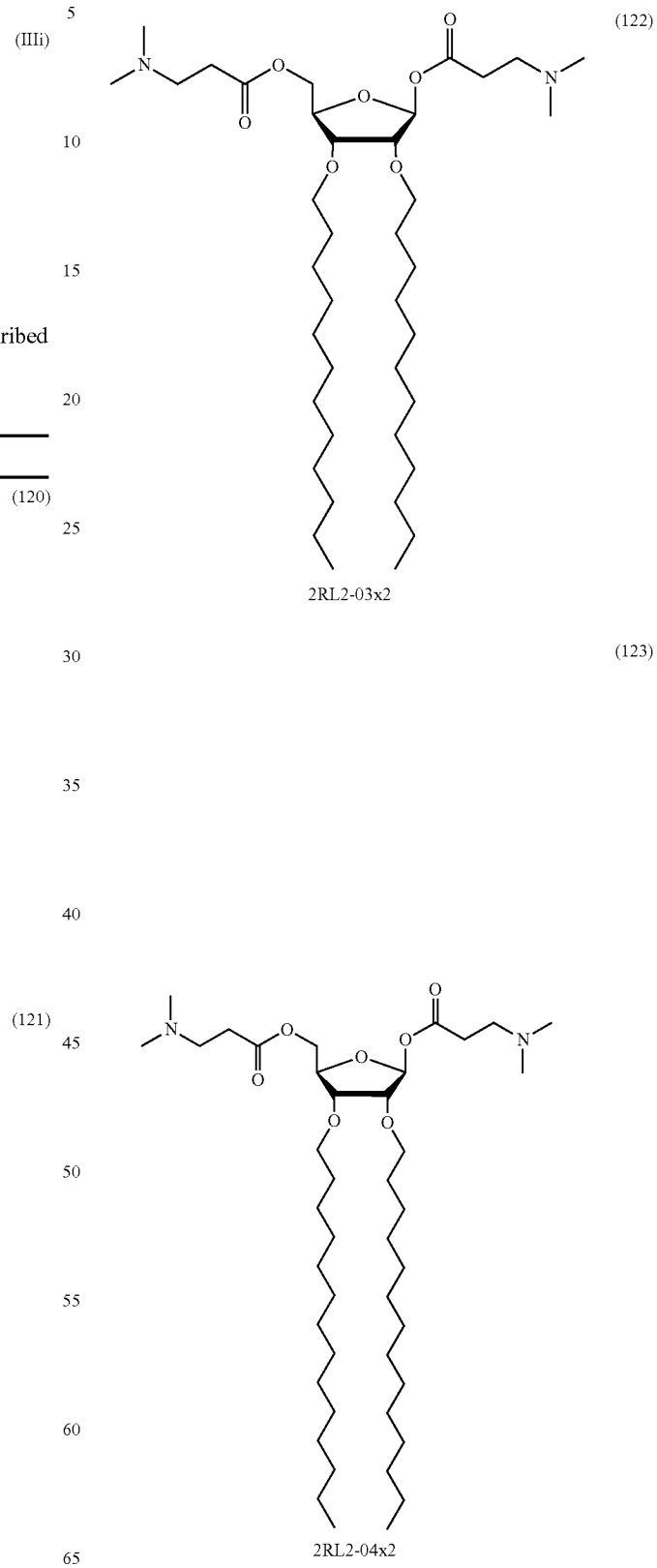
2RL2-03x2 (122)
2RL2-04x2 (123)

TABLE K-continued
Formula (IIIi) Cationic Lipids
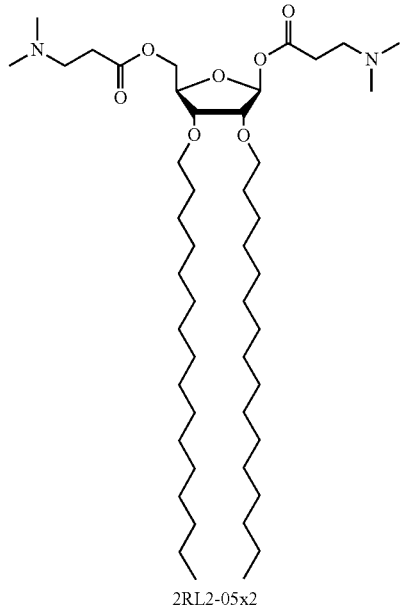
2RL2-05x2 (124)
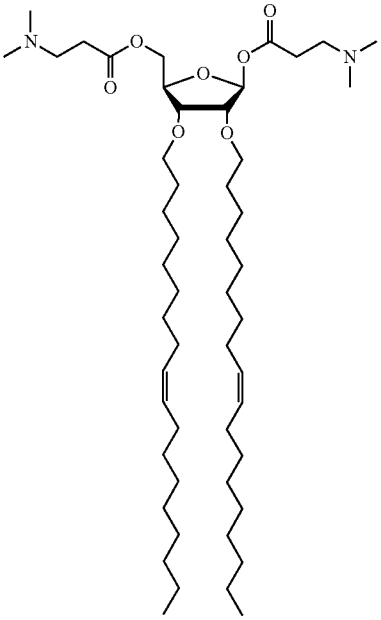
2RL2-07x2 (126)
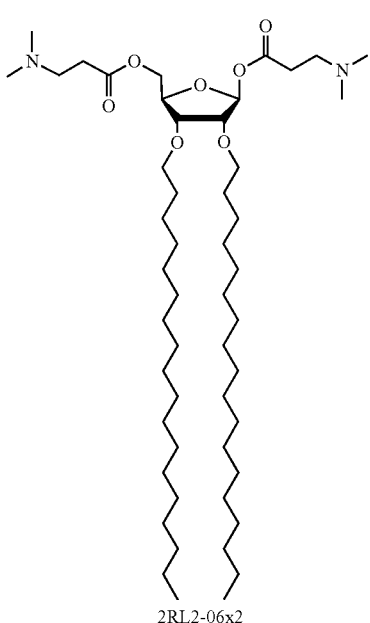
2RL2-06x2 (125)
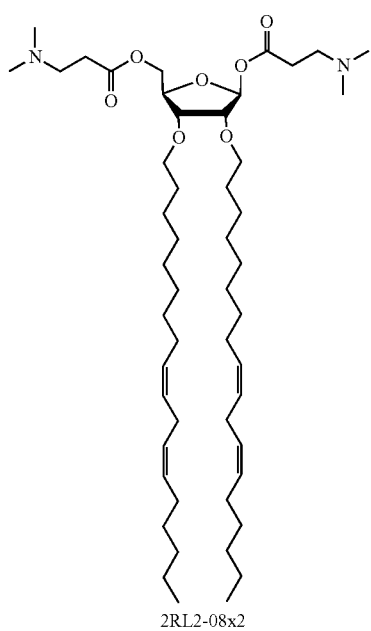
2RL2-08x2 (127)

TABLE K-continued
Formula (IIIi) Cationic Lipids
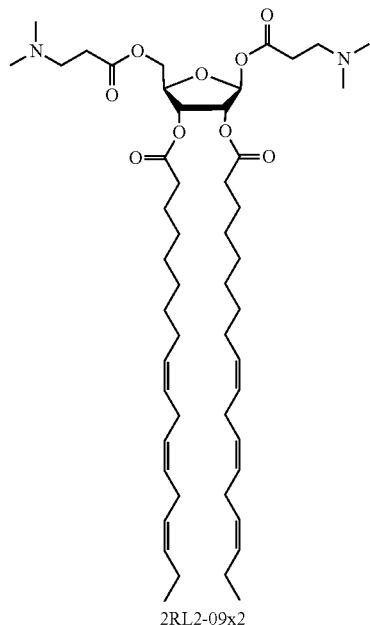
(128) 2RL2-09x2
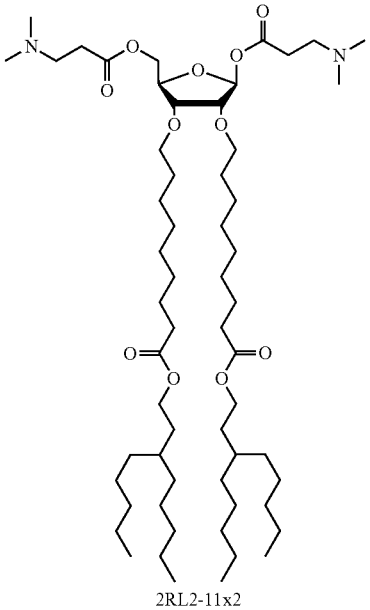
(130) 2RL2-11x2
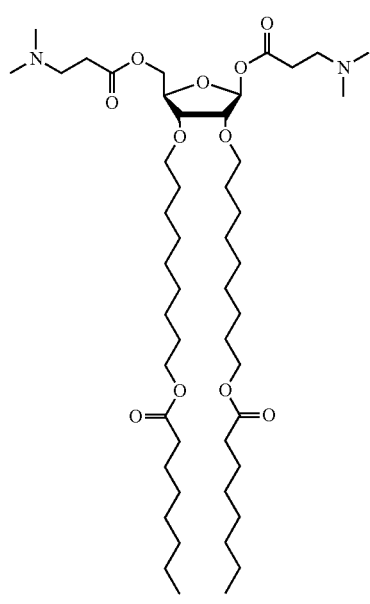
(129) 2RL2-10x2
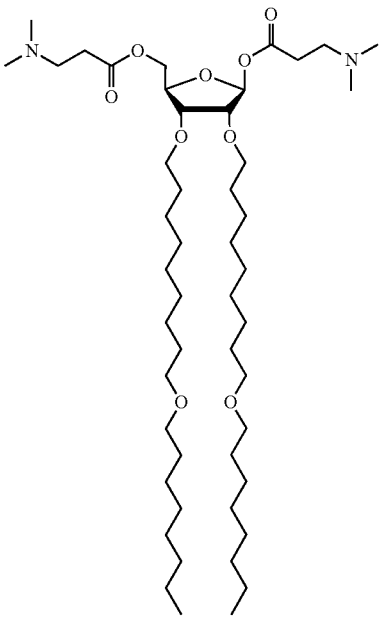
(131) 2RL2-12x2

TABLE K-continued

Formula (IIIi) Cationic Lipids

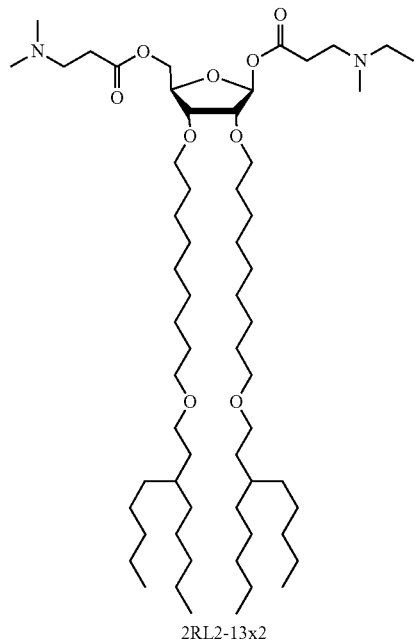

(132)

2RL2-13x2

---

In embodiments, a cationic lipid is cationic lipid (120). In embodiments, a cationic lipid is cationic lipid (121). In embodiments, a cationic lipid is cationic lipid (122). In embodiments, a cationic lipid is cationic lipid (123). In embodiments, a cationic lipid is cationic lipid (124). In embodiments, a cationic lipid is cationic lipid (125). In embodiments, a cationic lipid is cationic lipid (126). In embodiments, a cationic lipid is cationic lipid (127). In embodiments, a cationic lipid is cationic lipid (128). In embodiments, a cationic lipid is cationic lipid (129). In embodiments, a cationic lipid is cationic lipid (130). In embodiments, a cationic lipid is cationic lipid (131). In embodiments, a cationic lipid is cationic lipid (132).

Exemplary cationic lipids include cationic lipids according to formula (IIIj) such as cationic lipids (133)-(143) (Table L):

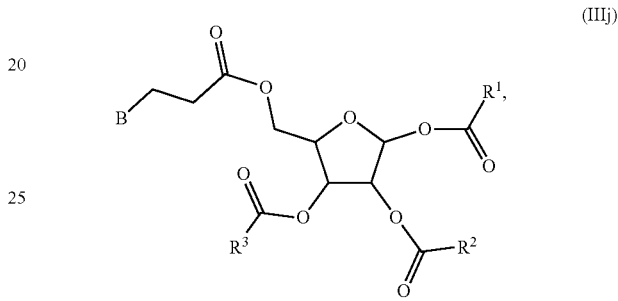

(IIIj)

where B, $R^1$, $R^2$, and $R^3$ are independently as described herein, including the exemplified groups of Table L.

TABLE L

Formula (IIIj) Cationic Lipids (133)

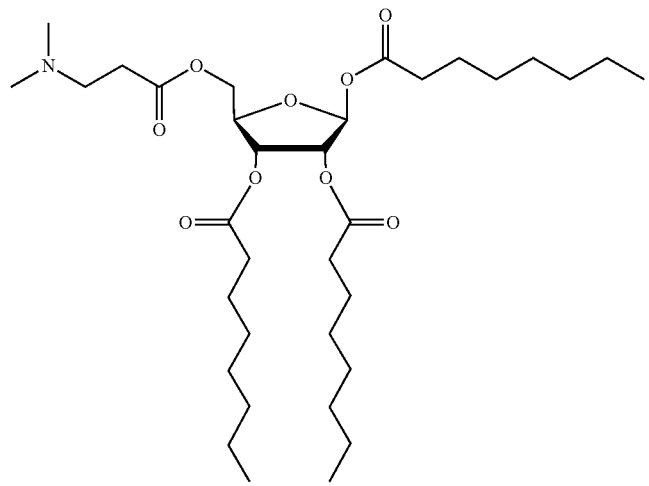

RL2-01D

TABLE L-continued
Formula (IIIj) Cationic Lipids
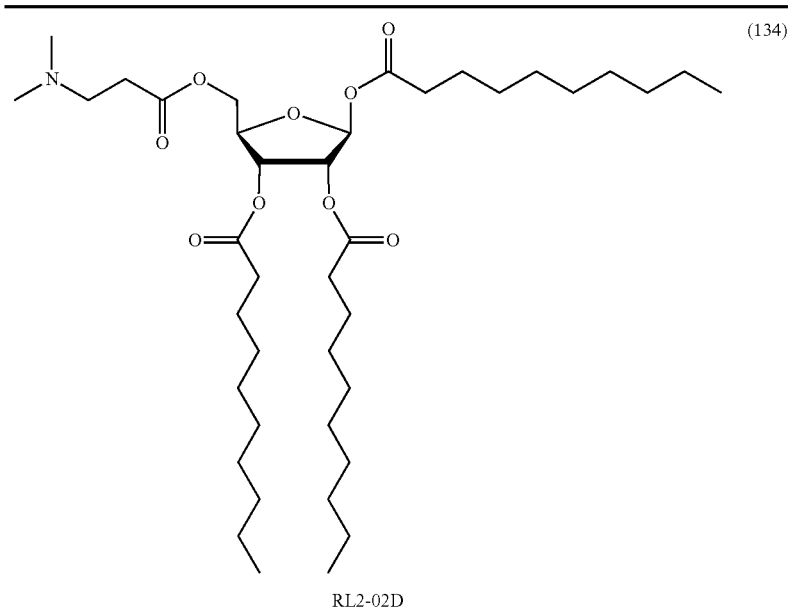
(134)
RL2-02D
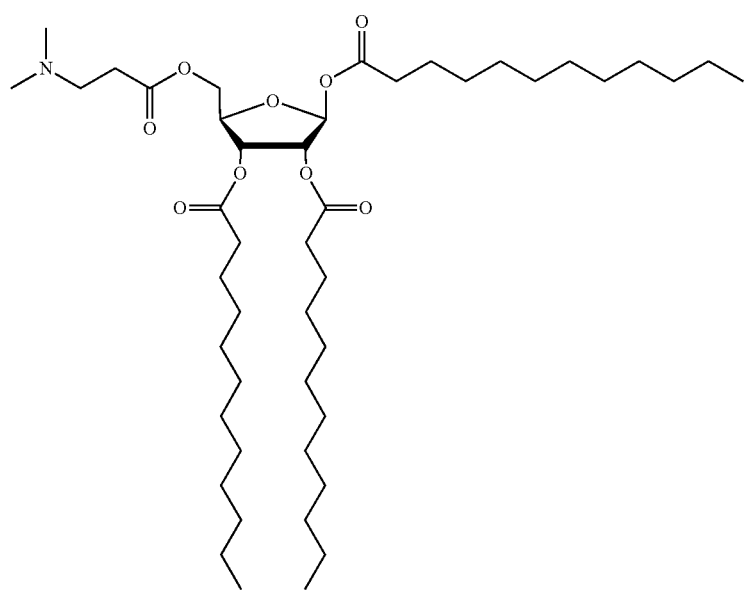
(135)
RL2-03D

TABLE L-continued
Formula (IIIj) Cationic Lipids
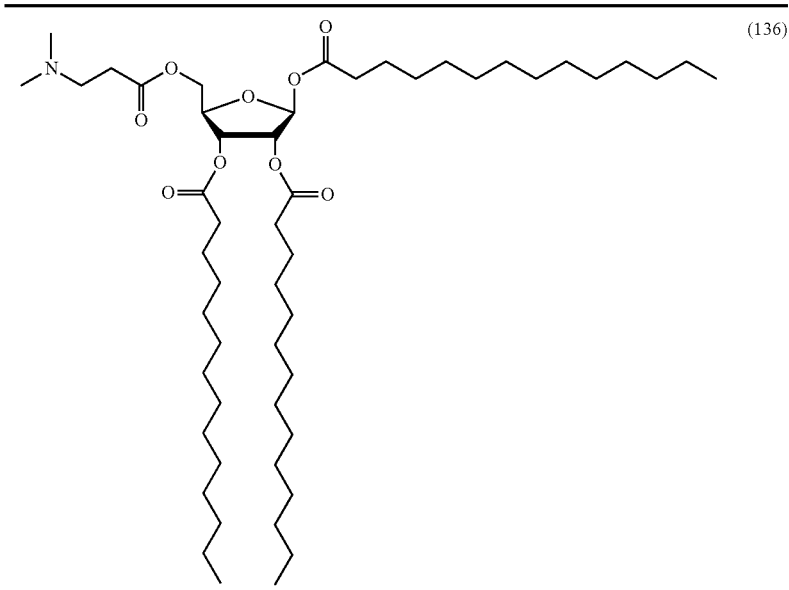
(136)
RL2-04D
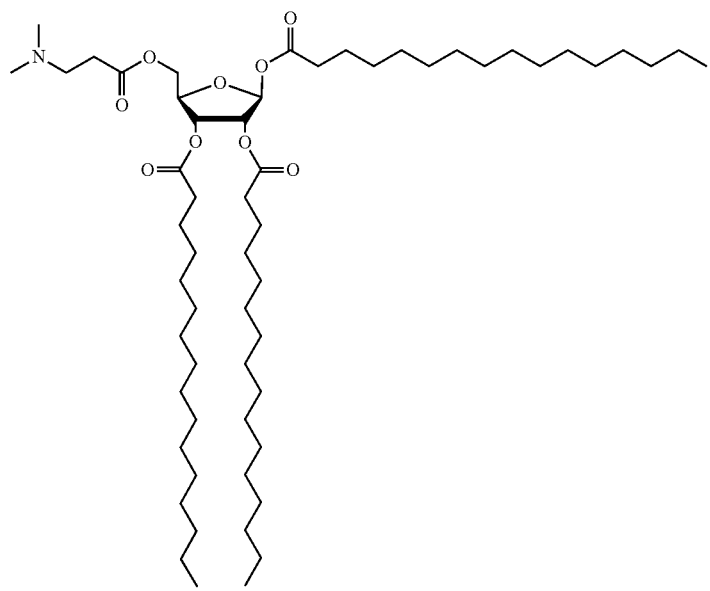
(137)
RL2-05D

TABLE L-continued
Formula (IIIj) Cationic Lipids
(138)
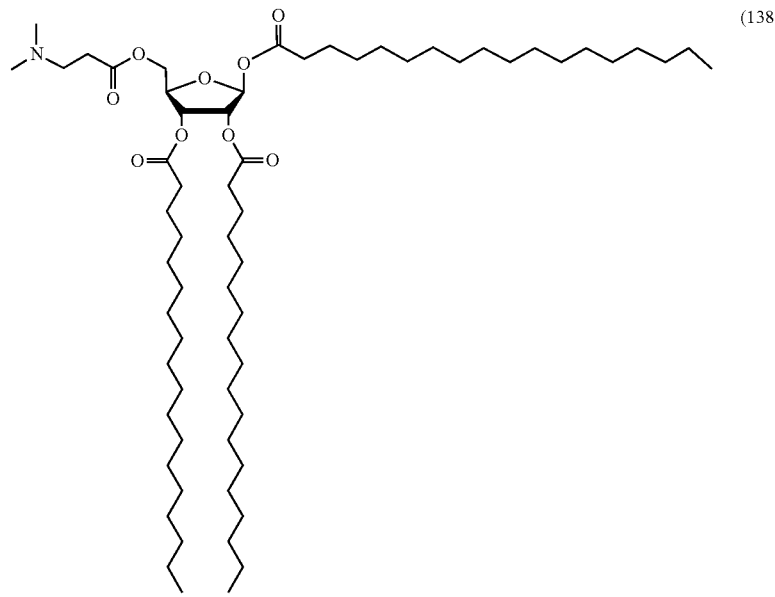
RL2-06D
(139)
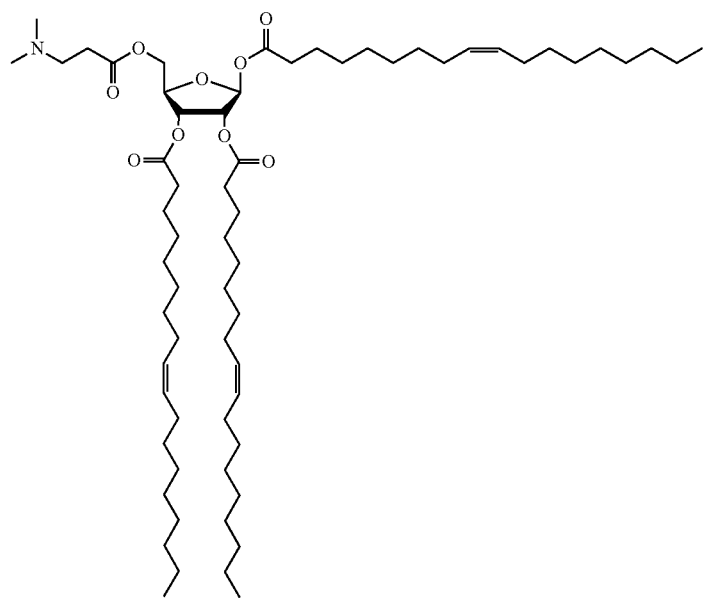
RL2-07D

TABLE L-continued
Formula (IIIj) Cationic Lipids
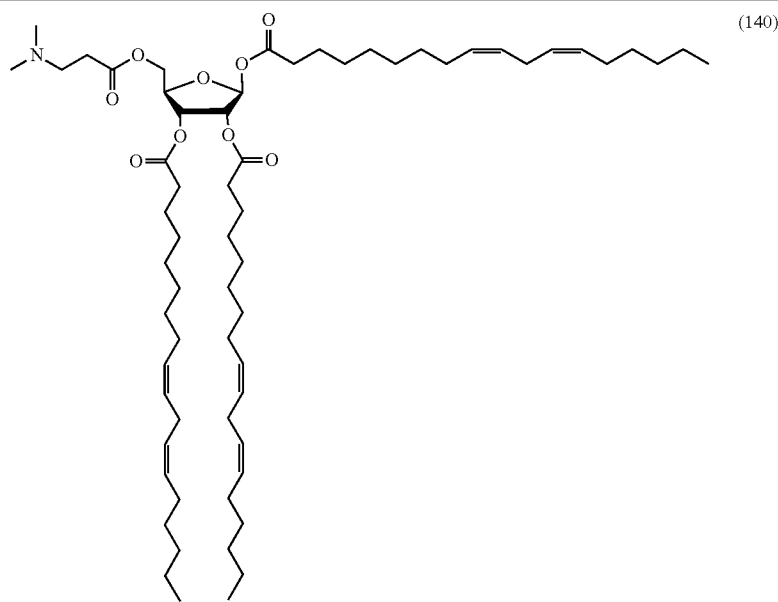
RL2-08D (140)
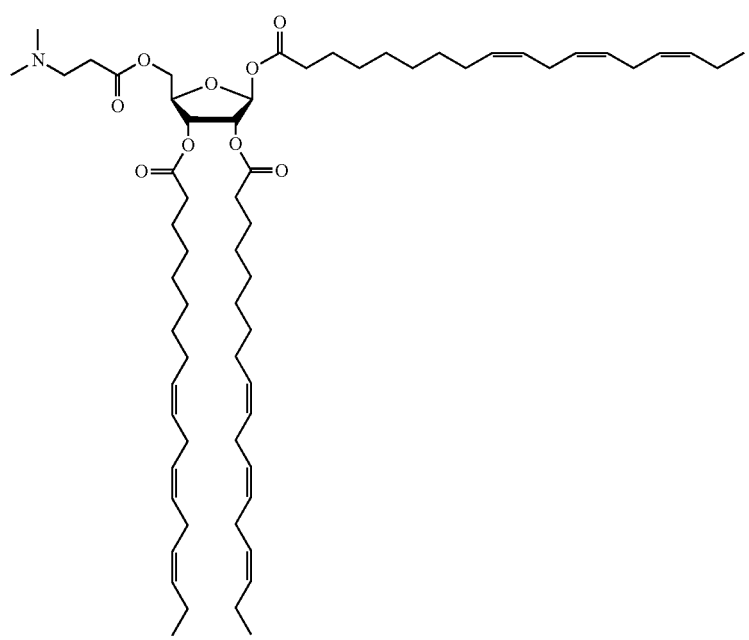
RL2-09D (141)

TABLE L-continued
Formula (IIIj) Cationic Lipids
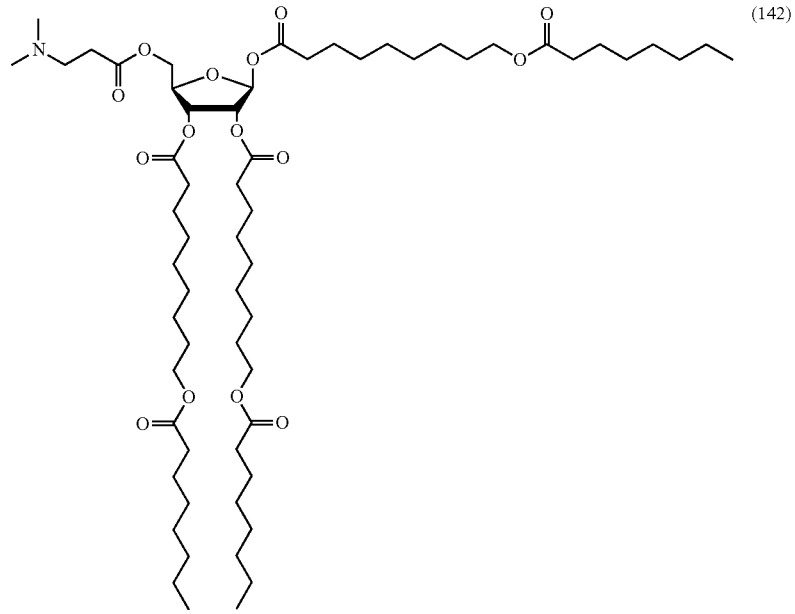
RL2-10D (142)
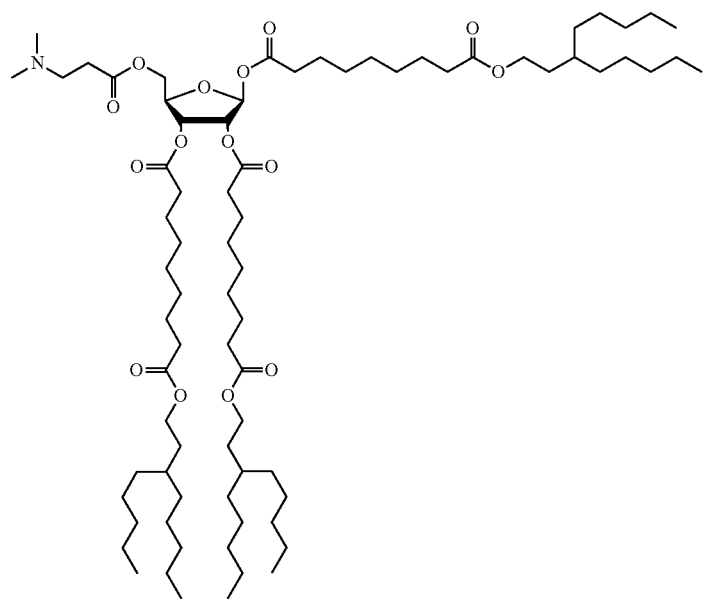
RL2-11D (143)

In embodiments, a cationic lipid is cationic lipid (133). In embodiments, a cationic lipid is cationic lipid (134). In embodiments, a cationic lipid is cationic lipid (135). In embodiments, a cationic lipid is cationic lipid (136). In embodiments, a cationic lipid is cationic lipid (137). In embodiments, a cationic lipid is cationic lipid (138). In embodiments, a cationic lipid is cationic lipid (139). In embodiments, a cationic lipid is cationic lipid (140). In embodiments, a cationic lipid is cationic lipid (141). In embodiments, a cationic lipid is cationic lipid (142). In embodiments, a cationic lipid is cationic lipid (143).

Exemplary cationic lipids include cationic lipids according to formula (IIIk) such as cationic lipids (144)-(154) (Table M):

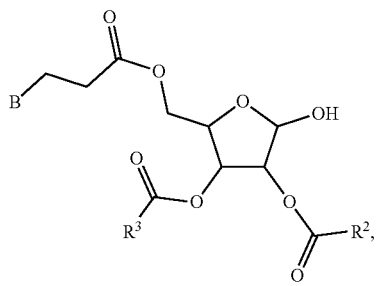

(IIIk)

where B, $R^2$, and $R^3$ are independently as described herein, including the exemplified groups of Table M.

TABLE M

Formula (IIIk) Cationic Lipids

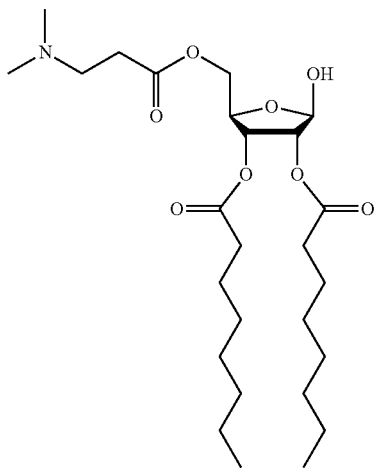

RL2-01Dx2 (144)

TABLE M-continued

Formula (IIIk) Cationic Lipids

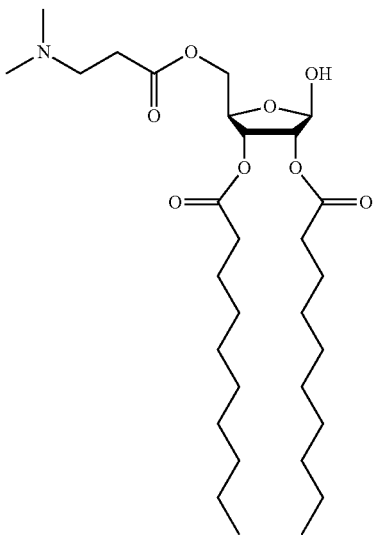

RL2-02Dx2 (145)

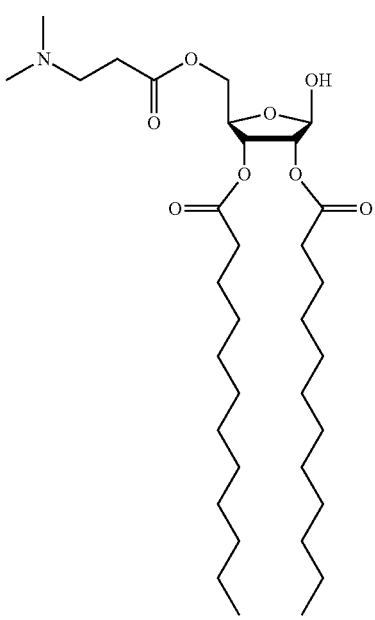

RL2-03Dx2 (146)

TABLE M-continued
Formula (IIIk) Cationic Lipids
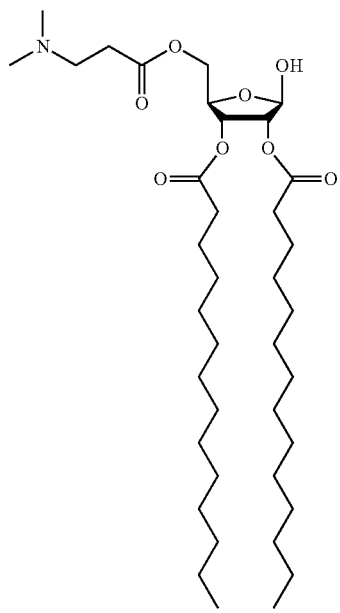
RL2-04Dx2 (147)
RL2-05Dx2 (148)
TABLE M-continued
Formula (IIIk) Cationic Lipids
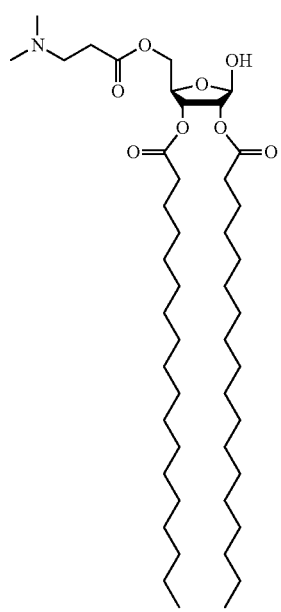
RL2-06Dx2 (149)
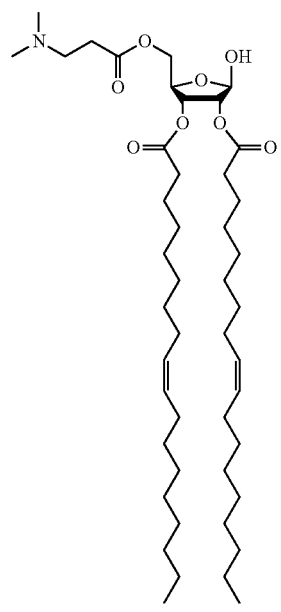
RL2-07Dx2 (150)

TABLE M-continued

Formula (IIIk) Cationic Lipids (151)

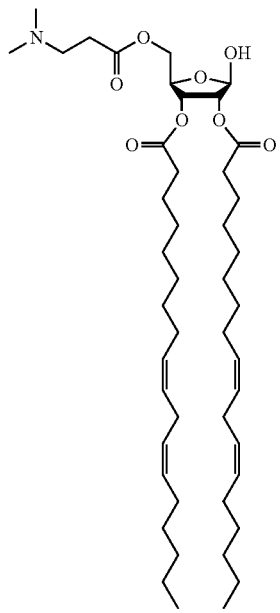

RL2-08Dx2

(152)

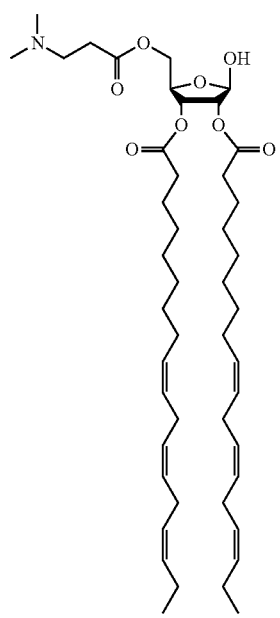

RL2-09Dx2

(153)

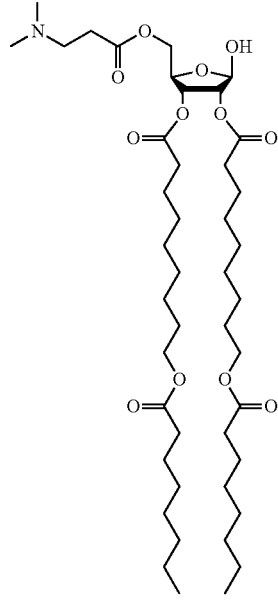

RL2-10Dx2

(154)

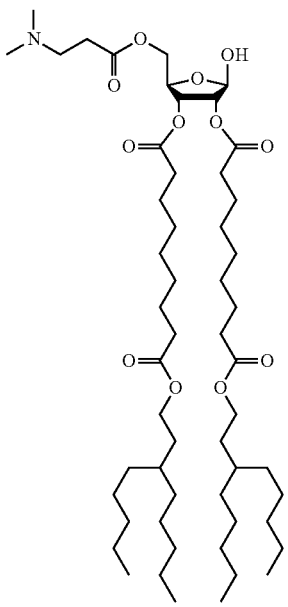

RL2-11Dx2

In embodiments, a cationic lipid is cationic lipid (144). In embodiments, a cationic lipid is cationic lipid (145). In embodiments, a cationic lipid is cationic lipid (146). In embodiments, a cationic lipid is cationic lipid (147). In embodiments, a cationic lipid is cationic lipid (148). In embodiments, a cationic lipid is cationic lipid (149). In embodiments, a cationic lipid is cationic lipid (150). In embodiments, a cationic lipid is cationic lipid (151). In embodiments, a cationic lipid is cationic lipid (152). In embodiments, a cationic lipid is cationic lipid (153). In embodiments, a cationic lipid is cationic lipid (154).

Exemplary cationic lipids include cationic lipids according to formula (IIIm) such as cationic lipids (155)-(165) (Table N):

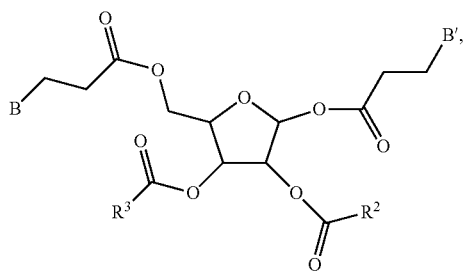
(IIIm)
where B, B', $R^2$, and $R^3$ are independently as described herein, including the exemplified groups of Table H.
TABLE N
Formula (IIIm) Cationic Lipids
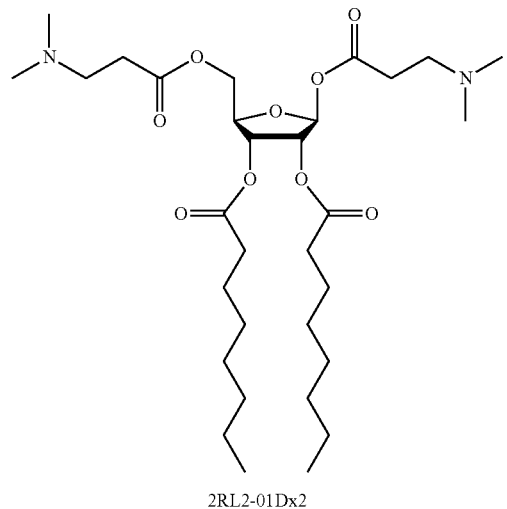
(155) 2RL2-01Dx2
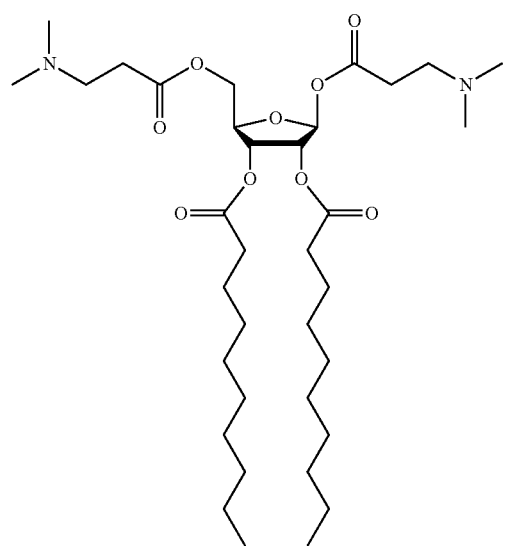
(156) 2RL2-02Dx2
TABLE N-continued
Formula (IIIm) Cationic Lipids
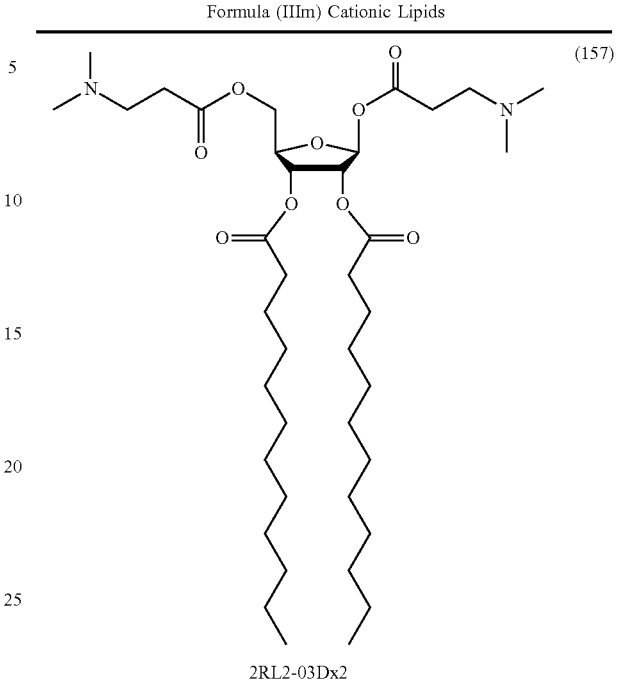
(157) 2RL2-03Dx2
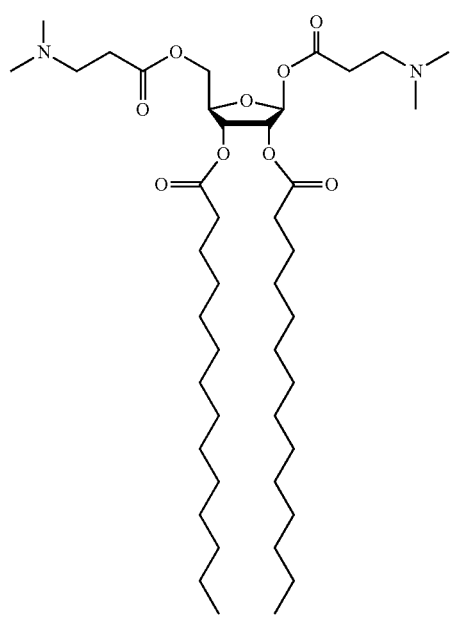
(158) 2RL2-04Dx2

TABLE N-continued
Formula (IIIm) Cationic Lipids
(159)
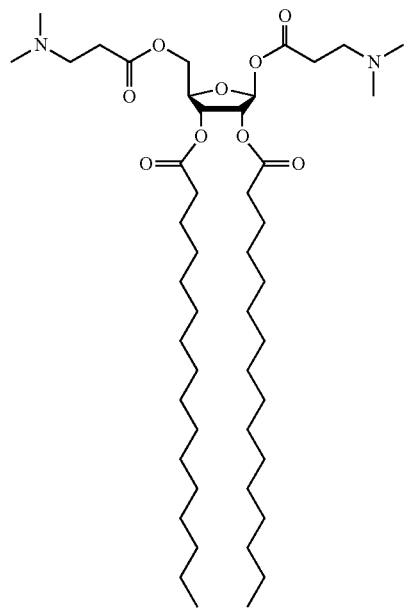
2RL2-05Dx2
(160)
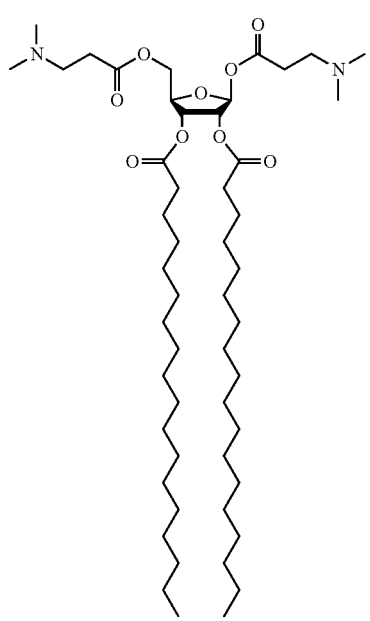
2RL2-06Dx2
(161)
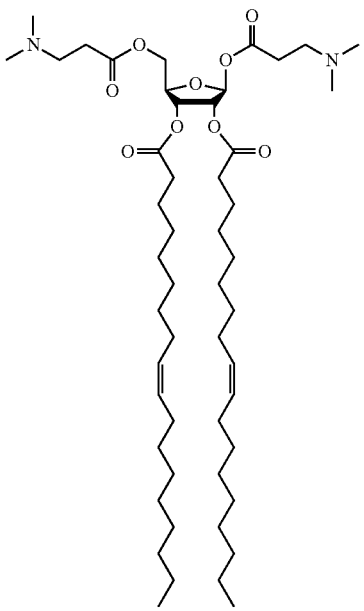
2RL2-07Dx2
(162)
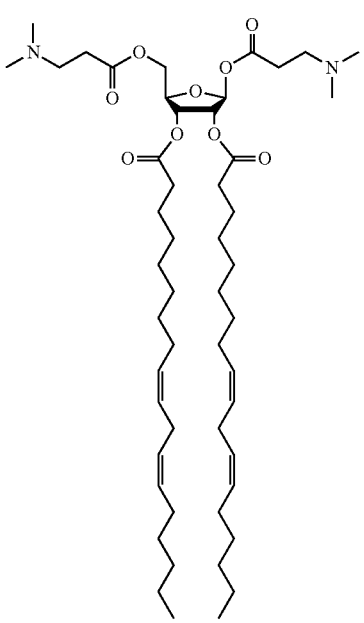
2RL2-08Dx2

TABLE N-continued

Formula (IIIm) Cationic Lipids

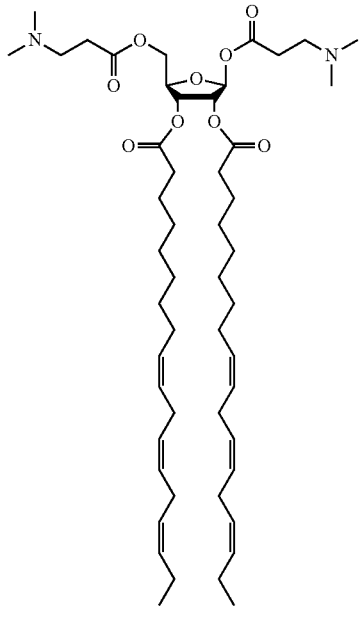

2RL2-09Dx2 (163)

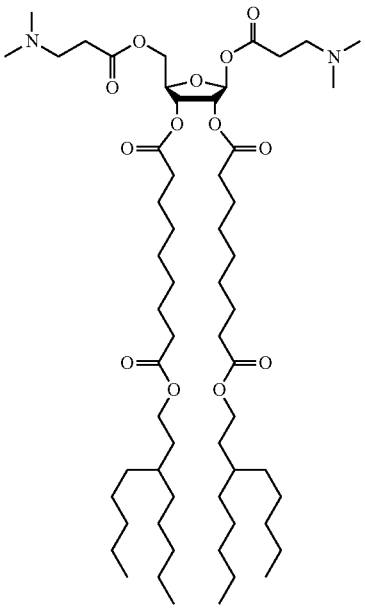

2RL2-11Dx2 (165)

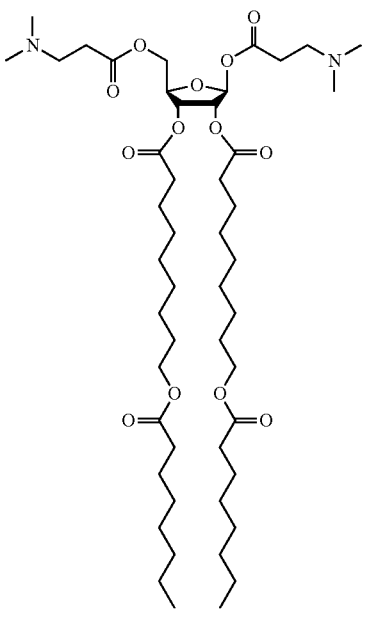

2RL2-10Dx2 (164)

In embodiments, a cationic lipid is cationic lipid (155). In embodiments, a cationic lipid is cationic lipid (156). In embodiments, a cationic lipid is cationic lipid (157). In embodiments, a cationic lipid is cationic lipid (158). In embodiments, a cationic lipid is cationic lipid (159). In embodiments, a cationic lipid is cationic lipid (160). In embodiments, a cationic lipid is cationic lipid (161). In embodiments, a cationic lipid is cationic lipid (162). In embodiments, a cationic lipid is cationic lipid (163). In embodiments, a cationic lipid is cationic lipid (164). In embodiments, a cationic lipid is cationic lipid (165).

Exemplary cationic lipids include cationic lipids according to formula (IIIn) such as cationic lipids (166)-(178) (Table O):

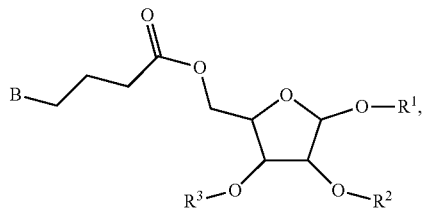

(IIIn)

where B, $R^1$, $R^2$, and $R^3$ are independently as described herein, including the exemplified groups of Table O.

In embodiments, a cationic lipid according to formula (IIIn) has the following structure,

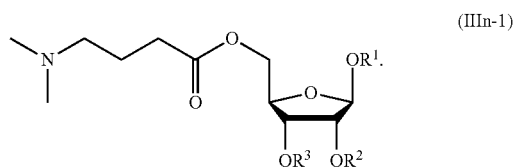
(IIIn-1)
In embodiments, each of $R^1$, $R^2$, and $R^3$ is any of the exemplified aliphatic groups described herein in (e.g., Table O).
TABLE O
Formula (IIIn) and (IIIn-1) Cationic Lipids
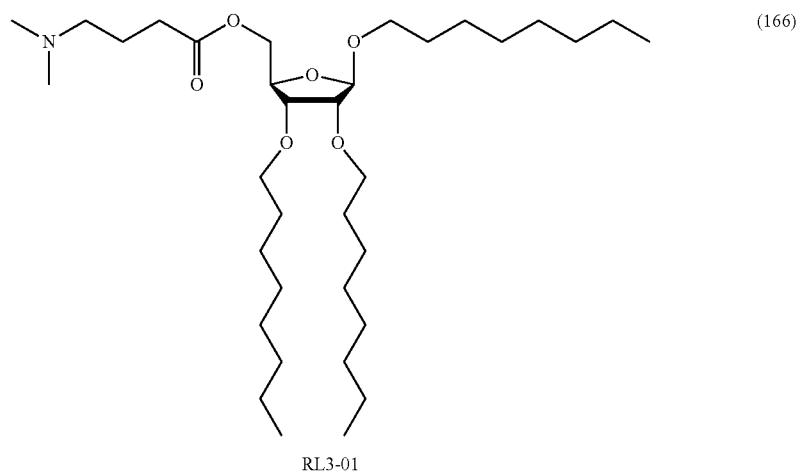
(166)
RL3-01
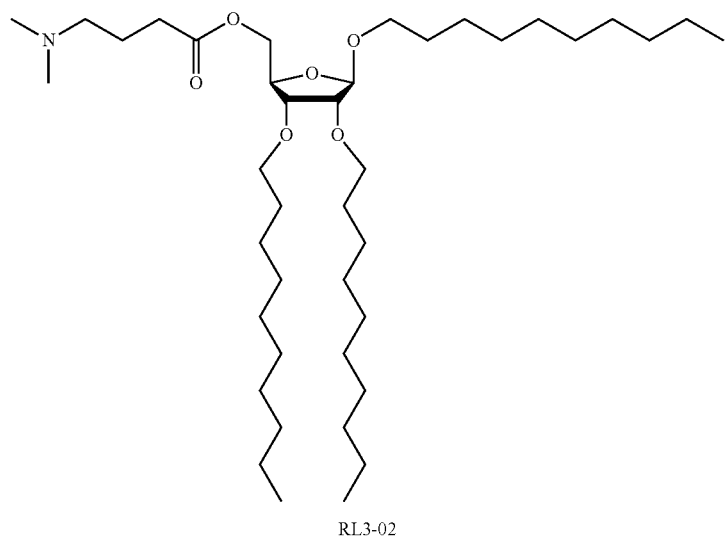
(167)
RL3-02

TABLE O-continued
Formula (IIIn) and (IIIn-1) Cationic Lipids
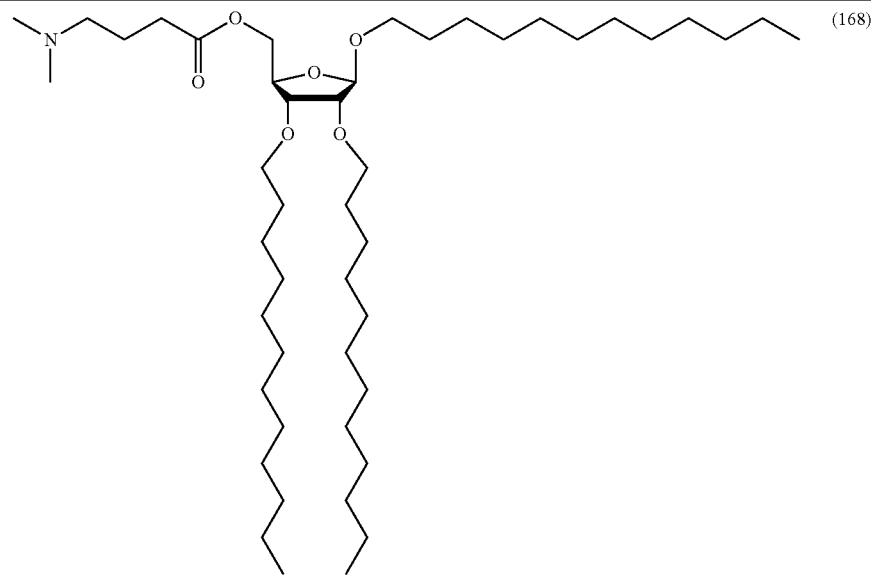
(168)
RL3-03
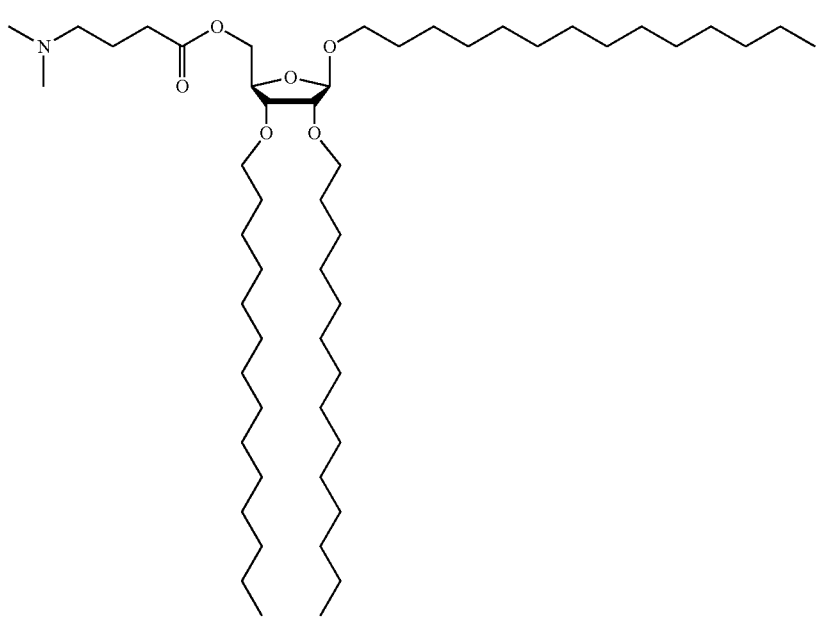
(169)
RL3-04

TABLE O-continued
Formula (IIIn) and (IIIn-1) Cationic Lipids
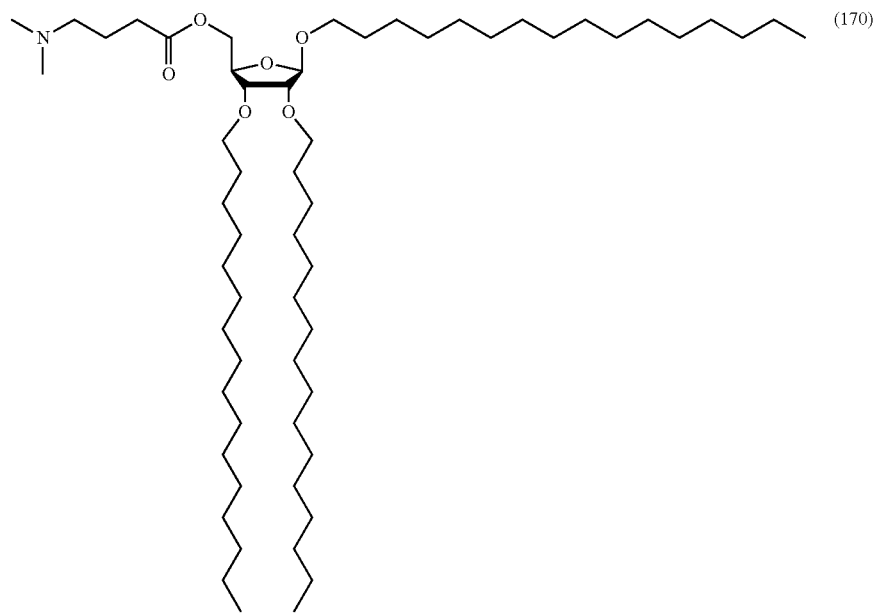
(170)
RL3-05
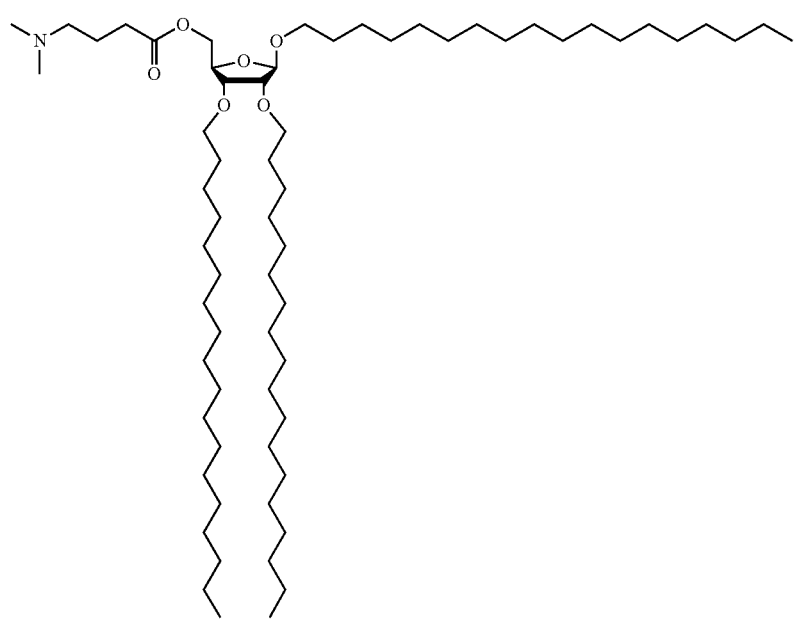
(171)
RL3-06

TABLE O-continued
Formula (IIIn) and (IIIn-1) Cationic Lipids
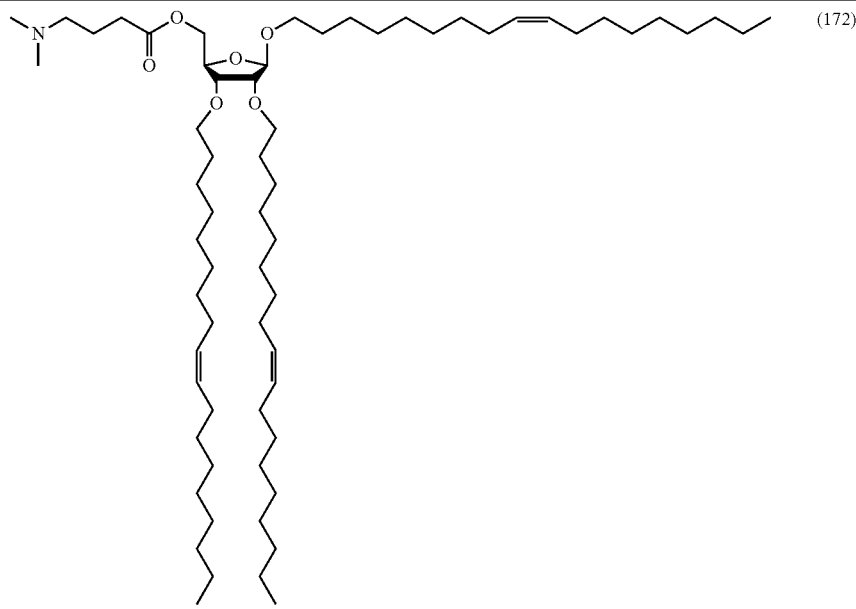
(172)
RL3-07
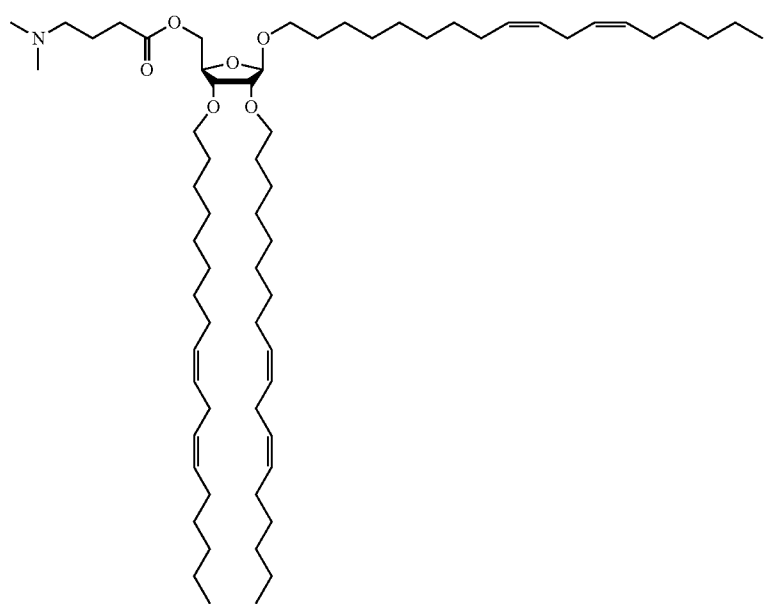
(173)
RL3-08

TABLE O-continued
Formula (IIIn) and (IIIn-1) Cationic Lipids
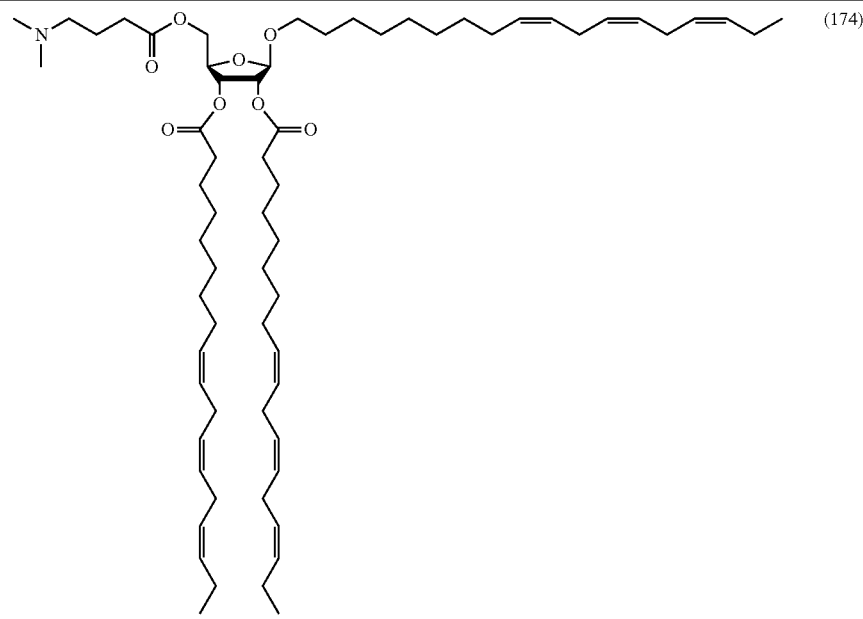
RL3-09 (174)
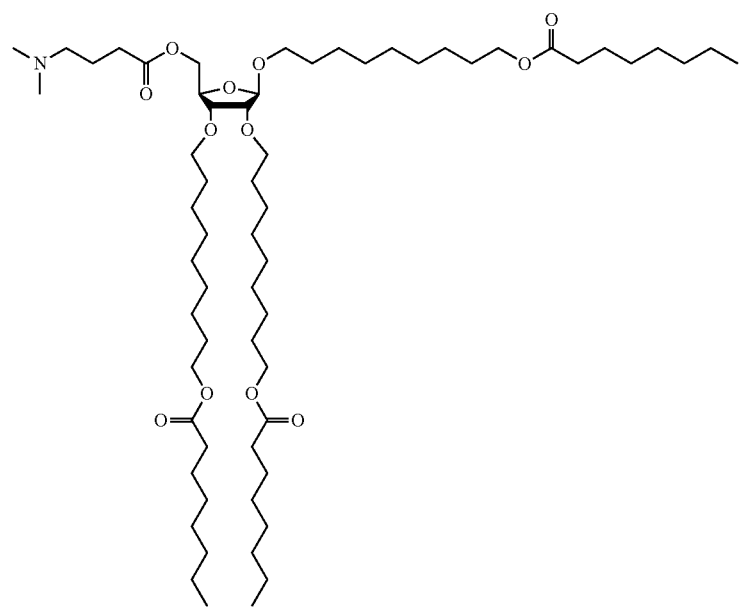
RL3-10 (175)

TABLE O-continued
Formula (IIIn) and (IIIn-1) Cationic Lipids
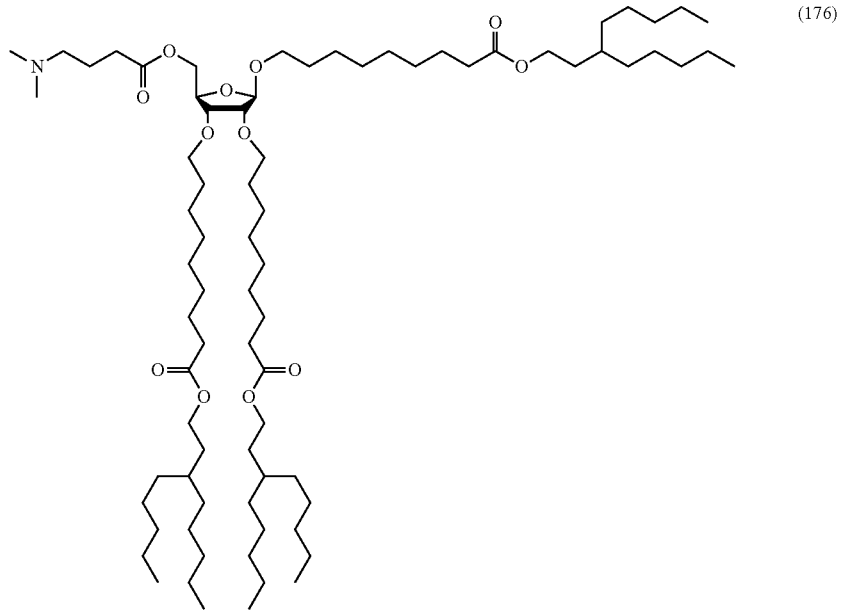
RL3-11 (176)
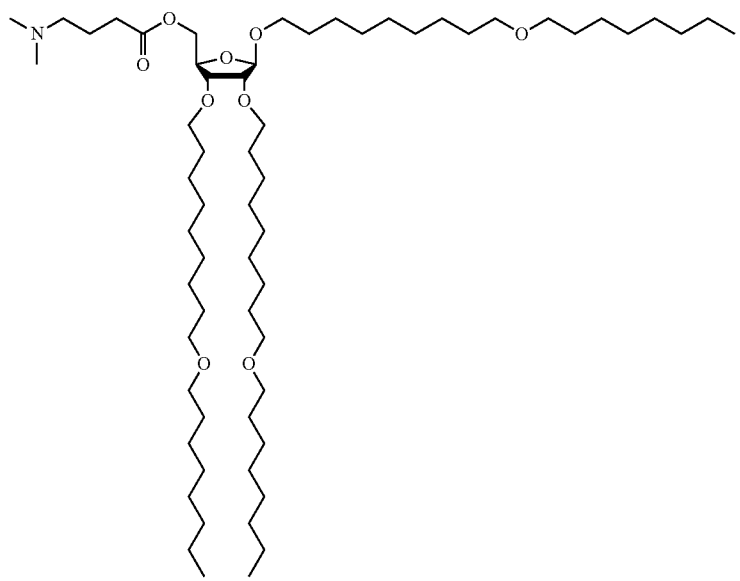
RL3-12 (177)

TABLE O-continued

Formula (IIIn) and (IIIn-1) Cationic Lipids

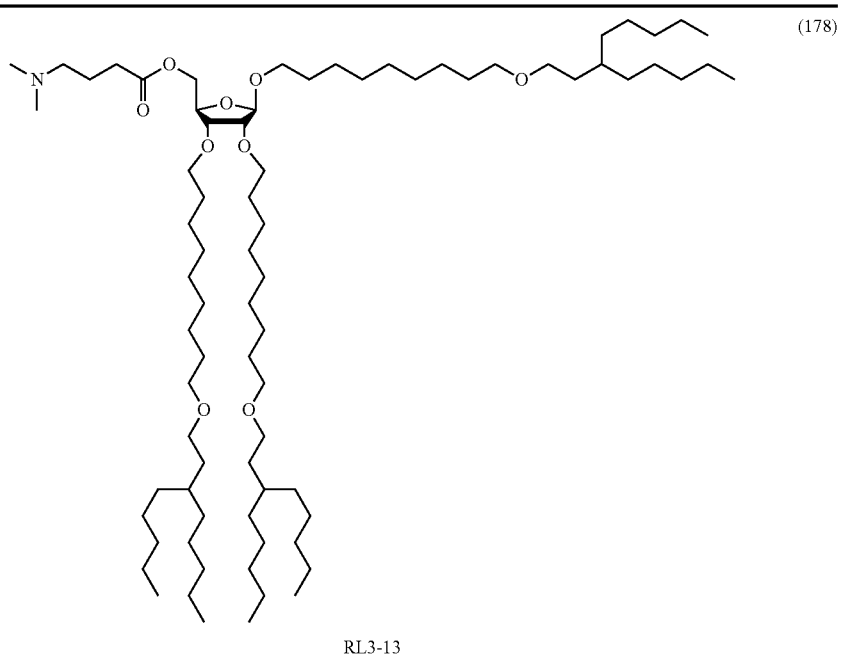

RL3-13 (178)

In embodiments, a cationic lipid is cationic lipid (166). In embodiments, a cationic lipid is cationic lipid (167). In embodiments, a cationic lipid is cationic lipid (168). In embodiments, a cationic lipid is cationic lipid (169). In embodiments, a cationic lipid is cationic lipid (170). In embodiments, a cationic lipid is cationic lipid (171). In embodiments, a cationic lipid is cationic lipid (172). In embodiments, a cationic lipid is cationic lipid (173). In embodiments, a cationic lipid is cationic lipid (174). In embodiments, a cationic lipid is cationic lipid (175). In embodiments, a cationic lipid is cationic lipid (176). In embodiments, a cationic lipid is cationic lipid (177). In embodiments, a cationic lipid is cationic lipid (178).

Exemplary cationic lipids include cationic lipids according to formula (IIIo) such as cationic lipids (179)-(191) (Table P):

(IIIo)

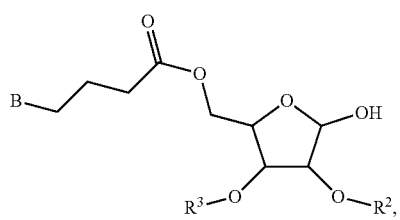

where B, $R^2$, and $R^3$ are independently as described herein, including the exemplified groups of Table P.

TABLE P

Formula (IIIo) Cationic Lipids

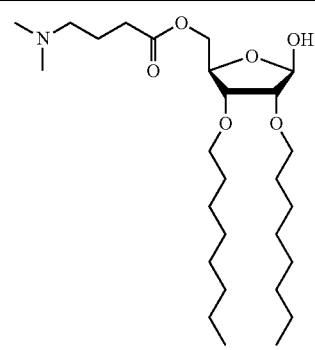

RL3-01x2 (179)

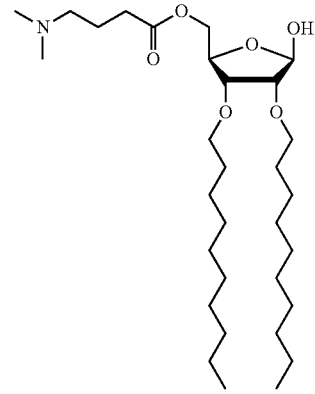

RL3-02x2 (180)

TABLE P-continued
Formula (IIIo) Cationic Lipids
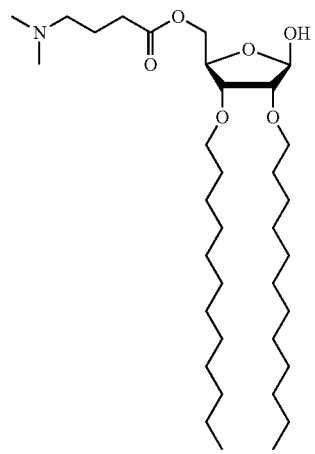
RL3-03x2 (181)
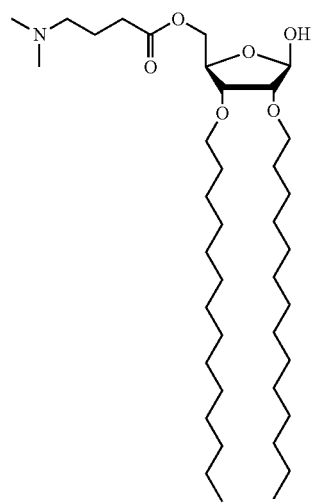
RL3-04x2 (182)
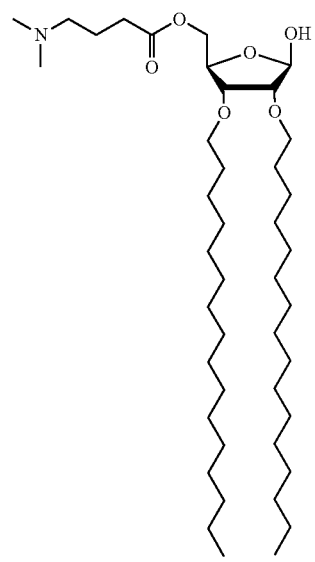
RL3-05x2 (183)
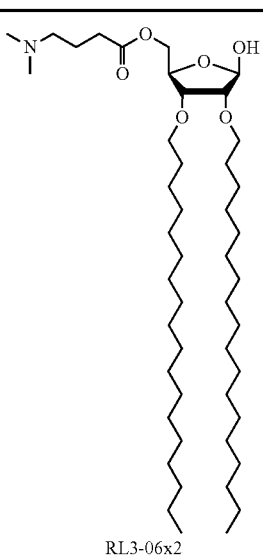
RL3-06x2 (184)
(185)
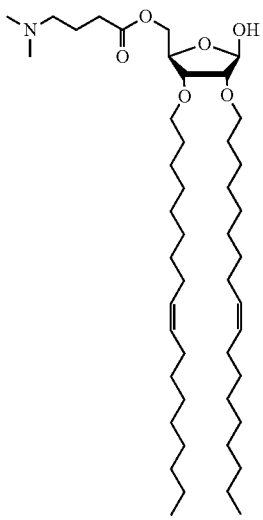
RL3-07x2

TABLE P-continued
Formula (IIIo) Cationic Lipids
(186)
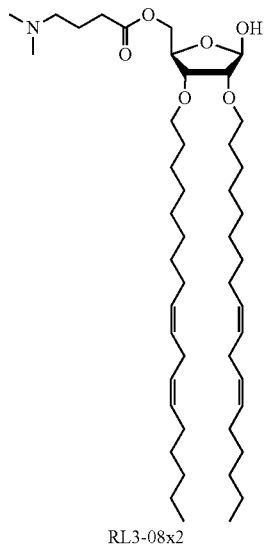
RL3-08x2
(187)
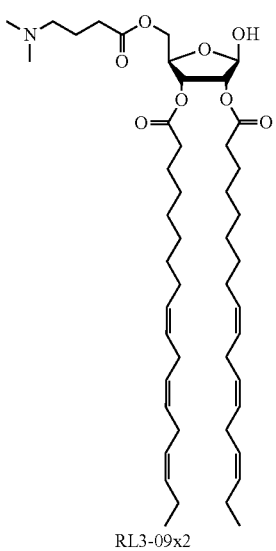
RL3-09x2
TABLE P-continued
Formula (IIIo) Cationic Lipids
(188)
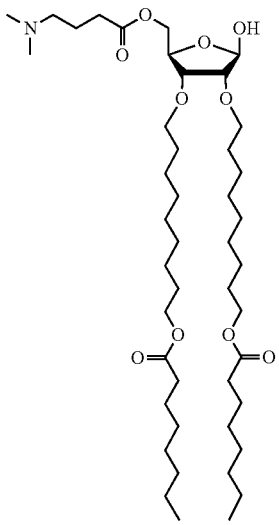
RL3-10x2
(189)
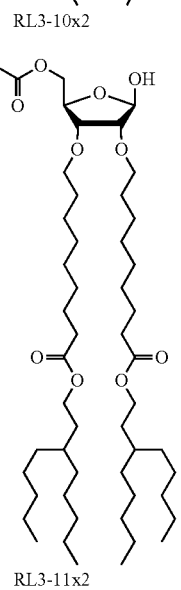
RL3-11x2
(190)
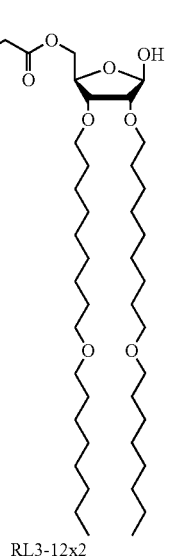
RL3-12x2

TABLE P-continued

Formula (IIIo) Cationic Lipids

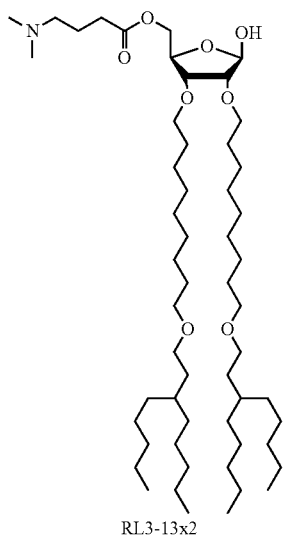

RL3-13x2 (191)

In embodiments, a cationic lipid is cationic lipid (179). In embodiments, a cationic lipid is cationic lipid (180). In embodiments, a cationic lipid is cationic lipid (181). In embodiments, a cationic lipid is cationic lipid (182). In embodiments, a cationic lipid is cationic lipid (183). In embodiments, a cationic lipid is cationic lipid (184). In embodiments, a cationic lipid is cationic lipid (185). In embodiments, a cationic lipid is cationic lipid (186). In embodiments, a cationic lipid is cationic lipid (187). In embodiments, a cationic lipid is cationic lipid (188). In embodiments, a cationic lipid is cationic lipid (189). In embodiments, a cationic lipid is cationic lipid (190). In embodiments, a cationic lipid is cationic lipid (191).

Exemplary cationic lipids include cationic lipids according to formula (IIIp) such as cationic lipids (192)-(204) (Table Q):

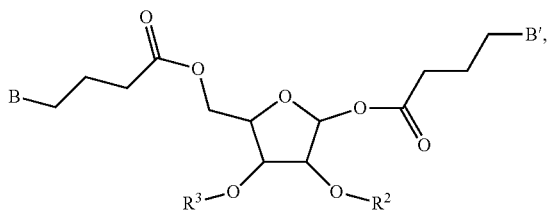

(IIIp)

where B, B', $R^2$, and $R^3$ are independently as described herein, including the exemplified groups of Table Q.

TABLE Q

Formula (IIIp) Cationic Lipids

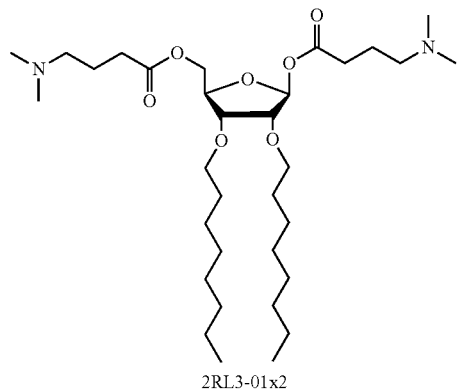

2RL3-01x2 (192)

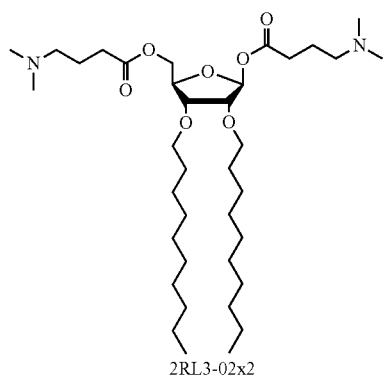

2RL3-02x2 (193)

TABLE Q-continued
Formula (IIIp) Cationic Lipids
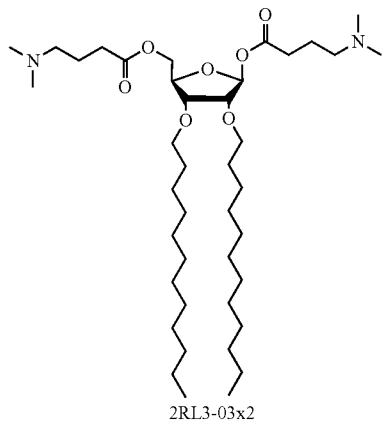
2RL3-03x2 (194)
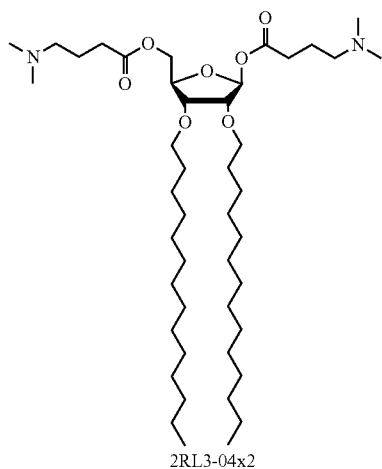
2RL3-04x2 (195)
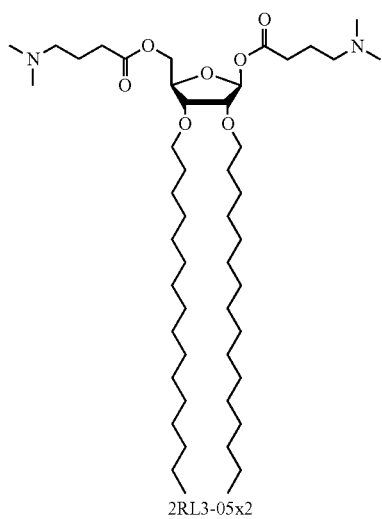
2RL3-05x2 (196)

TABLE Q-continued
Formula (IIIp) Cationic Lipids
(197)
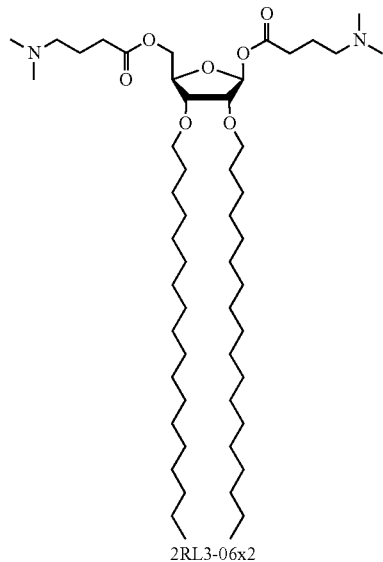
2RL3-06x2
(198)
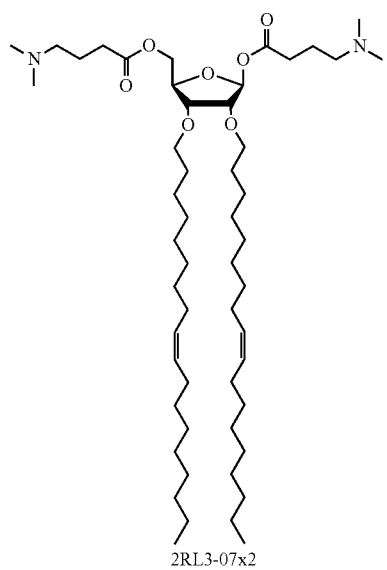
2RL3-07x2

TABLE Q-continued
Formula (IIIp) Cationic Lipids
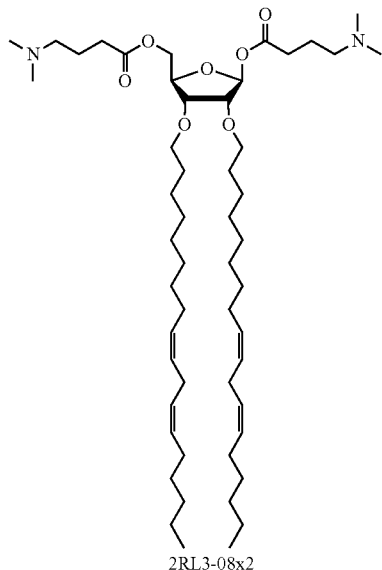
(199)
2RL3-08x2
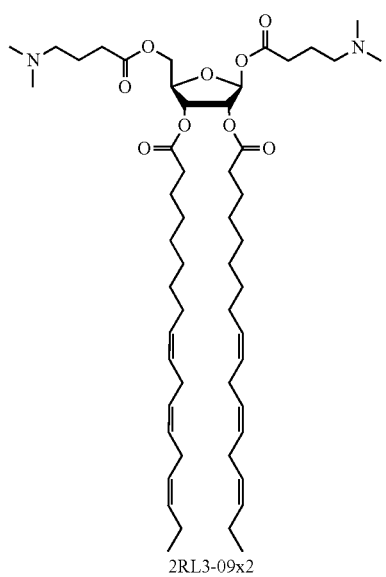
(200)
2RL3-09x2

TABLE Q-continued
Formula (IIIp) Cationic Lipids
(201)
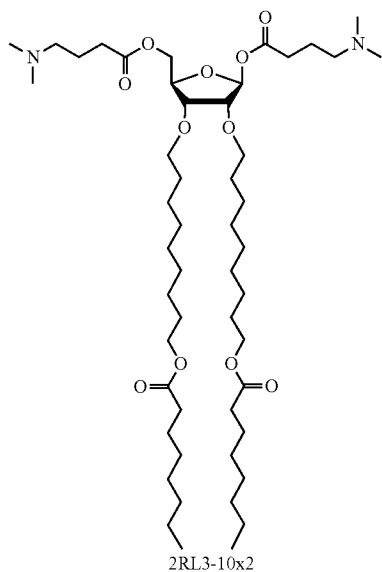
2RL3-10x2
(202)
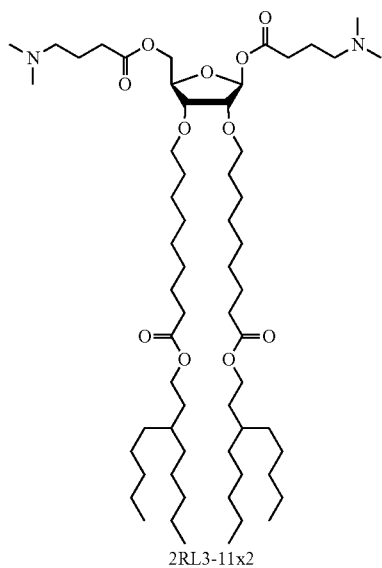
2RL3-11x2

TABLE Q-continued

Formula (IIIp) Cationic Lipids

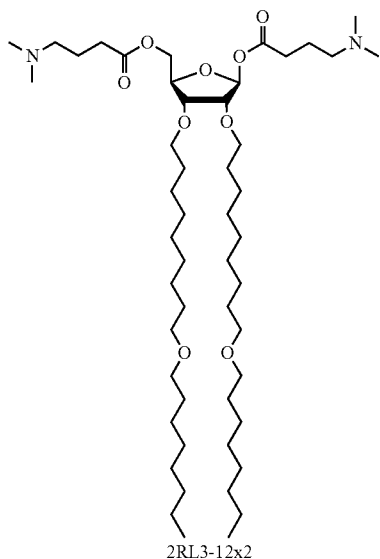

(203)

2RL3-12x2

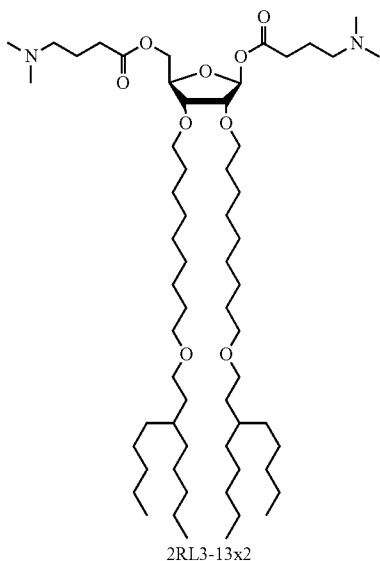

(204)

2RL3-13x2

In embodiments, a cationic lipid is cationic lipid (192). In embodiments, a cationic lipid is cationic lipid (193). In embodiments, a cationic lipid is cationic lipid (194). In embodiments, a cationic lipid is cationic lipid (195). In embodiments, a cationic lipid is cationic lipid (196). In embodiments, a cationic lipid is cationic lipid (197). In embodiments, a cationic lipid is cationic lipid (198). In embodiments, a cationic lipid is cationic lipid (199). In embodiments, a cationic lipid is cationic lipid (200). In embodiments, a cationic lipid is cationic lipid (201). In embodiments, a cationic lipid is cationic lipid (202). In embodiments, a cationic lipid is cationic lipid (203). In embodiments, a cationic lipid is cationic lipid (204).

Exemplary cationic lipids include cationic lipids according to formula (IIIq) such as cationic lipids (205)-(215) (Table R):

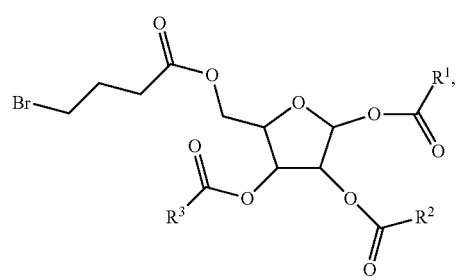

(IIIq)

where B, $R^1$, $R^2$, and $R^3$ are independently as described herein, including the exemplified groups of Table R.

In embodiments, a cationic lipid according to formula (IIIq) has the following structure,

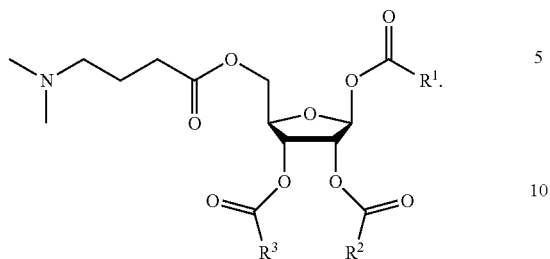
(IIIq-1)
In embodiments, each of R¹, R², and R³ is any of the exemplified aliphatic groups described in, e.g., Table R.
TABLE R
| Formula (IIIq) Cationic Lipids |
|---|
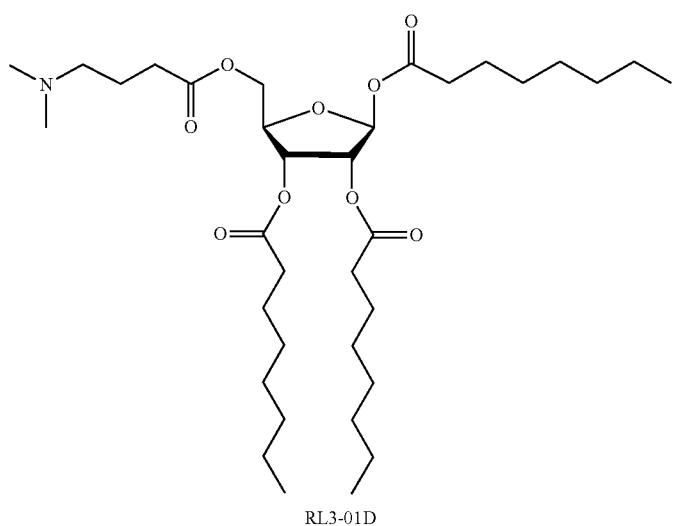
(205)
RL3-01D
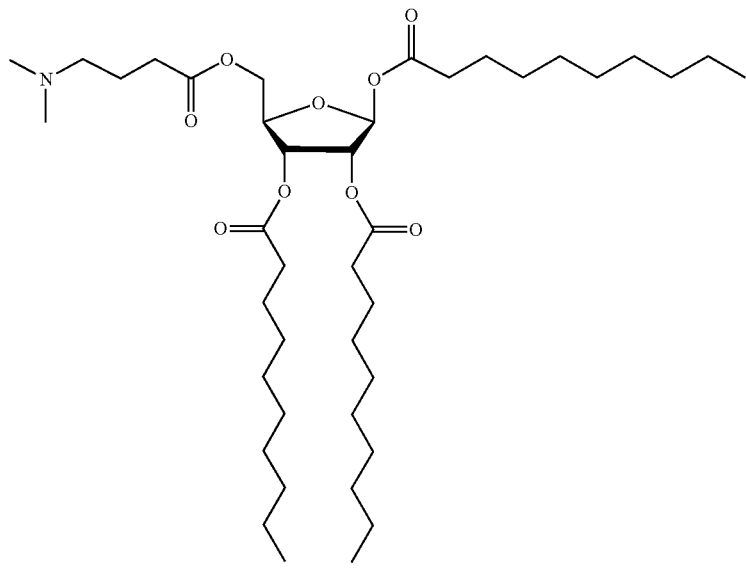
(206)
RL3-02D TABLE R-continued
Formula (IIIq) Cationic Lipids
(207)
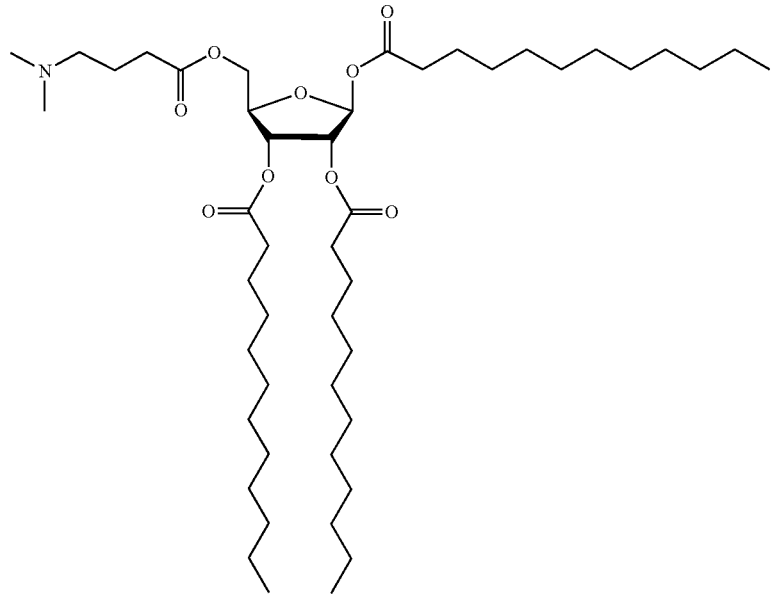
RL3-03D
(208)
RL3-04D

TABLE R-continued
Formula (IIIq) Cationic Lipids
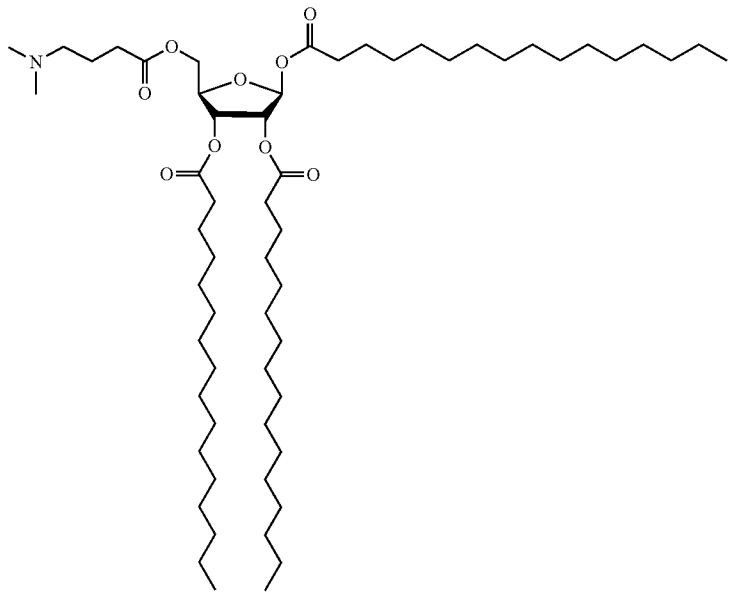
(209) RL3-05D
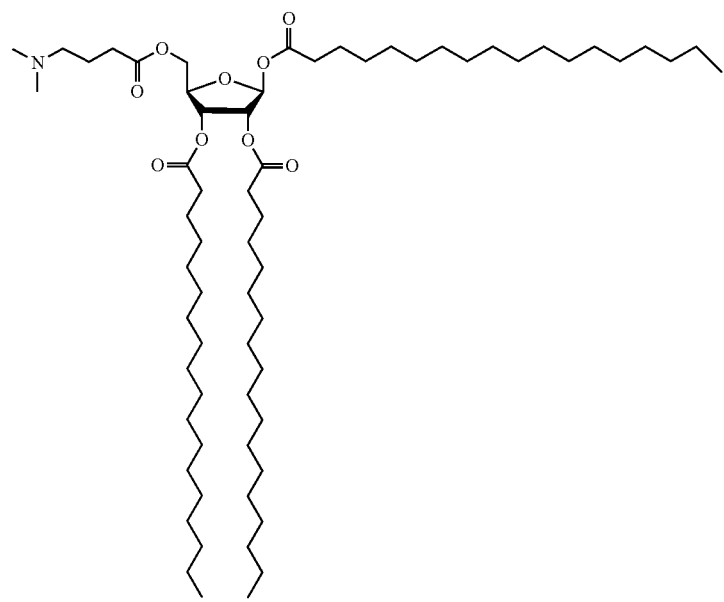
(210) RL3-06D

TABLE R-continued
Formula (IIIq) Cationic Lipids
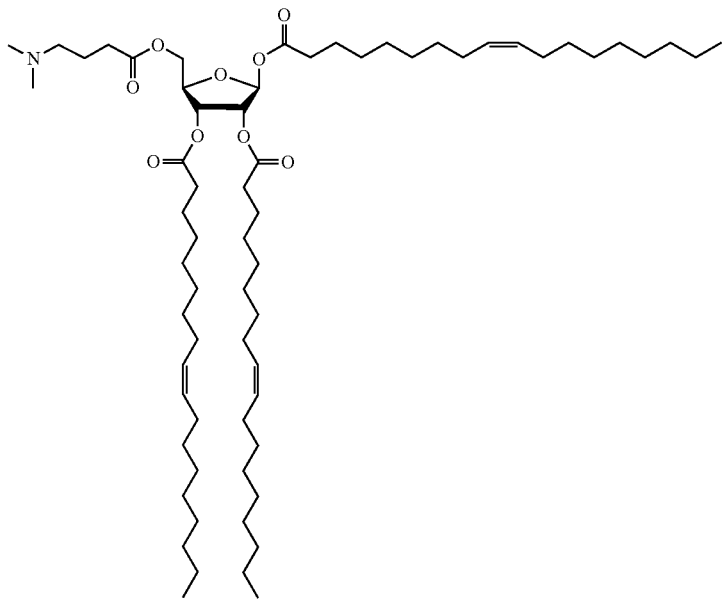
RL3-07D
(211)
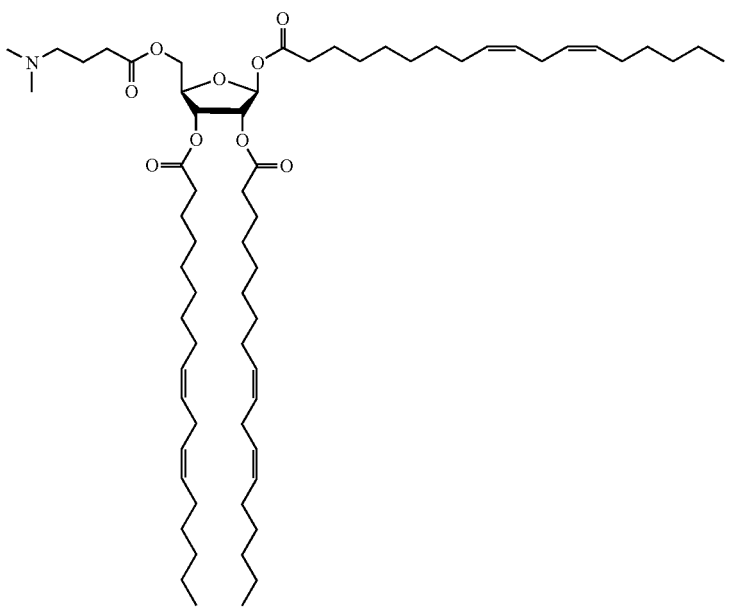
RL3-08D
(212)

TABLE R-continued
Formula (IIIq) Cationic Lipids
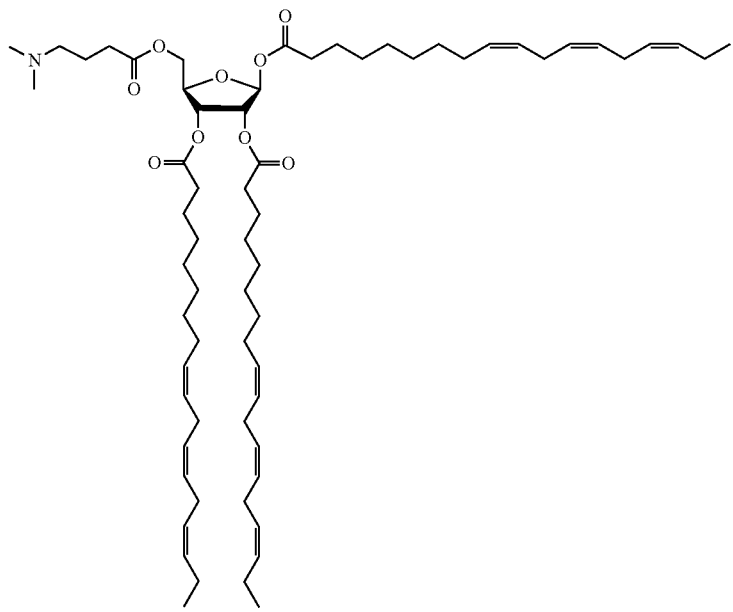
(213)
RL3-09D
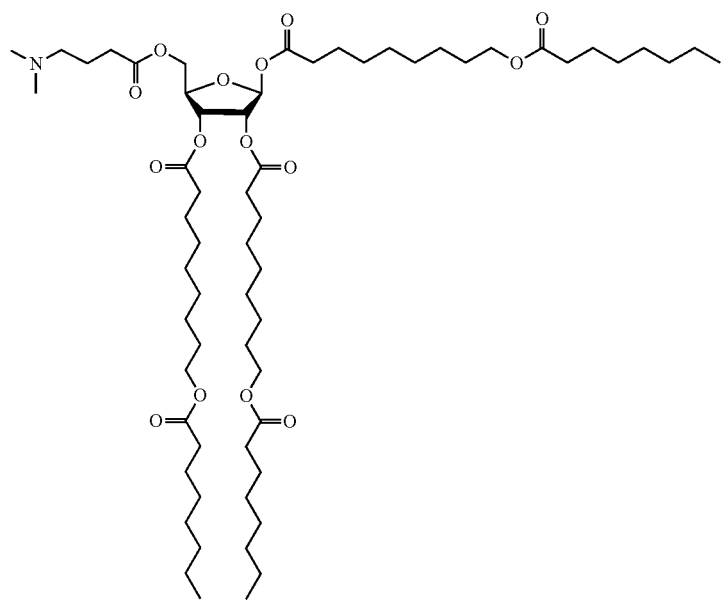
(214)
RL3-10D TABLE R-continued Formula (IIIq) Cationic Lipids (215)

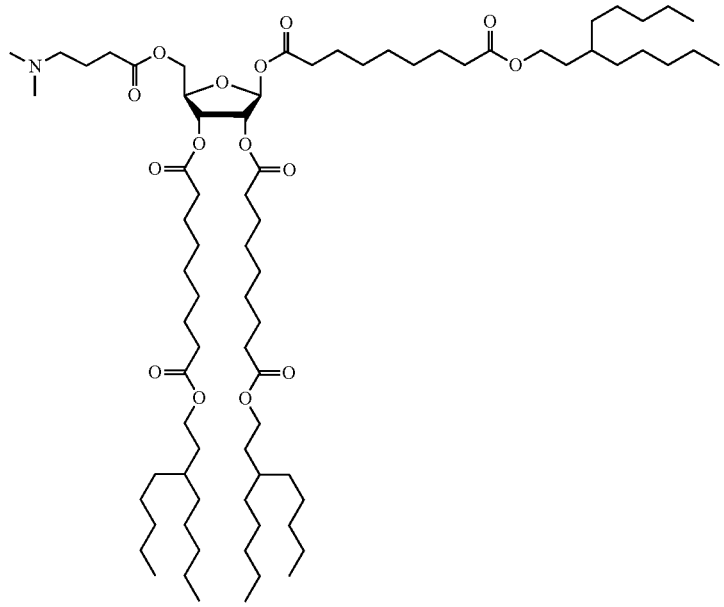

RL3-11D

In embodiments, a cationic lipid is cationic lipid (205). In embodiments, a cationic lipid is cationic lipid (206). In embodiments, a cationic lipid is cationic lipid (207). In embodiments, a cationic lipid is cationic lipid (208). In embodiments, a cationic lipid is cationic lipid (209). In embodiments, a cationic lipid is cationic lipid (210). In embodiments, a cationic lipid is cationic lipid (211). In embodiments, a cationic lipid is cationic lipid (212). In embodiments, a cationic lipid is cationic lipid (213). In embodiments, a cationic lipid is cationic lipid (214). In embodiments, a cationic lipid is cationic lipid (215).

Exemplary cationic lipids include cationic lipids according to formula (IIIr) such as cationic lipids (216)-(226) (Table S):

(IIIr)

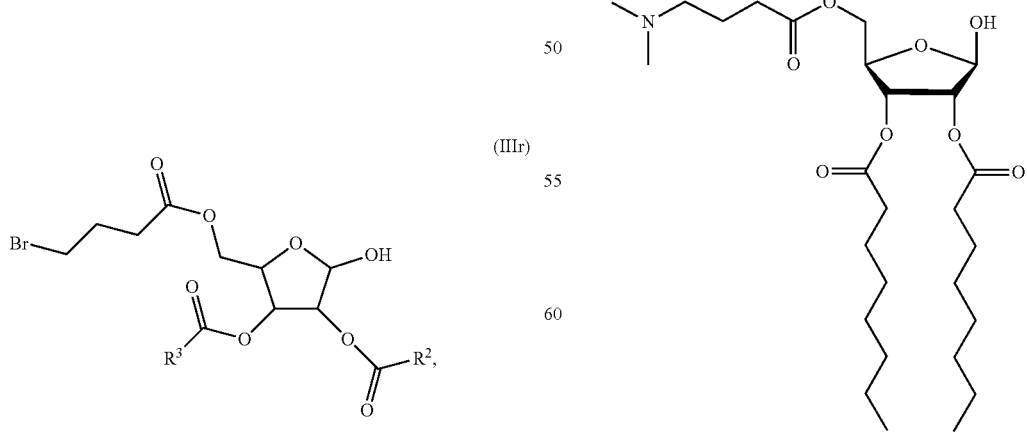

where B, $R^2$, and $R^3$ are independently as described herein, including the exemplified groups of Table S.

TABLE S

Formula (IIIr) Cationic Lipids (216)

RL3-01Dx2

TABLE S-continued
Formula (IIIr) Cationic Lipids
(217)
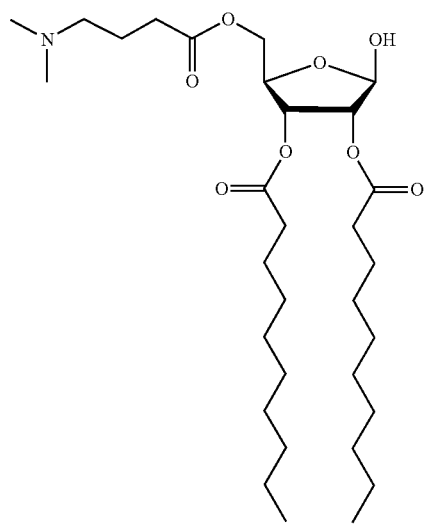
RL3-02Dx2
(218)
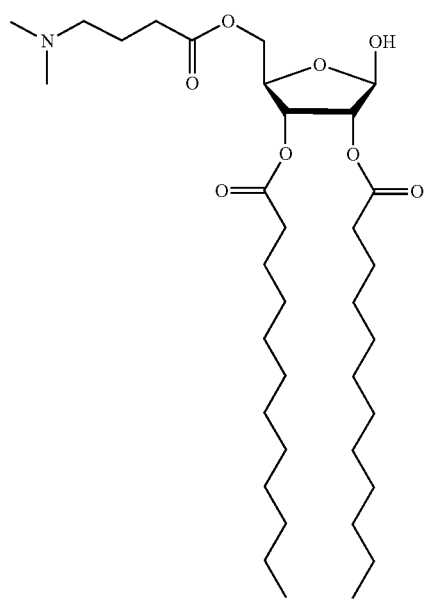
RL3-03Dx2
(219)
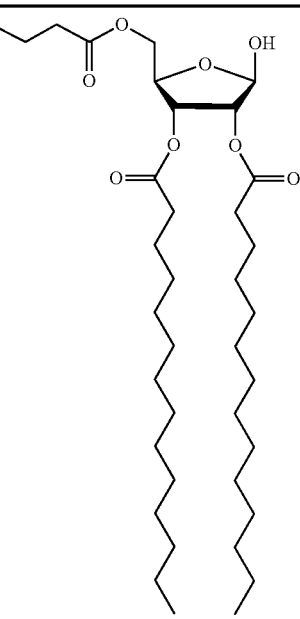
RL3-04Dx2
(220)
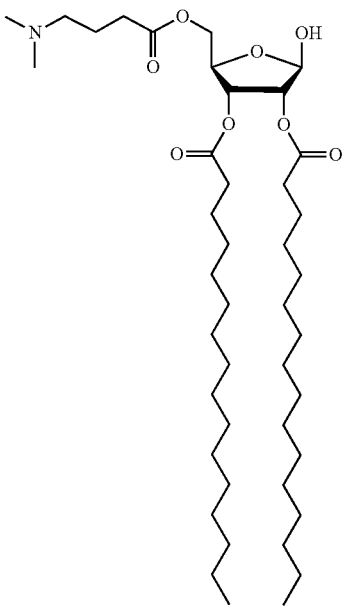
RL3-05Dx2

TABLE S-continued
Formula (IIIr) Cationic Lipids
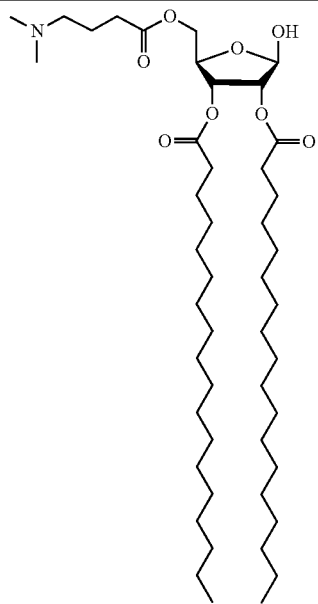
RL3-06Dx2 (221)
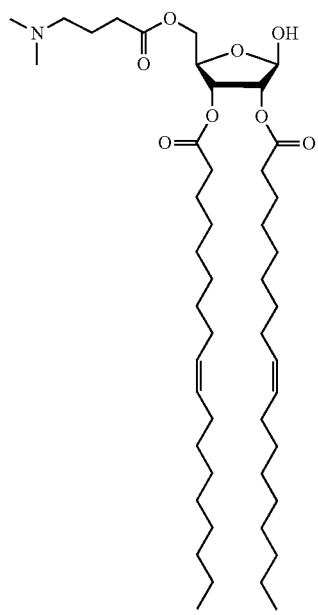
RL3-07Dx2 (222)
TABLE S-continued
Formula (IIIr) Cationic Lipids
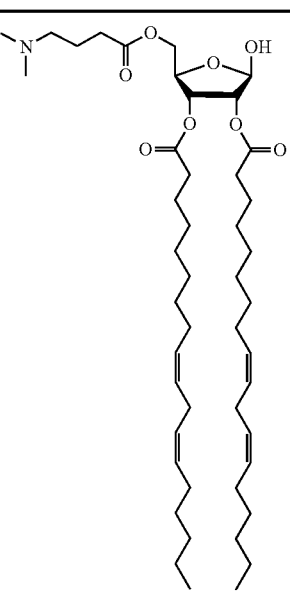
RL3-08Dx2 (223)
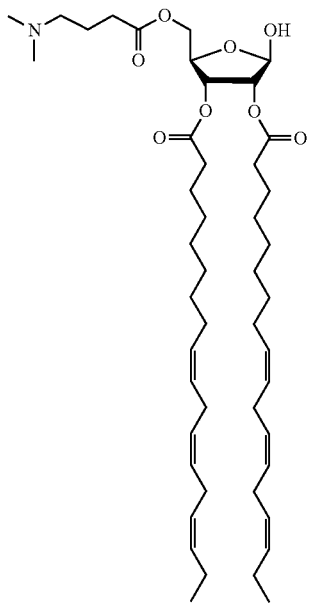
RL3-09Dx2 (224)

TABLE S-continued

Formula (IIIr) Cationic Lipids

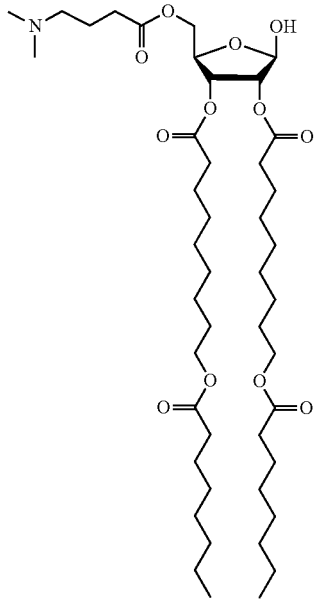

(225)

RL3-10Dx2

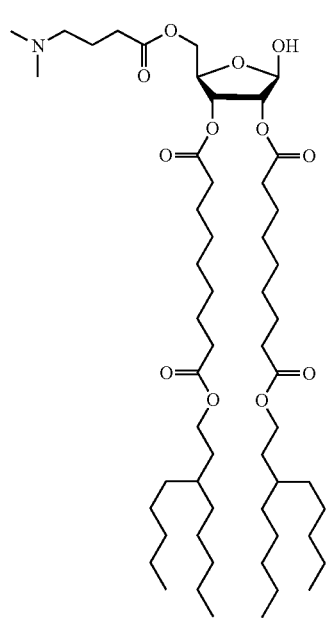

(226)

RL3-11Dx2

In embodiments, a cationic lipid is cationic lipid (216). In embodiments, a cationic lipid is cationic lipid (217). In embodiments, a cationic lipid is cationic lipid (218). In embodiments, a cationic lipid is cationic lipid (219). In embodiments, a cationic lipid is cationic lipid (220). In embodiments, a cationic lipid is cationic lipid (221). In embodiments, a cationic lipid is cationic lipid (222). In embodiments, a cationic lipid is cationic lipid (223). In embodiments, a cationic lipid is cationic lipid (224). In embodiments, a cationic lipid is cationic lipid (225). In embodiments, a cationic lipid is cationic lipid (226).

Exemplary cationic lipids include cationic lipids according to formula (IIIs) such as cationic lipids (227)-(237) (Table T):

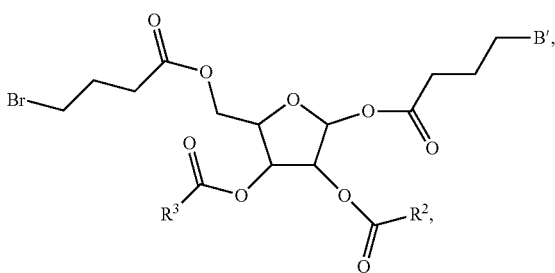

(IIIs)

where B, B', $R^2$, and $R^3$ are independently as described herein, including the exemplified groups of Table T.

TABLE T
Formula (IIIs) Cationic Lipids
(227)
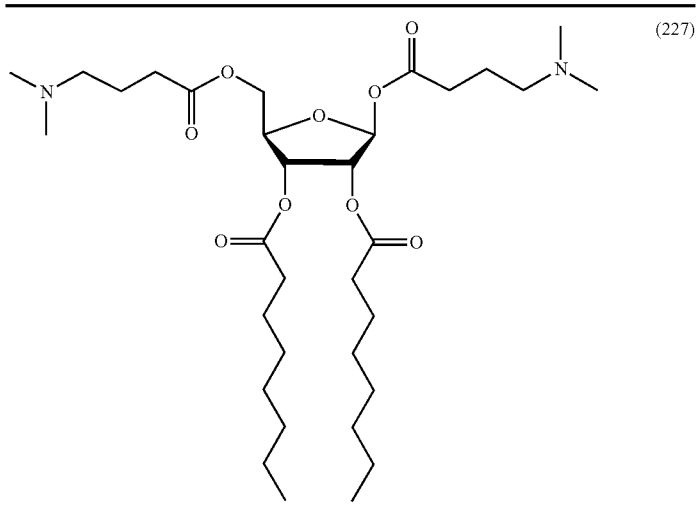
2RL3-01Dx2
(228)
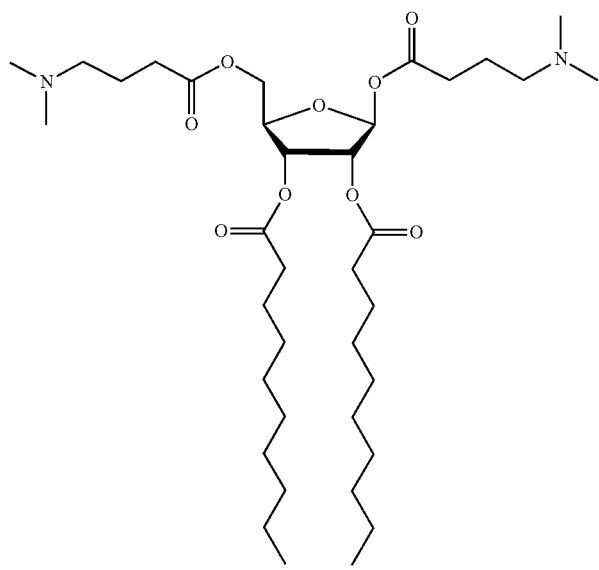
2RL3-02Dx2

TABLE T-continued
Formula (IIIs) Cationic Lipids
(229)
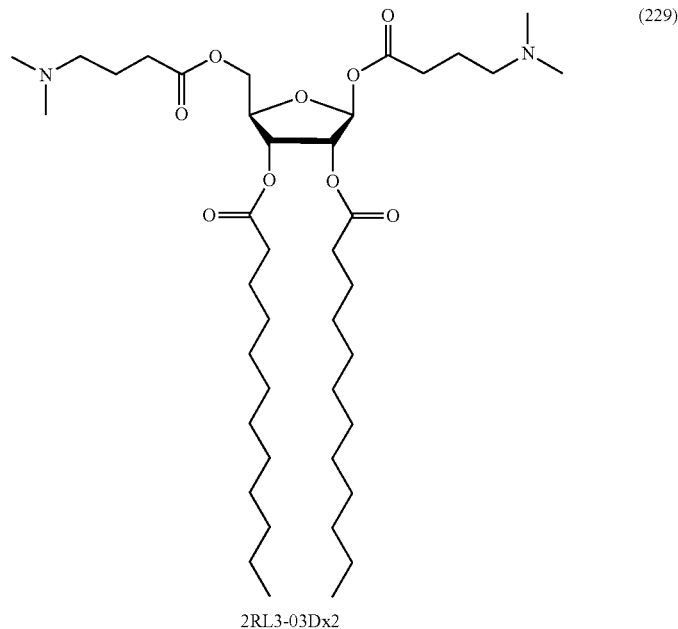
2RL3-03Dx2
(230)
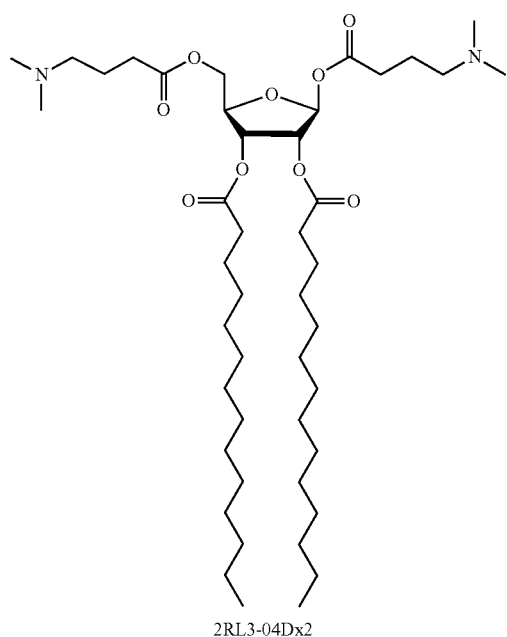
2RL3-04Dx2

TABLE T-continued
Formula (IIIs) Cationic Lipids
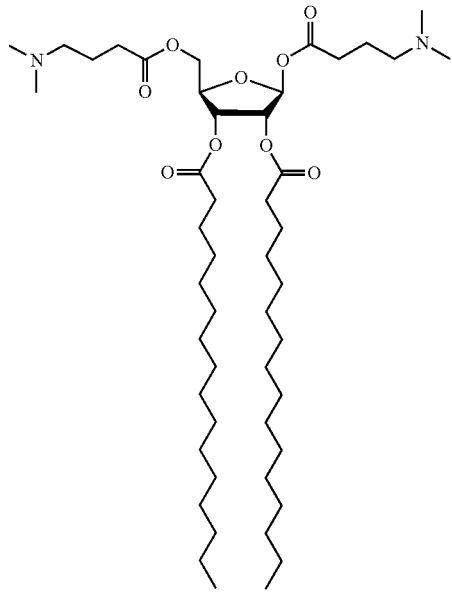
(231)
2RL3-05Dx2
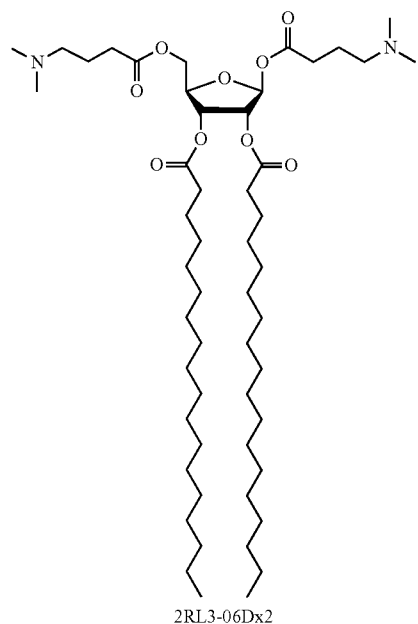
(232)
2RL3-06Dx2

TABLE T-continued
Formula (IIIs) Cationic Lipids
(233)
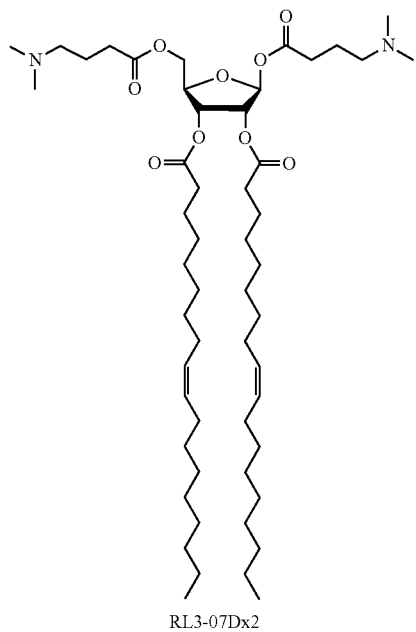
RL3-07Dx2
(234)
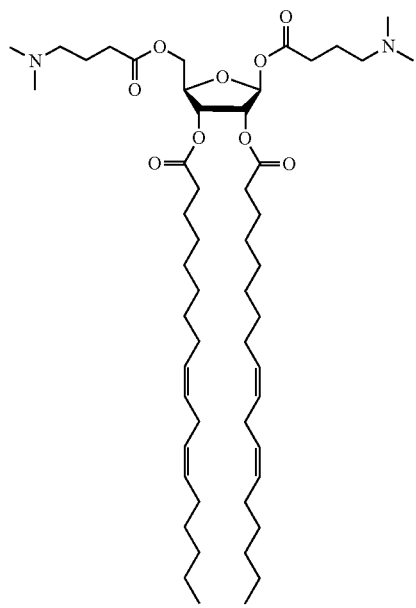
2RL3-08Dx2

TABLE T-continued
Formula (IIIs) Cationic Lipids
(235)
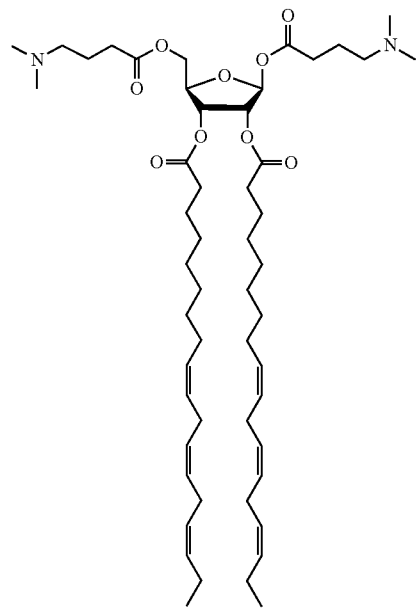
2RL3-09Dx2
(236)
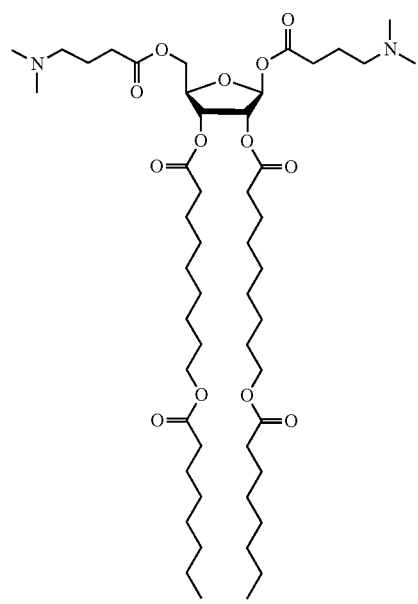
2RL3-10Dx2

TABLE T-continued

Formula (IIIs) Cationic Lipids (237)

[Structure: 2RL3-11Dx2]

In embodiments, a cationic lipid is cationic lipid (227). In embodiments, a cationic lipid is cationic lipid (228). In embodiments, a cationic lipid is cationic lipid (229). In embodiments, a cationic lipid is cationic lipid (230). In embodiments, a cationic lipid is cationic lipid (231). In embodiments, a cationic lipid is cationic lipid (232). In embodiments, a cationic lipid is cationic lipid (233). In embodiments, a cationic lipid is cationic lipid (234). In embodiments, a cationic lipid is cationic lipid (235). In embodiments, a cationic lipid is cationic lipid (236). In embodiments, a cationic lipid is cationic lipid (237).

Exemplary cationic lipids include cationic lipids according to formula (IIIt) such as cationic lipids (238)-(261) (Table U):

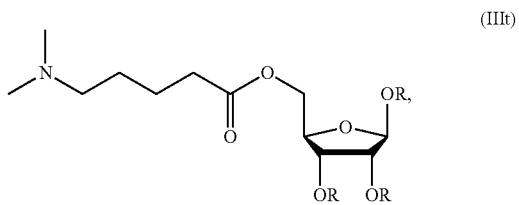
(IIIt)

wherein each R is independently as described herein, including the exemplified groups of Table U.

TABLE U

| Formula (IIIt) Cationic Lipids | |
|---|---|
| R = | Compound |
| [structure: C(=O)-(CH2)6-CH3] | (238) |
| [structure: C(=O)-(CH2)8-CH3] | (239) |
| [structure: C(=O)-(CH2)9-CH3] | (240) |

TABLE U-continued
Formula (IIIt) Cationic Lipids
| R = | Compound |
|---|---|
| 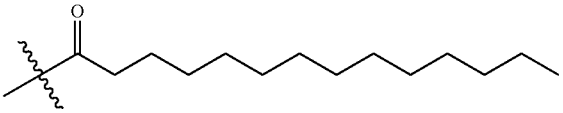 | (241) |
| 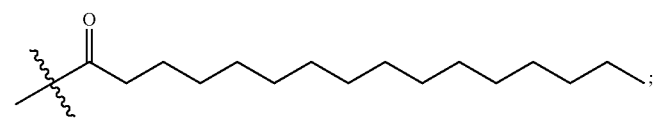 [SMILES: *C(=O)CCCCCCCCCCCCCCC] | (242) |
| 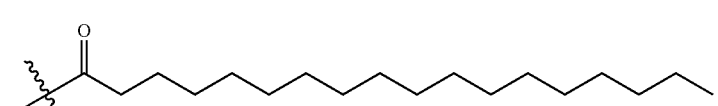 | (243) |
| 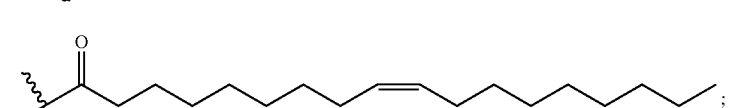 | (244) |
| 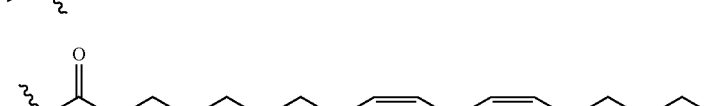 | (245) |
|  | (246) |
|  | (247) |
| 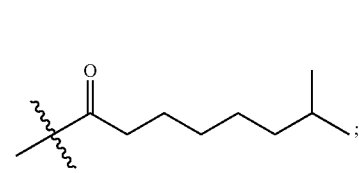 | (248) |
| 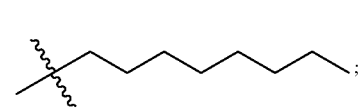 [SMILES: *CCCCCCCC] | (249) |
| 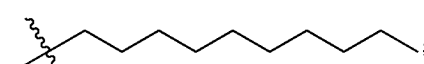 | (250) |
| 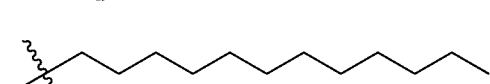 | (251) |
| 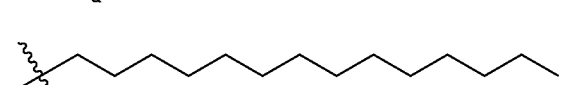 | (252) |
| 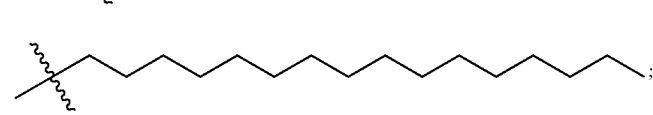 | (253) |

TABLE U-continued

Formula (IIIt) Cationic Lipids

| R = | Compound |
|---|---|
| 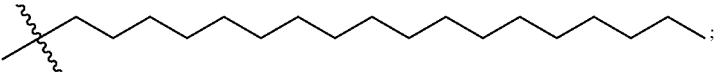 [SMILES: *CCCCCCCCCCCCCCCCCC] | (254) |
| 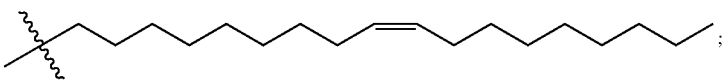 [SMILES: *CCCCCCCC/C=C\CCCCCCCC] | (255) |
| 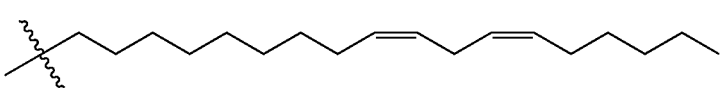 | (256) |
| 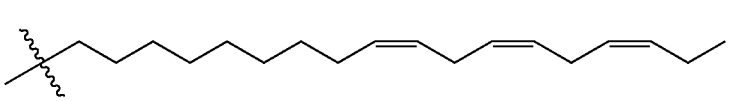 | (257) |
| 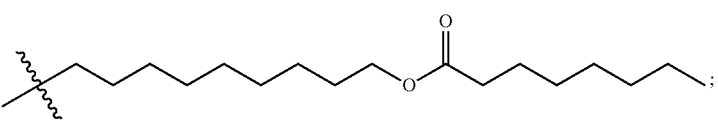 [SMILES: *CCCCCCCCCOC(=O)CCCCCCC] | (258) |
| 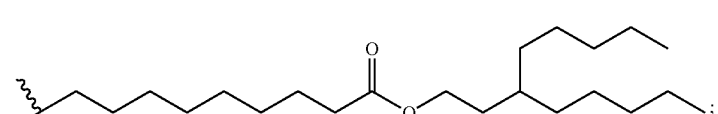 | (259) |
| 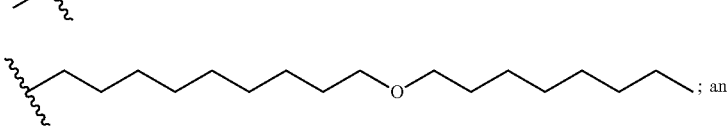 ; and | (260) |
| 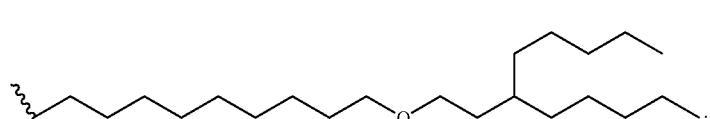 | (261) |

In embodiments, a cationic lipid is cationic lipid (238). In embodiments, a cationic lipid is cationic lipid (239). In embodiments, a cationic lipid is cationic lipid (240). In embodiments, a cationic lipid is cationic lipid (241). In embodiments, a cationic lipid is cationic lipid (242). In embodiments, a cationic lipid is cationic lipid (243). In embodiments, a cationic lipid is cationic lipid (244). In embodiments, a cationic lipid is cationic lipid (245). In embodiments, a cationic lipid is cationic lipid (246). In embodiments, a cationic lipid is cationic lipid (247). In embodiments, a cationic lipid is cationic lipid (248). In embodiments, a cationic lipid is cationic lipid (249). In embodiments, a cationic lipid is cationic lipid (250). In embodiments, a cationic lipid is cationic lipid (251). In embodiments, a cationic lipid is cationic lipid (252). In embodiments, a cationic lipid is cationic lipid (253). In embodiments, a cationic lipid is cationic lipid (254). In embodiments, a cationic lipid is cationic lipid (255). In embodiments, a cationic lipid is cationic lipid (256). In embodiments, a cationic lipid is cationic lipid (257). In embodiments, a cationic lipid is cationic lipid (258). In embodiments, a cationic lipid is cationic lipid (259). In embodiments, a cationic lipid is cationic lipid (260). In embodiments, a cationic lipid is cationic lipid (261).

Exemplary cationic lipids include cationic lipids according to formula (IIIu) such as cationic lipids (262)-(285) (Table V):

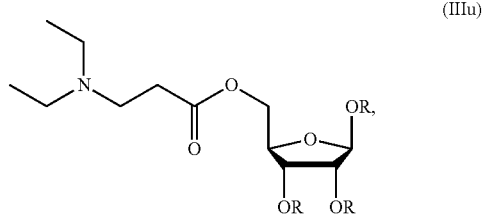

(IIIu)

wherein each R is independently as described herein, including the exemplified groups of Table V.

TABLE V
Formula (IIIu) Cationic Lipids
| R = | Compound |
|---|---|
| 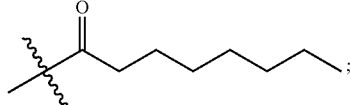 [SMILES: *C(=O)CCCCCCC] | (262) |
| 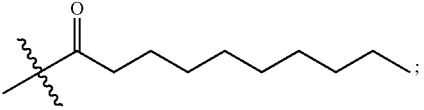 [SMILES: *C(=O)CCCCCCCCC] | (263) |
| 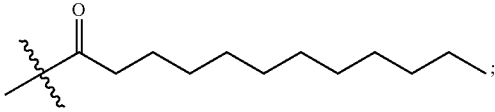 [SMILES: *C(=O)CCCCCCCCCCC] | (264) |
| 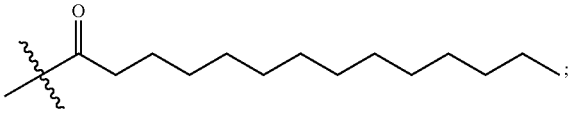 [SMILES: *C(=O)CCCCCCCCCCCCC] | (265) |
| 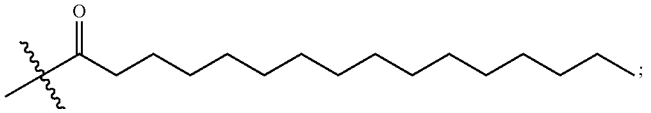 [SMILES: *C(=O)CCCCCCCCCCCCCCC] | (266) |
| 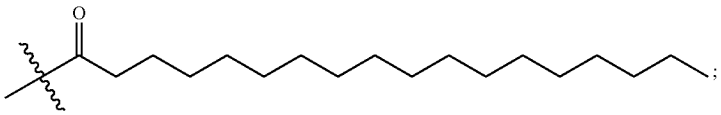 [SMILES: *C(=O)CCCCCCCCCCCCCCCCC] | (267) |
| 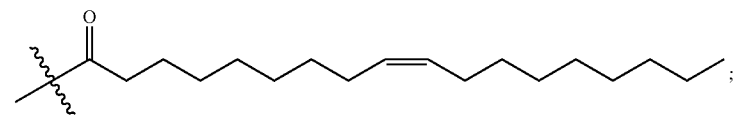 [SMILES: *C(=O)CCCCCCC/C=C\CCCCCCCC] | (268) |
| 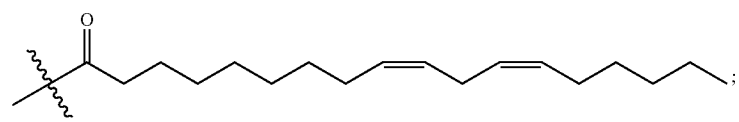 | (269) |
| 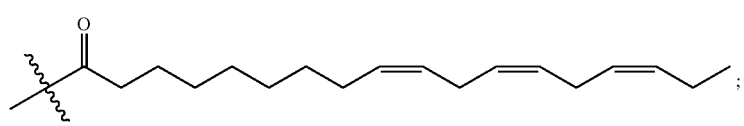 [SMILES: *C(=O)CCCCCCC/C=C\C/C=C\C/C=C\CC] | (270) |
| 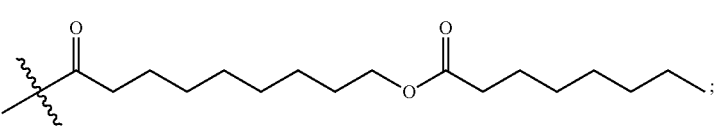 [SMILES: *C(=O)CCCCCCCCOC(=O)CCCCCCC] | (271) |
| 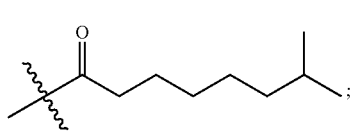 [SMILES: *C(=O)CCCCCC(C)C] | (272) |
| 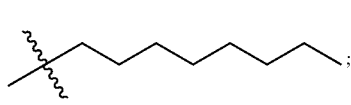 | (273) |

TABLE V-continued
Formula (IIIu) Cationic Lipids
| R = | Compound |
|---|---|
| 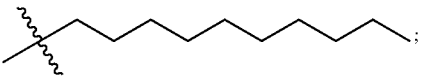 [SMILES: *CCCCCCCCCC] | (274) |
| 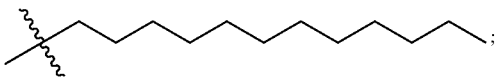 [SMILES: *CCCCCCCCCCCC] | (275) |
| 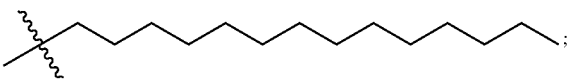 [SMILES: *CCCCCCCCCCCCCC] | (276) |
| 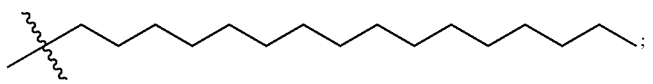 [SMILES: *CCCCCCCCCCCCCCCC] | (277) |
| 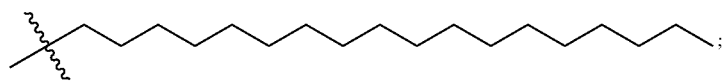 [SMILES: *CCCCCCCCCCCCCCCCCC] | (278) |
| 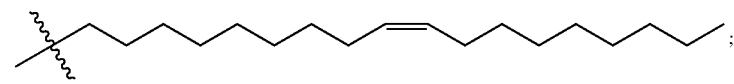 [SMILES: *CCCCCCCC/C=C\CCCCCCCC] | (279) |
| 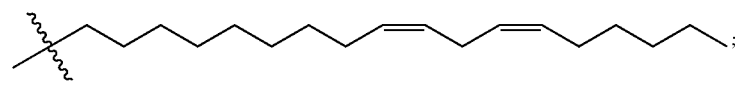 | (280) |
| 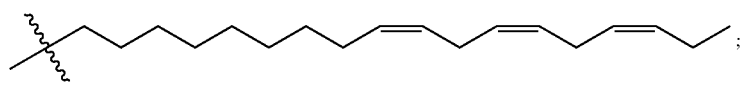 | (281) |
| 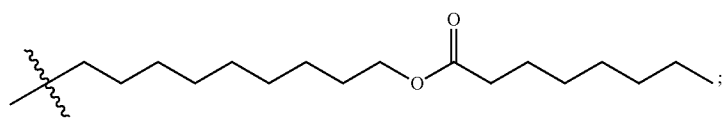 [SMILES: *CCCCCCCCCOC(=O)CCCCCCC] | (282) |
| 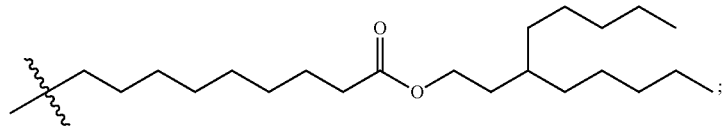 [SMILES: *CCCCCCCCC(=O)OCCC(CCCCC)CCCCC] | (283) |
| 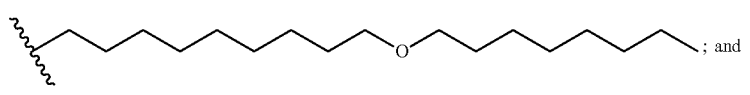 [SMILES: *CCCCCCCCCOCCCCCCCC]; and | (284) |
| 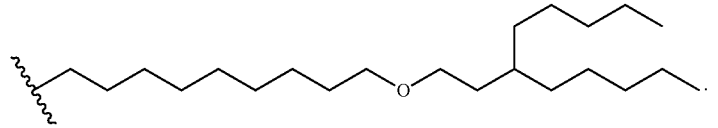 [SMILES: *CCCCCCCCCOCCC(CCCCC)CCCCC] | (285) |

In embodiments, a cationic lipid is cationic lipid (262). In embodiments, a cationic lipid is cationic lipid (263). In embodiments, a cationic lipid is cationic lipid (264). In embodiments, a cationic lipid is cationic lipid (265). In embodiments, a cationic lipid is cationic lipid (266). In embodiments, a cationic lipid is cationic lipid (267). In embodiments, a cationic lipid is cationic lipid (268). In embodiments, a cationic lipid is cationic lipid (269). In embodiments, a cationic lipid is cationic lipid (270). In embodiments, a cationic lipid is cationic lipid (271). In embodiments, a cationic lipid is cationic lipid (272). In embodiments, a cationic lipid is cationic lipid (273). In embodiments, a cationic lipid is cationic lipid (274). In embodiments, a cationic lipid is cationic lipid (275). In embodiments, a cationic lipid is cationic lipid (276). In embodiments, a cationic lipid is cationic lipid (277). In embodiments, a cationic lipid is cationic lipid (278). In embodiments, a cationic lipid is cationic lipid (279). In embodiments, a cationic lipid is cationic lipid (280). In embodiments, a cationic lipid is cationic lipid (281). In embodiments, a cationic lipid is cationic lipid (282). In embodiments, a cationic lipid is cationic lipid (283). In embodiments, a cationic lipid is cationic lipid (284). In embodiments, a cationic lipid is cationic lipid (285).

Exemplary cationic lipids include cationic lipids according to formula (IIIv) such as cationic lipids (286)-(309) (Table W):

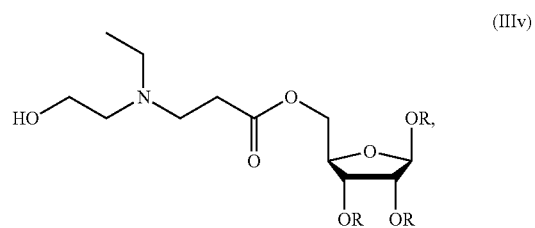

(IIIv)

wherein each R is independently as described herein, including the exemplified groups of Table W.

TABLE W

| Formula (IIIv) Cationic Lipids | |
|---|---|
| R = | Compound |
| ![structure] | (286) |
| ![structure] | (287) |
| ![structure] | (288) |
| ![structure] | (289) |
| ![structure] | (290) |
| ![structure] | (291) |
| ![structure] | (292) |

TABLE W-continued

Formula (IIIv) Cationic Lipids

| R = | Compound |
|---|---|
| | (293) |
| | (294) |
| | (295) |
| | (296) |
| | (297) |
| | (298) |
| | (299) |
| | (300) |
| | (301) |
| | (302) |
| | (303) |
| | (304) |
| | (305) |
| | (306) |

TABLE W-continued

Formula (IIIv) Cationic Lipids

| R = | Compound |
|---|---|
| 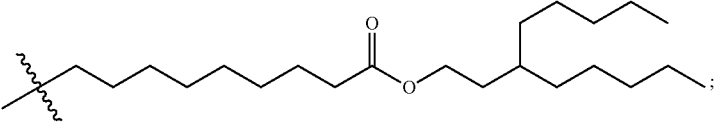 [SMILES: *CCCCCCCCC(=O)OCCC(CCCCC)CCCCC] | (307) |
| 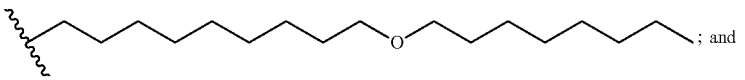 [SMILES: *CCCCCCCCCOCCCCCCCC] | (308) |
| 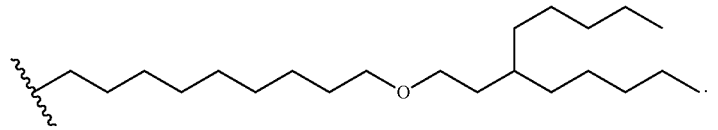 [SMILES: *CCCCCCCCCOCCC(CCCCC)CCCCC] | (309) |

In embodiments, a cationic lipid is cationic lipid (286). In embodiments, a cationic lipid is cationic lipid (287). In embodiments, a cationic lipid is cationic lipid (288). In embodiments, a cationic lipid is cationic lipid (289). In embodiments, a cationic lipid is cationic lipid (290). In embodiments, a cationic lipid is cationic lipid (291). In embodiments, a cationic lipid is cationic lipid (292). In embodiments, a cationic lipid is cationic lipid (293). In embodiments, a cationic lipid is cationic lipid (294). In embodiments, a cationic lipid is cationic lipid (295). In embodiments, a cationic lipid is cationic lipid (296). In embodiments, a cationic lipid is cationic lipid (297). In embodiments, a cationic lipid is cationic lipid (298). In embodiments, a cationic lipid is cationic lipid (299). In embodiments, a cationic lipid is cationic lipid (300). In embodiments, a cationic lipid is cationic lipid (301). In embodiments, a cationic lipid is cationic lipid (302). In embodiments, a cationic lipid is cationic lipid (303). In embodiments, a cationic lipid is cationic lipid (304). In embodiments, a cationic lipid is cationic lipid (305). In embodiments, a cationic lipid is cationic lipid (306). In embodiments, a cationic lipid is cationic lipid (307). In embodiments, a cationic lipid is cationic lipid (308). In embodiments, a cationic lipid is cationic lipid (309).

Exemplary cationic lipids include cationic lipids according to formula (IIIw) such as cationic lipids (310)-(333) (Table X):

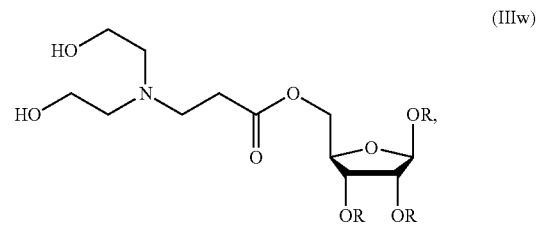

(IIIw)

wherein each R is independently as described herein, including the exemplified groups of Table X.

TABLE X

Formula (IIIw) Cationic Lipids

| R = | Compound |
|---|---|
| 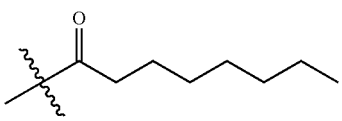 [SMILES: *C(=O)CCCCCCC] | (310); |
| 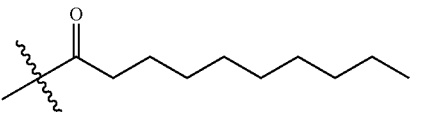 | (311); |
| 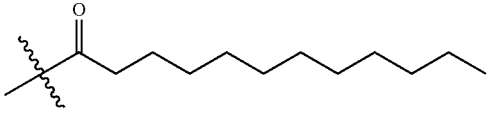 | (312); |

TABLE X-continued

Formula (IIIw) Cationic Lipids

| R = | Compound |
|---|---|
| | (313); |
| | (314); |
| | (315); |
| | (316); |
| | (317); |
| | (318); |
| | (319); |
| | (320); |
| | (321): |
| | (322); |
| | (323); |
| | (324); |
| | (325); |

TABLE X-continued

Formula (IIIw) Cationic Lipids

| R = | Compound |
|---|---|
| 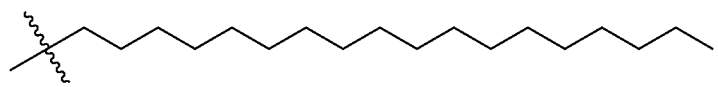 [SMILES: *CCCCCCCCCCCCCCCCCC] | (326); |
| 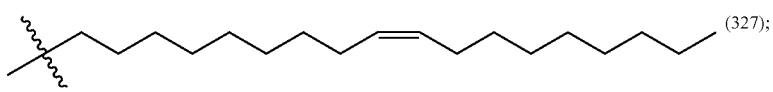 | (327); |
| 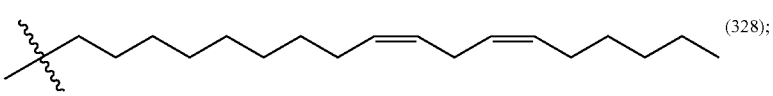 | (328); |
| 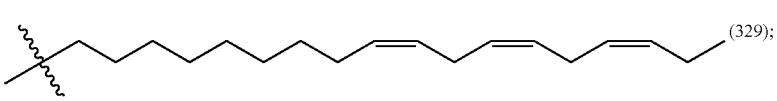 | (329); |
| 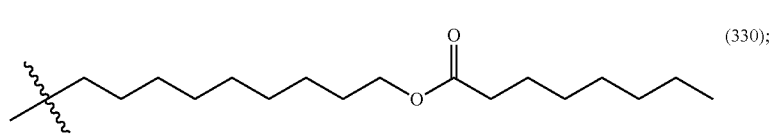 | (330); |
| 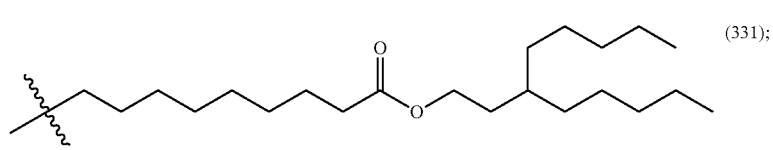 | (331); |
| 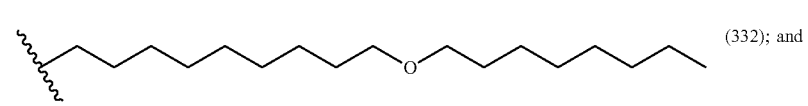 | (332); and |
| 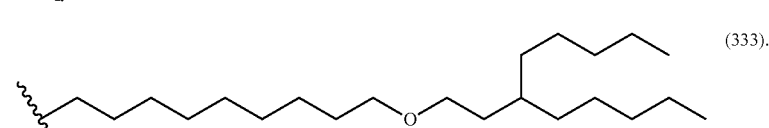 | (333). |

In embodiments, a cationic lipid is cationic lipid (310). In embodiments, a cationic lipid is cationic lipid (311). In embodiments, a cationic lipid is cationic lipid (312). In embodiments, a cationic lipid is cationic lipid (313). In embodiments, a cationic lipid is cationic lipid (314). In embodiments, a cationic lipid is cationic lipid (315). In embodiments, a cationic lipid is cationic lipid (316). In embodiments, a cationic lipid is cationic lipid (317). In embodiments, a cationic lipid is cationic lipid (318). In embodiments, a cationic lipid is cationic lipid (319). In embodiments, a cationic lipid is cationic lipid (320). In embodiments, a cationic lipid is cationic lipid (321). In embodiments, a cationic lipid is cationic lipid (322). In embodiments, a cationic lipid is cationic lipid (323). In embodiments, a cationic lipid is cationic lipid (324). In embodiments, a cationic lipid is cationic lipid (325). In embodiments, a cationic lipid is cationic lipid (326). In embodiments, a cationic lipid is cationic lipid (327). In embodiments, a cationic lipid is cationic lipid (328). In embodiments, a cationic lipid is cationic lipid (329). In embodiments, a cationic lipid is cationic lipid (330). In embodiments, a cationic lipid is cationic lipid (331). In embodiments, a cationic lipid is cationic lipid (332). In embodiments, a cationic lipid is cationic lipid (333).

Exemplary cationic lipids include cationic lipids according to formula (IIIx) such as cationic lipids (334)-(357) (Table Y):

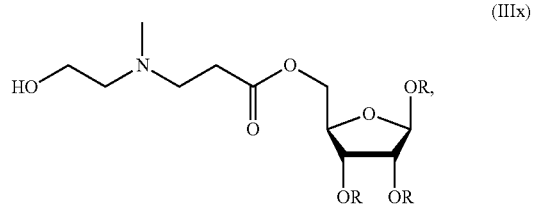

(IIIx)

wherein each R is independently as described herein, including the exemplified groups of Table Y.

TABLE Y
Formula (IIIx) Cationic Lipids
| R = | Compound |
|---|---|
| 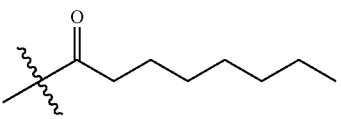 [SMILES: *C(=O)CCCCCCC] | (334); |
| 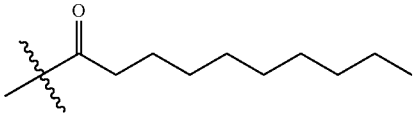 [SMILES: *C(=O)CCCCCCCCC] | (335); |
| 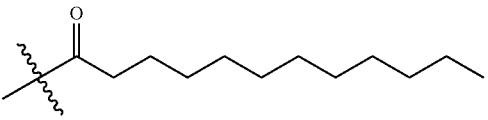 [SMILES: *C(=O)CCCCCCCCCCC] | (336); |
| 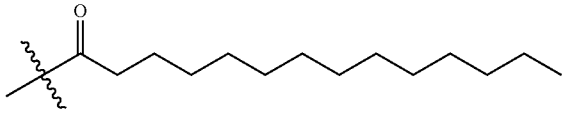 [SMILES: *C(=O)CCCCCCCCCCCCC] | (337); |
| 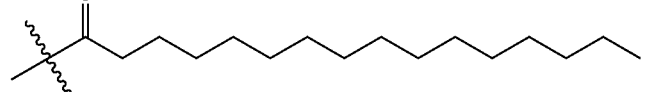 | (338); |
| 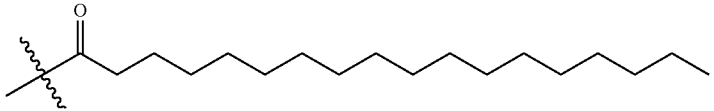 [SMILES: *C(=O)CCCCCCCCCCCCCCCCC] | (339); |
| 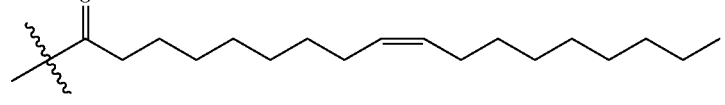 | (340); |
| 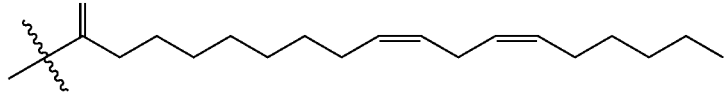 | (341); |
| 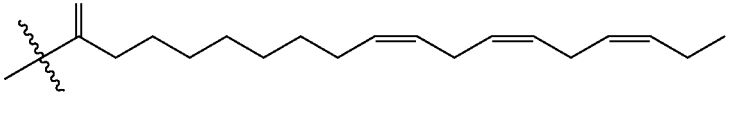 | (342); |
| 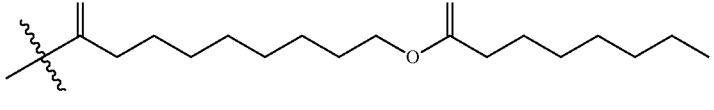 | (343); |
| 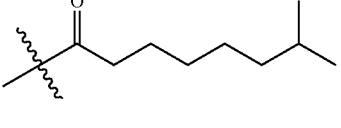 | (344); |
| 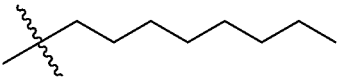 [SMILES: *CCCCCCCC] | (345); |

TABLE Y-continued
Formula (IIIx) Cationic Lipids
| R = | Compound |
|---|---|
|  | (346); |
| 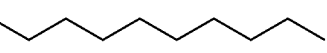 | (347); |
|  | (348); |
| 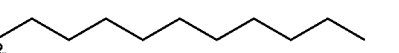 | (349); |
|  | (350); |
| 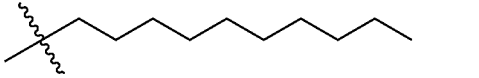 [SMILES: *CCCCCCCCCC] | (351); |
|  | (352); |
| 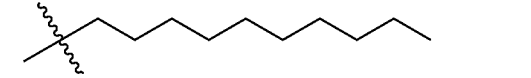 | (353); |
|  | (354); |
| 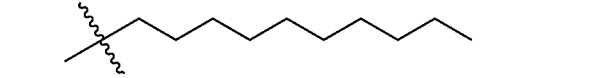 | (355); |
|  | (356); and |
| 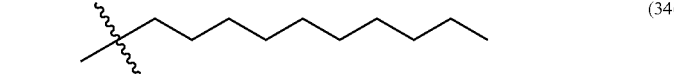 | (357). |

In embodiments, a cationic lipid is cationic lipid (334). In embodiments, a cationic lipid is cationic lipid (335). In embodiments, a cationic lipid is cationic lipid (336). In embodiments, a cationic lipid is cationic lipid (337). In embodiments, a cationic lipid is cationic lipid (338). In embodiments, a cationic lipid is cationic lipid (339). In embodiments, a cationic lipid is cationic lipid (340). In embodiments, a cationic lipid is cationic lipid (341). In embodiments, a cationic lipid is cationic lipid (342). In embodiments, a cationic lipid is cationic lipid (343). In embodiments, a cationic lipid is cationic lipid (344). In embodiments, a cationic lipid is cationic lipid (345). In embodiments, a cationic lipid is cationic lipid (346). In embodiments, a cationic lipid is cationic lipid (347). In embodiments, a cationic lipid is cationic lipid (348). In embodiments, a cationic lipid is cationic lipid (349). In embodiments, a cationic lipid is cationic lipid (350). In embodiments, a cationic lipid is cationic lipid (351). In embodiments, a cationic lipid is cationic lipid (352). In embodiments, a cationic lipid is cationic lipid (353). In embodiments, a cationic lipid is cationic lipid (354). In embodiments, a cationic lipid is cationic lipid (355). In embodiments, a cationic lipid is cationic lipid (356). In embodiments, a cationic lipid is cationic lipid (357).

Exemplary cationic lipids include cationic lipids according to formula (IIIy) such as cationic lipids (358)-(381) (Table Z):

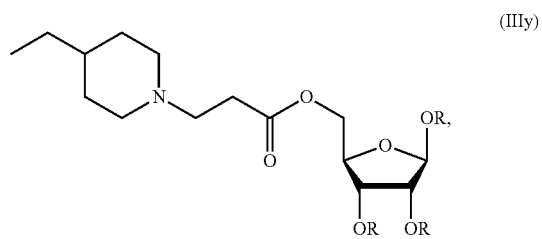

(IIIy)

wherein each R is independently as described herein, including the exemplified groups of Table Z.

TABLE Z

| Formula (IIIy) Cationic Lipids | |
|---|---|
| R = | Compound |
| ![structure] | (358); |
| ![structure] | (359); |
| ![structure] | (360); |
| ![structure] | (361); |
| ![structure] | (362); |
| ![structure] | (363); |
| ![structure] | (364); |

TABLE Z-continued

Formula (IIIy) Cationic Lipids

| R = | Compound |
|---|---|
| [structure] | (365); |
| [structure] | (366); |
| [structure] | (367); |
| [structure] | (368); |
| [structure] | (369); |
| [structure] | (370); |
| [structure] | (371); |
| [structure] | (372); |
| [structure] | (373); |
| [structure] | (374); |
| [structure] | (375); |
| [structure] | (376); |
| [structure] | (377); |
| [structure] | (378); |

TABLE Z-continued

Formula (IIIy) Cationic Lipids

| R = | Compound |
|---|---|
| 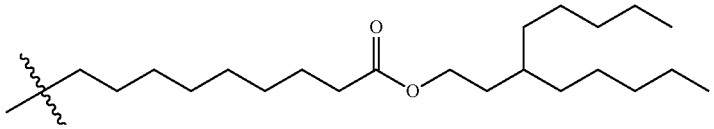 | (379); |
| 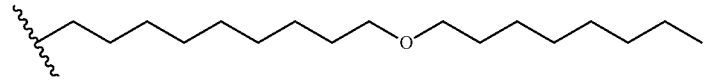 [SMILES: *CCCCCCCCCOCCCCCCCC] | (380); and |
| 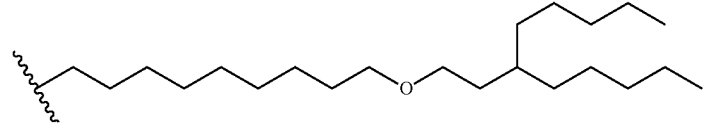 [SMILES: *CCCCCCCCCOCCC(CCCCC)CCCCC] | (381). |

In embodiments, a cationic lipid is cationic lipid (358). In embodiments, a cationic lipid is cationic lipid (359). In embodiments, a cationic lipid is cationic lipid (360). In embodiments, a cationic lipid is cationic lipid (361). In embodiments, a cationic lipid is cationic lipid (362). In embodiments, a cationic lipid is cationic lipid (363). In embodiments, a cationic lipid is cationic lipid (364). In embodiments, a cationic lipid is cationic lipid (365). In embodiments, a cationic lipid is cationic lipid (366). In embodiments, a cationic lipid is cationic lipid (367). In embodiments, a cationic lipid is cationic lipid (368). In embodiments, a cationic lipid is cationic lipid (369). In embodiments, a cationic lipid is cationic lipid (370). In embodiments, a cationic lipid is cationic lipid (371). In embodiments, a cationic lipid is cationic lipid (372). In embodiments, a cationic lipid is cationic lipid (373). In embodiments, a cationic lipid is cationic lipid (374). In embodiments, a cationic lipid is cationic lipid (375). In embodiments, a cationic lipid is cationic lipid (376). In embodiments, a cationic lipid is cationic lipid (377). In embodiments, a cationic lipid is cationic lipid (378). In embodiments, a cationic lipid is cationic lipid (379). In embodiments, a cationic lipid is cationic lipid (380). In embodiments, a cationic lipid is cationic lipid (381).

Exemplary cationic lipids include cationic lipids according to formula (IIIz) such as cationic lipids (382)-(405) (Table AA):

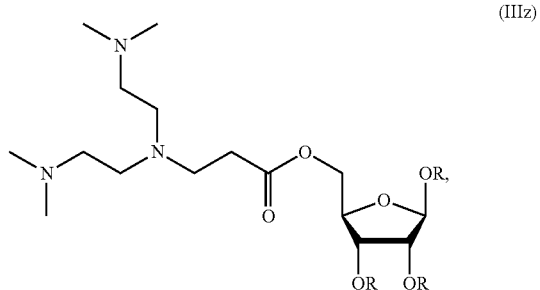

(IIIz)

wherein each R is independently as described herein, including the exemplified groups of Table AA.

TABLE AA

Formula (IIIz) Cationic Lipids

| R = | Compound |
|---|---|
| 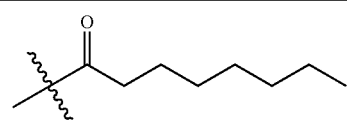 | (382); |
| 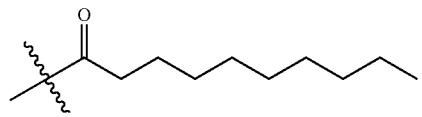 [SMILES: *C(=O)CCCCCCCCC] | (383); |
| 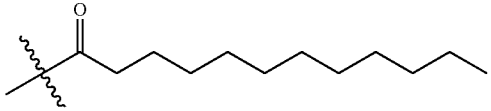 [SMILES: *C(=O)CCCCCCCCCCC] | (384); |

TABLE AA-continued
Formula (IIIz) Cationic Lipids
| R = | Compound |
|---|---|
| 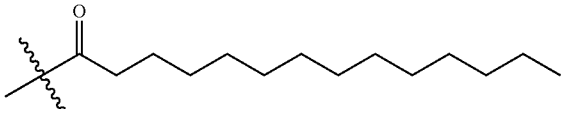 [SMILES: *C(=O)CCCCCCCCCCCCC] | (385); |
| 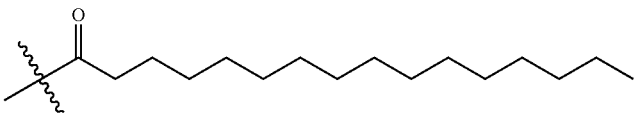 [SMILES: *C(=O)CCCCCCCCCCCCCCC] | (386); |
| 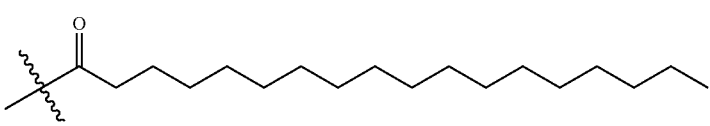 [SMILES: *C(=O)CCCCCCCCCCCCCCCCC] | (387); |
| 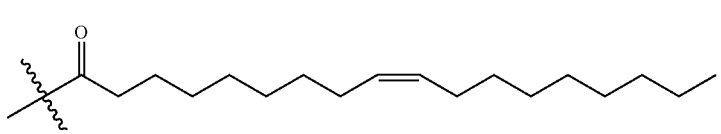 [SMILES: *C(=O)CCCCCCC/C=C\CCCCCCCC] | (388); |
| 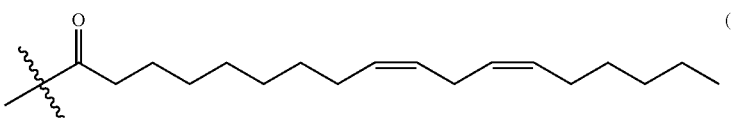 | (389); |
| 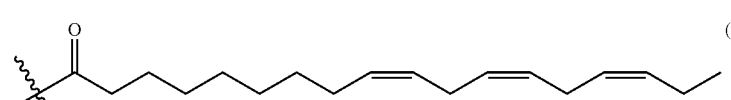 | (390); |
| 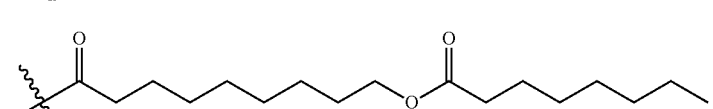 | (391); |
| 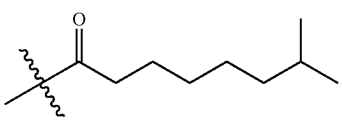 [SMILES: *C(=O)CCCCCC(C)C] | (392); |
| 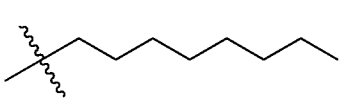 [SMILES: *CCCCCCCC] | (393); |
| 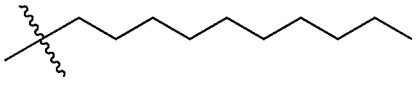 [SMILES: *CCCCCCCCCC] | (394); |
| 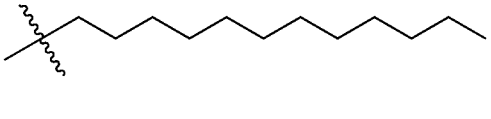 [SMILES: *CCCCCCCCCCCC] | (395); |
|  | (396); |
|  | (397); |

TABLE AA-continued

Formula (IIIz) Cationic Lipids

| R = | Compound |
|---|---|
| 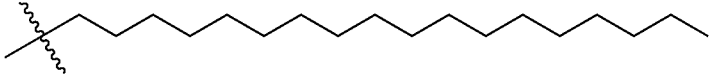 [SMILES: *CCCCCCCCCCCCCCCCCC] | (398); |
| 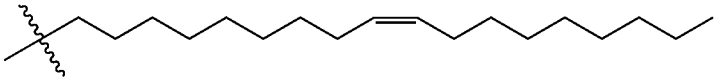 [SMILES: *CCCCCCCC/C=C\CCCCCCCC] | (399); |
| 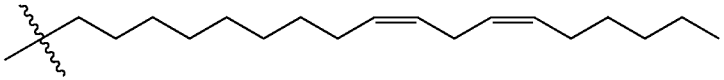 [SMILES: *CCCCCCCC/C=C\C/C=C\CCCCC] | (400); |
| 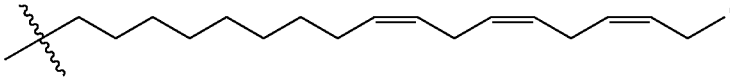 [SMILES: *CCCCCCCC/C=C\C/C=C\C/C=C\CC] | (401); |
| 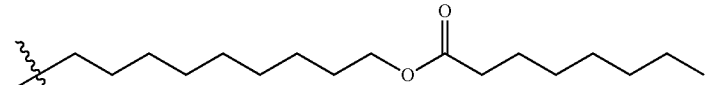 | (402); |
| 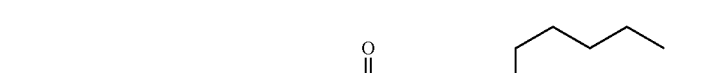 | (403); |
| 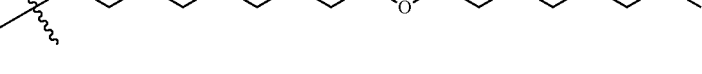 | (404); and |
|  | (405). |

In embodiments, a cationic lipid is cationic lipid (382). In embodiments, a cationic lipid is cationic lipid (383). In embodiments, a cationic lipid is cationic lipid (384). In embodiments, a cationic lipid is cationic lipid (385). In embodiments, a cationic lipid is cationic lipid (386). In embodiments, a cationic lipid is cationic lipid (387). In embodiments, a cationic lipid is cationic lipid (388). In embodiments, a cationic lipid is cationic lipid (389). In embodiments, a cationic lipid is cationic lipid (390). In embodiments, a cationic lipid is cationic lipid (391). In embodiments, a cationic lipid is cationic lipid (392). In embodiments, a cationic lipid is cationic lipid (393). In embodiments, a cationic lipid is cationic lipid (394). In embodiments, a cationic lipid is cationic lipid (395). In embodiments, a cationic lipid is cationic lipid (396). In embodiments, a cationic lipid is cationic lipid (397). In embodiments, a cationic lipid is cationic lipid (398). In embodiments, a cationic lipid is cationic lipid (399). In embodiments, a cationic lipid is cationic lipid (400). In embodiments, a cationic lipid is cationic lipid (401). In embodiments, a cationic lipid is cationic lipid (402). In embodiments, a cationic lipid is cationic lipid (403). In embodiments, a cationic lipid is cationic lipid (404). In embodiments, a cationic lipid is cationic lipid (405).

Exemplary cationic lipids include cationic lipids according to formula (IIIaa) such as cationic lipids (406)-(429) (Table AB):

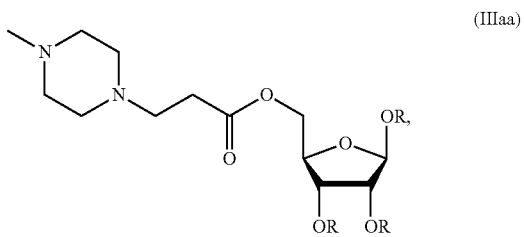

(IIIaa)

wherein each R is independently as described herein, including the exemplified groups of Table AB.

TABLE AB
Formula (IIIaa) Cationic Lipids
| R = | Compound |
|---|---|
| 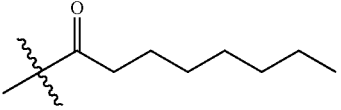 [SMILES: *C(=O)CCCCCCC] | (406); |
| 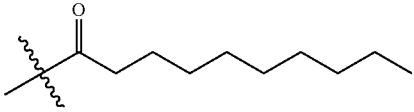 [SMILES: *C(=O)CCCCCCCCC] | (407); |
| 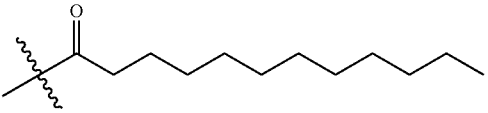 [SMILES: *C(=O)CCCCCCCCCCC] | (408); |
| 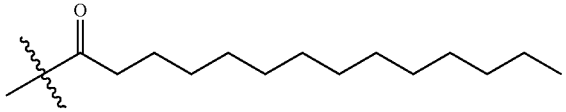 [SMILES: *C(=O)CCCCCCCCCCCCC] | (409); |
| 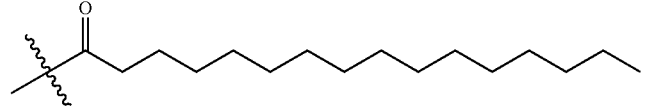 [SMILES: *C(=O)CCCCCCCCCCCCCCC] | (410); |
| 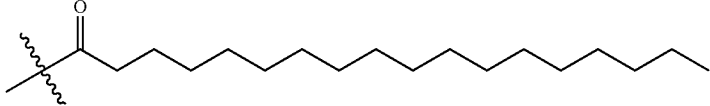 | (411); |
| 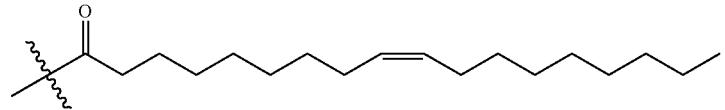 [SMILES: *C(=O)CCCCCCC/C=C\CCCCCCCC] | (412); |
| 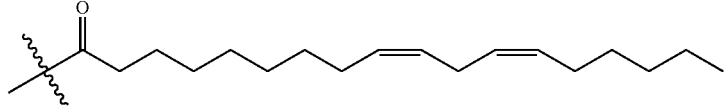 [SMILES: *C(=O)CCCCCCC/C=C\C/C=C\CCCCC] | (413); |
| 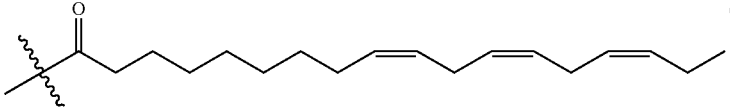 [SMILES: *C(=O)CCCCCCC/C=C\C/C=C\C/C=C\CC] | (414); |
| 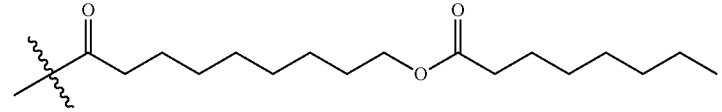 [SMILES: *C(=O)CCCCCCCCOC(=O)CCCCCCC] | (415); |
| 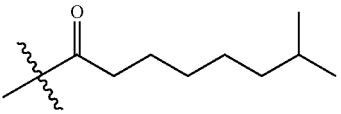 [SMILES: *C(=O)CCCCCC(C)C] | (416); |
| 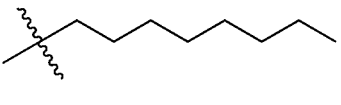 | (417); |

TABLE AB-continued
Formula (IIIaa) Cationic Lipids
| R = | Compound |
|---|---|
| 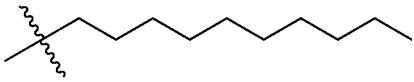 [SMILES: *CCCCCCCCCC] | (418); |
| 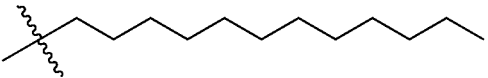 [SMILES: *CCCCCCCCCCCC] | (419); |
| 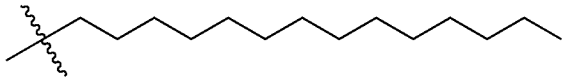 [SMILES: *CCCCCCCCCCCCCC] | (420); |
| 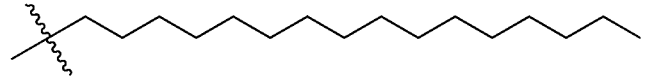 [SMILES: *CCCCCCCCCCCCCCCC] | (421); |
| 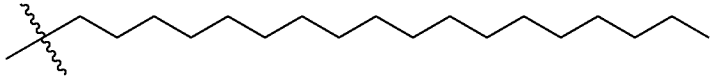 [SMILES: *CCCCCCCCCCCCCCCCCC] | (422); |
| 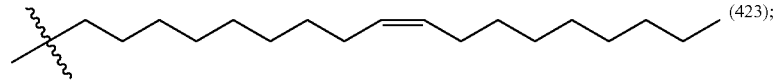 | (423); |
| 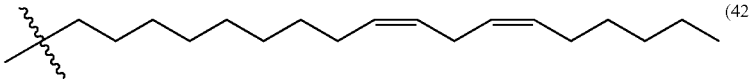 | (424); |
| 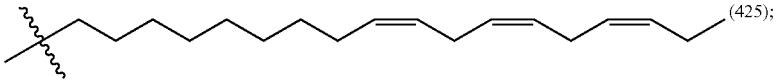 | (425); |
| 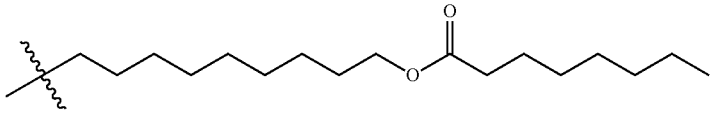 [SMILES: *CCCCCCCCCOC(=O)CCCCCCC] | (426); |
| 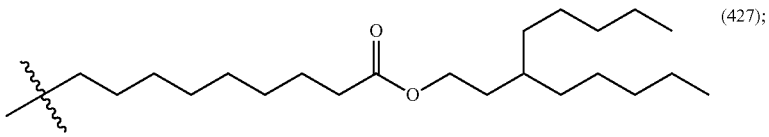 | (427); |
| 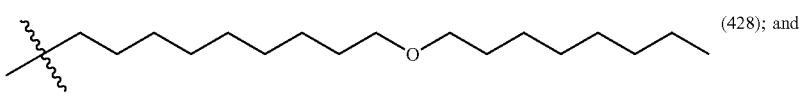 | (428); and |
| 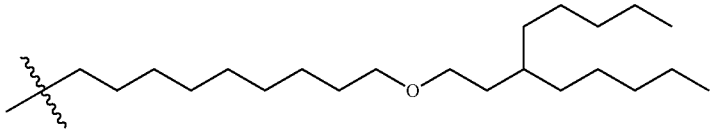 [SMILES: *CCCCCCCCCOCCC(CCCCC)CCCCC] | (429). |

In embodiments, a cationic lipid is cationic lipid (406). In embodiments, a cationic lipid is cationic lipid (407). In embodiments, a cationic lipid is cationic lipid (408). In embodiments, a cationic lipid is cationic lipid (409). In embodiments, a cationic lipid is cationic lipid (410). In embodiments, a cationic lipid is cationic lipid (411). In embodiments, a cationic lipid is cationic lipid (412). In embodiments, a cationic lipid is cationic lipid (413). In embodiments, a cationic lipid is cationic lipid (414). In embodiments, a cationic lipid is cationic lipid (415). In embodiments, a cationic lipid is cationic lipid (416). In embodiments, a cationic lipid is cationic lipid (417). In embodiments, a cationic lipid is cationic lipid (418). In embodiments, a cationic lipid is cationic lipid (419). In embodiments, a cationic lipid is cationic lipid (420). In embodiments, a cationic lipid is cationic lipid (421). In embodiments, a cationic lipid is cationic lipid (422). In embodiments, a cationic lipid is cationic lipid (423). In embodiments, a cationic lipid is cationic lipid (424). In embodiments, a cationic lipid is cationic lipid (425). In embodiments, a cationic lipid is cationic lipid (426). In embodiments, a cationic lipid is cationic lipid (427). In embodiments, a cationic lipid is cationic lipid (428). In embodiments, a cationic lipid is cationic lipid (429).

Exemplary cationic lipids include cationic lipids according to formula (IIIaa) such as cationic lipids (430)-(453) (Table AC):

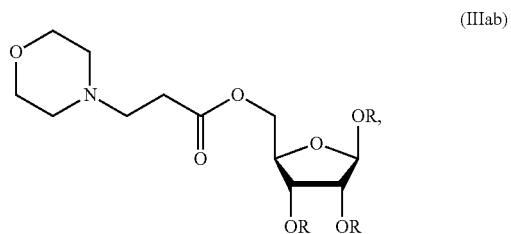

(IIIab)

wherein each R is independently as described herein, including the exemplified groups of Table AC.

TABLE AC

| Formula (IIIab) Cationic Lipids | |
|---|---|
| R = | Compound |
| [structure] | (430); |
| [structure] | (431); |
| [structure] | (432); |
| [structure] | (433); |
| [structure] | (434); |
| [structure] | (435); |
| [structure] | (436); |

TABLE AC-continued
Formula (IIIab) Cationic Lipids
| R = | Compound |
|---|---|
| 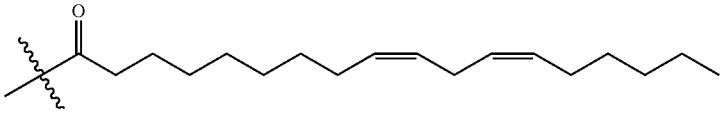 | (437); |
| 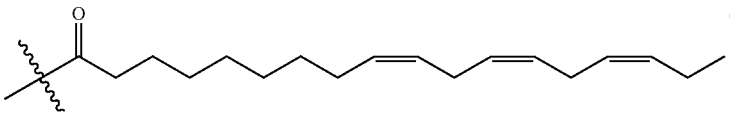 | (438); |
| 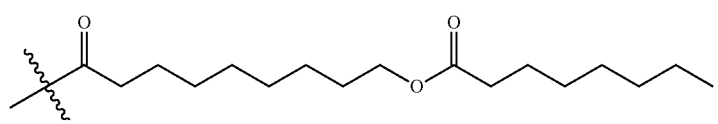 [SMILES: *C(=O)CCCCCCCCOC(=O)CCCCCCC] | (439); |
| 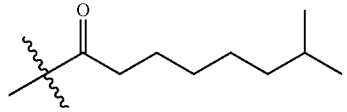 [SMILES: *C(=O)CCCCCC(C)C] | (440); |
| 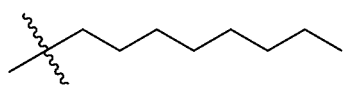 [SMILES: *CCCCCCCC] | (441); |
| 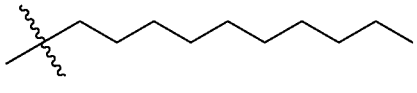 [SMILES: *CCCCCCCCCC] | (442); |
| 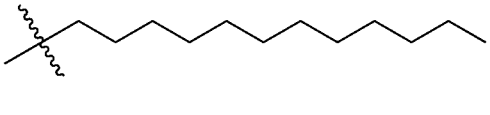 [SMILES: *CCCCCCCCCCCC] | (443); |
| 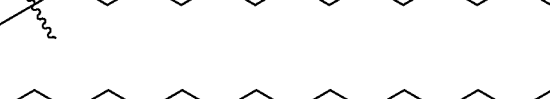 | (444); |
| 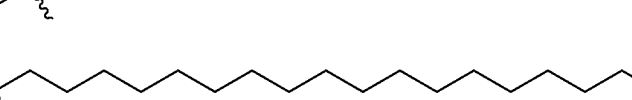 | (445); |
| 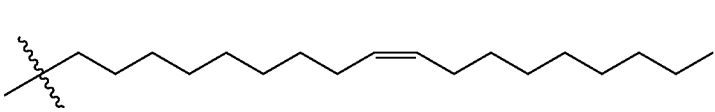 | (446); |
| 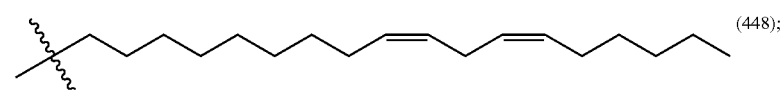 | (447); |
| 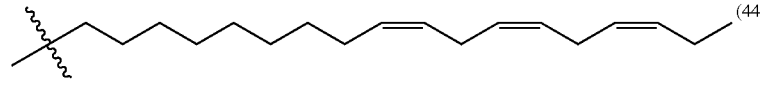 | (448); |
| 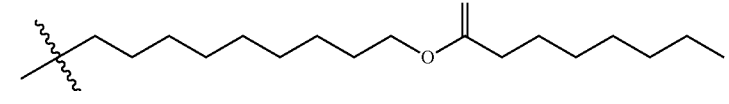 | (449); |
| 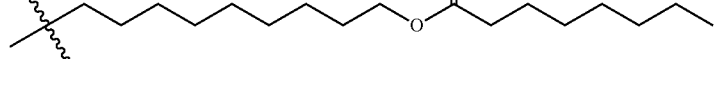 | (450); |

TABLE AC-continued

Formula (IIIab) Cationic Lipids

| R = | Compound |
|---|---|
| 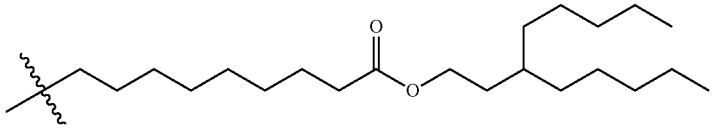 | (451); |
| 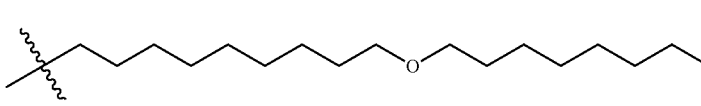 | (452); and |
| 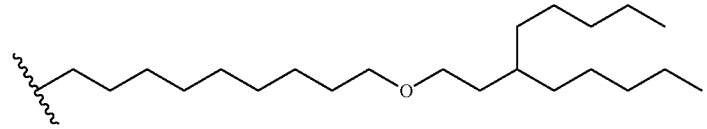 [SMILES: *CCCCCCCCCOCCC(CCCCC)CCCCC] | (453). |

In embodiments, a cationic lipid is cationic lipid (430). In embodiments, a cationic lipid is cationic lipid (431). In embodiments, a cationic lipid is cationic lipid (432). In embodiments, a cationic lipid is cationic lipid (433). In embodiments, a cationic lipid is cationic lipid (434). In embodiments, a cationic lipid is cationic lipid (435). In embodiments, a cationic lipid is cationic lipid (436). In embodiments, a cationic lipid is cationic lipid (437). In embodiments, a cationic lipid is cationic lipid (438). In embodiments, a cationic lipid is cationic lipid (439). In embodiments, a cationic lipid is cationic lipid (440). In embodiments, a cationic lipid is cationic lipid (441). In embodiments, a cationic lipid is cationic lipid (442). In embodiments, a cationic lipid is cationic lipid (443). In embodiments, a cationic lipid is cationic lipid (444). In embodiments, a cationic lipid is cationic lipid (445). In embodiments, a cationic lipid is cationic lipid (446). In embodiments, a cationic lipid is cationic lipid (447). In embodiments, a cationic lipid is cationic lipid (448). In embodiments, a cationic lipid is cationic lipid (449). In embodiments, a cationic lipid is cationic lipid (450). In embodiments, a cationic lipid is cationic lipid (451). In embodiments, a cationic lipid is cationic lipid (452). In embodiments, a cationic lipid is cationic lipid (453).

Exemplary cationic lipids include cationic lipids (454)-(462) of Table AD.

TABLE AD

Exemplary Cationic Lipids

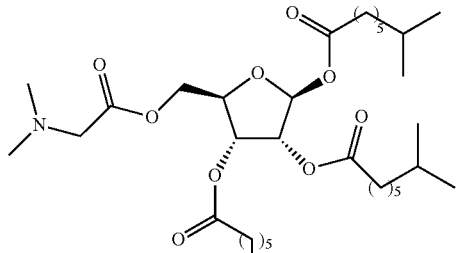 (454)

TABLE AD-continued

Exemplary Cationic Lipids

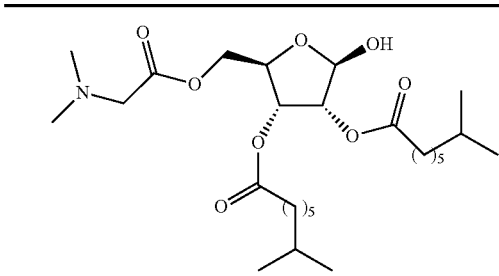 (455)

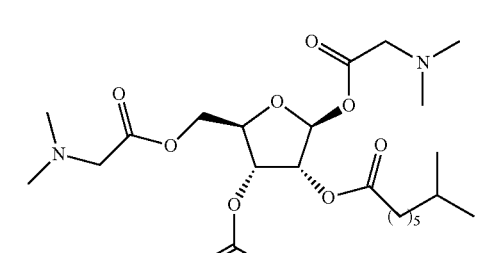 (456)

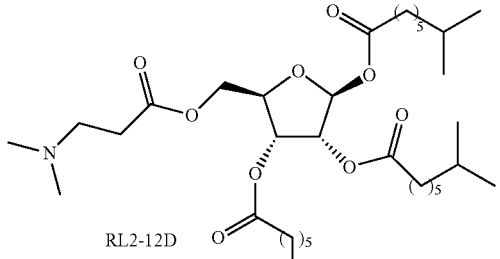 (457)

RL2-12D

TABLE AD-continued

Exemplary Cationic Lipids

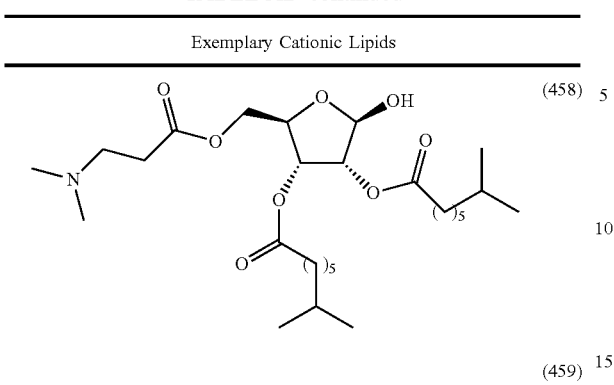
(458)

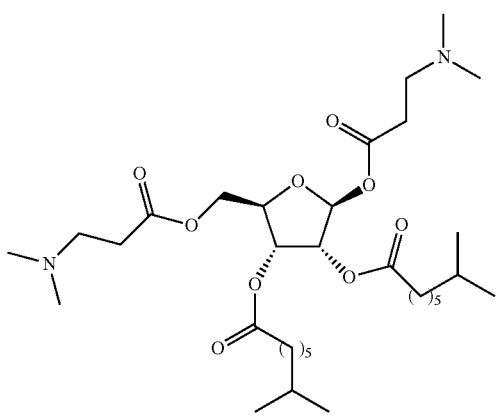
(459)

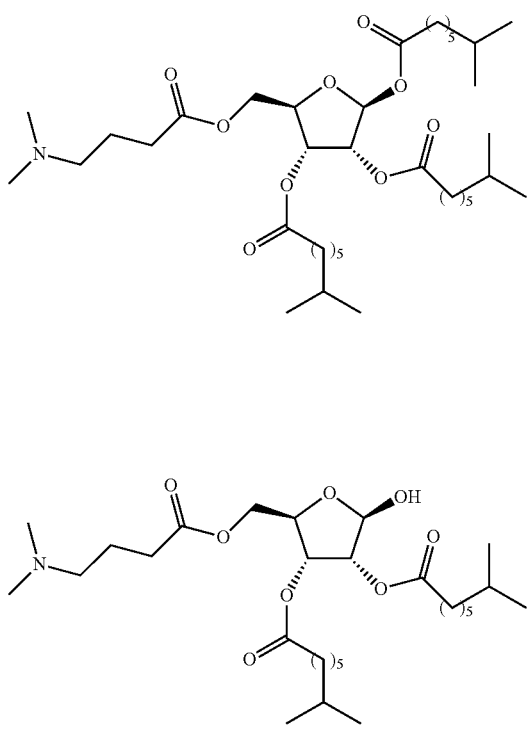
(460)

(461)

TABLE AD-continued

Exemplary Cationic Lipids

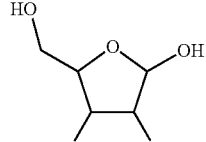
(462)

In embodiments, a cationic lipid is cationic lipid (454). In embodiments, a cationic lipid is cationic lipid (455). In embodiments, a cationic lipid is cationic lipid (456). In embodiments, a cationic lipid is cationic lipid (457). In embodiments, a cationic lipid is cationic lipid (458). In embodiments, a cationic lipid is cationic lipid (459). In embodiments, a cationic lipid is cationic lipid (460). In embodiments, a cationic lipid is cationic lipid (461). In embodiments, a cationic lipid is cationic lipid (462).

Synthesis of Cationic Lipids

Cationic lipids described herein (e.g., cationic lipids of Formula (I'), (I), (II), or (IIIa)-(IIIab) such as cationic lipids (1a)-(21a), (1b)-(21b), and (22)-(462)) can be prepared according to methods known in the art. Additional exemplary methods are provided in the Examples described herein.

Scheme 1 provides an exemplary synthesis for cationic lipids described herein.

Scheme 1. Exemplary Synthesis of Cationic Lipids

Compound A

+

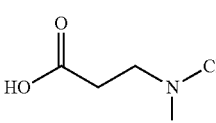
Compound B

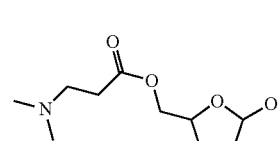
Compound C

Compound D

Compound F

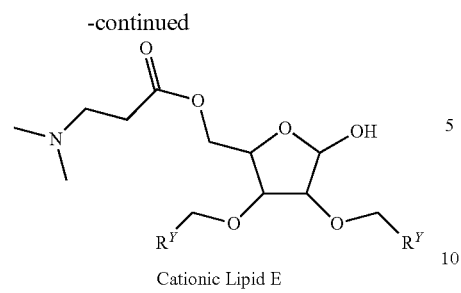

Cationic Lipid E

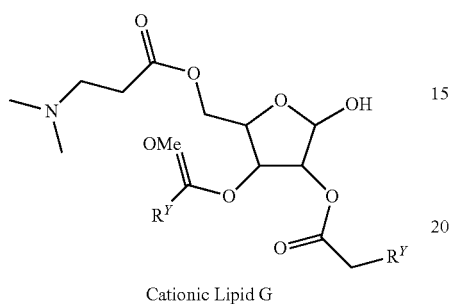

Cationic Lipid G

R$^Y$ = C$_1$-C$_{29}$ aliphatic group
LG = leaving group

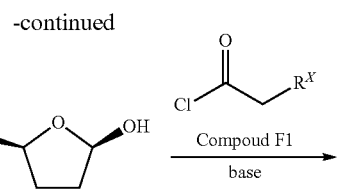

Compound C1

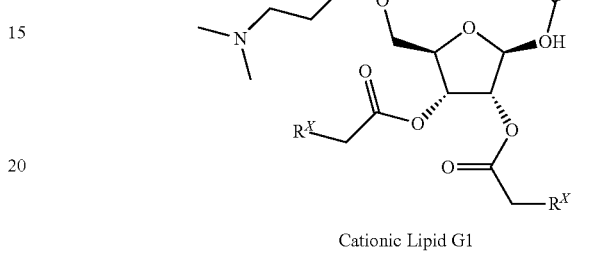

Cationic Lipid G1

R$^X$ = C$_1$-C$_{29}$ aliphatic group

In Scheme 1, combination of a carbohydrate such as Compound A with a cationic electrophile (e.g., Compound B, 3-(dimethylamino)propionic acid, or a salt thereof) can afford Compound C. This compound can be treated with various electrophiles to afford cationic lipids (e.g., cationic lipids of Formula (I) and (II)) as described herein. For example, Compound C can be treated with an aliphatic electrophile (e.g., alkyl halides or alkenyl halides) such as Compound D to afford product Cationic Lipid E. Alternatively, Compound C can be treated with an acylating agent such Compound F (e.g., acyl halides) to afford product Cationic Lipid G.

Scheme 2 provides an exemplary synthesis using D-ribose and acylating agents.

Scheme 2. Exemplary Synthesis of Ribose Cationic Lipids

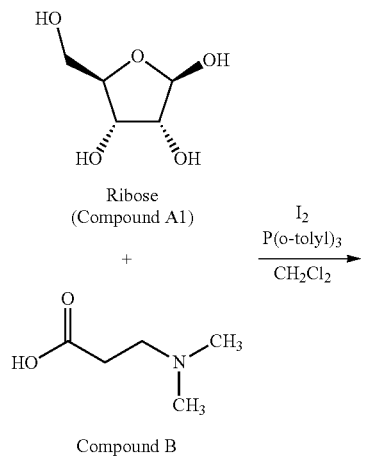

In Scheme 2, ribose (Compound A1) can be combined with 3-(dimethylamino)propionic acid (Compound B) using iodine and tri(p-tolyl)phosphine in dichloromethane to afford Compound C1. Treatment of Compound C1 with excess acyl halide (Compound F1) under basic conditions can afford peracylated Cationic Lipid G1.

Nucleic Acids

Cationic lipids described herein (e.g., a cationic lipid of Formula (I'), (I), (II), or (IIIa)-(IIIab) such as cationic lipids (1a)-(21a), (1b)-(21b), and (22)-(462)) can be used to prepare compositions useful for the delivery of nucleic acids.

Synthesis of Nucleic Acids

Nucleic acids according to the present invention may be synthesized according to any known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7, mutated T7 or SP6 RNA polymerase), DNAse I, pyrophosphatase, and/or RNAse inhibitor. The exact conditions will vary according to the specific application.

In some embodiments, for the preparation of mRNA according to the invention, a DNA template is transcribed in vitro. A suitable DNA template typically has a promoter, for example a T3, T7, mutated T7 or SP6 promoter, for in vitro transcription, followed by desired nucleotide sequence for desired mRNA and a termination signal.

Desired mRNA sequence(s) according to the invention may be determined and incorporated into a DNA template using standard methods. For example, starting from a desired amino acid sequence (e.g., an enzyme sequence), a virtual reverse translation is carried out based on the degenerated genetic code. Optimization algorithms may then be used for selection of suitable codons. Typically, the G/C content can be optimized to achieve the highest possible G/C content on one hand, taking into the best possible account the frequency of the tRNAs according to codon usage on the other hand. The optimized RNA sequence can be established and displayed, for example, with the aid of an appropriate display device and compared with the original (wild-type) sequence. A secondary structure can also be analyzed to calculate stabilizing and destabilizing properties or, respectively, regions of the RNA.

As described above, the term "nucleic acid," in its broadest sense, refers to any compound and/or substance that is or can be incorporated into a polynucleotide chain. DNA may be in the form of antisense DNA, plasmid DNA, parts of a plasmid DNA, pre-condensed DNA, a product of a polymerase chain reaction (PCR), vectors (e.g., P1, PAC, BAC, YAC, artificial chromosomes), expression cassettes, chimeric sequences, chromosomal DNA, or derivatives of these groups. RNA may be in the form of messenger RNA (mRNA), ribosomal RNA (rRNA), signal recognition particle RNA (7 SL RNA or SRP RNA), transfer RNA (tRNA), transfer-messenger RNA (tmRNA), small nuclear RNA (snRNA), small nucleolar RNA (snoRNA), SmY RNA, small Cajal body-specific RNA (scaRNA), guide RNA (gRNA), ribonuclease P (RNase P), Y RNA, telomerase RNA component (TERC), spliced leader RNA (SL RNA), antisense RNA (aRNA or asRNA), cis-natural antisense transcript (cis-NAT), CRISPR RNA (crRNA), long noncoding RNA (lncRNA), microRNA (miRNA), piwi-interacting RNA (piRNA), small interfering RNA (siRNA), transacting siRNA (tasiRNA), repeat associated siRNA (rasiRNA), 73K RNA, retrotransposons, a viral genome, a viroid, satellite RNA, or derivatives of these groups. In some embodiments, a nucleic acid is a mRNA encoding a protein.

Synthesis of mRNA mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application. The exact conditions will vary according to the specific application. The presence of these reagents is undesirable in the final product according to several embodiments and may thus be referred to as impurities and a preparation containing one or more of these impurities may be referred to as an impure preparation. In some embodiments, the in vitro transcribing occurs in a single batch.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for desired mRNA and a termination signal.

Desired mRNA sequence(s) according to the invention may be determined and incorporated into a DNA template using standard methods. For example, starting from a desired amino acid sequence (e.g., an enzyme sequence), a virtual reverse translation is carried out based on the degenerated genetic code. Optimization algorithms may then be used for selection of suitable codons. Typically, the G/C content can be optimized to achieve the highest possible G/C content on one hand, taking into the best possible account the frequency of the tRNAs according to codon usage on the other hand. The optimized RNA sequence can be established and displayed, for example, with the aid of an appropriate display device and compared with the original (wild-type) sequence. A secondary structure can also be analyzed to calculate stabilizing and destabilizing properties or, respectively, regions of the RNA.

Modified mRNA

In some embodiments, mRNA according to the present invention may be synthesized as unmodified or modified mRNA. Modified mRNA comprise nucleotide modifications in the RNA. A modified mRNA according to the invention can thus include nucleotide modification that are, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonyl-methyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g., from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, mRNAs may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, mRNAs may contain sugar modifications. A typical sugar modification is a chemical modification of the sugar of the nucleotides it contains including, but not limited to, sugar modifications chosen from the group consisting of 4'-thio-ribonucleotide (see, e.g., US Patent Application Publication No. US 2016/0031928, incorporated by reference herein), 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, mRNAs may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, O6-methylguanosine 5'-triphosphate, pseudouridine 5'-triphosphate, puromycin 5'-triphosphate or xanthosine 5'-triphosphate.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G(5')ppp(5')A and G(5')ppp(5')G.

In some embodiments, mRNAs include a 3' poly(A) tail structure. A poly-A tail on the 3' terminus of mRNA typically includes about 10 to 300 adenosine nucleotides (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Cap Structure

In some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G(5')ppp(5')A and G(5')ppp(5')G.

Naturally occurring cap structures comprise a 7-methyl guanosine that is linked via a triphosphate bridge to the 5'-end of the first transcribed nucleotide, resulting in a dinucleotide cap of $m^7G(5')ppp(5')N$, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is $m^7G(5')ppp(5')G$, which has been used as the dinucleotide cap in transcription with T7 or SP6 RNA polymerase in vitro to obtain RNAs having a cap structure in their 5'-termini. The prevailing method for the in vitro synthesis of caPPEd mRNA employs a pre-formed dinucleotide of the form $m^7G(5')ppp(5')G$ ("$m^7GpppG$") as an initiator of transcription.

To date, a usual form of a synthetic dinucleotide cap used in in vitro translation experiments is the Anti-Reverse Cap Analog ("ARCA") or modified ARCA, which is generally a modified cap analog in which the 2' or 3' OH group is replaced with —OCH$_3$.

Additional cap analogs include, but are not limited to, a chemical structures selected from the group consisting of $m^7GpppG$, $m^7GpppA$, $m^7GpppC$; unmethylated cap analogs (e.g., GpppG); dimethylated cap analog (e.g., $m^{2,7}GpppG$), trimethylated cap analog (e.g., $m^{2,2,7}GpppG$), dimethylated symmetrical cap analogs (e.g., $m^7Gpppm^7G$), or anti reverse cap analogs (e.g., ARCA; $m^{7,2'Ome}GpppG$, $m^{72'd}GpppG$, $m^{7,3'Ome}GpppG$, $m^{7,3'd}GpppG$ and their tetraphosphate derivatives) (see, e.g., Jemielity, J. et al., "Novel 'anti-reverse' cap analogs with superior translational properties", RNA, 9: 1108-1122 (2003)).

In some embodiments, a suitable cap is a 7-methyl guanylate ("m$^7$G") linked via a triphosphate bridge to the 5'-end of the first transcribed nucleotide, resulting in m$^7$G (5')ppp(5')N, where N is any nucleoside. A preferred embodiment of a m$^7$G cap utilized in embodiments of the invention is m$^7$G(5')ppp(5')G.

In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of m$^7$G cap analogs are known in the art, many of which are commercially available. These include the m$^7$GpppG described above, as well as the ARCA 3'-OCH$_3$ and 2'-OCH$_3$ cap analogs (Jemielity, J. et al., RNA, 9: 1108-1122 (2003)). Additional cap analogs for use in embodiments of the invention include N7-benzylated dinucleoside tetraphosphate analogs (described in Grudzien, E. et al., RNA, 10: 1479-1487 (2004)), phosphorothioate cap analogs (described in Grudzien-Nogalska, E., et al., RNA, 13: 1745-1755 (2007)), and cap analogs (including biotinylated cap analogs) described in U.S. Pat. Nos. 8,093,367 and 8,304,529, incorporated by reference herein.

Tail Structure

Typically, the presence of a "tail" serves to protect the mRNA from exonuclease degradation. The poly A tail is thought to stabilize natural messengers and synthetic sense RNA. Therefore, in certain embodiments a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)).

In some embodiments, mRNAs include a 3' poly(A) tail structure. Typically, the length of the poly A tail can be at least about 10, 50, 100, 200, 300, 400 at least 500 nucleotides. In some embodiments, a poly-A tail on the 3' terminus of mRNA typically includes about 10 to 300 adenosine nucleotides (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the length of the poly A or poly C tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression and/or polypeptide production in a target cell.

5' and 3' Untranslated Region

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

Pharmaceutical Formulations of Cationic Lipids and Nucleic Acids

In certain embodiments cationic lipids described herein described herein (e.g., a cationic lipid of Formula (I'), (I), (II), or (IIIa)-(IIIab) such as cationic lipids (1a)-(21a), (1b)-(21b), and (22)-(462)), as well as pharmaceutical and liposomal compositions comprising such lipids, can be used in formulations to facilitate the delivery of encapsulated materials (e.g., one or more polynucleotides such as mRNA) to, and subsequent transfection of one or more target cells. For example, in certain embodiments cationic lipids described herein (and compositions such as liposomal compositions comprising such lipids) are characterized as resulting in one or more receptor-mediated endocytosis, clathrin-mediated and caveolae-mediated endocytosis, phagocytosis and macropinocytosis, fusogenicity, endosomal or lysosomal disruption and/or releasable properties that afford such compounds advantages relative other similarly classified lipids.

According to the present invention, a nucleic acid, e.g., mRNA encoding a protein (e.g., a full length, fragment or portion of a protein) as described herein may be delivered via a delivery vehicle comprising a cationic lipid as described herein (e.g., a cationic lipid of Formula (I'), (I), (II), or (IIIa)-(IIIab) such as cationic lipids (1a)-(21a), (1b)-(21b), and (22)-(462)).

As used herein, the terms "delivery vehicle," "transfer vehicle," "nanoparticle" or grammatical equivalent, are used interchangeably.

For example, the present invention provides a composition (e.g., a pharmaceutical composition) comprising a cationic lipid described herein (e.g., a cationic lipid of Formula (I'), (I), (II), or (IIIa)-(IIIab) such as cationic lipids (1a)-(21a), (1b)-(21b), and (22)-(462)) and one or more polynucleotides. A composition (e.g., a pharmaceutical composition) may further comprise one or more cationic lipids, one or more non-cationic lipids, one or more cholesterol-based lipids and/or one or more PEG-modified lipids.

In certain embodiments a composition exhibits an enhanced (e.g., increased) ability to transfect one or more target cells. Accordingly, also provided herein are methods of transfecting one or more target cells. Such methods generally comprise the step of contacting the one or more target cells with the cationic lipids and/or pharmaceutical compositions disclosed herein (e.g., a liposomal formulation comprising a cationic lipid of Formula (I'), (I), (II), or (IIIa)-(IIIab) (e.g., any of cationic lipids (1a)-(21a), (1b)-(21b), and (22)-(462)) encapsulating one or more polynucleotides) such that the one or more target cells are transfected with the materials encapsulated therein (e.g., one or more polynucleotides). As used herein, the terms "transfect" or "transfection" refer to the intracellular introduction of one or more encapsulated materials (e.g., nucleic acids and/or polynucleotides) into a cell, or preferably into a target cell. The introduced polynucleotide may be stably or transiently maintained in the target cell. The term "transfection efficiency" refers to the relative amount of such encapsulated material (e.g., polynucleotides) up-taken by, introduced into and/or expressed by the target cell which is subject to transfection. In practice, transfection efficiency may be estimated by the amount of a reporter polynucleotide product produced by the target cells following transfection. In certain embodiments, the compounds and pharmaceutical compositions described herein demonstrate high transfection efficiencies thereby improving the likelihood that appropriate dosages of the encapsulated materials (e.g., one or more polynucleotides) will be delivered to the site of pathology and subsequently expressed, while at the same time minimizing potential systemic adverse effects or toxicity associated with the compound or their encapsulated contents.

Following transfection of one or more target cells by, for example, the polynucleotides encapsulated in the one or more lipid nanoparticles comprising the pharmaceutical or liposomal compositions disclosed herein, the production of the product (e.g., a polypeptide or protein) encoded by such polynucleotide may be preferably stimulated and the capability of such target cells to express the polynucleotide and produce, for example, a polypeptide or protein of interest is enhanced. For example, transfection of a target cell by one or more compounds or pharmaceutical compositions encapsulating mRNA will enhance (i.e., increase) the production of the protein or enzyme encoded by such mRNA.

Further, delivery vehicles described herein (e.g., liposomal delivery vehicles) may be prepared to preferentially distribute to other target tissues, cells or organs, such as the heart, lungs, kidneys, spleen. In embodiments, the lipid nanoparticles of the present invention may be prepared to achieve enhanced delivery to the target cells and tissues. For example, polynucleotides (e.g., mRNA) encapsulated in one or more of the compounds or pharmaceutical and liposomal compositions described herein can be delivered to and/or transfect targeted cells or tissues. In some embodiments, the encapsulated polynucleotides (e.g., mRNA) are capable of being expressed and functional polypeptide products produced (and in some instances excreted) by the target cell, thereby conferring a beneficial property to, for example the target cells or tissues. Such encapsulated polynucleotides (e.g., mRNA) may encode, for example, a hormone, enzyme, receptor, polypeptide, peptide or other protein of interest.

Liposomal Delivery Vehicles

In some embodiments, a composition is a suitable delivery vehicle. In embodiments, a composition is a liposomal delivery vehicle, e.g., a lipid nanoparticle.

The terms "liposomal delivery vehicle" and "liposomal composition" are used interchangeably.

Enriching liposomal compositions with one or more of the cationic lipids disclosed herein may be used as a means of improving (e.g., reducing) the toxicity or otherwise conferring one or more desired properties to such enriched liposomal composition (e.g., improved delivery of the encapsulated polynucleotides to one or more target cells and/or reduced in vivo toxicity of a liposomal composition). Accordingly, also contemplated are pharmaceutical compositions, and in particular liposomal compositions, that comprise one or more of the cationic lipids disclosed herein.

Thus, in certain embodiments, the compounds described herein (e.g., a cationic lipid of Formula (I'), (I), (II), or (IIIa)-(IIIab) such as cationic lipids (1a)-(21a), (1b)-(21b), and (22)-(462)) are cationic lipids that may be used as a component of a liposomal composition to facilitate or enhance the delivery and release of encapsulated materials (e.g., one or more therapeutic agents) to one or more target cells (e.g., by permeating or fusing with the lipid membranes of such target cells).

As used herein, liposomal delivery vehicles, e.g., lipid nanoparticles, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphophilic polymers and surfactants (e.g., polymerosomes, niosomes, etc.). In the context of the present invention, a liposomal delivery vehicle typically serves to transport a desired mRNA to a target cell or tissue.

In certain embodiments, such compositions (e.g., liposomal compositions) are loaded with or otherwise encapsulate materials, such as for example, one or more biologically-active polynucleotides (e.g., mRNA).

In embodiments, a composition (e.g., a pharmaceutical composition) comprises an mRNA encoding a protein, encapsulated within a liposome. In embodiments, a liposome comprises one or more cationic lipids, one or more non-cationic lipids, one or more cholesterol-based lipids and one or more PEG-modified lipids, and at least one cationic lipid is a cationic lipid as described herein (e.g., a cationic lipid of Formula (I'), (I), (II), or (IIIa)-(IIIab) such as cationic lipids (1a)-(21a), (1b)-(21b), and (22)-(462)). In embodiments, a composition comprises an mRNA encoding for a protein (e.g., any protein described herein). In embodiments, a composition comprises an mRNA encoding for cystic fibrosis transmembrane conductance regulator (CFTR) protein. In embodiments, a composition comprises an mRNA encoding for ornithine transcarbamylase (OTC) protein. In embodiments, an mRNA encodes for an antigen from an infectious agent.

In embodiments, a composition (e.g., a pharmaceutical composition) comprises a nucleic acid encapsulated within a liposome, wherein the liposome comprises any cationic lipid (e.g., a cationic lipid of Formula (I'), (I), (II), or (IIIa)-(IIIab) such as cationic lipids (1a)-(21a), (1b)-(21b), and (22)-(462)) as described herein.

In embodiments, a nucleic acid is an mRNA encoding a peptide or polypeptide. In embodiments, an mRNA encodes a peptide or polypeptide for use in the delivery to or treatment of the lung of a subject or a lung cell (e.g., an mRNA encodes cystic fibrosis transmembrane conductance regulator (CFTR) protein). In embodiments, an mRNA encodes a peptide or polypeptide for use in the delivery to or treatment of the liver of a subject or a liver cell (e.g., an mRNA encodes ornithine transcarbamylase (OTC) protein). In embodiments, an mRNA encodes for an antigen from an infectious agent. Still other exemplary mRNAs are described herein.

In embodiments, a liposomal delivery vehicle (e.g., a lipid nanoparticle) can have a net positive charge.

In embodiments, a liposomal delivery vehicle (e.g., a lipid nanoparticle) can have a net negative charge.

In embodiments, a liposomal delivery vehicle (e.g., a lipid nanoparticle) can have a net neutral charge.

In embodiments, a lipid nanoparticle that encapsulates a nucleic acid (e.g., mRNA encoding a peptide or polypeptide) comprises one or more cationic lipids described herein (e.g., a cationic lipid of Formula (I'), (I), (II), or (IIIa)-(IIIab) such as cationic lipids (1a)-(21a), (1b)-(21b), and (22)-(462)).

For example, the amount of a cationic lipid as described herein (e.g., a cationic lipid of Formula (I'), (I), (II), or (IIIa)-(IIIab) such as cationic lipids (1a)-(21a), (1b)-(21b), and (22)-(462)) in a composition can be described as a percentage ("wt %") of the combined dry weight of all lipids of a composition (e.g., the combined dry weight of all lipids present in a liposomal composition).

In embodiments of the pharmaceutical compositions described herein, a cationic lipid as described herein (e.g., a cationic lipid of Formula (I'), (I), (II), or (IIIa)-(IIIab) such as cationic lipids (1a)-(21a), (1b)-(21b), and (22)-(462)) is present in an amount that is about 0.5 wt % to about 30 wt % (e.g., about 0.5 wt % to about 20 wt %) of the combined dry weight of all lipids present in a composition (e.g., a liposomal composition).

In embodiments, a cationic lipid of Formula (I'), (I), (II), or (IIIa)-(IIIab) (e.g., any of cationic lipids (1a)-(21a), (1b)-(21b), and (22)-(462)) is present in an amount that is about 1 wt % to about 30 wt %, about 1 wt % to about 20 wt %, about 1 wt % to about 15 wt %, about 1 wt % to about 10 wt %, or about 5 wt % to about 25 wt % of the combined dry weight of all lipids present in a composition (e.g., a liposomal composition). In embodiments, a cationic lipid of Formula (I'), (I), (II), or (IIIa)-(IIIab) (e.g., any of cationic lipids (1a)-(21a), (1b)-(21b), and (22)-(462)) is present in an amount that is about 0.5 wt % to about 5 wt %, about 1 wt % to about 10 wt %, about 5 wt % to about 20 wt %, or about 10 wt % to about 20 wt % of the combined molar amounts of all lipids present in a composition such as a liposomal delivery vehicle.

In embodiments, the amount of a cationic lipid of Formula (I'), (I), (II), or (IIIa)-(IIIab) (e.g., any of cationic lipids (1a)-(21a), (1b)-(21b), and (22)-(462)) is present in an amount that is at least about 5 wt %, about 10 wt %, about 15 wt %, about 20 wt %, about 25 wt %, about 30 wt %, about 35 wt %, about 40 wt %, about 45 wt %, about 50 wt %, about 55 wt %, about 60 wt %, about 65 wt %, about 70 wt %, about 75 wt %, about 80 wt %, about 85 wt %, about 90 wt %, about 95 wt %, about 96 wt %, about 97 wt %, about 98 wt %, or about 99 wt % of the combined dry weight of total lipids in a composition (e.g., a liposomal composition).

In embodiments, the amount of a cationic lipid of Formula (I'), (I), (II), or (IIIa)-(IIIab) (e.g., any of cationic lipids (1a)-(21a), (1b)-(21b), and (22)-(462)) is present in an amount that is no more than about 5 wt %, about 10 wt %, about 15 wt %, about 20 wt %, about 25 wt %, about 30 wt %, about 35 wt %, about 40 wt %, about 45 wt %, about 50 wt %, about 55 wt %, about 60 wt %, about 65 wt %, about 70 wt %, about 75 wt %, about 80 wt %, about 85 wt %, about 90 wt %, about 95 wt %, about 96 wt %, about 97 wt %, about 98 wt %, or about 99 wt % of the combined dry weight of total lipids in a composition (e.g., a liposomal composition).

In embodiments, a composition (e.g., a liposomal delivery vehicle such as a lipid nanoparticle) comprises about 0.1 wt % to about 20 wt % (e.g., about 0.1 wt % to about 15 wt %) of a cationic lipid described herein (e.g., a cationic lipid of Formula (I'), (I), (II), or (IIIa)-(IIIab) such as cationic lipids (1a)-(21a), (1b)-(21b), and (22)-(462)). In embodiments, a delivery vehicle (e.g., a liposomal delivery vehicle such as a lipid nanoparticle) comprises about 0.5 wt %, about 1 wt %, about 3 wt %, about 5 wt %, or about 10 wt % a cationic lipid described herein (e.g., a cationic lipid of Formula (I'), (I), (II), or (IIIa)-(IIIab) such as cationic lipids (1a)-(21a), (1b)-(21b), and (22)-(462)). In embodiments, a delivery vehicle (e.g., a liposomal delivery vehicle such as a lipid nanoparticle) comprises up to about 0.5 wt %, about 1 wt %, about 3 wt %, about 5 wt %, about 10 wt %, about 15 wt %, or about 20 wt % of a cationic lipid described herein (e.g., a cationic lipid of Formula (I'), (I), (II), or (IIIa)-(IIIab) such as cationic lipids (1a)-(21a), (1b)-(21b), and (22)-(462)). In embodiments, the percentage results in an improved beneficial effect (e.g., improved delivery to targeted tissues such as the liver or the lung).

The amount of a cationic lipid of Formula (I'), (I), (II), or (IIIa)-(IIIab) (e.g., any of cationic lipids (1a)-(21a), (1b)-(21b), and (22)-(462)) in a composition also can be described as a percentage ("mol %") of the combined molar amounts of total lipids of a composition (e.g., the combined molar amounts of all lipids present in a liposomal delivery vehicle).

In embodiments of pharmaceutical compositions described herein, a cationic lipid of Formula (I'), (I), (II), or (IIIa)-(IIIab) (e.g., any of cationic lipids (1a)-(21a), (1b)-(21b), and (22)-(462)) is present in an amount that is about 0.5 mol % to about 30 mol % (e.g., about 0.5 mol % to about 20 mol %) of the combined molar amounts of all lipids present in a composition such as a liposomal delivery vehicle.

In embodiments, a cationic lipid of Formula (I'), (I), (II), or (IIIa)-(IIIab) (e.g., any of cationic lipids (1a)-(21a), (1b)-(21b), and (22)-(462)) is present in an amount that is about 0.5 mol % to about 5 mol %, about 1 mol % to about 10 mol %, about 5 mol % to about 20 mol %, or about 10 mol % to about 20 mol % of the combined molar amounts of all lipids present in a composition such as a liposomal delivery vehicle. In embodiments, a cationic lipid of Formula (I'), (I), (II), or (IIIa)-(IIIab) (e.g., any of cationic lipids (1a)-(21a), (1b)-(21b), and (22)-(462)) is present in an amount that is about 1 mol % to about 30 mol %, about 1 mol % to about 20 mol %, about 1 mol % to about 15 mol %, about 1 mol % to about 10 mol %, or about 5 mol % to about 25 mol % of the combined dry weight of all lipids present in a composition such as a liposomal delivery vehicle In certain embodiments, a cationic lipid described herein (e.g., a cationic lipid of Formula (I'), (I), (II), or (IIIa)-(IIIab) such as cationic lipids (1a)-(21a), (1b)-(21b), and (22)-(462)) can comprise from about 0.1 mol % to about 50 mol %, or from 0.5 mol % to about 50 mol %, or from about 1 mol % to about 25 mol %, or from about 1 mol % to about 10 mol % of the total amount of lipids in a composition (e.g., a liposomal delivery vehicle).

In certain embodiments, cationic lipids described herein (e.g., a cationic lipid of Formula (I'), (I), (II), or (IIIa)-(IIIab) such as cationic lipids (1a)-(21a), (1b)-(21b), and (22)-(462)) can comprise greater than about 0.1 mol %, or greater than about 0.5 mol %, or greater than about 1 mol %, or greater than about 5 mol % of the total amount of lipids in the lipid nanoparticle.

In certain embodiments, cationic lipid described herein (e.g., a cationic lipid of Formula (I'), (I), (II), or (IIIa)-(IIIab) such as cationic lipids (1a)-(21a), (1b)-(21b), and (22)-(462)) can comprise less than about 25 mol %, or less than about 10 mol %, or less than about 5 mol %, or less than about 1 mol % of the total amount of lipids in a composition (e.g., a liposomal delivery vehicle).

In embodiments, the amount of a cationic lipid of Formula (I'), (I), (II), or (IIIa)-(IIIab) (e.g., any of cationic lipids (1a)-(21a), (1b)-(21b), and (22)-(462)) is present in an amount that is at least about 5 mol %, about 10 mol %, about 15 mol %, about 20 mol %, about 25 mol %, about 30 mol %, about 35 mol %, about 40 mol %, about 45 mol %, about 50 mol %, about 55 mol %, about 60 mol %, about 65 mol %, about 70 mol %, about 75 mol %, about 80 mol %, about 85 mol %, about 90 mol %, about 95 mol %, about 96 mol %, about 97 mol %, about 98 mol %, or about 99 mol % of the combined dry weight of total lipids in a composition (e.g., a liposomal composition).

In embodiments, the amount of a cationic lipid of Formula (I'), (I), (II), or (IIIa)-(IIIab) (e.g., any of cationic lipids (1a)-(21a), (1b)-(21b), and (22)-(462)) is present in an amount that is no more than about 5 mol %, about 10 mol %, about 15 mol %, about 20 mol %, about 25 mol %, about 30 mol %, about 35 mol %, about 40 mol %, about 45 mol %, about 50 mol %, about 55 mol %, about 60 mol %, about 65 mol %, about 70 mol %, about 75 mol %, about 80 mol %, about 85 mol %, about 90 mol %, about 95 mol %, about 96 mol %, about 97 mol %, about 98 mol %, or about 99 mol % of the combined dry weight of total lipids in a composition (e.g., a liposomal composition).

In embodiments, the percentage results in an improved beneficial effect (e.g., improved delivery to targeted tissues such as the liver or the lung).

In embodiments, a composition further comprises one more lipids (e.g., one more lipids selected from the group consisting of one or more cationic lipids, one or more non-cationic lipids, and one or more PEG-modified lipids).

In certain embodiments, such pharmaceutical (e.g., liposomal) compositions comprise one or more of a PEG-modified lipid, a non-cationic lipid and a cholesterol lipid. In embodiments, such pharmaceutical (e.g., liposomal) compositions comprise: one or more PEG-modified lipids; one or more non-cationic lipids; and one or more cholesterol lipids. In embodiments, such pharmaceutical (e.g., liposomal) compositions comprise: one or more PEG-modified lipids and one or more cholesterol lipids.

In embodiments, a composition (e.g., lipid nanoparticle) that encapsulates a nucleic acid (e.g., mRNA encoding a peptide or polypeptide) comprises one or more cationic lipids described herein (e.g., a cationic lipid of Formula (I'), (I), (II), or (IIIa)-(IIIab) such as cationic lipids (1a)-(21a), (1b)-(21b), and (22)-(462)) and one or more lipids selected from the group consisting of a cationic lipid, a non-cationic lipid, and a PEGylated lipid.

In embodiments, a composition (e.g., lipid nanoparticle) that encapsulates a nucleic acid (e.g., mRNA encoding a peptide or polypeptide) comprises one or more cationic lipids described herein (e.g., a cationic lipid of Formula (I'), (I), (II), or (IIIa)-(IIIab) such as cationic lipids (1a)-(21a), (1b)-(21b), and (22)-(462)); one or more lipids selected from the group consisting of a cationic lipid, a non-cationic lipid, and a PEGylated lipid; and further comprises a cholesterol-based lipid.

In embodiments, a lipid nanoparticle that encapsulates a nucleic acid (e.g., mRNA encoding a peptide or polypeptide) comprises one or more cationic lipids described herein (e.g., a cationic lipid of Formula (I'), (I), (II), or (IIIa)-(IIIab) such as cationic lipids (1a)-(21a), (1b)-(21b), and (22)-(462)), as well as one or more lipids selected from the group consisting of a cationic lipid, a non-cationic lipid, a PEGylated lipid, and a cholesterol-based lipid.

In embodiments of lipid nanoparticles described herein, a lipid nanoparticle comprises one or more cationic lipids described herein (e.g., a cationic lipid of Formula (I'), (I), (II), or (IIIa)-(IIIab) such as cationic lipids (1a)-(21a), (1b)-(21b), and (22)-(462)), a non-cationic lipid (e.g., DOPE), a PEGylated lipid (e.g., DMG-PEG2000), and a cholesterol-based lipid (e.g., cholesterol).

According to various embodiments, the selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus, the molar ratios may be adjusted accordingly.

Further Cationic Lipids

In addition to any of the cationic lipids described herein (e.g., a cationic lipid of Formula (I'), (I), (II), or (IIIa)-(IIIab) such as cationic lipids (1a)-(21a), (1b)-(21b), and (22)-(462)), a composition may comprise one or more further cationic lipids.

In some embodiments, liposomes may comprise one or more further cationic lipids. As used herein, the phrase "cationic lipid" refers to any of a number of lipid species that have a net positive charge at a selected pH, such as physiological pH. Several cationic lipids have been described in the literature, many of which are commercially available.

Particularly suitable further cationic lipids for use in the compositions and methods of the invention include those described in international patent publications WO 2010/053572 (and particularly, C12-200 described at paragraph [00225]) and WO 2012/170930, both of which are incorporated herein by reference. In certain embodiments, the compositions and methods of the invention employ a lipid nanoparticles comprising a further cationic lipid described in U.S. provisional patent application 61/617,468, filed Mar. 29, 2012 (incorporated herein by reference), such as, e.g, (15Z, 18Z)—N,N-dimethyl-6-(9Z, 12Z)-octadeca-9,12-dien-1-yl)tetracosa-15,18-dien-1-amine (HGT5000), (15Z, 18Z)—N,N-dimethyl-6-((9Z, 12Z)-octadeca-9,12-dien-1-yl)tetracosa-4,15,18-trien-1-amine (HGT5001), and (15Z,18Z)—N,N-dimethyl-6-((9Z, 12Z)-octadeca-9,12-dien-1-yl)tetracosa-5, 15, 18-trien-1-amine (HGT5002).

In some embodiments, a composition (e.g., a liposomal composition) comprises a further cationic lipid described in WO 2013/063468, filed Oct. 26, 2012 and in U.S. provisional application 61/953,516, filed Mar. 14, 2014, both of which are incorporated by reference herein.

In particular embodiments, a composition (e.g., a liposomal composition) comprises a further cationic lipid cKK-E12, or (3,6-bis(4-(bis(2-hydroxydodecyl)amino)butyl)piperazine-2,5-dione). The structure of cKK-E12 is shown below:

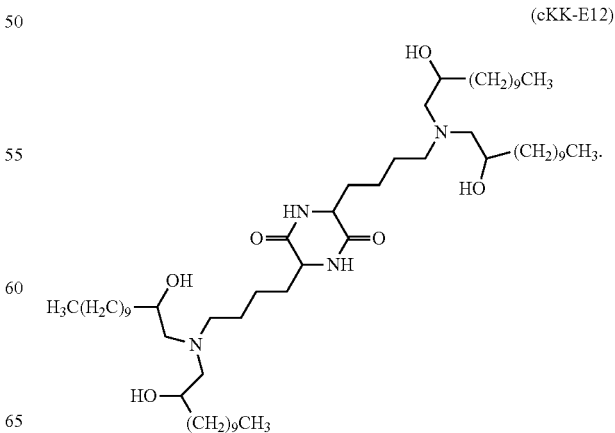

(cKK-E12)

In some embodiments, a further cationic lipid may be N-[1-(2,3-dioleyloxy)propyl]-N,N,N-trimethylammonium chloride or "DOTMA" (Feigner et al. (Proc. Nat'l Acad. Sci. 84, 7413 (1987); U.S. Pat. No. 4,897,355). DOTMA can be formulated alone or can be combined with a neutral lipid (e.g., dioleoylphosphatidyl-ethanolamine or "DOPE") or still other cationic or non-cationic lipids into a liposomal transfer vehicle or a lipid nanoparticle, and such liposomes can be used to enhance the delivery of nucleic acids into target cells. Other suitable further cationic lipids include, for example, 5-carboxyspermylglycinedioctadecylamide or "DOGS"; 2,3-dioleyloxy-N-[2(spermine-carboxamido) ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761); 1,2-dioleoyl-3-Dimethylammonium-Propane or "DODAP"; or 1,2-dioleoyl-3-trimethylammonium-propane or "DOTAP".

Additional exemplary further cationic lipids also include 1,2-distearyloxy-N,N-dimethyl-3-aminopropane or "DSDMA"; 1,2-dioleyloxy-N,N-dimethyl-3-aminopropane or "DODMA"; 1,2-dilinoleyloxy-N,N-dimethyl-3-aminopropane or "DLinDMA"; 1,2-dilinolenyloxy-N,N-dimethyl-3-aminopropane or "DLenDMA"; N-dioleyl-N,N-dimethyl-ammonium chloride or "DODAC"; N,N-distearyl-N,N-dimethylarnrnonium bromide or "DDAB"; N-(1,2-dimyristyloxyprop-3-yl)-N,N-dimethyl-N-hydroxyethyl ammonium bromide or "DMRIE"; 3-dimethylamino-2-(cholest-5-en-3-beta-oxybutan-4-oxy)-1-(cis,cis-9,12-octadecadienoxy)propane or "CLinDMA"; 2-[5'-(cholest-5-en-3-beta-oxy)-3'-oxapentoxy)-3-dimethy 1-1-(cis,cis-9', 1-2'-octadecadienoxy)propane or "CpLinDMA"; N,N-dimethyl-3,4-dioleyloxybenzylamine or "DMOBA"; 1,2-N,N'-dioleylcarbamyl-3-dimethylaminopropane or "DOcarbDAP"; 2,3-dilinoleoyloxy-N,N-dimethylpropylamine or "DLinDAP"; 1,2-N,N'-Dilinoleylcarbamyl-3-dimethylaminopropane or "DLincarbDAP"; 1,2-dilinoleoyl-carbamyl-3-dimethylaminopropane or "DLinCDAP"; 2,2-dilinoleyl-4-dimethylaminomethyl-[1,3]-dioxolane or "DLin-DMA"; 2,2-dilinoleyl-4-dimethylaminoethyl-[1,3]-dioxolane or "DLin-K-XTC2-DMA"; and 2-(2,2-di((9Z, 12Z)-octadeca-9,I 2-dien-1-yl)-1,3-dioxolan-4-yl)-N,N-dimethylethanamine (DLin-KC2-DMA)) (see WO 2010/042877; Semple et al., Nature Biotech. 28: 172-176 (2010)), or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1). In some embodiments, one or more of the further cationic lipids comprise at least one of an imidazole, dialkylamino, or guanidinium moiety.

In some embodiments, the one or more further cationic lipids may be chosen from XTC (2,2-dilinoleyl-4-dimethylaminoethyl-[1,3]-dioxolane), MC3 (((6Z,9Z,28Z,31Z)-heptatriaconta-6,9,28,31-tetraen-19-yl 4-(dimethylamino) butanoate), ALNY-100 ((3aR,5s,6aS)—N,N-dimethyl-2,2-di((9Z,12Z)-octadeca-9,12-dienyl)tetrahydro-3aH-cyclopenta[d] [1,3]dioxol-5-amine)), NC98-5 (4,7,13-tris(3-oxo-3-(undecylamino)propyl)-N1,N16-diundecyl-4,7,10, 13-tetraazahexadecane-1,16-diamide), DODAP (1,2-dioleyl-3-dimethylammonium propane), HGT4003 (WO 2012/170889, the teachings of which are incorporated herein by reference in their entirety), ICE (WO 2011/068810, the teachings of which are incorporated herein by reference in their entirety), HGT5000 (U.S. Provisional Patent Application No. 61/617,468, the teachings of which are incorporated herein by reference in their entirety) or HGT5001 (cis or trans) (Provisional Patent Application No. 61/617,468), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869).

In some embodiments, the percentage of total cationic lipids in a composition (e.g., a liposomal composition) may be no more than 10%, no more than 20%, no more than 30%, no more than 40%, no more than 50%, no more than 60%, no more than 70%, no more than 80%, no more than 90%, or no more than 95% of total lipids as measured by molar ratios (mol %) or by weight (wt %).

In some embodiments, the percentage of total cationic lipids in a composition (e.g., a liposomal composition) may be greater than 10%, greater than 20%, greater than 30%, greater than 40%, greater than 50%, greater than 60%, greater than 70%, greater than 80%, greater than 90%, or greater than 95% of total lipids as measured by molar ratios (mol %) or by weight (wt %).

In some embodiments, total cationic lipid(s) constitute(s) about 30-50% (e.g., about 30-45%, about 30-40%, about 35-50%, about 35-45%, or about 35-40%) of the liposome by weight. In some embodiments, the cationic lipid constitutes about 30%, about 35%, about 40%, about 45%, or about 50% of a composition (e.g., a liposomal composition) by molar ratio. In some embodiments, total cationic lipid(s) constitute(s) about 30-50% (e.g., about 30-45%, about 30-40%, about 35-50%, about 35-45%, or about 35-40%) of the liposome by weight. In some embodiments, the cationic lipid constitutes about 30%, about 35%, about 40%, about 45%, or about 50% of a composition (e.g., a liposomal composition) by weight.

Non-Cationic/Helper Lipids

Compositions (e.g., liposomal compositions) may also comprise one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-I-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, I-stearoyl-2-oleoyl-phosphatidyethanolamine (SOPE), or a mixture thereof.

In embodiments, a non-cationic or helper lipid is dioleoylphosphatidylethanolamine (DOPE).

In some embodiments, a non-cationic lipid is a neutral lipid, i.e., a lipid that does not carry a net charge in the conditions under which the composition is formulated and/or administered.

In some embodiments, a non-cationic lipid may be present in a molar ratio (mol %) of about 5% to about 90%, about 5% to about 70%, about 5% to about 50%, about 5% to about 40%, about 5% to about 30%, about 10% to about 70%, about 10% to about 50%, or about 10% to about 40% of the total lipids present in a composition. In some embodiments, total non-cationic lipids may be present in a molar ratio (mol %) of about 5% to about 90%, about 5% to about 70%, about 5% to about 50%, about 5% to about 40%, about 5% to about 30%, about 10% to about 70%, about 10% to about 50%, or about 10% to about 40% of the total lipids present in a composition. In some embodiments, the percentage of non-cationic lipid in a liposome may be greater than about 5 mol %, greater than about 10 mol %, greater than about 20 mol %, greater than about 30 mol %, or greater than about 40 mol %. In some embodiments, the percentage total non-cationic lipids in a liposome may be greater than about 5 mol %, greater than about 10 mol %, greater than about 20 mol %, greater than about 30 mol %, or greater than about 40 mol %. In some embodiments, the percentage of non-cationic lipid in a liposome is no more than about 5 mol %, no more than about 10 mol %, no more than about 20 mol %, no more than about 30 mol %, or no more than about 40 mol %. In some embodiments, the percentage total non-cationic lipids in a liposome may be no more than about 5 mol %, no more than about 10 mol %, no more than about 20 mol %, no more than about 30 mol %, or no more than about 40 mol %.

In some embodiments, a non-cationic lipid may be present in a weight ratio (wt %) of about 5% to about 90%, about 5% to about 70%, about 5% to about 50%, about 5% to about 40%, about 5% to about 30%, about 10% to about 70%, about 10% to about 50%, or about 10% to about 40% of the total lipids present in a composition. In some embodiments, total non-cationic lipids may be present in a weight ratio (wt %) of about 5% to about 90%, about 5% to about 70%, about 5% to about 50%, about 5% to about 40%, about 5% to about 30%, about 10% to about 70%, about 10% to about 50%, or about 10% to about 40% of the total lipids present in a composition. In some embodiments, the percentage of non-cationic lipid in a liposome may be greater than about 5 wt %, greater than about 10 wt %, greater than about 20 wt %, greater than about 30 wt %, or greater than about 40 wt %. In some embodiments, the percentage total non-cationic lipids in a liposome may be greater than about 5 wt %, greater than about 10 wt %, greater than about 20 wt %, greater than about 30 wt %, or greater than about 40 wt %. In some embodiments, the percentage of non-cationic lipid in a liposome is no more than about 5 wt %, no more than about 10 wt %, no more than about 20 wt %, no more than about 30 wt %, or no more than about 40 wt %. In some embodiments, the percentage total non-cationic lipids in a liposome may be no more than about 5 wt %, no more than about 10 wt %, no more than about 20 wt %, no more than about 30 wt %, or no more than about 40 wt %.

Cholesterol-Based Lipids

In some embodiments, a composition (e.g., a liposomal composition) comprises one or more cholesterol-based lipids. For example, suitable cholesterol-based lipids include cholesterol and, for example, DC-Chol (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or imidazole cholesterol ester (ICE), which has the following structure,

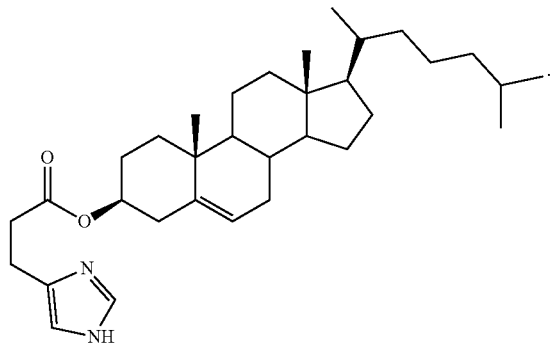

("ICE")

In embodiments, a cholesterol-based lipid is cholesterol.

In some embodiments, a cholesterol-based lipid may be present in a molar ratio (mol %) of about 1% to about 30%, or about 5% to about 20% of the total lipids present in a liposome. In some embodiments, the percentage of cholesterol-based lipid in the lipid nanoparticle may be greater than about 5 mol %, greater than about 10 mol %, greater than about 20 mol %, greater than about 30 mol %, or greater than about 40 mol %. In some embodiments, the percentage of cholesterol-based lipid in the lipid nanoparticle may be no more than about 5 mol %, no more than about 10 mol %, no more than about 20 mol %, no more than about 30 mol %, or no more than about 40 mol %.

In some embodiments, a cholesterol-based lipid may be present in a weight ratio (wt %) of about 1% to about 30%, or about 5% to about 20% of the total lipids present in a liposome. In some embodiments, the percentage of cholesterol-based lipid in the lipid nanoparticle may be greater than about 5 wt %, greater than about 10 wt %, greater than about 20 wt %, greater than about 30 wt %, or greater than about 40 wt %. In some embodiments, the percentage of cholesterol-based lipid in the lipid nanoparticle may be no more than about 5 wt %, no more than about 10 wt %, no more than about 20 wt %, no more than about 30 wt %, or no more than about 40 wt %.

PEGylated Lipids

In some embodiments, a composition (e.g., a liposomal composition) comprises one or more PEGylated lipids.

For example, the use of polyethylene glycol (PEG)-modified phospholipids and derivatized lipids such as derivatized ceramides (PEG-CER), including N-octanoyl-sphingosine-1-[succinyl(methoxy polyethylene glycol)-2000] (C8 PEG-2000 ceramide) is also contemplated by the present invention in combination with one or more of the cationic and, in some embodiments, other lipids together which comprise the liposome. In some embodiments, particularly useful exchangeable lipids are PEG-ceramides having shorter acyl chains (e.g., $C_{14}$ or $C_{18}$).

Contemplated PEG-modified lipids (also referred to herein as a PEGylated lipid, which term is interchangeable with PEG-modified lipid) include, but are not limited to, a polyethylene glycol chain of up to 5 kDa in length covalently attached to a lipid with alkyl chain(s) of $C_6$-$C_{20}$ length. In some embodiments, a PEG-modified or PEGylated lipid is PEGylated cholesterol or PEG-2K. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613).

In embodiments, a PEG-modified lipid is 1,2-dimyristoyl-sn-glycerol, methoxypolyethylene glycol (DMG-PEG2000).

A PEG-modified phospholipid and derivatized lipids of the present invention may be present in a molar ratio (mol %) from about 0% to about 15%, about 0.5% to about 15%, about 1% to about 15%, about 4% to about 10%, or about 2% of the total lipid present in the composition (e.g., a liposomal composition).

A PEG-modified phospholipid and derivatized lipids of the present invention may be present in a weight ratio (wt %) from about 0% to about 15%, about 0.5% to about 15%, about 1% to about 15%, about 4% to about 10%, or about 2% of the total lipid present in the composition (e.g., a liposomal composition).

Pharmaceutical Formulations and Therapeutic Uses

Cationic lipids described herein (e.g., a cationic lipid of Formula (I'), (I), (II), or (IIIa)-(IIIab) such as cationic lipids (1a)-(21a), (1b)-(21b), and (22)-(462)) may be used in the preparation of compositions (e.g., to construct liposomal compositions) that facilitate or enhance the delivery and release of encapsulated materials (e.g., one or more therapeutic polynucleotides) to one or more target cells (e.g., by permeating or fusing with the lipid membranes of such target cells).

For example, when a liposomal composition (e.g., a lipid nanoparticle) comprises or is otherwise enriched with one or more of the compounds disclosed herein, the phase transition in the lipid bilayer of the one or more target cells may facilitate the delivery of the encapsulated materials (e.g., one or more therapeutic polynucleotides encapsulated in a lipid nanoparticle) into the one or more target cells.

Similarly, in certain embodiments cationic lipids described herein (e.g., a cationic lipid of Formula (I'), (I), (II), or (IIIa)-(IIIab) such as cationic lipids (1a)-(21a), (1b)-(21b), and (22)-(462)) may be used to prepare liposomal vehicles that are characterized by their reduced toxicity in vivo. In certain embodiments, the reduced toxicity is a function of the high transfection efficiencies associated with the compositions disclosed herein, such that a reduced quantity of such composition may administered to the subject to achieve a desired therapeutic response or outcome.

Thus, pharmaceutical formulations comprising a cationic lipid described herein (e.g., a cationic lipid of Formula (I'), (I), (II), or (IIIa)-(IIIab) such as cationic lipids (1a)-(21a), (1b)-(21b), and (22)-(462)) and nucleic acids provided by the present invention may be used for various therapeutic purposes. To facilitate delivery of nucleic acids in vivo, a cationic lipid (e.g., a cationic lipid of Formula (I'), (I), (II), or (IIIa)-(IIIab) such as cationic lipids (1a)-(21a), (1b)-(21b), and (22)-(462)) and nucleic acids can be formulated in combination with one or more additional pharmaceutical carriers, targeting ligands or stabilizing reagents. In some embodiments, a cationic lipid (e.g., a cationic lipid of Formula (I'), (I), (II), or (IIIa)-(IIIab) such as cationic lipids (1a)-(21a), (1b)-(21b), and (22)-(462)) can be formulated via pre-mixed lipid solution. In other embodiments, a composition comprising a cationic lipid (e.g., a cationic lipid of Formula (I'), (I), (II), or (IIIa)-(IIIab) such as cationic lipids (1a)-(21a), (1b)-(21b), and (22)-(462)) can be formulated using post-insertion techniques into the lipid membrane of the nanoparticles. Techniques for formulation and administration of drugs may be found in "Remington's Pharmaceutical Sciences," Mack Publishing Co., Easton, Pa., latest edition.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal. In particular embodiments, the intramuscular administration is to a muscle selected from the group consisting of skeletal muscle, smooth muscle and cardiac muscle. In some embodiments the administration results in delivery of the nucleic acids to a muscle cell. In some embodiments the administration results in delivery of the nucleic acids to a hepatocyte (i.e., liver cell). In embodiments, administration is intramuscular. In embodiments, administration is intravenous.

Alternatively or additionally, pharmaceutical formulations of the invention may be administered in a local rather than systemic manner, for example, via injection of the pharmaceutical formulation directly into a targeted tissue, preferably in a sustained release formulation. Local delivery can be affected in various ways, depending on the tissue to be targeted. Exemplary tissues in which delivered mRNA may be delivered and/or expressed include, but are not limited to the liver, kidney, heart, spleen, serum, brain, skeletal muscle, lymph nodes, skin, and/or cerebrospinal fluid. In embodiments, the tissue to be targeted in the liver. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection.

In embodiments, administration is via pulmonary delivery. As used herein, pulmonary delivery refers to delivery to lung via, e.g., nasal cavity, trachea, bronchi, bronchioles, and/or other pulmonary system. In embodiments, a composition described herein is formulated for nebulization. In embodiments, the delivery vehicle may be in an aerosolized composition which can be inhaled. In embodiments, pulmonary delivery involves inhalation (e.g., for nasal, tracheal, or bronchial delivery). In embodiments, a composition is nebulized prior to inhalation.

The present invention provides methods for delivering a composition having full-length mRNA molecules encoding a peptide or polypeptide of interest for use in the treatment of a subject, e.g., a human subject or a cell of a human subject or a cell that is treated and delivered to a human subject.

Accordingly, in certain embodiments the present invention provides a method for producing a therapeutic composition comprising full-length mRNA that encodes a peptide or polypeptide for use in the delivery to or treatment of the lung of a subject or a lung cell. In certain embodiments the present invention provides a method for producing a therapeutic composition having full-length mRNA that encodes for cystic fibrosis transmembrane conductance regulator (CFTR) protein. In certain embodiments the present invention provides a method for producing a therapeutic composition having full-length mRNA that encodes for ATP-binding cassette sub-family A member 3 protein. In certain embodiments the present invention provides a method for producing a therapeutic composition having full-length mRNA that encodes for dynein axonemal intermediate chain 1 protein. In certain embodiments the present invention provides a method for producing a therapeutic composition having full-length mRNA that encodes for dynein axonemal heavy chain 5 (DNAH5) protein. In certain embodiments the present invention provides a method for producing a therapeutic composition having full-length mRNA that encodes for alpha-1-antitrypsin protein. In certain embodiments the present invention provides a method for producing a therapeutic composition having full-length mRNA that encodes for forkhead box P3 (FOXP3) protein. In certain embodiments the present invention provides a method for producing a therapeutic composition having full-length mRNA that encodes one or more surfactant protein, e.g., one or more of surfactant A protein, surfactant B protein, surfactant C protein, and surfactant D protein.

In certain embodiments the present invention provides a method for producing a therapeutic composition having full-length mRNA that encodes a peptide or polypeptide for use in the delivery to or treatment of the liver of a subject or a liver cell. Such peptides and polypeptides can include those associated with a urea cycle disorder, associated with a lysosomal storage disorder, with a glycogen storage disorder, associated with an amino acid metabolism disorder, associated with a lipid metabolism or fibrotic disorder, associated with methylmalonic acidemia, or associated with any other metabolic disorder for which delivery to or treatment of the liver or a liver cell with enriched full-length mRNA provides therapeutic benefit.

In certain embodiments the present invention provides a method for producing a therapeutic composition having full-length mRNA that encodes for a protein associated with a urea cycle disorder. In certain embodiments the present invention provides a method for producing a therapeutic composition having full-length mRNA that encodes for ornithine transcarbamylase (OTC) protein. In certain embodiments the present invention provides a method for producing a therapeutic composition having full-length mRNA that encodes for arginosuccinate synthetase 1 protein. In certain embodiments the present invention provides a method for producing a therapeutic composition having full-length mRNA that encodes for carbamoyl phosphate synthetase I protein. In certain embodiments the present invention provides a method for producing a therapeutic composition having full-length mRNA that encodes for arginosuccinate lyase protein. In certain embodiments the present invention provides a method for producing a therapeutic composition having full-length mRNA that encodes for arginase protein.

In certain embodiments the present invention provides a method for producing a therapeutic composition having full-length mRNA that encodes for a protein associated with a lysosomal storage disorder. In certain embodiments the present invention provides a method for producing a therapeutic composition having full-length mRNA that encodes for alpha galactosidase protein. In certain embodiments the present invention provides a method for producing a therapeutic composition having full-length mRNA that encodes for glucocerebrosidase protein. In certain embodiments the present invention provides a method for producing a therapeutic composition having full-length mRNA that encodes for iduronate-2-sulfatase protein. In certain embodiments the present invention provides a method for producing a therapeutic composition having full-length mRNA that encodes for iduronidase protein. In certain embodiments the present invention provides a method for producing a therapeutic composition having full-length mRNA that encodes for N-acetyl-alpha-D-glucosaminidase protein. In certain embodiments the present invention provides a method for producing a therapeutic composition having full-length mRNA that encodes for heparan N-sulfatase protein. In certain embodiments the present invention provides a method for producing a therapeutic composition having full-length mRNA that encodes for galactosamine-6 sulfatase protein. In certain embodiments the present invention provides a method for producing a therapeutic composition having full-length mRNA that encodes for beta-galactosidase protein. In certain embodiments the present invention provides a method for producing a therapeutic composition having full-length mRNA that encodes for lysosomal lipase protein. In certain embodiments the present invention provides a method for producing a therapeutic composition having full-length mRNA that encodes for arylsulfatase B (N-acetylgalactosamine-4-sulfatase) protein. In certain embodiments the present invention provides a method for producing a therapeutic composition having full-length mRNA that encodes for transcription factor EB (TFEB).

In certain embodiments the present invention provides a method for producing a therapeutic composition having full-length mRNA that encodes for a protein associated with a glycogen storage disorder. In certain embodiments the present invention provides a method for producing a therapeutic composition having full-length mRNA that encodes for acid alpha-glucosidase protein. In certain embodiments the present invention provides a method for producing a therapeutic composition having full-length mRNA that encodes for glucose-6-phosphatase (G6PC) protein. In certain embodiments the present invention provides a method for producing a therapeutic composition having full-length mRNA that encodes for liver glycogen phosphorylase protein. In certain embodiments the present invention provides a method for producing a therapeutic composition having full-length mRNA that encodes for muscle phosphoglycerate mutase protein. In certain embodiments the present invention provides a method for producing a therapeutic composition having full-length mRNA that encodes for glycogen debranching enzyme.

In certain embodiments the present invention provides a method for producing a therapeutic composition having full-length mRNA that encodes for a protein associated with amino acid metabolism. In certain embodiments the present invention provides a method for producing a therapeutic composition having full-length mRNA that encodes for phenylalanine hydroxylase enzyme. In certain embodiments the present invention provides a method for producing a therapeutic composition having full-length mRNA that encodes for glutaryl-CoA dehydrogenase enzyme. In certain embodiments the present invention provides a method for producing a therapeutic composition having full-length mRNA that encodes for propionyl-CoA carboxylase enzyme. In certain embodiments the present invention provides a method for producing a therapeutic composition having full-length mRNA that encodes for oxalase alanine-glyoxylate aminotransferase enzyme.

In certain embodiments the present invention provides a method for producing a therapeutic composition having full-length mRNA that encodes for a protein associated with a lipid metabolism or fibrotic disorder. In certain embodiments the present invention provides a method for producing a therapeutic composition having full-length mRNA that encodes for a mTOR inhibitor. In certain embodiments the present invention provides a method for producing a therapeutic composition having full-length mRNA that encodes for ATPase phospholipid transporting 8B1 (ATP8B1) protein. In certain embodiments the present invention provides a method for producing a therapeutic composition having full-length mRNA that encodes for one or more NF-kappa B inhibitors, such as one or more of I-kappa B alpha, interferon-related development regulator 1 (IFRD1), and Sirtuin 1 (SIRT1). In certain embodiments the present invention provides a method for producing a therapeutic composition having full-length mRNA that encodes for PPAR-gamma protein or an active variant.

In certain embodiments the present invention provides a method for producing a therapeutic composition having full-length mRNA that encodes for a protein associated with methylmalonic acidemia. For example, in certain embodiments the present invention provides a method for producing a therapeutic composition having full-length mRNA that encodes for methylmalonyl CoA mutase protein. In certain embodiments the present invention provides a method for producing a therapeutic composition having full-length mRNA that encodes for methylmalonyl CoA epimerase protein.

In certain embodiments the present invention provides a method for producing a therapeutic composition having full-length mRNA for which delivery to or treatment of the liver can provide therapeutic benefit. In certain embodiments the present invention provides a method for producing a therapeutic composition having full-length mRNA that encodes for ATP7B protein, also known as Wilson disease protein. In certain embodiments the present invention provides a method for producing a therapeutic composition having full-length mRNA that encodes for porphobilinogen deaminase enzyme. In certain embodiments the present invention provides a method for producing a therapeutic composition having full-length mRNA that encodes for one or clotting enzymes, such as Factor VIII, Factor IX, Factor VII, and Factor X. In certain embodiments the present invention provides a method for producing a therapeutic composition having full-length mRNA that encodes for human hemochromatosis (HFE) protein.

In certain embodiments the present invention provides a method for producing a therapeutic composition having full-length mRNA that encodes a peptide or polypeptide for use in the delivery to or treatment of the cardiovasculature of a subject or a cardiovascular cell. In certain embodiments the present invention provides a method for producing a therapeutic composition having full-length mRNA that encodes for vascular endothelial growth factor A protein. In certain embodiments the present invention provides a method for producing a therapeutic composition having full-length mRNA that encodes for relaxin protein. In certain embodiments the present invention provides a method for producing a therapeutic composition having full-length mRNA that encodes for bone morphogenetic protein-9 protein. In certain embodiments the present invention provides a method for producing a therapeutic composition having full-length mRNA that encodes for bone morphogenetic protein-2 receptor protein.

In certain embodiments the present invention provides a method for producing a therapeutic composition having full-length mRNA that encodes a peptide or polypeptide for use in the delivery to or treatment of the muscle of a subject or a muscle cell. In certain embodiments the present invention provides a method for producing a therapeutic composition having full-length mRNA that encodes for dystrophin protein. In certain embodiments the present invention provides a method for producing a therapeutic composition having full-length mRNA that encodes for frataxin protein. In certain embodiments the present invention provides a method for producing a therapeutic composition having full-length mRNA that encodes a peptide or polypeptide for use in the delivery to or treatment of the cardiac muscle of a subject or a cardiac muscle cell. In certain embodiments the present invention provides a method for producing a therapeutic composition having full-length mRNA that encodes for a protein that modulates one or both of a potassium channel and a sodium channel in muscle tissue or in a muscle cell. In certain embodiments the present invention provides a method for producing a therapeutic composition having full-length mRNA that encodes for a protein that modulates a Kv7.1 channel in muscle tissue or in a muscle cell. In certain embodiments the present invention provides a method for producing a therapeutic composition having full-length mRNA that encodes for a protein that modulates a Nav1.5 channel in muscle tissue or in a muscle cell.

In certain embodiments the present invention provides a method for producing a therapeutic composition having full-length mRNA that encodes a peptide or polypeptide for use in the delivery to or treatment of the nervous system of a subject or a nervous system cell. For example, in certain embodiments the present invention provides a method for producing a therapeutic composition having full-length mRNA that encodes for survival motor neuron 1 protein. For example, in certain embodiments the present invention provides a method for producing a therapeutic composition having full-length mRNA that encodes for survival motor neuron 2 protein. In certain embodiments the present invention provides a method for producing a therapeutic composition having full-length mRNA that encodes for frataxin protein. In certain embodiments the present invention provides a method for producing a therapeutic composition having full-length mRNA that encodes for ATP binding cassette subfamily D member 1 (ABCD1) protein. In certain embodiments the present invention provides a method for producing a therapeutic composition having full-length mRNA that encodes for CLN3 protein.

In certain embodiments the present invention provides a method for producing a therapeutic composition having full-length mRNA that encodes a peptide or polypeptide for use in the delivery to or treatment of the blood or bone marrow of a subject or a blood or bone marrow cell. In certain embodiments the present invention provides a method for producing a therapeutic composition having full-length mRNA that encodes for beta globin protein. In certain embodiments the present invention provides a method for producing a therapeutic composition having full-length mRNA that encodes for Bruton's tyrosine kinase protein. In certain embodiments the present invention provides a method for producing a therapeutic composition having full-length mRNA that encodes for one or clotting enzymes, such as Factor VIII, Factor IX, Factor VII, and Factor X.

In certain embodiments the present invention provides a method for producing a therapeutic composition having full-length mRNA that encodes a peptide or polypeptide for use in the delivery to or treatment of the kidney of a subject or a kidney cell. In certain embodiments the present invention provides a method for producing a therapeutic composition having full-length mRNA that encodes for collagen type IV alpha 5 chain (COL4A5) protein.

In certain embodiments the present invention provides a method for producing a therapeutic composition having full-length mRNA that encodes a peptide or polypeptide for use in the delivery to or treatment of the eye of a subject or an eye cell. In certain embodiments the present invention provides a method for producing a therapeutic composition having full-length mRNA that encodes for ATP-binding cassette sub-family A member 4 (ABCA4) protein. In certain embodiments the present invention provides a method for producing a therapeutic composition having full-length mRNA that encodes for retinoschisin protein. In certain embodiments the present invention provides a method for producing a therapeutic composition having full-length mRNA that encodes for retinal pigment epithelium-specific 65 kDa (RPE65) protein. In certain embodiments the present invention provides a method for producing a therapeutic composition having full-length mRNA that encodes for centrosomal protein of 290 kDa (CEP290).

In embodiments, an mRNA encodes for an antigen from an infectious agent.

In certain embodiments the present invention provides a method for producing a therapeutic composition having full-length mRNA that encodes a peptide or polypeptide for use in the delivery of or treatment with a vaccine for a subject or a cell of a subject. For example, in certain embodiments the present invention provides a method for producing a therapeutic composition having full-length mRNA that encodes for an antigen from an infectious agent, such as a virus. In certain embodiments the present invention provides a method for producing a therapeutic composition having full-length mRNA that encodes for an antigen from influenza virus. In certain embodiments the present invention provides a method for producing a therapeutic composition having full-length mRNA that encodes for an antigen from respiratory syncytial virus. In certain embodiments the present invention provides a method for producing a therapeutic composition having full-length mRNA that encodes for an antigen from rabies virus. In certain embodiments the present invention provides a method for producing a therapeutic composition having full-length mRNA that encodes for an antigen from cytomegalovirus. In certain embodiments the present invention provides a method for producing a therapeutic composition having full-length mRNA that encodes for an antigen from rotavirus. In certain embodiments the present invention provides a method for producing a therapeutic composition having full-length mRNA that encodes for an antigen from a hepatitis virus, such as hepatitis A virus, hepatitis B virus, or hepatis C virus. In certain embodiments the present invention provides a method for producing a therapeutic composition having full-length mRNA that encodes for an antigen from human papillomavirus. In certain embodiments the present invention provides a method for producing a therapeutic composition having full-length mRNA that encodes for an antigen from a herpes simplex virus, such as herpes simplex virus 1 or herpes simplex virus 2. In certain embodiments the present invention provides a method for producing a therapeutic composition having full-length mRNA that encodes for an antigen from a human immunodeficiency virus, such as human immunodeficiency virus type 1 or human immunodeficiency virus type 2. In certain embodiments the present invention provides a method for producing a therapeutic composition having full-length mRNA that encodes for an antigen from a human metapneumovirus. In certain embodiments the present invention provides a method for producing a therapeutic composition having full-length mRNA that encodes for an antigen from a human parainfluenza virus, such as human parainfluenza virus type 1, human parainfluenza virus type 2, or human parainfluenza virus type 3. In certain embodiments the present invention provides a method for producing a therapeutic composition having full-length mRNA that encodes for an antigen from malaria virus. In certain embodiments the present invention provides a method for producing a therapeutic composition having full-length mRNA that encodes for an antigen from zika virus. In certain embodiments the present invention provides a method for producing a therapeutic composition having full-length mRNA that encodes for an antigen from chikungunya virus.

In certain embodiments the present invention provides a method for producing a therapeutic composition having full-length mRNA that encodes for an antigen associated with a cancer of a subject or identified from a cancer cell of a subject. In certain embodiments the present invention provides a method for producing a therapeutic composition having full-length mRNA that encodes for an antigen determined from a subject's own cancer cell, i.e., to provide a personalized cancer vaccine. In certain embodiments the present invention provides a method for producing a therapeutic composition having full-length mRNA that encodes for an antigen expressed from a mutant KRAS gene.

In certain embodiments the present invention provides a method for producing a therapeutic composition having full-length mRNA that encodes for an antibody. In certain embodiments, the antibody can be a bi-specific antibody. In certain embodiments, the antibody can be part of a fusion protein. In certain embodiments the present invention provides a method for producing a therapeutic composition having full-length mRNA that encodes for an antibody to OX40. In certain embodiments the present invention provides a method for producing a therapeutic composition having full-length mRNA that encodes for an antibody to VEGF. In certain embodiments the present invention provides a method for producing a therapeutic composition having full-length mRNA that encodes for an antibody to tissue necrosis factor alpha. In certain embodiments the present invention provides a method for producing a therapeutic composition having full-length mRNA that encodes for an antibody to CD3. In certain embodiments the present invention provides a method for producing a therapeutic composition having full-length mRNA that encodes for an antibody to CD19.

In certain embodiments the present invention provides a method for producing a therapeutic composition having full-length mRNA that encodes for an immunomodulator. In certain embodiments the present invention provides a method for producing a therapeutic composition having full-length mRNA that encodes for Interleukin 12. In certain embodiments the present invention provides a method for producing a therapeutic composition having full-length mRNA that encodes for Interleukin 23. In certain embodiments the present invention provides a method for producing a therapeutic composition having full-length mRNA that encodes for Interleukin 36 gamma. In certain embodiments the present invention provides a method for producing a therapeutic composition having full-length mRNA that encodes for a constitutively active variant of one or more stimulator of interferon genes (STING) proteins.

In certain embodiments the present invention provides a method for producing a therapeutic composition having full-length mRNA that encodes for an endonuclease. In certain embodiments the present invention provides a method for producing a therapeutic composition having full-length mRNA that encodes for an RNA-guided DNA endonuclease protein, such as Cas 9 protein. In certain embodiments the present invention provides a method for producing a therapeutic composition having full-length mRNA that encodes for a meganuclease protein. In certain embodiments the present invention provides a method for producing a therapeutic composition having full-length mRNA that encodes for a transcription activator-like effector nuclease protein. In certain embodiments the present invention provides a method for producing a therapeutic composition having full-length mRNA that encodes for a zinc finger nuclease protein.

In embodiments, exemplary therapeutic uses result from the delivery of mRNA encoding a secreted protein. Accordingly, in embodiments, the compositions and methods of the invention provide for delivery of mRNA encoding a secreted protein. In some embodiments, the compositions and methods of the invention provide for delivery of mRNA encoding one or more secreted proteins listed in Table 1; thus, compositions of the invention may comprise an mRNA encoding a protein listed in Table 1 (or a homolog thereof) along with other components set out herein, and methods of the invention may comprise preparing and/or administering a composition comprising an mRNA encoding a protein listed in Table 1 (or a homolog thereof) along with other components set out herein

TABLE 1

Secreted Proteins

| Uniprot ID | Protein Name | Gene Name |
|---|---|---|
| A1E959 | Odontogenic ameloblast-associated protein | ODAM |
| A1KZ92 | Peroxidasin-like protein | PXDNL |
| A1L453 | Serine protease 38 | PRSS38 |
| A1L4H1 | Soluble scavenger receptor cysteine-rich domain-containing protein SSC5D | SSC5D |
| A2RUU4 | Colipase-like protein 1 | CLPSL1 |
| A2VDF0 | Fucose mutarotase | FUOM |
| A2VEC9 | SCO-spondin | SSPO |
| A3KMH1 | von Willebrand factor A domain-containing protein 8 | VWA8 |
| A4D0S4 | Laminin subunit beta-4 | LAMB4 |
| A4D1T9 | Probable inactive serine protease 37 | PRSS37 |
| A5D8T8 | C-type lectin domain family 18 member A | CLEC18A |
| A6NC86 | phospholipase A2 inhibitor and Ly6/PLAUR domain-containing protein | PINLYP |
| A6NCI4 | von Willebrand factor A domain-containing protein 3A | VWA3A |
| A6ND01 | Probable folate receptor delta | FOLR4 |
| A6NDD2 | Beta-defensin 108B-like | |
| A6NE02 | BTB/POZ domain-containing protein 17 | BTBD17 |
| A6NEF6 | Growth hormone 1 | GH1 |
| A6NF02 | NPIP-like protein LOC730153 | |
| A6NFB4 | HCG1749481, isoform CRA_k | CSH1 |
| A6NFZ4 | Protein FAM24A | FAM24A |
| A6NG13 | Glycosyltransferase 54 domain-containing protein | |
| A6NGN9 | IgLON family member 5 | IGLON5 |
| A6NHN0 | Otolin-1 | OTOL1 |
| A6NHN6 | Nuclear pore complex-interacting protein-like 2 | NPIPL2 |
| A6NI73 | Leukocyte immunoglobulin-like receptor subfamily A member 5 | LILRA5 |
| A6NIT4 | Chorionic somatomammotropin hormone 2 isoform 2 | CSH2 |
| A6NJ69 | IgA-inducing protein homolog | IGIP |
| A6NKQ9 | Choriogonadotropin subunit beta variant 1 | CGB1 |
| A6NMZ7 | Collagen alpha-6(VI) chain | COL6A6 |
| A6NNS2 | Dehydrogenase/reductase SDR family member 7C | DHRS7C |
| A6XGL2 | Insulin A chain | INS |
| A8K0G1 | Protein Wnt | WNT7B |
| A8K2U0 | Alpha-2-macroglobulin-like protein 1 | A2ML1 |
| A8K7I4 | Calcium-activated chloride channel regulator 1 | CLCA1 |
| A8MTL9 | Serpin-like protein HMSD | HMSD |
| A8MV23 | Serpin E3 | SERPINE3 |
| A8MZH6 | Oocyte-secreted protein 1 homolog | OOSP1 |
| A8TX70 | Collagen alpha-5(VI) chain | COL6A5 |
| B0ZBE8 | Natriuretic peptide | NPPA |
| B1A4G9 | Somatotropin | GH1 |
| B1A4H2 | HCG1749481, isoform CRA_d | CSH1 |
| B1A4H9 | Chorionic somatomammotropin hormone | CSH2 |
| B1AJZ6 | Protein Wnt | WNT4 |
| B1AKI9 | Isthmin-1 | ISM1 |
| B2RNN3 | Complement C1q and tumor necrosis factor-related protein 9B | C1QTNF9B |
| B2RUY7 | von Willebrand factor C domain-containing protein 2-like | VWC2L |
| B3GLJ2 | Prostate and testis expressed protein 3 | PATE3 |
| B4DI03 | SEC11-like 3 (S. cerevisiae), isoform CRA_a | SEC11L3 |
| B4DJF9 | Protein Wnt | WNT4 |
| B4DUL4 | SEC11-like 1 (S. cerevisiae), isoform CRA_d | SEC11L1 |
| B5MCC8 | Protein Wnt | WNT10B |
| B8A595 | Protein Wnt | WNT7B |
| B8A597 | Protein Wnt | WNT7B |
| B8A598 | Protein Wnt | WNT7B |
| B9A064 | Immunoglobulin lambda-like polypeptide 5 | IGLL5 |

TABLE 1-continued

Secreted Proteins

| Uniprot ID | Protein Name | Gene Name |
| --- | --- | --- |
| C9J3H3 | Protein Wnt | WNT10B |
| C9J8I8 | Protein Wnt | WNT5A |
| C9JAF2 | Insulin-like growth factor II Ala-25 Del | IGF2 |
| C9JCI2 | Protein Wnt | WNT10B |
| C9JL84 | HERV-H LTR-associating protein 1 | HHLA1 |
| C9JNR5 | Insulin A chain | INS |
| C9JUI2 | Protein Wnt | WNT2 |
| D6RF47 | Protein Wnt | WNT8A |
| D6RF94 | Protein Wnt | WNT8A |
| E2RYF7 | Protein PBMUCL2 | HCG22 |
| E5RFR1 | PENK(114-133) | PENK |
| E7EML9 | Serine protease 44 | PRSS44 |
| E7EPC3 | Protein Wnt | WNT9B |
| E7EVP0 | Nociceptin | PNOC |
| E9PD02 | Insulin-like growth factor I | IGF1 |
| E9PH60 | Protein Wnt | WNT16 |
| E9PJL6 | Protein Wnt | WNT11 |
| F5GYM2 | Protein Wnt | WNT5B |
| F5H034 | Protein Wnt | WNT5B |
| F5H364 | Protein Wnt | WNT5B |
| F5H7Q6 | Protein Wnt | WNT5B |
| F8WCM5 | Protein INS-IGF2 | INS-IGF2 |
| F8WDR1 | Protein Wnt | WNT2 |
| H0Y663 | Protein Wnt | WNT4 |
| H0YK72 | Signal peptidase complex catalytic subunit SEC11A | SEC11A |
| H0YK83 | Signal peptidase complex catalytic subunit SEC11A | SEC11A |
| H0YM39 | Chorionic somatomammotropin hormone | CSH2 |
| H0YMT7 | Chorionic somatomammotropin hormone | CSH1 |
| H0YN17 | Chorionic somatomammotropin hormone | CSH2 |
| H0YNA5 | Signal peptidase complex catalytic subunit SEC11A | SEC11A |
| H0YNG3 | Signal peptidase complex catalytic subunit SEC11A | SEC11A |
| H0YNX5 | Signal peptidase complex catalytic subunit SEC11A | SEC11A |
| H7BZB8 | Protein Wnt | WNT10A |
| H9KV56 | Choriogonadotropin subunit beta variant 2 | CGB2 |
| I3L0L8 | Protein Wnt | WNT9B |
| J3KNZ1 | Choriogonadotropin subunit beta variant 1 | CGB1 |
| J3KP00 | Choriogonadotropin subunit beta | CGB7 |
| J3QT02 | Choriogonadotropin subunit beta variant 1 | CGB1 |
| O00175 | C-C motif chemokine 24 | CCL24 |
| O00182 | Galectin-9 | LGALS9 |
| O00187 | Mannan-binding lectin serine protease 2 | MASP2 |
| O00230 | Cortistatin | CORT |
| O00253 | Agouti-related protein | AGRP |
| O00270 | 12-(S)-hydroxy-5,8,10,14-eicosatetraenoic acid receptor | GPR31 |
| O00292 | Left-right determination factor 2 | LEFTY2 |
| O00294 | Tubby-related protein 1 | TULP1 |
| O00295 | Tubby-related protein 2 | TULP2 |
| O00300 | Tumor necrosis factor receptor superfamily member 11B | TNFRSF11B |
| O00339 | Matrilin-2 | MATN2 |
| O00391 | Sulfhydryl oxidase 1 | QSOX1 |
| O00468 | Agrin | AGRN |
| O00515 | Ladinin-1 | LAD1 |
| O00533 | Processed neural cell adhesion molecule L1-like protein | CHL1 |
| O00584 | Ribonuclease T2 | RNASET2 |
| O00585 | C-C motif chemokine 21 | CCL21 |
| O00602 | Ficolin-1 | FCN1 |
| O00622 | Protein CYR61 | CYR61 |
| O00626 | MDC(5-69) | CCL22 |
| O00634 | Netrin-3 | NTN3 |
| O00744 | Protein Wnt-10b | WNT10B |
| O00755 | Protein Wnt-7a | WNT7A |
| O14498 | Immunoglobulin superfamily containing leucine-rich repeat protein | ISLR |

TABLE 1-continued

Secreted Proteins

| Uniprot ID | Protein Name | Gene Name |
|---|---|---|
| O14511 | Pro-neuregulin-2, membrane-bound isoform | NRG2 |
| O14594 | Neurocan core protein | NCAN |
| O14625 | C-X-C motif chemokine 11 | CXCL11 |
| O14638 | Ectonucleotide pyrophosphatase/phosphodiesterase family member 3 | ENPP3 |
| O14656 | Torsin-1A | TOR1A |
| O14657 | Torsin-1B | TOR1B |
| O14786 | Neuropilin-1 | NRP1 |
| O14788 | Tumor necrosis factor ligand superfamily member 11, membrane form | TNFSF11 |
| O14791 | Apolipoprotein L1 | APOL1 |
| O14793 | Growth/differentiation factor 8 | MSTN |
| O14904 | Protein Wnt-9a | WNT9A |
| O14905 | Protein Wnt-9b | WNT9B |
| O14944 | Proepiregulin | EREG |
| O14960 | Leukocyte cell-derived chemotaxin-2 | LECT2 |
| O15018 | Processed PDZ domain-containing protein 2 | PDZD2 |
| O15041 | Semaphorin-3E | SEMA3E |
| O15072 | A disintegrin and metalloproteinase with thrombospondin motifs 3 | ADAMTS3 |
| O15123 | Angiopoietin-2 | ANGPT2 |
| O15130 | Neuropeptide FF | NPFF |
| O15197 | Ephrin type-B receptor 6 | EPHB6 |
| O15204 | ADAM DEC1 | ADAMDEC1 |
| O15230 | Laminin subunit alpha-5 | LAMA5 |
| O15232 | Matrilin-3 | MATN3 |
| O15240 | Neuroendocrine regulatory peptide-1 | VGF |
| O15263 | Beta-defensin 4A | DEFB4A |
| O15335 | Chondroadherin | CHAD |
| O15393 | Transmembrane protease serine 2 catalytic chain | TMPRSS2 |
| O15444 | C-C motif chemokine 25 | CCL25 |
| O15467 | C-C motif chemokine 16 | CCL16 |
| O15496 | Group 10 secretory phospholipase A2 | PLA2G10 |
| O15520 | Fibroblast growth factor 10 | FGF10 |
| O15537 | Retinoschisin | RS1 |
| O43157 | Plexin-B1 | PLXNB1 |
| O43184 | Disintegrin and metalloproteinase domain-containing protein 12 | ADAM12 |
| O43240 | Kallikrein-10 | KLK10 |
| O43278 | Kunitz-type protease inhibitor 1 | SPINT1 |
| O43320 | Fibroblast growth factor 16 | FGF16 |
| O43323 | Desert hedgehog protein C-product | DHH |
| O43405 | Cochlin | COCH |
| O43508 | Tumor necrosis factor ligand superfamily member 12, membrane form | TNFSF12 |
| O43555 | Progonadoliberin-2 | GNRH2 |
| O43557 | Tumor necrosis factor ligand superfamily member 14, soluble form | TNFSF14 |
| O43692 | Peptidase inhibitor 15 | PI15 |
| O43699 | Sialic acid-binding Ig-like lectin 6 | SIGLEC6 |
| O43820 | Hyaluronidase-3 | HYAL3 |
| O43827 | Angiopoietin-related protein 7 | ANGPTL7 |
| O43852 | Calumenin | CALU |
| O43854 | EGF-like repeat and discoidin I-like domain-containing protein 3 | EDIL3 |
| O43866 | CD5 antigen-like | CD5L |
| O43897 | Tolloid-like protein 1 | TLL1 |
| O43915 | Vascular endothelial growth factor D | FIGF |
| O43927 | C-X-C motif chemokine 13 | CXCL13 |
| O60218 | Aldo-keto reductase family 1 member B10 | AKR1B10 |
| O60235 | Transmembrane protease serine 11D | TMPRSS11D |
| O60258 | Fibroblast growth factor 17 | FGF17 |
| O60259 | Kallikrein-8 | KLK8 |
| O60383 | Growth/differentiation factor 9 | GDF9 |
| O60469 | Down syndrome cell adhesion molecule | DSCAM |
| O60542 | Persephin | PSPN |
| O60565 | Gremlin-1 | GREM1 |
| O60575 | Serine protease inhibitor Kazal-type 4 | SPINK4 |
| O60676 | Cystatin-8 | CST8 |
| O60687 | Sushi repeat-containing protein SRPX2 | SRPX2 |
| O60844 | Zymogen granule membrane protein 16 | ZG16 |
| O60882 | Matrix metalloproteinase-20 | MMP20 |
| O60938 | Keratocan | KERA |
| O75015 | Low affinity immunoglobulin gamma Fc region receptor III-B | FCGR3B |

TABLE 1-continued

Secreted Proteins

| Uniprot ID | Protein Name | Gene Name |
| --- | --- | --- |
| O75077 | Disintegrin and metalloproteinase domain-containing protein 23 | ADAM23 |
| O75093 | Slit homolog 1 protein | SLIT1 |
| O75094 | Slit homolog 3 protein | SLIT3 |
| O75095 | Multiple epidermal growth factor-like domains protein 6 | MEGF6 |
| O75173 | A disintegrin and metalloproteinase with thrombospondin motifs 4 | ADAMTS4 |
| O75200 | Nuclear pore complex-interacting protein-like 1 | NPIPL1 |
| O75339 | Cartilage intermediate layer protein 1 C1 | CILP |
| O75354 | Ectonucleoside triphosphate diphosphohydrolase 6 | ENTPD6 |
| O75386 | Tubby-related protein 3 | TULP3 |
| O75398 | Deformed epidermal autoregulatory factor 1 homolog | DEAF1 |
| O75443 | Alpha-tectorin | TECTA |
| O75445 | Usherin | USH2A |
| O75462 | Cytokine receptor-like factor 1 | CRLF1 |
| O75487 | Glypican-4 | GPC4 |
| O75493 | Carbonic anhydrase-related protein 11 | CA11 |
| O75594 | Peptidoglycan recognition protein 1 | PGLYRP1 |
| O75596 | C-type lectin domain family 3 member A | CLEC3A |
| O75610 | Left-right determination factor 1 | LEFTY1 |
| O75629 | Protein CREG1 | CREG1 |
| O75636 | Ficolin-3 | FCN3 |
| O75711 | Scrapie-responsive protein 1 | SCRG1 |
| O75715 | Epididymal secretory glutathione peroxidase | GPX5 |
| O75718 | Cartilage-associated protein | CRTAP |
| O75829 | Chondrosurfactant protein | LECT1 |
| O75830 | Serpin I2 | SERPINI2 |
| O75882 | Attractin | ATRN |
| O75888 | Tumor necrosis factor ligand superfamily member 13 | TNFSF13 |
| O75900 | Matrix metalloproteinase-23 | MMP23A |
| O75951 | Lysozyme-like protein 6 | LYZL6 |
| O75973 | C1q-related factor | C1QL1 |
| O76038 | Secretagogin | SCGN |
| O76061 | Stanniocalcin-2 | STC2 |
| O76076 | WNT1-inducible-signaling pathway protein 2 | WISP2 |
| O76093 | Fibroblast growth factor 18 | FGF18 |
| O76096 | Cystatin-F | CST7 |
| O94769 | Extracellular matrix protein 2 | ECM2 |
| O94813 | Slit homolog 2 protein C-product | SLIT2 |
| O94907 | Dickkopf-related protein 1 | DKK1 |
| O94919 | Endonuclease domain-containing 1 protein | ENDOD1 |
| O94964 | N-terminal form | SOGA1 |
| O95025 | Semaphorin-3D | SEMA3D |
| O95084 | Serine protease 23 | PRSS23 |
| O95150 | Tumor necrosis factor ligand superfamily member 15 | TNFSF15 |
| O95156 | Neurexophilin-2 | NXPH2 |
| O95157 | Neurexophilin-3 | NXPH3 |
| O95158 | Neurexophilin-4 | NXPH4 |
| O95388 | WNT1-inducible-signaling pathway protein 1 | WISP1 |
| O95389 | WNT1-inducible-signaling pathway protein 3 | WISP3 |
| O95390 | Growth/differentiation factor 11 | GDF11 |
| O95393 | Bone morphogenetic protein 10 | BMP10 |
| O95399 | Urotensin-2 | UTS2 |
| O95407 | Tumor necrosis factor receptor superfamily member 6B | TNFRSF6B |
| O95428 | Papilin | PAPLN |
| O95445 | Apolipoprotein M | APOM |
| O95450 | A disintegrin and metalloproteinase with thrombospondin motifs 2 | ADAMTS2 |
| O95460 | Matrilin-4 | MATN4 |
| O95467 | LHAL tetrapeptide | GNAS |
| O95631 | Netrin-1 | NTN1 |
| O95633 | Follistatin-related protein 3 | FSTL3 |
| O95711 | Lymphocyte antigen 86 | LY86 |
| O95715 | C-X-C motif chemokine 14 | CXCL14 |
| O95750 | Fibroblast growth factor 19 | FGF19 |
| O95760 | Interleukin-33 | IL33 |
| O95813 | Cerberus | CER1 |
| O95841 | Angiopoietin-related protein 1 | ANGPTL1 |
| O95897 | Noelin-2 | OLFM2 |
| O95925 | Eppin | EPPIN |
| O95965 | Integrin beta-like protein 1 | ITGBL1 |

TABLE 1-continued

Secreted Proteins

| Uniprot ID | Protein Name | Gene Name |
|---|---|---|
| O95967 | EGF-containing fibulin-like extracellular matrix protein 2 | EFEMP2 |
| O95968 | Secretoglobin family 1D member 1 | SCGB1D1 |
| O95969 | Secretoglobin family 1D member 2 | SCGB1D2 |
| O95970 | Leucine-rich glioma-inactivated protein 1 | LGI1 |
| O95972 | Bone morphogenetic protein 15 | BMP15 |
| O95994 | Anterior gradient protein 2 homolog | AGR2 |
| O95998 | Interleukin-18-binding protein | IL18BP |
| O96009 | Napsin-A | NAPSA |
| O96014 | Protein Wnt-11 | WNT11 |
| P00450 | Ceruloplasmin | CP |
| P00451 | Factor VIIIa light chain | F8 |
| P00488 | Coagulation factor XIII A chain | F13A1 |
| P00533 | Epidermal growth factor receptor | EGFR |
| P00709 | Alpha-lactalbumin | LALBA |
| P00734 | Prothrombin | F2 |
| P00738 | Haptoglobin beta chain | HP |
| P00739 | Haptoglobin-related protein | HPR |
| P00740 | Coagulation factor IXa heavy chain | F9 |
| P00742 | Factor X heavy chain | F10 |
| P00746 | Complement factor D | CFD |
| P00747 | Plasmin light chain B | PLG |
| P00748 | Coagulation factor XIIa light chain | F12 |
| P00749 | Urokinase-type plasminogen activator long chain A | PLAU |
| P00750 | Tissue-type plasminogen activator | PLAT |
| P00751 | Complement factor B Ba fragment | CFB |
| P00797 | Renin | REN |
| P00973 | 2'-5'-oligoadenylate synthase 1 | OAS1 |
| P00995 | Pancreatic secretory trypsin inhibitor | SPINK1 |
| P01008 | Antithrombin-III | SERPINC1 |
| P01009 | Alpha-1-antitrypsin | SERPINA1 |
| P01011 | Alpha-1-antichymotrypsin His-Pro-less | SERPINA3 |
| P01019 | Angiotensin-1 | AGT |
| P01023 | Alpha-2-macroglobulin | A2M |
| P01024 | Acylation stimulating protein | C3 |
| P01031 | Complement C5 beta chain | C5 |
| P01033 | Metalloproteinase inhibitor 1 | TIMP1 |
| P01034 | Cystatin-C | CST3 |
| P01036 | Cystatin-S | CST4 |
| P01037 | Cystatin-SN | CST1 |
| P01042 | Kininogen-1 light chain | KNG1 |
| P01127 | Platelet-derived growth factor subunit B | PDGFB |
| P01135 | Transforming growth factor alpha | TGFA |
| P01137 | Transforming growth factor beta-1 | TGFB1 |
| P01138 | Beta-nerve growth factor | NGF |
| P01148 | Gonadoliberin-1 | GNRH1 |
| P01160 | Atrial natriuretic factor | NPPA |
| P01178 | Oxytocin | OXT |
| P01185 | Vasopressin-neurophysin 2-copeptin | AVP |
| P01189 | Corticotropin | POMC |
| P01210 | PENK(237-258) | PENK |
| P01213 | Alpha-neoendorphin | PDYN |
| P01215 | Glycoprotein hormones alpha chain | CGA |
| P01222 | Thyrotropin subunit beta | TSHB |
| P01225 | Follitropin subunit beta | FSHB |
| P01229 | Lutropin subunit beta | LHB |
| P01233 | Choriogonadotropin subunit beta | CGB8 |
| P01236 | Prolactin | PRL |
| P01241 | Somatotropin | GH1 |
| P01242 | Growth hormone variant | GH2 |
| P01243 | Chorionic somatomammotropin hormone | CSH2 |
| P01258 | Katacalcin | CALCA |
| P01266 | Thyroglobulin | TG |
| P01270 | Parathyroid hormone | PTH |
| P01275 | Glucagon | GCG |
| P01282 | Intestinal peptide PHM-27 | VIP |
| P01286 | Somatoliberin | GHRH |
| P01298 | Pancreatic prohormone | PPY |
| P01303 | C-flanking peptide of NPY | NPY |
| P01308 | Insulin | INS |
| P01344 | Insulin-like growth factor II | IGF2 |
| P01350 | Big gastrin | GAST |
| P01374 | Lymphotoxin-alpha | LTA |
| P01375 | C-domain 1 | TNF |
| P01562 | Interferon alpha-1/13 | IFNA1 |

TABLE 1-continued

| Secreted Proteins | | |
|---|---|---|
| Uniprot ID | Protein Name | Gene Name |
| P01563 | Interferon alpha-2 | IFNA2 |
| P01566 | Interferon alpha-10 | IFNA10 |
| P01567 | Interferon alpha-7 | IFNA7 |
| P01568 | Interferon alpha-21 | IFNA21 |
| P01569 | Interferon alpha-5 | IFNA5 |
| P01570 | Interferon alpha-14 | IFNA14 |
| P01571 | Interferon alpha-17 | IFNA17 |
| P01574 | Interferon beta | IFNB1 |
| P01579 | Interferon gamma | IFNG |
| P01583 | Interleukin-1 alpha | IL1A |
| P01584 | Interleukin-1 beta | IL1B |
| P01588 | Erythropoietin | EPO |
| P01591 | Immunoglobulin J chain | IGJ |
| P01732 | T-cell surface glycoprotein CD8 alpha chain | CD8A |
| P01833 | Polymeric immunoglobulin receptor | PIGR |
| P01857 | Ig gamma-1 chain C region | IGHG1 |
| P01859 | Ig gamma-2 chain C region | IGHG2 |
| P01860 | Ig gamma-3 chain C region | IGHG3 |
| P01861 | Ig gamma-4 chain C region | IGHG4 |
| P01871 | Ig mu chain C region | IGHM |
| P01880 | Ig delta chain C region | IGHD |
| P02452 | Collagen alpha-1(I) chain | COL1A1 |
| P02458 | Chondrocalcin | COL2A1 |
| P02461 | Collagen alpha-1(III) chain | COL3A1 |
| P02462 | Collagen alpha-1(IV) chain | COL4A1 |
| P02647 | Apolipoprotein A-I | APOA1 |
| P02649 | Apolipoprotein E | APOE |
| P02652 | Apolipoprotein A-II | APOA2 |
| P02654 | Apolipoprotein C-I | APOC1 |
| P02655 | Apolipoprotein C-II | APOC2 |
| P02656 | Apolipoprotein C-III | APOC3 |
| P02671 | Fibrinogen alpha chain | FGA |
| P02675 | Fibrinopeptide B | FGB |
| P02679 | Fibrinogen gamma chain | FGG |
| P02741 | C-reactive protein | CRP |
| P02743 | Serum amyloid P-component(1-203) | APCS |
| P02745 | Complement C1q subcomponent subunit A | C1QA |
| P02746 | Complement C1q subcomponent subunit B | C1QB |
| P02747 | Complement C1q subcomponent subunit C | C1QC |
| P02748 | Complement component C9b | C9 |
| P02749 | Beta-2-glycoprotein 1 | APOH |
| P02750 | Leucine-rich alpha-2-glycoprotein | LRG1 |
| P02751 | Ugl-Y2 | FN1 |
| P02753 | Retinol-binding protein 4 | RBP4 |
| P02760 | Trypstatin | AMBP |
| P02763 | Alpha-1-acid glycoprotein 1 | ORM1 |
| P02765 | Alpha-2-HS-glycoprotein chain A | AHSG |
| P02766 | Transthyretin | TTR |
| P02768 | Serum albumin | ALB |
| P02771 | Alpha-fetoprotein | AFP |
| P02774 | Vitamin D-binding protein | GC |
| P02775 | Connective tissue-activating peptide III | PPBP |
| P02776 | Platelet factor 4 | PF4 |
| P02778 | CXCL10(1-73) | CXCL10 |
| P02786 | Transferrin receptor protein 1 | TFRC |
| P02787 | Serotransferrin | TF |
| P02788 | Lactoferroxin-C | LTF |
| P02790 | Hemopexin | HPX |
| P02808 | Statherin | STATH |
| P02810 | Salivary acidic proline-rich phosphoprotein 1/2 | PRH2 |
| P02812 | Basic salivary proline-rich protein 2 | PRB2 |
| P02814 | Peptide D1A | SMR3B |
| P02818 | Osteocalcin | BGLAP |
| P03950 | Angiogenin | ANG |
| P03951 | Coagulation factor XIa heavy chain | F11 |
| P03952 | Plasma kallikrein | KLKB1 |
| P03956 | 27 kDa interstitial collagenase | MMP1 |
| P03971 | Muellerian-inhibiting factor | AMH |
| P03973 | Antileukoproteinase | SLPI |
| P04003 | C4b-binding protein alpha chain | C4BPA |
| P04004 | Somatomedin-B | VTN |
| P04054 | Phospholipase A2 | PLA2G1B |
| P04085 | Platelet-derived growth factor subunit A | PDGFA |
| P04090 | Relaxin A chain | RLN2 |
| P04114 | Apolipoprotein B-100 | APOB |
| P04118 | Colipase | CLPS |

TABLE 1-continued

Secreted Proteins

| Uniprot ID | Protein Name | Gene Name |
|---|---|---|
| P04141 | Granulocyte-macrophage colony-stimulating factor | CSF2 |
| P04155 | Trefoil factor 1 | TFF1 |
| P04180 | Phosphatidylcholine-sterol acyltransferase | LCAT |
| P04196 | Histidine-rich glycoprotein | HRG |
| P04217 | Alpha-1B-glycoprotein | A1BG |
| P04275 | von Willebrand antigen 2 | VWF |
| P04278 | Sex hormone-binding globulin | SHBG |
| P04279 | Alpha-inhibin-31 | SEMG1 |
| P04280 | Basic salivary proline-rich protein 1 | PRB1 |
| P04628 | Proto-oncogene Wnt-1 | WNT1 |
| P04745 | Alpha-amylase 1 | AMY1A |
| P04746 | Pancreatic alpha-amylase | AMY2A |
| P04808 | Prorelaxin H1 | RLN1 |
| P05000 | Interferon omega-1 | IFNW1 |
| P05013 | Interferon alpha-6 | IFNA6 |
| P05014 | Interferon alpha-4 | IFNA4 |
| P05015 | Interferon alpha-16 | IFNA16 |
| P05019 | Insulin-like growth factor I | IGF1 |
| P05060 | GAWK peptide | CHGB |
| P05090 | Apolipoprotein D | APOD |
| P05109 | Protein S100-A8 | S100A8 |
| P05111 | Inhibin alpha chain | INHA |
| P05112 | Interleukin-4 | IL4 |
| P05113 | Interleukin-5 | IL5 |
| P05120 | Plasminogen activator inhibitor 2 | SERPINB2 |
| P05121 | Plasminogen activator inhibitor 1 | SERPINE1 |
| P05154 | Plasma serine protease inhibitor | SERPINA5 |
| P05155 | Plasma protease C1 inhibitor | SERPING1 |
| P05156 | Complement factor I heavy chain | CFI |
| P05160 | Coagulation factor XIII B chain | F13B |
| P05161 | Ubiquitin-like protein ISG15 | ISG15 |
| P05230 | Fibroblast growth factor 1 | FGF1 |
| P05231 | Interleukin-6 | IL6 |
| P05305 | Big endothelin-1 | EDN1 |
| P05408 | C-terminal peptide | SCG5 |
| P05451 | Lithostathine-1-alpha | REG1A |
| P05452 | Tetranectin | CLEC3B |
| P05543 | Thyroxine-binding globulin | SERPINA7 |
| P05814 | Beta-casein | CSN2 |
| P05997 | Collagen alpha-2(V) chain | COL5A2 |
| P06276 | Cholinesterase | BCHE |
| P06307 | Cholecystokinin-12 | CCK |
| P06396 | Gelsolin | GSN |
| P06681 | Complement C2 | C2 |
| P06702 | Protein S100-A9 | S100A9 |
| P06727 | Apolipoprotein A-IV | APOA4 |
| P06734 | Low affinity immunoglobulin epsilon Fc receptor soluble form | FCER2 |
| P06744 | Glucose-6-phosphate isomerase | GPI |
| P06850 | Corticoliberin | CRH |
| P06858 | Lipoprotein lipase | LPL |
| P06881 | Calcitonin gene-related peptide 1 | CALCA |
| P07093 | Glia-derived nexin | SERPINE2 |
| P07098 | Gastric triacylglycerol lipase | LIPF |
| P07225 | Vitamin K-dependent protein S | PROS1 |
| P07237 | Protein disulfide-isomerase | P4HB |
| P07288 | Prostate-specific antigen | KLK3 |
| P07306 | Asialoglycoprotein receptor 1 | ASGR1 |
| P07355 | Annexin A2 | ANXA2 |
| P07357 | Complement component C8 alpha chain | C8A |
| P07358 | Complement component C8 beta chain | C8B |
| P07360 | Complement component C8 gamma chain | C8G |
| P07477 | Alpha-trypsin chain 2 | PRSS1 |
| P07478 | Trypsin-2 | PRSS2 |
| P07492 | Neuromedin-C | GRP |
| P07498 | Kappa-casein | CSN3 |
| P07585 | Decorin | DCN |
| P07911 | Uromodulin | UMOD |
| P07942 | Laminin subunit beta-1 | LAMB1 |
| P07988 | Pulmonary surfactant-associated protein B | SFTPB |
| P07998 | Ribonuclease pancreatic | RNASE1 |
| P08118 | Beta-microseminoprotein | MSMB |
| P08123 | Collagen alpha-2(I) chain | COL1A2 |
| P08185 | Corticosteroid-binding globulin | SERPINA6 |
| P08217 | Chymotrypsin-like elastase family member 2A | CELA2A |

TABLE 1-continued

Secreted Proteins

| Uniprot ID | Protein Name | Gene Name |
|---|---|---|
| P08218 | Chymotrypsin-like elastase family member 2B | CELA2B |
| P08253 | 72 kDa type IV collagenase | MMP2 |
| P08254 | Stromelysin-1 | MMP3 |
| P08294 | Extracellular superoxide dismutase [Cu—Zn] | SOD3 |
| P08476 | Inhibin beta A chain | INHBA |
| P08493 | Matrix Gla protein | MGP |
| P08572 | Collagen alpha-2(IV) chain | COL4A2 |
| P08581 | Hepatocyte growth factor receptor | MET |
| P08603 | Complement factor H | CFH |
| P08620 | Fibroblast growth factor 4 | FGF4 |
| P08637 | Low affinity immunoglobulin gamma Fc region receptor III-A | FCGR3A |
| P08697 | Alpha-2-antiplasmin | SERPINF2 |
| P08700 | Interleukin-3 | IL3 |
| P08709 | Coagulation factor VII | F7 |
| P08833 | Insulin-like growth factor-binding protein 1 | IGFBP1 |
| P08887 | Interleukin-6 receptor subunit alpha | IL6R |
| P08949 | Neuromedin-B-32 | NMB |
| P08F94 | Fibrocystin | PKHD1 |
| P09038 | Fibroblast growth factor 2 | FGF2 |
| P09228 | Cystatin-SA | CST2 |
| P09237 | Matrilysin | MMP7 |
| P09238 | Stromelysin-2 | MMP10 |
| P09341 | Growth-regulated alpha protein | CXCL1 |
| P09382 | Galectin-1 | LGALS1 |
| P09466 | Glycodelin | PAEP |
| P09486 | SPARC | SPARC |
| P09529 | Inhibin beta B chain | INHBB |
| P09544 | Protein Wnt-2 | WNT2 |
| P09603 | Processed macrophage colony-stimulating factor 1 | CSF1 |
| P09681 | Gastric inhibitory polypeptide | GIP |
| P09683 | Secretin | SCT |
| P09919 | Granulocyte colony-stimulating factor | CSF3 |
| P0C091 | FRAS1-related extracellular matrix protein 3 | FREM3 |
| P0C0L4 | C4d-A | C4A |
| P0C0L5 | Complement C4-B alpha chain | C4B |
| P0C0P6 | Neuropeptide S | NPS |
| P0C7L1 | Serine protease inhibitor Kazal-type 8 | SPINK8 |
| P0C862 | Complement C1q and tumor necrosis factor-related protein 9A | C1QTNF9 |
| P0C8F1 | Prostate and testis expressed protein 4 | PATE4 |
| P0CG01 | Gastrokine-3 | GKN3P |
| P0CG36 | Cryptic family protein 1B | CFC1B |
| P0CG37 | Cryptic protein | CFC1 |
| P0CJ68 | Humanin-like protein 1 | MTRNR2L1 |
| P0CJ69 | Humanin-like protein 2 | MTRNR2L2 |
| P0CJ70 | Humanin-like protein 3 | MTRNR2L3 |
| P0CJ71 | Humanin-like protein 4 | MTRNR2L4 |
| P0CJ72 | Humanin-like protein 5 | MTRNR2L5 |
| P0CJ73 | Humanin-like protein 6 | MTRNR2L6 |
| P0CJ74 | Humanin-like protein 7 | MTRNR2L7 |
| P0CJ75 | Humanin-like protein 8 | MTRNR2L8 |
| P0CJ76 | Humanin-like protein 9 | MTRNR2L9 |
| P0CJ77 | Humanin-like protein 10 | MTRNR2L10 |
| P0DJD7 | Pepsin A-4 | PGA4 |
| P0DJD8 | Pepsin A-3 | PGA3 |
| P0DJD9 | Pepsin A-5 | PGA5 |
| P0DJI8 | Amyloid protein A | SAA1 |
| P0DJI9 | Serum amyloid A-2 protein | SAA2 |
| P10082 | Peptide YY(3-36) | PYY |
| P10092 | Calcitonin gene-related peptide 2 | CALCB |
| P10124 | Serglycin | SRGN |
| P10145 | MDNCF-a | IL8 |
| P10147 | MIP-1-alpha(4-69) | CCL3 |
| P10163 | Peptide P-D | PRB4 |
| P10451 | Osteopontin | SPP1 |
| P10599 | Thioredoxin | TXN |
| P10600 | Transforming growth factor beta-3 | TGFB3 |
| P10643 | Complement component C7 | C7 |
| P10645 | Vasostatin-2 | CHGA |
| P10646 | Tissue factor pathway inhibitor | TFPI |
| P10720 | Platelet factor 4 variant(4-74) | PF4V1 |
| P10745 | Retinol-binding protein 3 | RBP3 |
| P10767 | Fibroblast growth factor 6 | FGF6 |
| P10909 | Clusterin alpha chain | CLU |
| P10912 | Growth hormone receptor | GHR |

TABLE 1-continued

Secreted Proteins

| Uniprot ID | Protein Name | Gene Name |
| --- | --- | --- |
| P10915 | Hyaluronan and proteoglycan link protein 1 | HAPLN1 |
| P10966 | T-cell surface glycoprotein CD8 beta chain | CD8B |
| P10997 | Islet amyloid polypeptide | IAPP |
| P11047 | Laminin subunit gamma-1 | LAMC1 |
| P11150 | Hepatic triacylglycerol lipase | LIPC |
| P11226 | Mannose-binding protein C | MBL2 |
| P11464 | Pregnancy-specific beta-1-glycoprotein 1 | PSG1 |
| P11465 | Pregnancy-specific beta-1-glycoprotein 2 | PSG2 |
| P11487 | Fibroblast growth factor 3 | FGF3 |
| P11597 | Cholesteryl ester transfer protein | CETP |
| P11684 | Uteroglobin | SCGB1A1 |
| P11686 | Pulmonary surfactant-associated protein C | SFTPC |
| P12034 | Fibroblast growth factor 5 | FGF5 |
| P12107 | Collagen alpha-1(XI) chain | COL11A1 |
| P12109 | Collagen alpha-1(VI) chain | COL6A1 |
| P12110 | Collagen alpha-2(VI) chain | COL6A2 |
| P12111 | Collagen alpha-3(VI) chain | COL6A3 |
| P12259 | Coagulation factor V | F5 |
| P12272 | PTHrP[1-36] | PTHLH |
| P12273 | Prolactin-inducible protein | PIP |
| P12544 | Granzyme A | GZMA |
| P12643 | Bone morphogenetic protein 2 | BMP2 |
| P12644 | Bone morphogenetic protein 4 | BMP4 |
| P12645 | Bone morphogenetic protein 3 | BMP3 |
| P12724 | Eosinophil cationic protein | RNASE3 |
| P12821 | Angiotensin-converting enzyme, soluble form | ACE |
| P12838 | Neutrophil defensin 4 | DEFA4 |
| P12872 | Motilin | MLN |
| P13232 | Interleukin-7 | IL7 |
| P13236 | C-C motif chemokine 4 | CCL4 |
| P13284 | Gamma-interferon-inducible lysosomal thiol reductase | IFI30 |
| P13500 | C-C motif chemokine 2 | CCL2 |
| P13501 | C-C motif chemokine 5 | CCL5 |
| P13521 | Secretogranin-2 | SCG2 |
| P13591 | Neural cell adhesion molecule 1 | NCAM1 |
| P13611 | Versican core protein | VCAN |
| P13671 | Complement component C6 | C6 |
| P13688 | Carcinoembryonic antigen-related cell adhesion molecule 1 | CEACAM1 |
| P13725 | Oncostatin-M | OSM |
| P13726 | Tissue factor | F3 |
| P13727 | Eosinophil granule major basic protein | PRG2 |
| P13942 | Collagen alpha-2(XI) chain | COL11A2 |
| P13987 | CD59 glycoprotein | CD59 |
| P14138 | Endothelin-3 | EDN3 |
| P14174 | Macrophage migration inhibitory factor | MIF |
| P14207 | Folate receptor beta | FOLR2 |
| P14222 | Perforin-1 | PRF1 |
| P14543 | Nidogen-1 | NID1 |
| P14555 | Phospholipase A2, membrane associated | PLA2G2A |
| P14625 | Endoplasmin | HSP90B1 |
| P14735 | Insulin-degrading enzyme | IDE |
| P14778 | Interleukin-1 receptor type 1, soluble form | IL1R1 |
| P14780 | 82 kDa matrix metalloproteinase-9 | MMP9 |
| P15018 | Leukemia inhibitory factor | LIF |
| P15085 | Carboxypeptidase A1 | CPA1 |
| P15086 | Carboxypeptidase B | CPB1 |
| P15151 | Poliovirus receptor | PVR |
| P15169 | Carboxypeptidase N catalytic chain | CPN1 |
| P15248 | Interleukin-9 | IL9 |
| P15291 | N-acetyllactosamine synthase | B4GALT1 |
| P15309 | PAPf39 | ACPP |
| P15328 | Folate receptor alpha | FOLR1 |
| P15374 | Ubiquitin carboxyl-terminal hydrolase isozyme L3 | UCHL3 |
| P15502 | Elastin | ELN |
| P15509 | Granulocyte-macrophage colony-stimulating factor receptor subunit alpha | CSF2RA |
| P15515 | Histatin-1 | HTN1 |
| P15516 | His3-(31-51)-peptide | HTN3 |
| P15692 | Vascular endothelial growth factor A | VEGFA |
| P15814 | Immunoglobulin lambda-like polypeptide 1 | IGLL1 |
| P15907 | Beta-galactoside alpha-2,6-sialyltransferase 1 | ST6GAL1 |
| P15941 | Mucin-1 subunit beta | MUC1 |
| P16035 | Metalloproteinase inhibitor 2 | TIMP2 |
| P16112 | Aggrecan core protein 2 | ACAN |

TABLE 1-continued

Secreted Proteins

| Uniprot ID | Protein Name | Gene Name |
|---|---|---|
| P16233 | Pancreatic triacylglycerol lipase | PNLIP |
| P16442 | Histo-blood group ABO system transferase | ABO |
| P16471 | Prolactin receptor | PRLR |
| P16562 | Cysteine-rich secretory protein 2 | CRISP2 |
| P16619 | C-C motif chemokine 3-like 1 | CCL3L1 |
| P16860 | BNP(3-29) | NPPB |
| P16870 | Carboxypeptidase E | CPE |
| P16871 | Interleukin-7 receptor subunit alpha | IL7R |
| P17213 | Bactericidal permeability-increasing protein | BPI |
| P17538 | Chymotrypsinogen B | CTRB1 |
| P17931 | Galectin-3 | LGALS3 |
| P17936 | Insulin-like growth factor-binding protein 3 | IGFBP3 |
| P17948 | Vascular endothelial growth factor receptor 1 | FLT1 |
| P18065 | Insulin-like growth factor-binding protein 2 | IGFBP2 |
| P18075 | Bone morphogenetic protein 7 | BMP7 |
| P18428 | Lipopolysaccharide-binding protein | LBP |
| P18509 | PACAP-related peptide | ADCYAP1 |
| P18510 | Interleukin-1 receptor antagonist protein | IL1RN |
| P18827 | Syndecan-1 | SDC1 |
| P19021 | Peptidylglycine alpha-hydroxylating monooxygenase | PAM |
| P19235 | Erythropoietin receptor | EPOR |
| P19438 | Tumor necrosis factor-binding protein 1 | TNFRSF1A |
| P19652 | Alpha-1-acid glycoprotein 2 | ORM2 |
| P19801 | Amiloride-sensitive amine oxidase [copper-containing] | ABP1 |
| P19823 | Inter-alpha-trypsin inhibitor heavy chain H2 | ITIH2 |
| P19827 | Inter-alpha-trypsin inhibitor heavy chain H1 | ITIH1 |
| P19835 | Bile salt-activated lipase | CEL |
| P19875 | C-X-C motif chemokine 2 | CXCL2 |
| P19876 | C-X-C motif chemokine 3 | CXCL3 |
| P19883 | Follistatin | FST |
| P19957 | Elafin | PI3 |
| P19961 | Alpha-amylase 2B | AMY2B |
| P20061 | Transcobalamin-1 | TCN1 |
| P20062 | Transcobalamin-2 | TCN2 |
| P20142 | Gastricsin | PGC |
| P20155 | Serine protease inhibitor Kazal-type 2 | SPINK2 |
| P20231 | Tryptase beta-2 | TPSB2 |
| P20333 | Tumor necrosis factor receptor superfamily member 1B | TNFRSF1B |
| P20366 | Substance P | TAC1 |
| P20382 | Melanin-concentrating hormone | PMCH |
| P20396 | Thyroliberin | TRH |
| P20742 | Pregnancy zone protein | PZP |
| P20774 | Mimecan | OGN |
| P20783 | Neurotrophin-3 | NTF3 |
| P20800 | Endothelin-2 | EDN2 |
| P20809 | Interleukin-11 | IL11 |
| P20827 | Ephrin-A1 | EFNA1 |
| P20849 | Collagen alpha-1(IX) chain | COL9A1 |
| P20851 | C4b-binding protein beta chain | C4BPB |
| P20908 | Collagen alpha-1(V) chain | COL5A1 |
| P21128 | Poly(U)-specific endoribonuclease | ENDOU |
| P21246 | Pleiotrophin | PTN |
| P21583 | Kit ligand | KITLG |
| P21741 | Midkine | MDK |
| P21754 | Zona pellucida sperm-binding protein 3 | ZP3 |
| P21781 | Fibroblast growth factor 7 | FGF7 |
| P21802 | Fibroblast growth factor receptor 2 | FGFR2 |
| P21810 | Biglycan | BGN |
| P21815 | Bone sialoprotein 2 | IBSP |
| P21860 | Receptor tyrosine-protein kinase erbB-3 | ERBB3 |
| P21941 | Cartilage matrix protein | MATN1 |
| P22003 | Bone morphogenetic protein 5 | BMP5 |
| P22004 | Bone morphogenetic protein 6 | BMP6 |
| P22079 | Lactoperoxidase | LPO |
| P22105 | Tenascin-X | TNXB |
| P22301 | Interleukin-10 | IL10 |
| P22303 | Acetylcholinesterase | ACHE |
| P22352 | Glutathione peroxidase 3 | GPX3 |
| P22362 | C-C motif chemokine 1 | CCL1 |
| P22455 | Fibroblast growth factor receptor 4 | FGFR4 |
| P22466 | Galanin message-associated peptide | GAL |
| P22692 | Insulin-like growth factor-binding protein 4 | IGFBP4 |
| P22749 | Granulysin | GNLY |

TABLE 1-continued

Secreted Proteins

| Uniprot ID | Protein Name | Gene Name |
| --- | --- | --- |
| P22792 | Carboxypeptidase N subunit 2 | CPN2 |
| P22891 | Vitamin K-dependent protein Z | PROZ |
| P22894 | Neutrophil collagenase | MMP8 |
| P23142 | Fibulin-1 | FBLN1 |
| P23280 | Carbonic anhydrase 6 | CA6 |
| P23352 | Anosmin-1 | KAL1 |
| P23435 | Cerebellin-1 | CBLN1 |
| P23560 | Brain-derived neurotrophic factor | BDNF |
| P23582 | C-type natriuretic peptide | NPPC |
| P23946 | Chymase | CMA1 |
| P24043 | Laminin subunit alpha-2 | LAMA2 |
| P24071 | Immunoglobulin alpha Fc receptor | FCAR |
| P24347 | Stromelysin-3 | MMP11 |
| P24387 | Corticotropin-releasing factor-binding protein | CRHBP |
| P24592 | Insulin-like growth factor-binding protein 6 | IGFBP6 |
| P24593 | Insulin-like growth factor-binding protein 5 | IGFBP5 |
| P24821 | Tenascin | TNC |
| P24855 | Deoxyribonuclease-1 | DNASE1 |
| P25067 | Collagen alpha-2(VIII) chain | COL8A2 |
| P25311 | Zinc-alpha-2-glycoprotein | AZGP1 |
| P25391 | Laminin subunit alpha-1 | LAMA1 |
| P25445 | Tumor necrosis factor receptor superfamily member 6 | FAS |
| P25940 | Collagen alpha-3(V) chain | COL5A3 |
| P25942 | Tumor necrosis factor receptor superfamily member 5 | CD40 |
| P26022 | Pentraxin-related protein PTX3 | PTX3 |
| P26927 | Hepatocyte growth factor-like protein beta chain | MST1 |
| P27169 | Serum paraoxonase/arylesterase 1 | PON1 |
| P27352 | Gastric intrinsic factor | GIF |
| P27487 | Dipeptidyl peptidase 4 membrane form | DPP4 |
| P27539 | Embryonic growth/differentiation factor 1 | GDF1 |
| P27658 | Vastatin | COL8A1 |
| P27797 | Calreticulin | CALR |
| P27918 | Properdin | CFP |
| P28039 | Acyloxyacyl hydrolase | AOAH |
| P28300 | Protein-lysine 6-oxidase | LOX |
| P28325 | Cystatin-D | CST5 |
| P28799 | Granulin-1 | GRN |
| P29122 | Proprotein convertase subtilisin/kexin type 6 | PCSK6 |
| P29279 | Connective tissue growth factor | CTGF |
| P29320 | Ephrin type-A receptor 3 | EPHA3 |
| P29400 | Collagen alpha-5(IV) chain | COL4A5 |
| P29459 | Interleukin-12 subunit alpha | IL12A |
| P29460 | Interleukin-12 subunit beta | IL12B |
| P29508 | Serpin B3 | SERPINB3 |
| P29622 | Kallistatin | SERPINA4 |
| P29965 | CD40 ligand, soluble form | CD40LG |
| P30990 | Neurotensin/neuromedin N | NTS |
| P31025 | Lipocalin-1 | LCN1 |
| P31151 | Protein S100-A7 | S100A7 |
| P31371 | Fibroblast growth factor 9 | FGF9 |
| P31431 | Syndecan-4 | SDC4 |
| P31947 | 14-3-3 protein sigma | SFN |
| P32455 | Interferon-induced guanylate-binding protein 1 | GBP1 |
| P32881 | Interferon alpha-8 | IFNA8 |
| P34096 | Ribonuclease 4 | RNASE4 |
| P34130 | Neurotrophin-4 | NTF4 |
| P34820 | Bone morphogenetic protein 8B | BMP8B |
| P35030 | Trypsin-3 | PRSS3 |
| P35052 | Secreted glypican-1 | GPC1 |
| P35070 | Betacellulin | BTC |
| P35225 | Interleukin-13 | IL13 |
| P35247 | Pulmonary surfactant-associated protein D | SFTPD |
| P35318 | ADM | ADM |
| P35542 | Serum amyloid A-4 protein | SAA4 |
| P35555 | Fibrillin-1 | FBN1 |
| P35556 | Fibrillin-2 | FBN2 |
| P35625 | Metalloproteinase inhibitor 3 | TIMP3 |
| P35858 | Insulin-like growth factor-binding protein complex acid labile subunit | IGFALS |
| P35916 | Vascular endothelial growth factor receptor 3 | FLT4 |
| P35968 | Vascular endothelial growth factor receptor 2 | KDR |
| P36222 | Chitinase-3-like protein 1 | CHI3L1 |
| P36952 | Serpin B5 | SERPINB5 |
| P36955 | Pigment epithelium-derived factor | SERPINF1 |

TABLE 1-continued

Secreted Proteins

| Uniprot ID | Protein Name | Gene Name |
|---|---|---|
| P36980 | Complement factor H-related protein 2 | CFHR2 |
| P39059 | Collagen alpha-1(XV) chain | COL15A1 |
| P39060 | Collagen alpha-1(XVIII) chain | COL18A1 |
| P39877 | Calcium-dependent phospholipase A2 | PLA2G5 |
| P39900 | Macrophage metalloelastase | MMP12 |
| P39905 | Glial cell line-derived neurotrophic factor | GDNF |
| P40225 | Thrombopoietin | THPO |
| P40967 | M-alpha | PMEL |
| P41159 | Leptin | LEP |
| P41221 | Protein Wnt-5a | WNT5A |
| P41222 | Prostaglandin-H2 D-isomerase | PTGDS |
| P41271 | Neuroblastoma suppressor of tumorigenicity 1 | NBL1 |
| P41439 | Folate receptor gamma | FOLR3 |
| P42127 | Agouti-signaling protein | ASIP |
| P42702 | Leukemia inhibitory factor receptor | LIFR |
| P42830 | ENA-78(9-78) | CXCL5 |
| P43026 | Growth/differentiation factor 5 | GDF5 |
| P43251 | Biotinidase | BTD |
| P43652 | Afamin | AFM |
| P45452 | Collagenase 3 | MMP13 |
| P47710 | Casoxin-D | CSN1S1 |
| P47929 | Galectin-7 | LGALS7B |
| P47972 | Neuronal pentraxin-2 | NPTX2 |
| P47989 | Xanthine oxidase | XDH |
| P47992 | Lymphotactin | XCL1 |
| P48023 | Tumor necrosis factor ligand superfamily member 6, membrane form | FASLG |
| P48052 | Carboxypeptidase A2 | CPA2 |
| P48061 | Stromal cell-derived factor 1 | CXCL12 |
| P48304 | Lithostathine-1-beta | REG1B |
| P48307 | Tissue factor pathway inhibitor 2 | TFPI2 |
| P48357 | Leptin receptor | LEPR |
| P48594 | Serpin B4 | SERPINB4 |
| P48645 | Neuromedin-U-25 | NMU |
| P48740 | Mannan-binding lectin serine protease 1 | MASP1 |
| P48745 | Protein NOV homolog | NOV |
| P48960 | CD97 antigen subunit beta | CD97 |
| P49223 | Kunitz-type protease inhibitor 3 | SPINT3 |
| P49747 | Cartilage oligomeric matrix protein | COMP |
| P49763 | Placenta growth factor | PGF |
| P49765 | Vascular endothelial growth factor B | VEGFB |
| P49767 | Vascular endothelial growth factor C | VEGFC |
| P49771 | Fms-related tyrosine kinase 3 ligand | FLT3LG |
| P49862 | Kallikrein-7 | KLK7 |
| P49863 | Granzyme K | GZMK |
| P49908 | Selenoprotein P | SEPP1 |
| P49913 | Antibacterial protein FALL-39 | CAMP |
| P50607 | Tubby protein homolog | TUB |
| P51124 | Granzyme M | GZMM |
| P51512 | Matrix metalloproteinase-16 | MMP16 |
| P51654 | Glypican-3 | GPC3 |
| P51671 | Eotaxin | CCL11 |
| P51884 | Lumican | LUM |
| P51888 | Prolargin | PRELP |
| P52798 | Ephrin-A4 | EFNA4 |
| P52823 | Stanniocalcin-1 | STC1 |
| P53420 | Collagen alpha-4(IV) chain | COL4A4 |
| P53621 | Coatomer subunit alpha | COPA |
| P54108 | Cysteine-rich secretory protein 3 | CRISP3 |
| P54315 | Pancreatic lipase-related protein 1 | PNLIPRP1 |
| P54317 | Pancreatic lipase-related protein 2 | PNLIPRP2 |
| P54793 | Arylsulfatase F | ARSF |
| P55000 | Secreted Ly-6/uPAR-related protein 1 | SLURP 1 |
| P55001 | Microfibrillar-associated protein 2 | MFAP2 |
| P55056 | Apolipoprotein C-IV | APOC4 |
| P55058 | Phospholipid transfer protein | PLTP |
| P55075 | Fibroblast growth factor 8 | FGF8 |
| P55081 | Microfibrillar-associated protein 1 | MFAP1 |
| P55083 | Microfibril-associated glycoprotein 4 | MFAP4 |
| P55107 | Bone morphogenetic protein 3B | GDF10 |
| P55145 | Mesencephalic astrocyte-derived neurotrophic factor | MANF |
| P55259 | Pancreatic secretory granule membrane major glycoprotein GP2 | GP2 |
| P55268 | Laminin subunit beta-2 | LAMB2 |
| P55773 | CCL23(30-99) | CCL23 |

TABLE 1-continued

Secreted Proteins

| Uniprot ID | Protein Name | Gene Name |
|---|---|---|
| P55774 | C-C motif chemokine 18 | CCL18 |
| P55789 | FAD-linked sulfhydryl oxidase ALR | GFER |
| P56703 | Proto-oncogene Wnt-3 | WNT3 |
| P56704 | Protein Wnt-3a | WNT3A |
| P56705 | Protein Wnt-4 | WNT4 |
| P56706 | Protein Wnt-7b | WNT7B |
| P56730 | Neurotrypsin | PRSS12 |
| P56851 | Epididymal secretory protein E3-beta | EDDM3B |
| P56975 | Neuregulin-3 | NRG3 |
| P58062 | Serine protease inhibitor Kazal-type 7 | SPINK7 |
| P58215 | Lysyl oxidase homolog 3 | LOXL3 |
| P58294 | Prokineticin-1 | PROK1 |
| P58335 | Anthrax toxin receptor 2 | ANTXR2 |
| P58397 | A disintegrin and metalloproteinase with thrombospondin motifs 12 | ADAMTS12 |
| P58417 | Neurexophilin-1 | NXPH1 |
| P58499 | Protein FAM3B | FAM3B |
| P59510 | A disintegrin and metalloproteinase with thrombospondin motifs 20 | ADAMTS20 |
| P59665 | Neutrophil defensin 1 | DEFA1B |
| P59666 | Neutrophil defensin 3 | DEFA3 |
| P59796 | Glutathione peroxidase 6 | GPX6 |
| P59826 | BPI fold-containing family B member 3 | BPIFB3 |
| P59827 | BPI fold-containing family B member 4 | BPIFB4 |
| P59861 | Beta-defensin 131 | DEFB131 |
| P60022 | Beta-defensin 1 | DEFB1 |
| P60153 | Inactive ribonuclease-like protein 9 | RNASE9 |
| P60827 | Complement C1q tumor necrosis factor-related protein 8 | C1QTNF8 |
| P60852 | Zona pellucida sperm-binding protein 1 | ZP1 |
| P60985 | Keratinocyte differentiation-associated protein | KRTDAP |
| P61109 | Kidney androgen-regulated protein | KAP |
| P61278 | Somatostatin-14 | SST |
| P61366 | Osteocrin | OSTN |
| P61626 | Lysozyme C | LYZ |
| P61769 | Beta-2-microglobulin | B2M |
| P61812 | Transforming growth factor beta-2 | TGFB2 |
| P61916 | Epididymal secretory protein E1 | NPC2 |
| P62502 | Epididymal-specific lipocalin-6 | LCN6 |
| P62937 | Peptidyl-prolyl cis-trans isomerase A | PPIA |
| P67809 | Nuclease-sensitive element-binding protein 1 | YBX1 |
| P67812 | Signal peptidase complex catalytic subunit SEC11A | SEC11A |
| P78310 | Coxsackievirus and adenovirus receptor | CXADR |
| P78333 | Secreted glypican-5 | GPC5 |
| P78380 | Oxidized low-density lipoprotein receptor 1 | OLR1 |
| P78423 | Processed fractalkine | CX3CL1 |
| P78509 | Reelin | RELN |
| P78556 | CCL20(2-70) | CCL20 |
| P80075 | MCP-2(6-76) | CCL8 |
| P80098 | C-C motif chemokine 7 | CCL7 |
| P80108 | Phosphatidylinositol-glycan-specific phospholipase D | GPLD1 |
| P80162 | C-X-C motif chemokine 6 | CXCL6 |
| P80188 | Neutrophil gelatinase-associated lipocalin | LCN2 |
| P80303 | Nucleobindin-2 | NUCB2 |
| P80511 | Calcitermin | S100A12 |
| P81172 | Hepcidin-25 | HAMP |
| P81277 | Prolactin-releasing peptide | PRLH |
| P81534 | Beta-defensin 103 | DEFB103A |
| P81605 | Dermcidin | DCD |
| P82279 | Protein crumbs homolog 1 | CRB1 |
| P82987 | ADAMTS-like protein 3 | ADAMTSL3 |
| P83105 | Serine protease HTRA4 | HTRA4 |
| P83110 | Serine protease HTRA3 | HTRA3 |
| P83859 | Orexigenic neuropeptide QRFP | QRFP |
| P98088 | Mucin-5AC | MUC5AC |
| P98095 | Fibulin-2 | FBLN2 |
| P98160 | Basement membrane-specific heparan sulfate proteoglycan core protein | HSPG2 |
| P98173 | Protein FAM3A | FAM3A |
| Q00604 | Norrin | NDP |
| Q00796 | Sorbitol dehydrogenase | SORD |
| Q00887 | Pregnancy-specific beta-1-glycoprotein 9 | PSG9 |
| Q00888 | Pregnancy-specific beta-1-glycoprotein 4 | PSG4 |
| Q00889 | Pregnancy-specific beta-1-glycoprotein 6 | PSG6 |

TABLE 1-continued

Secreted Proteins

| Uniprot ID | Protein Name | Gene Name |
|---|---|---|
| Q01523 | HD5(56-94) | DEFA5 |
| Q01524 | Defensin-6 | DEFA6 |
| Q01955 | Collagen alpha-3(IV) chain | COL4A3 |
| Q02297 | Pro-neuregulin-1, membrane-bound isoform | NRG1 |
| Q02325 | Plasminogen-like protein B | PLGLB1 |
| Q02383 | Semenogelin-2 | SEMG2 |
| Q02388 | Collagen alpha-1(VII) chain | COL7A1 |
| Q02505 | Mucin-3A | MUC3A |
| Q02509 | Otoconin-90 | OC90 |
| Q02747 | Guanylin | GUCA2A |
| Q02763 | Angiopoietin-1 receptor | TEK |
| Q02817 | Mucin-2 | MUC2 |
| Q02985 | Complement factor H-related protein 3 | CFHR3 |
| Q03167 | Transforming growth factor beta receptor type 3 | TGFBR3 |
| Q03403 | Trefoil factor 2 | TFF2 |
| Q03405 | Urokinase plasminogen activator surface receptor | PLAUR |
| Q03591 | Complement factor H-related protein 1 | CFHR1 |
| Q03692 | Collagen alpha-1(X) chain | COL10A1 |
| Q04118 | Basic salivary proline-rich protein 3 | PRB3 |
| Q04756 | Hepatocyte growth factor activator short chain | HGFAC |
| Q04900 | Sialomucin core protein 24 | CD164 |
| Q05315 | Eosinophil lysophospholipase | CLC |
| Q05707 | Collagen alpha-1(XIV) chain | COL14A1 |
| Q05996 | Processed zona pellucida sperm-binding protein 2 | ZP2 |
| Q06033 | Inter-alpha-trypsin inhibitor heavy chain H3 | ITIH3 |
| Q06141 | Regenerating islet-derived protein 3-alpha | REG3A |
| Q06828 | Fibromodulin | FMOD |
| Q07092 | Collagen alpha-1(XVI) chain | COL16A1 |
| Q07325 | C-X-C motif chemokine 9 | CXCL9 |
| Q07507 | Dermatopontin | DPT |
| Q075Z2 | Binder of sperm protein homolog 1 | BSPH1 |
| Q07654 | Trefoil factor 3 | TFF3 |
| Q07699 | Sodium channel subunit beta-1 | SCN1B |
| Q08345 | Epithelial discoidin domain-containing receptor 1 | DDR1 |
| Q08380 | Galectin-3-binding protein | LGALS3BP |
| Q08397 | Lysyl oxidase homolog 1 | LOXL1 |
| Q08431 | Lactadherin | MFGE8 |
| Q08629 | Testican-1 | SPOCK1 |
| Q08648 | Sperm-associated antigen 11B | SPAG11B |
| Q08830 | Fibrinogen-like protein 1 | FGL1 |
| Q10471 | Polypeptide N-acetylgalactosaminyltransferase 2 | GALNT2 |
| Q10472 | Polypeptide N-acetylgalactosaminyltransferase 1 | GALNT1 |
| Q11201 | CMP-N-acetylneuraminate-beta-galactosamide-alpha-2,3-sialyltransferase 1 | ST3GAL1 |
| Q11203 | CMP-N-acetylneuraminate-beta-1,4-galactoside alpha-2,3-sialyltransferase | ST3GAL3 |
| Q11206 | CMP-N-acetylneuraminate-beta-galactosamide-alpha-2,3-sialyltransferase 4 | ST3GAL4 |
| Q12794 | Hyaluronidase-1 | HYAL1 |
| Q12805 | EGF-containing fibulin-like extracellular matrix protein 1 | EFEMP1 |
| Q12836 | Zona pellucida sperm-binding protein 4 | ZP4 |
| Q12841 | Follistatin-related protein 1 | FSTL1 |
| Q12904 | Aminoacyl tRNA synthase complex-interacting multifunctional protein 1 | AIMP1 |
| Q13018 | Soluble secretory phospholipase A2 receptor | PLA2R1 |
| Q13072 | B melanoma antigen 1 | BAGE |
| Q13093 | Platelet-activating factor acetylhydrolase | PLA2G7 |
| Q13103 | Secreted phosphoprotein 24 | SPP2 |
| Q13162 | Peroxiredoxin-4 | PRDX4 |
| Q13201 | Platelet glycoprotein Ia* | MMRN1 |
| Q13214 | Semaphorin-3B | SEMA3B |
| Q13219 | Pappalysin-1 | PAPPA |
| Q13231 | Chitotriosidase-1 | CHIT1 |
| Q13253 | Noggin | NOG |
| Q13261 | Interleukin-15 receptor subunit alpha | IL15RA |
| Q13275 | Semaphorin-3F | SEMA3F |
| Q13291 | Signaling lymphocytic activation molecule | SLAMF1 |
| Q13316 | Dentin matrix acidic phosphoprotein 1 | DMP1 |
| Q13361 | Microfibrillar-associated protein 5 | MFAP5 |
| Q13410 | Butyrophilin subfamily 1 member A1 | BTN1A1 |
| Q13421 | Mesothelin, cleaved form | MSLN |
| Q13429 | Insulin-like growth factor I | IGF-I |
| Q13443 | Disintegrin and metalloproteinase domain-containing protein 9 | ADAM9 |

TABLE 1-continued

Secreted Proteins

| Uniprot ID | Protein Name | Gene Name |
|---|---|---|
| Q13519 | Neuropeptide 1 | PNOC |
| Q13751 | Laminin subunit beta-3 | LAMB3 |
| Q13753 | Laminin subunit gamma-2 | LAMC2 |
| Q13790 | Apolipoprotein F | APOF |
| Q13822 | Ectonucleotide pyrophosphatase/phosphodiesterase family member 2 | ENPP2 |
| Q14031 | Collagen alpha-6(IV) chain | COL4A6 |
| Q14050 | Collagen alpha-3(IX) chain | COL9A3 |
| Q14055 | Collagen alpha-2(IX) chain | COL9A2 |
| Q14112 | Nidogen-2 | NID2 |
| Q14114 | Low-density lipoprotein receptor-related protein 8 | LRP8 |
| Q14118 | Dystroglycan | DAG1 |
| Q14314 | Fibroleukin | FGL2 |
| Q14393 | Growth arrest-specific protein 6 | GAS6 |
| Q14406 | Chorionic somatomammotropin hormone-like 1 | CSHL1 |
| Q14507 | Epididymal secretory protein E3-alpha | EDDM3A |
| Q14508 | WAP four-disulfide core domain protein 2 | WFDC2 |
| Q14512 | Fibroblast growth factor-binding protein 1 | FGFBP1 |
| Q14515 | SPARC-like protein 1 | SPARCL1 |
| Q14520 | Hyaluronan-binding protein 2 27 kDa light chain | HABP2 |
| Q14563 | Semaphorin-3A | SEMA3A |
| Q14623 | Indian hedgehog protein | IHH |
| Q14624 | Inter-alpha-trypsin inhibitor heavy chain H4 | ITIH4 |
| Q14667 | UPF0378 protein KIAA0100 | KIAA0100 |
| Q14703 | Membrane-bound transcription factor site-1 protease | MBTPS1 |
| Q14766 | Latent-transforming growth factor beta-binding protein 1 | LTBP1 |
| Q14767 | Latent-transforming growth factor beta-binding protein 2 | LTBP2 |
| Q14773 | Intercellular adhesion molecule 4 | ICAM4 |
| Q14993 | Collagen alpha-1(XIX) chain | COL19A1 |
| Q14CN2 | Calcium-activated chloride channel regulator 4, 110 kDa form | CLCA4 |
| Q15046 | Lysine--tRNA ligase | KARS |
| Q15063 | Periostin | POSTN |
| Q15109 | Advanced glycosylation end product-specific receptor | AGER |
| Q15113 | Procollagen C-endopeptidase enhancer 1 | PCOLCE |
| Q15166 | Serum paraoxonase/lactonase 3 | PON3 |
| Q15195 | Plasminogen-like protein A | PLGLA |
| Q15198 | Platelet-derived growth factor receptor-like protein | PDGFRL |
| Q15223 | Poliovirus receptor-related protein 1 | PVRL1 |
| Q15238 | Pregnancy-specific beta-1-glycoprotein 5 | PSG5 |
| Q15363 | Transmembrane emp24 domain-containing protein 2 | TMED2 |
| Q15375 | Ephrin type-A receptor 7 | EPHA7 |
| Q15389 | Angiopoietin-1 | ANGPT1 |
| Q15465 | Sonic hedgehog protein | SHH |
| Q15485 | Ficolin-2 | FCN2 |
| Q15517 | Corneodesmosin | CDSN |
| Q15582 | Transforming growth factor-beta-induced protein ig-h3 | TGFBI |
| Q15661 | Tryptase alpha/beta-1 | TPSAB1 |
| Q15726 | Metastin | KISS1 |
| Q15782 | Chitinase-3-like protein 2 | CHI3L2 |
| Q15828 | Cystatin-M | CST6 |
| Q15846 | Clusterin-like protein 1 | CLUL1 |
| Q15848 | Adiponectin | ADIPOQ |
| Q16206 | Protein disulfide-thiol oxidoreductase | ENOX2 |
| Q16270 | Insulin-like growth factor-binding protein 7 | IGFBP7 |
| Q16363 | Laminin subunit alpha-4 | LAMA4 |
| Q16378 | Proline-rich protein 4 | PRR4 |
| Q16557 | Pregnancy-specific beta-1-glycoprotein 3 | PSG3 |
| Q16568 | CART(42-89) | CARTPT |
| Q16610 | Extracellular matrix protein 1 | ECM1 |
| Q16619 | Cardiotrophin-1 | CTF1 |
| Q16623 | Syntaxin-1A | STX1A |
| Q16627 | HCC-1(9-74) | CCL14 |
| Q16651 | Prostasin light chain | PRSS8 |
| Q16661 | Guanylate cyclase C-activating peptide 2 | GUCA2B |
| Q16663 | CCL15(29-92) | CCL15 |
| Q16674 | Melanoma-derived growth regulatory protein | MIA |
| Q16769 | Glutaminyl-peptide cyclotransferase | QPCT |

TABLE 1-continued

Secreted Proteins

| Uniprot ID | Protein Name | Gene Name |
|---|---|---|
| Q16787 | Laminin subunit alpha-3 | LAMA3 |
| Q16842 | CMP-N-acetylneuraminate-beta-galactosamide-alpha-2,3-sialyltransferase 2 | ST3GAL2 |
| Q17RR3 | Pancreatic lipase-related protein 3 | PNLIPRP3 |
| Q17RW2 | Collagen alpha-1(XXIV) chain | COL24A1 |
| Q17RY6 | Lymphocyte antigen 6K | LY6K |
| Q1L6U9 | Prostate-associated microseminoprotein | MSMP |
| Q1W4C9 | Serine protease inhibitor Kazal-type 13 | SPINK13 |
| Q1ZYL8 | Izumo sperm-egg fusion protein 4 | IZUMO4 |
| Q29960 | HLA class I histocompatibility antigen, Cw-16 alpha chain | HLA-C |
| Q2I0M5 | R-spondin-4 | RSPO4 |
| Q2L4Q9 | Serine protease 53 | PRSS53 |
| Q2MKA7 | R-spondin-1 | RSPO1 |
| Q2MV58 | Tectonic-1 | TCTN1 |
| Q2TAL6 | Brorin | VWC2 |
| Q2UY09 | Collagen alpha-1(XXVIII) chain | COL28A1 |
| Q2VPA4 | Complement component receptor 1-like protein | CR1L |
| Q2WEN9 | Carcinoembryonic antigen-related cell adhesion molecule 16 | CEACAM16 |
| Q30KP8 | Beta-defensin 136 | DEFB136 |
| Q30KP9 | Beta-defensin 135 | DEFB135 |
| Q30KQ1 | Beta-defensin 133 | DEFB133 |
| Q30KQ2 | Beta-defensin 130 | DEFB130 |
| Q30KQ4 | Beta-defensin 116 | DEFB116 |
| Q30KQ5 | Beta-defensin 115 | DEFB115 |
| Q30KQ6 | Beta-defensin 114 | DEFB114 |
| Q30KQ7 | Beta-defensin 113 | DEFB113 |
| Q30KQ8 | Beta-defensin 112 | DEFB112 |
| Q30KQ9 | Beta-defensin 110 | DEFB110 |
| Q30KR1 | Beta-defensin 109 | DEFB109P1 |
| Q32P28 | Prolyl 3-hydroxylase 1 | LEPRE1 |
| Q3B7J2 | Glucose-fructose oxidoreductase domain-containing protein 2 | GFOD2 |
| Q3SY79 | Protein Wnt | WNT3A |
| Q3T906 | N-acetylglucosamine-1-phosphotransferase subunits alpha/beta | GNPTAB |
| Q495T6 | Membrane metallo-endopeptidase-like 1 | MMEL1 |
| Q49AH0 | Cerebral dopamine neurotrophic factor | CDNF |
| Q4G0G5 | Secretoglobin family 2B member 2 | SCGB2B2 |
| Q4G0M1 | Protein FAM132B | FAM132B |
| Q4LDE5 | Sushi, von Willebrand factor type A, EGF and pentraxin domain-containing protein 1 | SVEP1 |
| Q4QY38 | Beta-defensin 134 | DEFB134 |
| Q4VAJ4 | Protein Wnt | WNT10B |
| Q4W5P6 | Protein TMEM155 | TMEM155 |
| Q4ZHG4 | Fibronectin type III domain-containing protein 1 | FNDC1 |
| Q53H76 | Phospholipase A1 member A | PLA1A |
| Q53RD9 | Fibulin-7 | FBLN7 |
| Q53S33 | BolA-like protein 3 | BOLA3 |
| Q5BLP8 | Neuropeptide-like protein C4orf48 | C4orf48 |
| Q5DT21 | Serine protease inhibitor Kazal-type 9 | SPINK9 |
| Q5EBL8 | PDZ domain-containing protein 11 | PDZD11 |
| Q5FYB0 | Arylsulfatase J | ARSJ |
| Q5FYB1 | Arylsulfatase I | ARSI |
| Q5GAN3 | Ribonuclease-like protein 13 | RNASE13 |
| Q5GAN4 | Ribonuclease-like protein 12 | RNASE12 |
| Q5GAN6 | Ribonuclease-like protein 10 | RNASE10 |
| Q5GFL6 | von Willebrand factor A domain-containing protein 2 | VWA2 |
| Q5H8A3 | Neuromedin-S | NMS |
| Q5H8C1 | FRAS1-related extracellular matrix protein 1 | FREM1 |
| Q5IJ48 | Protein crumbs homolog 2 | CRB2 |
| Q5J5C9 | Beta-defensin 121 | DEFB121 |
| Q5JS37 | NHL repeat-containing protein 3 | NHLRC3 |
| Q5JTB6 | Placenta-specific protein 9 | PLAC9 |
| Q5JU69 | Torsin-2A | TOR2A |
| Q5JXM2 | Methyltransferase-like protein 24 | METTL24 |
| Q5JZY3 | Ephrin type-A receptor 10 | EPHA10 |
| Q5K4E3 | Polyserase-2 | PRSS36 |
| Q5SRR4 | Lymphocyte antigen 6 complex locus protein G5c | LY6G5C |
| Q5T1H1 | Protein eyes shut homolog | EYS |
| Q5T4F7 | Secreted frizzled-related protein 5 | SFRP5 |
| Q5T4W7 | Artemin | ARTN |
| Q5T7M4 | Protein FAM132A | FAM132A |
| Q5TEH8 | Protein Wnt | WNT2B |

TABLE 1-continued

Secreted Proteins

| Uniprot ID | Protein Name | Gene Name |
| --- | --- | --- |
| Q5TIE3 | von Willebrand factor A domain-containing protein 5B1 | VWA5B1 |
| Q5UCC4 | ER membrane protein complex subunit 10 | EMC10 |
| Q5VST6 | Abhydrolase domain-containing protein FAM108B1 | FAM108B1 |
| Q5VTL7 | Fibronectin type III domain-containing protein 7 | FNDC7 |
| Q5VUM1 | UPF0369 protein C6orf57 | C6orf57 |
| Q5VV43 | Dyslexia-associated protein KIAA0319 | KIAA0319 |
| Q5VWW1 | Complement C1q-like protein 3 | C1QL3 |
| Q5VXI9 | Lipase member N | LIPN |
| Q5VXJ0 | Lipase member K | LIPK |
| Q5VXM1 | CUB domain-containing protein 2 | CDCP2 |
| Q5VYX0 | Renalase | RNLS |
| Q5VYY2 | Lipase member M | LIPM |
| Q5W186 | Cystatin-9 | CST9 |
| Q5W5W9 | Regulated endocrine-specific protein 18 | RESP18 |
| Q5XG92 | Carboxylesterase 4A | CES4A |
| Q63HQ2 | Pikachurin | EGFLAM |
| Q641Q3 | Meteorin-like protein | METRNL |
| Q66K79 | Carboxypeptidase Z | CPZ |
| Q685J3 | Mucin-17 | MUC17 |
| Q68BL7 | Olfactomedin-like protein 2A | OLFML2A |
| Q68BL8 | Olfactomedin-like protein 2B | OLFML2B |
| Q68DV7 | E3 ubiquitin-protein ligase RNF43 | RNF43 |
| Q6B9Z1 | Insulin growth factor-like family member 4 | IGFL4 |
| Q6BAA4 | Fc receptor-like B | FCRLB |
| Q6E0U4 | Dermokine | DMKN |
| Q6EMK4 | Vasorin | VASN |
| Q6FHJ7 | Secreted frizzled-related protein 4 | SFRP4 |
| Q6GPI1 | Chymotrypsin B2 chain B | CTRB2 |
| Q6GTS8 | Probable Carboxypeptidase PM20D1 | PM20D1 |
| Q6H9L7 | Isthmin-2 | ISM2 |
| Q6IE36 | Ovostatin homolog 2 | OVOS2 |
| Q6IE37 | Ovostatin homolog 1 | OVOS1 |
| Q6IE38 | Serine protease inhibitor Kazal-type 14 | SPINK14 |
| Q6ISS4 | Leukocyte-associated immunoglobulin-like receptor 2 | LAIR2 |
| Q6JVE5 | Epididymal-specific lipocalin-12 | LCN12 |
| Q6JVE6 | Epididymal-specific lipocalin-10 | LCN10 |
| Q6JVE9 | Epididymal-specific lipocalin-8 | LCN8 |
| Q6KF10 | Growth/differentiation factor 6 | GDF6 |
| Q6MZW2 | Follistatin-related protein 4 | FSTL4 |
| Q6NSX1 | Coiled-coil domain-containing protein 70 | CCDC70 |
| Q6NT32 | Carboxylesterase 5A | CES5A |
| Q6NT52 | Choriogonadotropin subunit beta variant 2 | CGB2 |
| Q6NUI6 | Chondroactherin-like protein | CHADL |
| Q6NUJ1 | Saposin A-like | PSAPL1 |
| Q6P093 | Arylacetamide deacetylase-like 2 | AADACL2 |
| Q6P4A8 | Phospholipase B-like 1 | PLBD1 |
| Q6P5S2 | UPF0762 protein C6orf58 | C6orf58 |
| Q6P988 | Protein notum homolog | NOTUM |
| Q6PCB0 | von Willebrand factor A domain-containing protein 1 | VWA1 |
| Q6PDA7 | Sperm-associated antigen 11A | SPAG11A |
| Q6PEW0 | Inactive serine protease 54 | PRSS54 |
| Q6PEZ8 | Podocan-like protein 1 | PODNL1 |
| Q6PKH6 | Dehydrogenase/reductase SDR family member 4-like 2 | DHRS4L2 |
| Q6Q788 | Apolipoprotein A-V | APOA5 |
| Q6SPF0 | Atherin | SAMD1 |
| Q6UDR6 | Kunitz-type protease inhibitor 4 | SPINT4 |
| Q6URK8 | Testis, prostate and placenta-expressed protein | TEPP |
| Q6UW01 | Cerebellin-3 | CBLN3 |
| Q6UW10 | Surfactant-associated protein 2 | SFTA2 |
| Q6UW15 | Regenerating islet-derived protein 3-gamma | REG3G |
| Q6UW32 | Insulin growth factor-like family member 1 | IGFL1 |
| Q6UW78 | UPF0723 protein C11orf83 | C11orf83 |
| Q6UW88 | Epigen | EPGN |
| Q6UWE3 | Colipase-like protein 2 | CLPSL2 |
| Q6UWF7 | NXPE family member 4 | NXPE4 |
| Q6UWF9 | Protein FAM180A | FAM180A |
| Q6UWM5 | GLIPR1-like protein 1 | GLIPR1L1 |
| Q6UWN8 | Serine protease inhibitor Kazal-type 6 | SPINK6 |
| Q6UWP2 | Dehydrogenase/reductase SDR family member 11 | DHRS11 |
| Q6UWP8 | Suprabasin | SBSN |
| Q6UWQ5 | Lysozyme-like protein 1 | LYZL1 |

TABLE 1-continued

Secreted Proteins

| Uniprot ID | Protein Name | Gene Name |
| --- | --- | --- |
| Q6UWQ7 | Insulin growth factor-like family member 2 | IGFL2 |
| Q6UWR7 | Ectonucleotide pyrophosphatase/phosphodiesterase family member 6 soluble form | ENPP6 |
| Q6UWT2 | Adropin | ENHO |
| Q6UWU2 | Beta-galactosidase-1-like protein | GLB1L |
| Q6UWW0 | Lipocalin-15 | LCN15 |
| Q6UWX4 | HHIP-like protein 2 | HHIPL2 |
| Q6UWY0 | Arylsulfatase K | ARSK |
| Q6UWY2 | Serine protease 57 | PRSS57 |
| Q6UWY5 | Olfactomedin-like protein 1 | OLFML1 |
| Q6UX06 | Olfactomedin-4 | OLFM4 |
| Q6UX07 | Dehydrogenase/reductase SDR family member 13 | DHRS13 |
| Q6UX39 | Amelotin | AMTN |
| Q6UX46 | Protein FAM150B | FAM150B |
| Q6UX73 | UPF0764 protein C16orf89 | C16orf89 |
| Q6UXB0 | Protein FAM131A | FAM131A |
| Q6UXB1 | Insulin growth factor-like family member 3 | IGFL3 |
| Q6UXB2 | VEGF co-regulated chemokine 1 | CXCL17 |
| Q6UXF7 | C-type lectin domain family 18 member B | CLEC18B |
| Q6UXH0 | Hepatocellular carcinoma-associated protein TD26 | C19orf80 |
| Q6UXH1 | Cysteine-rich with EGF-like domain protein 2 | CRELD2 |
| Q6UXH8 | Collagen and calcium-binding EGF domain-containing protein 1 | CCBE1 |
| Q6UXH9 | Inactive serine protease PAMR1 | PAMR1 |
| Q6UXI7 | Vitrin | VIT |
| Q6UXI9 | Nephronectin | NPNT |
| Q6UXN2 | Trem-like transcript 4 protein | TREML4 |
| Q6UXS0 | C-type lectin domain family 19 member A | CLEC19A |
| Q6UXT8 | Protein FAM150A | FAM150A |
| Q6UXT9 | Abhydrolase domain-containing protein 15 | ABHD15 |
| Q6UXV4 | Apolipoprotein O-like | APOOL |
| Q6UXX5 | Inter-alpha-trypsin inhibitor heavy chain H6 | ITIH6 |
| Q6UXX9 | R-spondin-2 | RSPO2 |
| Q6UY14 | ADAMTS-like protein 4 | ADAMTSL4 |
| Q6UY27 | Prostate and testis expressed protein 2 | PATE2 |
| Q6W4X9 | Mucin-6 | MUC6 |
| Q6WN34 | Chordin-like protein 2 | CHRDL2 |
| Q6WRI0 | Immunoglobulin superfamily member 10 | IGSF10 |
| Q6X4U4 | Sclerostin domain-containing protein 1 | SOSTDC1 |
| Q6X784 | Zona pellucida-binding protein 2 | ZPBP2 |
| Q6XE38 | Secretoglobin family 1D member 4 | SCGB1D4 |
| Q6XPR3 | Repetin | RPTN |
| Q6XZB0 | Lipase member I | LIPI |
| Q6ZMM2 | ADAMTS-like protein 5 | ADAMTSL5 |
| Q6ZMP0 | Thrombospondin type-1 domain-containing protein 4 | THSD4 |
| Q6ZNF0 | Iron/zinc purple acid phosphatase-like protein | PAPL |
| Q6ZRI0 | Otogelin | OTOG |
| Q6ZRP7 | Sulfhydryl oxidase 2 | QSOX2 |
| Q6ZWJ8 | Kielin/chordin-like protein | KCP |
| Q75N90 | Fibrillin-3 | FBN3 |
| Q765I0 | Urotensin-2B | UTS2D |
| Q76B58 | Protein FAM5C | FAM5C |
| Q76LX8 | A disintegrin and metalloproteinase with thrombospondin motifs 13 | ADAMTS13 |
| Q76M96 | Coiled-coil domain-containing protein 80 | CCDC80 |
| Q7L1S5 | Carbohydrate sulfotransferase 9 | CHST9 |
| Q7L513 | Fc receptor-like A | FCRLA |
| Q7L8A9 | Vasohibin-1 | VASH1 |
| Q7RTM1 | Otopetrin-1 | OTOP1 |
| Q7RTW8 | Otoancorin | OTOA |
| Q7RTY5 | Serine protease 48 | PRSS48 |
| Q7RTY7 | Ovochymase-1 | OVCH1 |
| Q7RTZ1 | Ovochymase-2 | OVCH2 |
| Q7Z304 | MAM domain-containing protein 2 | MAMDC2 |
| Q7Z3S9 | Notch homolog 2 N-terminal-like protein | NOTCH2NL |
| Q7Z4H4 | Intermedin-short | ADM2 |
| Q7Z4P5 | Growth/differentiation factor 7 | GDF7 |
| Q7Z4R8 | UPF0669 protein C6orf120 | C6orf120 |
| Q7Z4W2 | Lysozyme-like protein 2 | LYZL2 |
| Q7Z5A4 | Serine protease 42 | PRSS42 |
| Q7Z5A7 | Protein FAM19A5 | FAM19A5 |
| Q7Z5A8 | Protein FAM19A3 | FAM19A3 |

TABLE 1-continued

Secreted Proteins

| Uniprot ID | Protein Name | Gene Name |
|---|---|---|
| Q7Z5A9 | Protein FAM19A1 | FAM19A1 |
| Q7Z5J1 | Hydroxysteroid 11-beta-dehydrogenase 1-like protein | HSD11B1L |
| Q7Z5L0 | Vitelline membrane outer layer protein 1 homolog | VMO1 |
| Q7Z5L3 | Complement C1q-like protein 2 | C1QL2 |
| Q7Z5L7 | Podocan | PODN |
| Q7Z5P4 | 17-beta-hydroxysteroid dehydrogenase 13 | HSD17B13 |
| Q7Z5P9 | Mucin-19 | MUC19 |
| Q7Z5Y6 | Bone morphogenetic protein 8A | BMP8A |
| Q7Z7B7 | Beta-defensin 132 | DEFB132 |
| Q7Z7B8 | Beta-defensin 128 | DEFB128 |
| Q7Z7C8 | Transcription initiation factor TFIID subunit 8 | TAF8 |
| Q7Z7H5 | Transmembrane emp24 domain-containing protein 4 | TMED4 |
| Q86SG7 | Lysozyme g-like protein 2 | LYG2 |
| Q86SI9 | Protein CEI | C5orf38 |
| Q86TE4 | Leucine zipper protein 2 | LUZP2 |
| Q86TH1 | ADAMTS-like protein 2 | ADAMTSL2 |
| Q86U17 | Serpin A11 | SERPINA11 |
| Q86UU9 | Endokinin-A | TAC4 |
| Q86UW8 | Hyaluronan and proteoglycan link protein 4 | HAPLN4 |
| Q86UX2 | Inter-alpha-trypsin inhibitor heavy chain H5 | ITIH5 |
| Q86V24 | Adiponectin receptor protein 2 | ADIPOR2 |
| Q86VB7 | Soluble CD163 | CD163 |
| Q86VR8 | Four-jointed box protein 1 | FJX1 |
| Q86WD7 | Serpin A9 | SERPINA9 |
| Q86WN2 | Interferon epsilon | IFNE |
| Q86WS3 | Placenta-specific 1-like protein | PLAC1L |
| Q86X52 | Chondroitin sulfate synthase 1 | CHSY1 |
| Q86XP6 | Gastrokine-2 | GKN2 |
| Q86XS5 | Angiopoietin-related protein 5 | ANGPTL5 |
| Q86Y27 | B melanoma antigen 5 | BAGE5 |
| Q86Y28 | B melanoma antigen 4 | BAGE4 |
| Q86Y29 | B melanoma antigen 3 | BAGE3 |
| Q86Y30 | B melanoma antigen 2 | BAGE2 |
| Q86Y38 | Xylosyltransferase 1 | XYLT1 |
| Q86Y78 | Ly6/PLAUR domain-containing protein 6 | LYPD6 |
| Q86YD3 | Transmembrane protein 25 | TMEM25 |
| Q86YJ6 | Threonine synthase-like 2 | THNSL2 |
| Q86YW7 | Glycoprotein hormone beta-5 | GPHB5 |
| Q86Z23 | Complement C1q-like protein 4 | C1QL4 |
| Q8IU57 | Interleukin-28 receptor subunit alpha | IL28RA |
| Q8IUA0 | WAP four-disulfide core domain protein 8 | WFDC8 |
| Q8IUB2 | WAP four-disulfide core domain protein 3 | WFDC3 |
| Q8IUB3 | Protein WFDC10B | WFDC10B |
| Q8IUB5 | WAP four-disulfide core domain protein 13 | WFDC13 |
| Q8IUH2 | Protein CREG2 | CREG2 |
| Q8IUK5 | Plexin domain-containing protein 1 | PLXDC1 |
| Q8IUL8 | Cartilage intermediate layer protein 2 C2 | CILP2 |
| Q8IUX7 | Adipocyte enhancer-binding protein 1 | AEBP1 |
| Q8IUX8 | Epidermal growth factor-like protein 6 | EGFL6 |
| Q8IVL8 | Carboxypeptidase O | CPO |
| Q8IVN8 | Somatomedin-B and thrombospondin type-1 domain-containing protein | SBSPON |
| Q8IVW8 | Protein spinster homolog 2 | SPNS2 |
| Q8IW75 | Serpin A12 | SERPINA12 |
| Q8IW92 | Beta-galactosidase-1-like protein 2 | GLB1L2 |
| Q8IWL1 | Pulmonary surfactant-associated protein A2 | SFTPA2 |
| Q8IWL2 | Pulmonary surfactant-associated protein A1 | SFTPA1 |
| Q8IWV2 | Contactin-4 | CNTN4 |
| Q8IWY4 | Signal peptide, CUB and EGF-like domain-containing protein 1 | SCUBE1 |
| Q8IX30 | Signal peptide, CUB and EGF-like domain-containing protein 3 | SCUBE3 |
| Q8IXA5 | Sperm acrosome membrane-associated protein 3, membrane form | SPACA3 |
| Q8IXB1 | DnaJ homolog subfamily C member 10 | DNAJC10 |
| Q8IXL6 | Extracellular serine/threonine protein kinase Fam20C | FAM20C |
| Q8IYD9 | Lung adenoma susceptibility protein 2 | LAS2 |
| Q8IYP2 | Serine protease 58 | PRSS58 |
| Q8IYS5 | Osteoclast-associated immunoglobulin-like receptor | OSCAR |
| Q8IZC6 | Collagen alpha-1(XXVII) chain | COL27A1 |
| Q8IZJ3 | C3 and PZP-like alpha-2-macroglobulin domain-containing protein 8 | CPAMD8 |

TABLE 1-continued

Secreted Proteins

| Uniprot ID | Protein Name | Gene Name |
|---|---|---|
| Q8IZN7 | Beta-defensin 107 | DEFB107B |
| Q8N0V4 | Leucine-rich repeat LGI family member 2 | LGI2 |
| Q8N104 | Beta-defensin 106 | DEFB106B |
| Q8N119 | Matrix metalloproteinase-21 | MMP21 |
| Q8N129 | Protein canopy homolog 4 | CNPY4 |
| Q8N135 | Leucine-rich repeat LGI family member 4 | LGI4 |
| Q8N145 | Leucine-rich repeat LGI family member 3 | LGI3 |
| Q8N158 | Glypican-2 | GPC2 |
| Q8N1E2 | Lysozyme g-like protein 1 | LYG1 |
| Q8N2E2 | von Willebrand factor D and EGF domain-containing protein | VWDE |
| Q8N2E6 | Prosalusin | TOR2A |
| Q8N2S1 | Latent-transforming growth factor beta-binding protein 4 | LTBP4 |
| Q8N302 | Angiogenic factor with G patch and FHA domains 1 | AGGF1 |
| Q8N307 | Mucin-20 | MUC20 |
| Q8N323 | NXPE family member 1 | NXPE1 |
| Q8N387 | Mucin-15 | MUC15 |
| Q8N3Z0 | Inactive serine protease 35 | PRSS35 |
| Q8N436 | Inactive carboxypeptidase-like protein X2 | CPXM2 |
| Q8N474 | Secreted frizzled-related protein 1 | SFRP1 |
| Q8N475 | Follistatin-related protein 5 | FSTL5 |
| Q8N4F0 | BPI fold-containing family B member 2 | BPIFB2 |
| Q8N4T0 | Carboxypeptidase A6 | CPA6 |
| Q8N5W8 | Protein FAM24B | FAM24B |
| Q8N687 | Beta-defensin 125 | DEFB125 |
| Q8N688 | Beta-defensin 123 | DEFB123 |
| Q8N690 | Beta-defensin 119 | DEFB119 |
| Q8N6C5 | Immunoglobulin superfamily member 1 | IGSF1 |
| Q8N6C8 | Leukocyte immunoglobulin-like receptor subfamily A member 3 | LILRA3 |
| Q8N6G6 | ADAMTS-like protein 1 | ADAMTSL1 |
| Q8N6Y2 | Leucine-rich repeat-containing protein 17 | LRRC17 |
| Q8N729 | Neuropeptide W-23 | NPW |
| Q8N8U9 | BMP-binding endothelial regulator protein | BMPER |
| Q8N907 | DAN domain family member 5 | DAND5 |
| Q8NAT1 | Glycosyltransferase-like domain-containing protein 2 | GTDC2 |
| Q8NAU1 | Fibronectin type III domain-containing protein 5 | FNDC5 |
| Q8NB37 | Parkinson disease 7 domain-containing protein 1 | PDDC1 |
| Q8NBI3 | Draxin | DRAXIN |
| Q8NBM8 | Prenylcysteine oxidase-like | PCYOX1L |
| Q8NBP7 | Proprotein convertase subtilisin/kexin type 9 | PCSK9 |
| Q8NBQ5 | Estradiol 17-beta-dehydrogenase 11 | HSD17B11 |
| Q8NBV8 | Synaptotagmin-8 | SYT8 |
| Q8NCC3 | Group XV phospholipase A2 | PLA2G15 |
| Q8NCF0 | C-type lectin domain family 18 member C | CLEC18C |
| Q8NCW5 | NAD(P)H-hydrate epimerase | APOA1BP |
| Q8NDA2 | Hemicentin-2 | HMCN2 |
| Q8NDX9 | Lymphocyte antigen 6 complex locus protein G5b | LY6G5B |
| Q8NDZ4 | Deleted in autism protein 1 | C3orf58 |
| Q8NEB7 | Acrosin-binding protein | ACRBP |
| Q8NES8 | Beta-defensin 124 | DEFB124 |
| Q8NET1 | Beta-defensin 108B | DEFB108B |
| Q8NEX5 | Protein WFDC9 | WFDC9 |
| Q8NEX6 | Protein WFDC11 | WFDC11 |
| Q8NF86 | Serine protease 33 | PRSS33 |
| Q8NFM7 | Interleukin-17 receptor D | IL17RD |
| Q8NFQ5 | BPI fold-containing family B member 6 | BPIFB6 |
| Q8NFQ6 | BPI fold-containing family C protein | BPIFC |
| Q8NFU4 | Follicular dendritic cell secreted peptide | FDCSP |
| Q8NFW1 | Collagen alpha-1(XXII) chain | COL22A1 |
| Q8NG35 | Beta-defensin 105 | DEFB105B |
| Q8NG41 | Neuropeptide B-23 | NPB |
| Q8NHW6 | Otospiralin | OTOS |
| Q8NI99 | Angiopoietin-related protein 6 | ANGPTL6 |
| Q8TAA1 | Probable ribonuclease 11 | RNASE11 |
| Q8TAG5 | V-set and transmembrane domain-containing protein 2A | VSTM2A |
| Q8TAL6 | Fin bud initiation factor homolog | FIBIN |
| Q8TAT2 | Fibroblast growth factor-binding protein 3 | FGFBP3 |
| Q8TAX7 | Mucin-7 | MUC7 |
| Q8TB22 | Spermatogenesis-associated protein 20 | SPATA20 |
| Q8TB73 | Protein NDNF | NDNF |
| Q8TB96 | T-cell immunomodulatory protein | ITFG1 |
| Q8TC92 | Protein disulfide-thiol oxidoreductase | ENOX1 |

TABLE 1-continued

Secreted Proteins

| Uniprot ID | Protein Name | Gene Name |
|---|---|---|
| Q8TCV5 | WAP four-disulfide core domain protein 5 | WFDC5 |
| Q8TD06 | Anterior gradient protein 3 homolog | AGR3 |
| Q8TD33 | Secretoglobin family 1C member 1 | SCGB1C1 |
| Q8TD46 | Cell surface glycoprotein CD200 receptor 1 | CD200R1 |
| Q8TDE3 | Ribonuclease 8 | RNASE8 |
| Q8TDF5 | Neuropilin and tolloid-like protein 1 | NETO1 |
| Q8TDL5 | BPI fold-containing family B member 1 | BPIFB1 |
| Q8TE56 | A disintegrin and metalloproteinase with thrombospondin motifs 17 | ADAMTS17 |
| Q8TE57 | A disintegrin and metalloproteinase with thrombospondin motifs 16 | ADAMTS16 |
| Q8TE58 | A disintegrin and metalloproteinase with thrombospondin motifs 15 | ADAMTS15 |
| Q8TE59 | A disintegrin and metalloproteinase with thrombospondin motifs 19 | ADAMTS19 |
| Q8TE60 | A disintegrin and metalloproteinase with thrombospondin motifs 18 | ADAMTS18 |
| Q8TE99 | Acid phosphatase-like protein 2 | ACPL2 |
| Q8TER0 | Sushi, nidogen and EGF-like domain-containing protein 1 | SNED1 |
| Q8TEU8 | WAP, kazal, immunoglobulin, kunitz and NTR domain-containing protein 2 | WFIKKN2 |
| Q8WTQ1 | Beta-defensin 104 | DEFB104B |
| Q8WTR8 | Netrin-5 | NTN5 |
| Q8WTU2 | Scavenger receptor cysteine-rich domain-containing group B protein | SRCRB4D |
| Q8WU66 | Protein TSPEAR | TSPEAR |
| Q8WUA8 | Tsukushin | TSKU |
| Q8WUF8 | Protein FAM172A | FAM172A |
| Q8WUJ1 | Neuferricin | CYB5D2 |
| Q8WUY1 | UPF0670 protein THEM6 | THEM6 |
| Q8WVN6 | Secreted and transmembrane protein 1 | SECTM1 |
| Q8WVQ1 | Soluble calcium-activated nucleotidase 1 | CANT1 |
| Q8WWA0 | Intelectin-1 | ITLN1 |
| Q8WWG1 | Neuregulin-4 | NRG4 |
| Q8WWQ2 | Inactive heparanase-2 | HPSE2 |
| Q8WWU7 | Intelectin-2 | ITLN2 |
| Q8WWY7 | WAP four-disulfide core domain protein 12 | WFDC12 |
| Q8WWY8 | Lipase member H | LIPH |
| Q8WWZ8 | Oncoprotein-induced transcript 3 protein | OIT3 |
| Q8WX39 | Epididymal-specific lipocalin-9 | LCN9 |
| Q8WXA2 | Prostate and testis expressed protein 1 | PATE1 |
| Q8WXD2 | Secretogranin-3 | SCG3 |
| Q8WXF3 | Relaxin-3 A chain | RLN3 |
| Q8WXI7 | Mucin-16 | MUC16 |
| Q8WXQ8 | Carboxypeptidase A5 | CPA5 |
| Q8WXS8 | A disintegrin and metalloproteinase with thrombospondin motifs 14 | ADAMTS14 |
| Q92484 | Acid sphingomyelinase-like phosphodiesterase 3a | SMPDL3A |
| Q92485 | Acid sphingomyelinase-like phosphodiesterase 3b | SMPDL3B |
| Q92496 | Complement factor H-related protein 4 | CFHR4 |
| Q92520 | Protein FAM3C | FAM3C |
| Q92563 | Testican-2 | SPOCK2 |
| Q92583 | C-C motif chemokine 17 | CCL17 |
| Q92626 | Peroxidasin homolog | PXDN |
| Q92743 | Serine protease HTRA1 | HTRA1 |
| Q92752 | Tenascin-R | TNR |
| Q92765 | Secreted frizzled-related protein 3 | FRZB |
| Q92819 | Hyaluronan synthase 2 | HAS2 |
| Q92820 | Gamma-glutamyl hydrolase | GGH |
| Q92824 | Proprotein convertase subtilisin/kexin type 5 | PCSK5 |
| Q92832 | Protein kinase C-binding protein NELL1 | NELL1 |
| Q92838 | Ectodysplasin-A, membrane form | EDA |
| Q92874 | Deoxyribonuclease-1-like 2 | DNASE1L2 |
| Q92876 | Kallikrein-6 | KLK6 |
| Q92913 | Fibroblast growth factor 13 | FGF13 |
| Q92954 | Proteoglycan 4 C-terminal part | PRG4 |
| Q93038 | Tumor necrosis factor receptor superfamily member 25 | TNFRSF25 |
| Q93091 | Ribonuclease K6 | RNASE6 |
| Q93097 | Protein Wnt-2b | WNT2B |
| Q93098 | Protein Wnt-8b | WNT8B |
| Q95460 | Major histocompatibility complex class I-related gene protein | MR1 |
| Q969D9 | Thymic stromal lymphopoietin | TSLP |
| Q969E1 | Liver-expressed antimicrobial peptide 2 | LEAP2 |

TABLE 1-continued

Secreted Proteins

| Uniprot ID | Protein Name | Gene Name |
|---|---|---|
| Q969H8 | UPF0556 protein C19orf10 | C19orf10 |
| Q969Y0 | NXPE family member 3 | NXPE3 |
| Q96A54 | Adiponectin receptor protein 1 | ADIPOR1 |
| Q96A83 | Collagen alpha-1(XXVI) chain | EMID2 |
| Q96A84 | EMI domain-containing protein 1 | EMID1 |
| Q96A98 | Tuberoinfundibular peptide of 39 residues | PTH2 |
| Q96A99 | Pentraxin-4 | PTX4 |
| Q96BH3 | Epididymal sperm-binding protein 1 | ELSPBP1 |
| Q96BQ1 | Protein FAM3D | FAM3D |
| Q96CG8 | Collagen triple helix repeat-containing protein 1 | CTHRC1 |
| Q96DA0 | Zymogen granule protein 16 homolog B | ZG16B |
| Q96DN2 | von Willebrand factor C and EGF domain-containing protein | VWCE |
| Q96DR5 | BPI fold-containing family A member 2 | BPIFA2 |
| Q96DR8 | Mucin-like protein 1 | MUCL1 |
| Q96DX4 | RING finger and SPRY domain-containing protein 1 | RSPRY1 |
| Q96EE4 | Coiled-coil domain-containing protein 126 | CCDC126 |
| Q96GS6 | Abhydrolase domain-containing protein FAM108A1 | FAM108A1 |
| Q96GW7 | Brevican core protein | BCAN |
| Q96HF1 | Secreted frizzled-related protein 2 | SFRP2 |
| Q96I82 | Kazal-type serine protease inhibitor domain-containing protein 1 | KAZALD1 |
| Q96ID5 | Immunoglobulin superfamily member 21 | IGSF21 |
| Q96II8 | Leucine-rich repeat and calponin homology domain-containing protein 3 | LRCH3 |
| Q96IY4 | Carboxypeptidase B2 | CPB2 |
| Q96JB6 | Lysyl oxidase homolog 4 | LOXL4 |
| Q96JK4 | HHIP-like protein 1 | HHIPL1 |
| Q96KN2 | Beta-Ala-His dipeptidase | CNDP1 |
| Q96KW9 | Protein SPACA7 | SPACA7 |
| Q96KX0 | Lysozyme-like protein 4 | LYZL4 |
| Q96L15 | Ecto-ADP-ribosyltransferase 5 | ART5 |
| Q96LB8 | Peptidoglycan recognition protein 4 | PGLYRP4 |
| Q96LB9 | Peptidoglycan recognition protein 3 | PGLYRP3 |
| Q96LC7 | Sialic acid-binding Ig-like lectin 10 | SIGLEC10 |
| Q96LR4 | Protein FAM19A4 | FAM19A4 |
| Q96MK3 | Protein FAM20A | FAM20A |
| Q96MS3 | Glycosyltransferase 1 domain-containing protein 1 | GLT1D1 |
| Q96NY8 | Processed poliovirus receptor-related protein 4 | PVRL4 |
| Q96NZ8 | WAP, kazal, immunoglobulin, kunitz and NTR domain-containing protein 1 | WFIKKN1 |
| Q96NZ9 | Proline-rich acidic protein 1 | PRAP1 |
| Q96P44 | Collagen alpha-1(XXI) chain | COL21A1 |
| Q96PB7 | Noelin-3 | OLFM3 |
| Q96PC5 | Melanoma inhibitory activity protein 2 | MIA2 |
| Q96PD5 | N-acetylmuramoyl-L-alanine amidase | PGLYRP2 |
| Q96PH6 | Beta-defensin 118 | DEFB118 |
| Q96PL1 | Secretoglobin family 3A member 2 | SCGB3A2 |
| Q96PL2 | Beta-tectorin | TECTB |
| Q96QH8 | Sperm acrosome-associated protein 5 | SPACA5 |
| Q96QR1 | Secretoglobin family 3A member 1 | SCGB3A1 |
| Q96QU1 | Protocadherin-15 | PCDH15 |
| Q96QV1 | Hedgehog-interacting protein | HHIP |
| Q96RW7 | Hemicentin-1 | HMCN1 |
| Q96S42 | Nodal homolog | NODAL |
| Q96S86 | Hyaluronan and proteoglycan link protein 3 | HAPLN3 |
| Q96SL4 | Glutathione peroxidase 7 | GPX7 |
| Q96SM3 | Probable carboxypeptidase X1 | CPXM1 |
| Q96T91 | Glycoprotein hormone alpha-2 | GPHA2 |
| Q99062 | Granulocyte colony-stimulating factor receptor | CSF3R |
| Q99102 | Mucin-4 alpha chain | MUC4 |
| Q99217 | Amelogenin, X isoform | AMELX |
| Q99218 | Amelogenin, Y isoform | AMELY |
| Q99435 | Protein kinase C-binding protein NELL2 | NELL2 |
| Q99470 | Stromal cell-derived factor 2 | SDF2 |
| Q99542 | Matrix metalloproteinase-19 | MMP19 |
| Q99574 | Neuroserpin | SERPINI1 |
| Q99584 | Protein S100-A13 | S100A13 |
| Q99616 | C-C motif chemokine 13 | CCL13 |
| Q99645 | Epiphycan | EPYC |
| Q99674 | Cell growth regulator with EF hand domain protein 1 | CGREF1 |
| Q99715 | Collagen alpha-1(XII) chain | COL12A1 |
| Q99727 | Metalloproteinase inhibitor 4 | TIMP4 |
| Q99731 | C-C motif chemokine 19 | CCL19 |

TABLE 1-continued

Secreted Proteins

| Uniprot ID | Protein Name | Gene Name |
|---|---|---|
| Q99748 | Neurturin | NRTN |
| Q99935 | Proline-rich protein 1 | PROL1 |
| Q99942 | E3 ubiquitin-protein ligase RNF5 | RNF5 |
| Q99944 | Epidermal growth factor-like protein 8 | EGFL8 |
| Q99954 | Submaxillary gland androgen-regulated protein 3A | SMR3A |
| Q99969 | Retinoic acid receptor responder protein 2 | RARRES2 |
| Q99972 | Myocilin | MYOC |
| Q99983 | Osteomodulin | OMD |
| Q99985 | Semaphorin-3C | SEMA3C |
| Q99988 | Growth/differentiation factor 15 | GDF15 |
| Q9BPW4 | Apolipoprotein L4 | APOL4 |
| Q9BQ08 | Resistin-like beta | RETNLB |
| Q9BQ16 | Testican-3 | SPOCK3 |
| Q9BQ51 | Programmed cell death 1 ligand 2 | PDCD1LG2 |
| Q9BQB4 | Sclerostin | SOST |
| Q9BQI4 | Coiled-coil domain-containing protein 3 | CCDC3 |
| Q9BQP9 | BPI fold-containing family A member 3 | BPIFA3 |
| Q9BQR3 | Serine protease 27 | PRSS27 |
| Q9BQY6 | WAP four-disulfide core domain protein 6 | WFDC6 |
| Q9BRR6 | ADP-dependent glucokinase | ADPGK |
| Q9BS86 | Zona pellucida-binding protein 1 | ZPBP |
| Q9BSG0 | Protease-associated domain-containing protein 1 | PRADC1 |
| Q9BSG5 | Retbindin | RTBDN |
| Q9BT30 | Probable alpha-ketoglutarate-dependent dioxygenase ABH7 | ALKBH7 |
| Q9BT56 | Spexin | C12orG9 |
| Q9BT67 | NEDD4 family-interacting protein 1 | NDFIP1 |
| Q9BTY2 | Plasma alpha-L-fucosidase | FUCA2 |
| Q9BU40 | Chordin-like protein 1 | CHRDL1 |
| Q9BUD6 | Spondin-2 | SPON2 |
| Q9BUN1 | Protein MENT | MENT |
| Q9BUR5 | Apolipoprotein O | APOO |
| Q9BV94 | ER degradation-enhancing alpha-mannosidase-like 2 | EDEM2 |
| Q9BWP8 | Collectin-11 | COLEC11 |
| Q9BWS9 | Chitinase domain-containing protein 1 | CHID1 |
| Q9BX67 | Junctional adhesion molecule C | JAM3 |
| Q9BX93 | Group XIIB secretory phospholipase A2-like protein | PLA2G12B |
| Q9BXI9 | Complement C1q tumor necrosis factor-related protein 6 | C1QTNF6 |
| Q9BXJ0 | Complement C1q tumor necrosis factor-related protein 5 | C1QTNF5 |
| Q9BXJ1 | Complement C1q tumor necrosis factor-related protein 1 | C1QTNF1 |
| Q9BXJ2 | Complement C1q tumor necrosis factor-related protein 7 | C1QTNF7 |
| Q9BXJ3 | Complement C1q tumor necrosis factor-related protein 4 | C1QTNF4 |
| Q9BXJ4 | Complement C1q tumor necrosis factor-related protein 3 | C1QTNF3 |
| Q9BXJ5 | Complement C1q tumor necrosis factor-related protein 2 | C1QTNF2 |
| Q9BXN1 | Asporin | ASPN |
| Q9BXP8 | Pappalysin-2 | PAPPA2 |
| Q9BXR6 | Complement factor H-related protein 5 | CFHR5 |
| Q9BXS0 | Collagen alpha-1(XXV) chain | COL25A1 |
| Q9BXX0 | EMILIN-2 | EMILIN2 |
| Q9BXY4 | R-spondin-3 | RSPO3 |
| Q9BY15 | EGF-like module-containing mucin-like hormone receptor-like 3 subunit beta | EMR3 |
| Q9BY50 | Signal peptidase complex catalytic subunit SEC11C | SEC11C |
| Q9BY76 | Angiopoietin-related protein 4 | ANGPTL4 |
| Q9BYF1 | Processed angiotensin-converting enzyme 2 | ACE2 |
| Q9BYJ0 | Fibroblast growth factor-binding protein 2 | FGFBP2 |
| Q9BYW3 | Beta-defensin 126 | DEFB126 |
| Q9BYX4 | Interferon-induced helicase C domain-containing protein 1 | IFIH1 |
| Q9BYZ8 | Regenerating islet-derived protein 4 | REG4 |
| Q9BZ76 | Contactin-associated protein-like 3 | CNTNAP3 |
| Q9BZG9 | Ly-6/neurotoxin-like protein 1 | LYNX1 |
| Q9BZJ3 | Tryptase delta | TPSD1 |
| Q9BZM1 | Group XIIA secretory phospholipase A2 | PLA2G12A |
| Q9BZM2 | Group IIF secretory phospholipase A2 | PLA2G2F |
| Q9BZM5 | NKG2D ligand 2 | ULBP2 |
| Q9BZP6 | Acidic mammalian chitinase | CHIA |

TABLE 1-continued

Secreted Proteins

| Uniprot ID | Protein Name | Gene Name |
|---|---|---|
| Q9BZZ2 | Sialoadhesin | SIGLEC1 |
| Q9C0B6 | Protein FAM5B | FAM5B |
| Q9GZM7 | Tubulointerstitial nephritis antigen-like | TINAGL1 |
| Q9GZN4 | Brain-specific serine protease 4 | PRSS22 |
| Q9GZP0 | Platelet-derived growth factor D, receptor-binding form | PDGFD |
| Q9GZT5 | Protein Wnt-10a | WNT10A |
| Q9GZU5 | Nyctalopin | NYX |
| Q9GZV7 | Hyaluronan and proteoglycan link protein 2 | HAPLN2 |
| Q9GZV9 | Fibroblast growth factor 23 | FGF23 |
| Q9GZX9 | Twisted gastrulation protein homolog 1 | TWSG1 |
| Q9GZZ7 | GDNF family receptor alpha-4 | GFRA4 |
| Q9GZZ8 | Extracellular glycoprotein lacritin | LACRT |
| Q9H0B8 | Cysteine-rich secretory protein LCCL domain-containing 2 | CRISPLD2 |
| Q9H106 | Signal-regulatory protein delta | SIRPD |
| Q9H114 | Cystatin-like 1 | CSTL1 |
| Q9H173 | Nucleotide exchange factor SIL1 | SIL1 |
| Q9H1E1 | Ribonuclease 7 | RNASE7 |
| Q9H1F0 | WAP four-disulfide core domain protein 10A | WFDC10A |
| Q9H1J5 | Protein Wnt-8a | WNT8A |
| Q9H1J7 | Protein Wnt-5b | WNT5B |
| Q9H1M3 | Beta-defensin 129 | DEFB129 |
| Q9H1M4 | Beta-defensin 127 | DEFB127 |
| Q9H1Z8 | Augurin | C2orf40 |
| Q9H239 | Matrix metalloproteinase-28 | MMP28 |
| Q9H2A7 | C-X-C motif chemokine 16 | CXCL16 |
| Q9H2A9 | Carbohydrate sulfotransferase 8 | CHST8 |
| Q9H2R5 | Kallikrein-15 | KLK15 |
| Q9H2X0 | Chordin | CHRD |
| Q9H2X3 | C-type lectin domain family 4 member M | CLEC4M |
| Q9H306 | Matrix metalloproteinase-27 | MMP27 |
| Q9H324 | A disintegrin and metalloproteinase with thrombospondin motifs 10 | ADAMTS10 |
| Q9H336 | Cysteine-rich secretory protein LCCL domain-containing 1 | CRISPLD1 |
| Q9H3E2 | Sorting nexin-25 | SNX25 |
| Q9H3R2 | Mucin-13 | MUC13 |
| Q9H3U7 | SPARC-related modular calcium-binding protein 2 | SMOC2 |
| Q9H3Y0 | Peptidase inhibitor R3HDML | R3HDML |
| Q9H4A4 | Aminopeptidase B | RNPEP |
| Q9H4F8 | SPARC-related modular calcium-binding protein 1 | SMOC1 |
| Q9H4G1 | Cystatin-9-like | CST9L |
| Q9H5V8 | CUB domain-containing protein 1 | CDCP1 |
| Q9H6B9 | Epoxide hydrolase 3 | EPHX3 |
| Q9H6E4 | Coiled-coil domain-containing protein 134 | CCDC134 |
| Q9H741 | UPF0454 protein C12orf49 | C12orf49 |
| Q9H772 | Gremlin-2 | GREM2 |
| Q9H7Y0 | Deleted in autism-related protein 1 | CXorf36 |
| Q9H8L6 | Multimerin-2 | MMRN2 |
| Q9H9S5 | Fukutin-related protein | FKRP |
| Q9HAT2 | Sialate O-acetylesterase | SIAE |
| Q9HB40 | Retinoid-inducible serine carboxypeptidase | SCPEP1 |
| Q9HB63 | Netrin-4 | NTN4 |
| Q9HBJ0 | Placenta-specific protein 1 | PLAC1 |
| Q9HC23 | Prokineticin-2 | PROK2 |
| Q9HC57 | WAP four-disulfide core domain protein 1 | WFDC1 |
| Q9HC73 | Cytokine receptor-like factor 2 | CRLF2 |
| Q9HC84 | Mucin-5B | MUC5B |
| Q9HCB6 | Spondin-1 | SPON1 |
| Q9HCQ7 | Neuropeptide NPSF | NPVF |
| Q9HCT0 | Fibroblast growth factor 22 | FGF22 |
| Q9HD89 | Resistin | RETN |
| Q9NNX1 | Tuftelin | TUFT1 |
| Q9NNX6 | CD209 antigen | CD209 |
| Q9NP55 | BPI fold-containing family A member 1 | BPIFA1 |
| Q9NP70 | Ameloblastin | AMBN |
| Q9NP95 | Fibroblast growth factor 20 | FGF20 |
| Q9NP99 | Triggering receptor expressed on myeloid cells 1 | TREM1 |
| Q9NPA2 | Matrix metalloproteinase-25 | MMP25 |
| Q9NPE2 | Neugrin | NGRN |
| Q9NPH0 | Lysophosphatidic acid phosphatase type 6 | ACP6 |
| Q9NPH6 | Odorant-binding protein 2b | OBP2B |
| Q9NQ30 | Endothelial cell-specific molecule 1 | ESM1 |
| Q9NQ36 | Signal peptide, CUB and EGF-like domain-containing protein 2 | SCUBE2 |

TABLE 1-continued

Secreted Proteins

| Uniprot ID | Protein Name | Gene Name |
| --- | --- | --- |
| Q9NQ38 | Serine protease inhibitor Kazal-type 5 | SPINK5 |
| Q9NQ76 | Matrix extracellular phosphoglycoprotein | MEPE |
| Q9NQ79 | Cartilage acidic protein 1 | CRTAC1 |
| Q9NR16 | Scavenger receptor cysteine-rich type 1 protein M160 | CD163L1 |
| Q9NR23 | Growth/differentiation factor 3 | GDF3 |
| Q9NR71 | Neutral ceramidase | ASAH2 |
| Q9NR99 | Matrix-remodeling-associated protein 5 | MXRA5 |
| Q9NRA1 | Platelet-derived growth factor C | PDGFC |
| Q9NRC9 | Otoraplin | OTOR |
| Q9NRE1 | Matrix metalloproteinase-26 | MMP26 |
| Q9NRJ3 | C-C motif chemokine 28 | CCL28 |
| Q9NRM1 | Enamelin | ENAM |
| Q9NRN5 | Olfactomedin-like protein 3 | OLFML3 |
| Q9NRR1 | Cytokine-like protein 1 | CYTL1 |
| Q9NS15 | Latent-transforming growth factor beta-binding protein 3 | LTBP3 |
| Q9NS62 | Thrombospondin type-1 domain-containing protein 1 | THSD1 |
| Q9NS71 | Gastrokine-1 | GKN1 |
| Q9NS98 | Semaphorin-3G | SEMA3G |
| Q9NSA1 | Fibroblast growth factor 21 | FGF21 |
| Q9NT22 | EMILIN-3 | EMILIN3 |
| Q9NTU7 | Cerebellin-4 | CBLN4 |
| Q9NVR0 | Kelch-like protein 11 | KLHL11 |
| Q9NWH7 | Spermatogenesis-associated protein 6 | SPATA6 |
| Q9NXC2 | Glucose-fructose oxidoreductase domain-containing protein 1 | GFOD1 |
| Q9NY56 | Odorant-binding protein 2a | OBP2A |
| Q9NY84 | Vascular non-inflammatory molecule 3 | VNN3 |
| Q9NZ20 | Group 3 secretory phospholipase A2 | PLA2G3 |
| Q9NZC2 | Triggering receptor expressed on myeloid cells 2 | TREM2 |
| Q9NZK5 | Adenosine deaminase CECR1 | CECR1 |
| Q9NZK7 | Group IIE secretory phospholipase A2 | PLA2G2E |
| Q9NZP8 | Complement C1r subcomponent-like protein | C1RL |
| Q9NZV1 | Cysteine-rich motor neuron 1 protein | CRIM1 |
| Q9NZW4 | Dentin sialoprotein | DSPP |
| Q9P0G3 | Kallikrein-14 | KLK14 |
| Q9P0W0 | Interferon kappa | IFNK |
| Q9P218 | Collagen alpha-1(XX) chain | COL20A1 |
| Q9P2C4 | Transmembrane protein 181 | TMEM181 |
| Q9P2K2 | Thioredoxin domain-containing protein 16 | TXNDC16 |
| Q9P2N4 | A disintegrin and metalloproteinase with thrombospondin motifs 9 | ADAMTS9 |
| Q9UBC7 | Galanin-like peptide | GALP |
| Q9UBD3 | Cytokine SCM-1 beta | XCL2 |
| Q9UBD9 | Cardiotrophin-like cytokine factor 1 | CLCF1 |
| Q9UBM4 | Opticin | OPTC |
| Q9UBP4 | Dickkopf-related protein 3 | DKK3 |
| Q9UBQ6 | Exostosin-like 2 | EXTL2 |
| Q9UBR5 | Chemokine-like factor | CKLF |
| Q9UBS5 | Gamma-aminobutyric acid type B receptor subunit 1 | GABBR1 |
| Q9UBT3 | Dickkopf-related protein 4 short form | DKK4 |
| Q9UBU2 | Dickkopf-related protein 2 | DKK2 |
| Q9UBU3 | Ghrelin-28 | GHRL |
| Q9UBV4 | Protein Wnt-16 | WNT16 |
| Q9UBX5 | Fibulin-5 | FBLN5 |
| Q9UBX7 | Kallikrein-11 | KLK11 |
| Q9UEF7 | Klotho | KL |
| Q9UFP1 | Protein FAM198A | FAM198A |
| Q9UGM3 | Deleted in malignant brain tumors 1 protein | DMBT1 |
| Q9UGM5 | Fetuin-B | FETUB |
| Q9UGP8 | Translocation protein SEC63 homolog | SEC63 |
| Q9UHF0 | Neurokinin-B | TAC3 |
| Q9UHF1 | Epidermal growth factor-like protein 7 | EGFL7 |
| Q9UHG2 | ProSAAS | PCSK1N |
| Q9UHI8 | A disintegrin and metalloproteinase with thrombospondin motifs 1 | ADAMTS1 |
| Q9UHL4 | Dipeptidyl peptidase 2 | DPP7 |
| Q9UI42 | Carboxypeptidase A4 | CPA4 |
| Q9UIG4 | Psoriasis susceptibility 1 candidate gene 2 protein | PSORS1C2 |
| Q9UIK5 | Tomoregulin-2 | TMEFF2 |
| Q9UIQ6 | Leucyl-cystinyl aminopeptidase, pregnancy serum form | LNPEP |

TABLE 1-continued

Secreted Proteins

| Uniprot ID | Protein Name | Gene Name |
|---|---|---|
| Q9UJA9 | Ectonucleotide pyrophosphatase/phosphodiesterase family member 5 | ENPP5 |
| Q9UJH8 | Meteorin | METRN |
| Q9UJJ9 | N-acetylglucosamine-1-phosphotransferase subunit gamma | GNPTG |
| Q9UJW2 | Tubulointerstitial nephritis antigen | TINAG |
| Q9UK05 | Growth/differentiation factor 2 | GDF2 |
| Q9UK55 | Protein Z-dependent protease inhibitor | SERPINA10 |
| Q9UK85 | Dickkopf-like protein 1 | DKKL1 |
| Q9UKJ1 | Paired immunoglobulin-like type 2 receptor alpha | PILRA |
| Q9UKP4 | A disintegrin and metalloproteinase with thrombospondin motifs 7 | ADAMTS7 |
| Q9UKP5 | A disintegrin and metalloproteinase with thrombospondin motifs 6 | ADAMTS6 |
| Q9UKQ2 | Disintegrin and metalloproteinase domain-containing protein 28 | ADAM28 |
| Q9UKQ9 | Kallikrein-9 | KLK9 |
| Q9UKR0 | Kallikrein-12 | KLK12 |
| Q9UKR3 | Kallikrein-13 | KLK13 |
| Q9UKU9 | Angiopoietin-related protein 2 | ANGPTL2 |
| Q9UKZ9 | Procollagen C-endopeptidase enhancer 2 | PCOLCE2 |
| Q9UL52 | Transmembrane protease serine 11E non-catalytic chain | TMPRSS11E |
| Q9ULC0 | Endomucin | EMCN |
| Q9ULI3 | Protein HEG homolog 1 | HEG1 |
| Q9ULZ1 | Apelin-13 | APLN |
| Q9ULZ9 | Matrix metalloproteinase-17 | MMP17 |
| Q9UM21 | Alpha-1,3-mannosyl-glycoprotein 4-beta-N-acetylglucosaminyltransferase A soluble form | MGAT4A |
| Q9UM22 | Mammalian ependymin-related protein 1 | EPDR1 |
| Q9UM73 | ALK tyrosine kinase receptor | ALK |
| Q9UMD9 | 97 kDa linear IgA disease antigen | COL17A1 |
| Q9UMX5 | Neudesin | NENF |
| Q9UN73 | Protocadherin alpha-6 | PCDHA6 |
| Q9UNA0 | A disintegrin and metalloproteinase with thrombospondin motifs 5 | ADAMTS5 |
| Q9UNI1 | Chymotrypsin-like elastase family member 1 | CELA1 |
| Q9UNK4 | Group IID secretory phospholipase A2 | PLA2G2D |
| Q9UP79 | A disintegrin and metalloproteinase with thrombospondin motifs 8 | ADAMTS8 |
| Q9UPZ6 | Thrombospondin type-1 domain-containing protein 7A | THSD7A |
| Q9UQ72 | Pregnancy-specific beta-1-glycoprotein 11 | PSG11 |
| Q9UQ74 | Pregnancy-specific beta-1-glycoprotein 8 | PSG8 |
| Q9UQC9 | Calcium-activated chloride channel regulator 2 | CLCA2 |
| Q9UQE7 | Structural maintenance of chromosomes protein 3 | SMC3 |
| Q9UQP3 | Tenascin-N | TNN |
| Q9Y223 | UDP-N-acetylglucosamine 2-epimerase | GNE |
| Q9Y240 | C-type lectin domain family 11 member A | CLEC11A |
| Q9Y251 | Heparanase 8 kDa subunit | HPSE |
| Q9Y258 | C-C motif chemokine 26 | CCL26 |
| Q9Y264 | Angiopoietin-4 | ANGPT4 |
| Q9Y275 | Tumor necrosis factor ligand superfamily member 13b, membrane form | TNFSF13B |
| Q9Y287 | BRI2 intracellular domain | ITM2B |
| Q9Y2E5 | Epididymis-specific alpha-mannosidase | MAN2B2 |
| Q9Y334 | von Willebrand factor A domain-containing protein 7 | VWA7 |
| Q9Y337 | Kallikrein-5 | KLK5 |
| Q9Y3B3 | Transmembrane emp24 domain-containing protein 7 | TMED7 |
| Q9Y3E2 | BolA-like protein 1 | BOLA1 |
| Q9Y426 | C2 domain-containing protein 2 | C2CD2 |
| Q9Y4K0 | Lysyl oxidase homolog 2 | LOXL2 |
| Q9Y4X3 | C-C motif chemokine 27 | CCL27 |
| Q9Y5C1 | Angiopoietin-related protein 3 | ANGPTL3 |
| Q9Y5I2 | Protocadherin alpha-10 | PCDHA10 |
| Q9Y5I3 | Protocadherin alpha-1 | PCDHA1 |
| Q9Y5K2 | Kallikrein-4 | KLK4 |
| Q9Y5L2 | Hypoxia-inducible lipid droplet-associated protein | HILPDA |
| Q9Y5Q5 | Atrial natriuretic peptide-converting enzyme | CORIN |
| Q9Y5R2 | Matrix metalloproteinase-24 | MMP24 |
| Q9Y5U5 | Tumor necrosis factor receptor superfamily member 18 | TNFRSF18 |
| Q9Y5W5 | Wnt inhibitory factor 1 | WIF1 |
| Q9Y5X9 | Endothelial lipase | LIPG |

TABLE 1-continued

Secreted Proteins

| Uniprot ID | Protein Name | Gene Name |
|---|---|---|
| Q9Y625 | Secreted glypican-6 | GPC6 |
| Q9Y646 | Carboxypeptidase Q | CPQ |
| Q9Y6C2 | EMILIN-1 | EMILIN1 |
| Q9Y6F9 | Protein Wnt-6 | WNT6 |
| Q9Y6I9 | Testis-expressed sequence 264 protein | TEX264 |
| Q9Y6L7 | Tolloid-like protein 2 | TLL2 |
| Q9Y6N3 | Calcium-activated chloride channel regulator family member 3 | CLCA3P |
| Q9Y6N6 | Laminin subunit gamma-3 | LAMC3 |
| Q9Y6R7 | IgGFc-binding protein | FCGBP |
| Q9Y6Y9 | Lymphocyte antigen 96 | LY96 |
| Q9Y6Z7 | Collectin-10 | COLEC10 |

In some embodiments, the compositions and methods of the invention provide for the delivery of one or more mRNAs encoding one or more additional exemplary proteins listed in Table 2; thus, compositions of the invention may comprise an mRNA encoding a protein listed in Table 2 (or a homolog thereof) along with other components set out herein, and methods of the invention may comprise preparing and/or administering composition comprising an mRNA encoding a protein chosen from the proteins listed in Table 2 (or a homolog thereof) along with other components set out herein.

TABLE 2

Additional Exemplary Proteins

| Uniprot ID | Protein Name | Gene Name |
|---|---|---|
| A6NGW2 | Putative stereocilin-like protein | STRCP1 |
| A6NIE9 | Putative serine protease 29 | PRSS29P |
| A6NJ16 | Putative V-set and immunoglobulin domain-containing-like protein IGHV4OR15-8 | IGHV4OR15-8 |
| A6NJS3 | Putative V-set and immunoglobulin domain-containing-like protein IGHV1OR21-1 | IGHV1OR21-1 |
| A6NMY6 | Putative annexin A2-like protein | ANXA2P2 |
| A8MT79 | Putative zinc-alpha-2-glycoprotein-like 1 | |
| A8MWS1 | Putative killer cell immunoglobulin-like receptor like protein KIR3DP1 | KIR3DP1 |
| A8MXU0 | Putative beta-defensin 108A | DEFB108P1 |
| C9JUS6 | Putative adrenomedullin-5-like protein | ADM5 |
| P0C7V7 | Putative signal peptidase complex catalytic subunit SEC11B | SEC11B |
| P0C854 | Putative cat eye syndrome critical region protein 9 | CECR9 |
| Q13046 | Putative pregnancy-specific beta-1-glycoprotein 7 | PSG7 |
| Q16609 | Putative apolipoprotein(a)-like protein 2 | LPAL2 |
| Q2TV78 | Putative macrophage-stimulating protein MSTP9 | MST1P9 |
| Q5JQD4 | Putative peptide YY-3 | PYY3 |
| Q5R387 | Putative inactive group IIC secretory phospholipase A2 | PLA2G2C |
| Q5VSP4 | Putative lipocalin 1-like protein 1 | LCN1P1 |
| Q5W188 | Putative cystatin-9-like protein CST9LP1 | CST9LP1 |
| Q6UXR4 | Putative serpin A13 | SERPINA13P |
| Q86SH4 | Putative testis-specific prion protein | PRNT |
| Q86YQ2 | Putative latherin | LATH |
| Q8IVG9 | Putative humanin peptide | MT-RNR2 |
| Q8NHM4 | Putative trypsin-6 | TRY6 |
| Q8NHW4 | C-C motif chemokine 4-like | CCL4L2 |
| Q9H7L2 | Putative killer cell immunoglobulin-like receptor-like protein KIR3DX1 | KIR3DX1 |
| Q9NRI6 | Putative peptide YY-2 | PYY2 |
| Q9UF72 | Putative TP73 antisense gene protein 1 | TP73-AS1 |
| Q9UKY3 | Putative inactive carboxylesterase 4 | CES1P1 |

The Uniprot IDs set forth in Table 1 and Table 2 refer to the human versions the listed proteins and the sequences of each are available from the Uniprot database. Sequences of the listed proteins are also generally available for various animals, including various mammals and animals of veterinary or industrial interest. Accordingly, in some embodiments, compositions and methods of the invention provide for the delivery of one or more mRNAs encoding one or more proteins chosen from mammalian homologs or homologs from an animal of veterinary or industrial interest of the secreted proteins listed in Table 1 and Table 2; thus, compositions of the invention may comprise an mRNA encoding a protein chosen from mammalian homologs or homologs from an animal of veterinary or industrial interest of a protein listed in Table 1 and Table 2 along with other components set out herein, and methods of the invention may comprise preparing and/or administering a composition comprising an mRNA encoding a protein chosen from mammalian homologs or homologs from an animal of veterinary or industrial interest of a protein listed in Table 1 and Table 2 along with other components set out herein. In some embodiments, mammalian homologs are chosen from mouse, rat, hamster, gerbil, horse, pig, cow, llama, alpaca, mink, dog, cat, ferret, sheep, goat, or camel homologs. In some embodiments, the animal of veterinary or industrial interest is chosen from the mammals listed above and/or chicken, duck, turkey, salmon, catfish, or tilapia.

In embodiments, the compositions and methods of the invention provide for the delivery of mRNA encoding a lysosomal protein chosen from Table 3. In some embodiments, the compositions and methods of the invention provide for the delivery of one or more mRNAs encoding one or more lysosomal and/or related proteins listed in Table 3; thus, compositions of the invention may comprise an mRNA encoding a protein listed in Table 3 (or a homolog thereof) along with other components set out herein, and methods of the invention may comprise preparing and/or administering a composition comprising an mRNA encoding a protein chosen from the proteins listed in Table 3 (or a homolog thereof) along with other components set out herein.

TABLE 3

Lysosomal and Related Proteins

α-fucosidase
α-galactosidase
α-glucosidase
α-Iduronidase

TABLE 3-continued

Lysosomal and Related Proteins

α-mannosidase
α-N-acetylgalactosaminidase (α-galactosidase B)
β-galactosidase
β-glucuronidase
β-hexosaminidase
β-mannosidase
3-hydroxy-3-methylglutaryl-CoA (HMG-CoA) lyase
3-methylcrotonyl-CoA carboxylase
3-O-sulfogalactosyl cerebroside sulfatase (arylsulfatase A)
acetyl-CoA transferase
acid alpha-glucosidase
acid ceramidase
acid lipase
acid phosphatase
acid sphingomyelinase
alpha-galactosidase A
arylsulfatase A
beta-galactosidase
beta-glucocerebrosidase
beta-hexosaminidase
biotinidase
cathepsin A
cathepsin K
CLN3
CLN5
CLN6
CLN8
CLN9
cystine transporter (cystinosin)
cytosolic protein beta3A subunit of the adaptor protein-3 complex, AP3
formyl-Glycine generating enzyme (FGE)
Galactocerebrosidase
galactose-1-phosphate uridyltransferase (GALT)
galactose 6-sulfate sulfatase
(also known as N-acetylgalactosamine-6-sulfatase)
Glucocerebrosidase
glucuronate sulfatase
glucuronidase
glycoprotein cleaving enzymes
glycosaminoglycan cleaving enzymes
glycosylasparaginase (aspartylglucosaminidase)
GM2-AP
Heparan-alpha-glucosaminide N-acetyltransferase (HGSNAT, TMEM76)
Heparan sulfatase
hexosaminidase A lysosomal proteases methylmalonyl-CoA mutase
Hyaluronidase
Iduronate sulfatase
LAMP-2
lysosomal α-mannosidase
Lysosomal p40 (C2orf18)
Major facilitator superfamily domain containing 8 protein

TABLE 3-continued

Lysosomal and Related Proteins (MFSD8 or CLN7)
N-acetylgalactosamine 4-sulfatase
N-acetyl glucosamine 6-sulfatase
N-acetyl glucosaminidase
N-acetylglucosamine-1-phosphate transferase
NPC1
NPC2
palmitoyl-protein thioesterase
palmitoyl-protein thioesterase (CLN1)
Saposin A (Sphingolipid activator protein A)
Saposin B (Sphingolipid activator protein B)
Saposin C (Sphingolipid activator protein C)
Saposin D (Sphingolipid activator protein D)
sialic acid transporter (sialin)
Sialidase
Sialin
Sulfatase
Transmembrane protein 74 (TMEM74)
tripeptidyl-peptidase
tripeptidyl-peptidase I (CLN2)
UDP-N-acetylglucosamine- phosphotransferase Information regarding lysosomal proteins is available from Lubke et al., "Proteomics of the Lysosome," *Bichim Biophys Acta*. (2009) 1793: 625-635. In some embodiments, the protein listed in Table 3 and encoded by mRNA in the compositions and methods of the invention is a human protein. Sequences of the listed proteins are also available for various animals, including various mammals and animals of veterinary or industrial interest as described above.

In some embodiments, the compositions and methods of the invention provide for the delivery of mRNA encoding a therapeutic protein (e.g., cytosolic, transmembrane or secreted) such as those listed in Table 4. In some embodiments, the compositions and methods of the invention provide for the delivery of an mRNA encoding a therapeutic protein useful in treating a disease or disorder (i.e., indication) listed in Table 4; thus, compositions of the invention may comprise an mRNA encoding a therapeutic protein listed or not listed in Table 4 (or a homolog thereof, as discussed below) along with other components set out herein for treating a disease or disorder (i.e., indication) listed in Table 4, and methods of the invention may comprise preparing and/or administering a composition comprising an mRNA encoding a such a protein (or a homolog thereof, as discussed below) along with other components set out herein for treatment of a disease or disorder listed in Table 4.

TABLE 4

Exemplary Indications and Related Proteins

| Indication | Therapeutic Protein |
| --- | --- |
| 3-Methylcrotonyl-CoA carboxylase deficiency | Methylcrotonoyl-CoA carboxylase |
| 3-Methylglutaconic aciduria | Methylglutaconyl-CoA hydratase |
| Actinic keratosis | |
| Acute intermittent porphyria | Porphobilinogen deaminase |
| Acute lymphocytic leukemia | |
| Acute myeloid leukemia | |
| Addison's disease | |
| Adenosine deaminase deficiency | Adenosine deaminase |
| Adrenoleukodystrophy | ABCD1 |
| Adrenomyeloneuropathy | |
| AIDS/HIV | |
| Alcohol use disorders | |
| Alkaptonuria | Homogentisate 1,2-dioxygenase |
| Allergic asthma | Anti-IgE mAb |
| Allergies (dermatitis, rhinitis) | |
| Alopecia areata | |
| Alpers' disease | POLG |
| Alpers-Huttenlocher syndrome | |

TABLE 4-continued

Exemplary Indications and Related Proteins

| Indication | Therapeutic Protein |
|---|---|
| Alpha 1-antitrypsin deficiency | Alpha 1 protease inhibitor |
| Alpha-mannosidosis | Alpha-D-mannosidase |
| Alport syndrome | |
| Alzheimer's disease | |
| Amyloid light-chain amyloidosis | |
| Amyotrophic lateral sclerosis (ALS) | |
| Anemia | Erythropoietin |
| Aortic valve stenosis | |
| Argininemia | Arginase |
| Argininosuccinic acidemia | Argininosuccinate lyase |
| Arrhythmogenic right ventricular dysplasia | |
| Autism | |
| Autosomal dominant and recessive progressive external ophthalmoplegia with mitochondrial DNA deletions | |
| Autosomal recessive polycystic kidney disease | ARPKD |
| Bacterial infections | |
| Basal cell carcinoma | |
| Batten disease | Battenin + others |
| B-cell chronic lymphocytic leukemia | |
| Becker muscular dystrophy | Dystrophin |
| Beta-thalassemia | Beta globin |
| Binge eating disorder | |
| Bipolar disorder | |
| Bladder cancer | |
| Blepharospasm, Cervical dystonia, Chronic migraine, more | Botulinum toxin |
| Bronchiolitis obliterans | |
| Brugada syndrome | |
| Buerger's disease | |
| CACNA1A | |
| CACNB4-related Episodic Ataxia Type 2 | |
| Cancer and depression | |
| Cancer and sexual dysfunction | |
| Cancer in pregnancy | |
| Carbamylphosphate synthetase deficiency | Carbamylphosphate synthetase |
| Carcinoma of the gallbladder | |
| Cardiomyopathy (diabetic) | |
| Cardiomyopathy (hypertrophic) | |
| Carnitine uptake defect | SLC22A5 |
| Catecholaminergic polymorphic ventricular tachycardia | |
| CDKL5-related Atypical Rett Syndrome | |
| Celiac disease | |
| Cellulitis | |
| Cerebrovascular disease | |
| Cervix uteri cancer | |
| Chronic fatigue syndrome | |
| Chronic graft versus host disease | |
| Chronic idiopathic urticaria | |
| Chronic immune thrombocytopenia | Thrombopoietin |
| Chronic kidney kisease | |
| Chronic liver disease | |
| Chronic lymphocytic leukemia | |
| Chronic myeloid leukemia | |
| Chronic pancreatitis | |
| Cirrhosis of the liver | |
| Citrullinemia, type I | Argininosuccinate synthase |
| Classic Rett Syndrome | |
| Classical galactosemia | Galactose-1-phosphate uridylyltransferase |
| Clostridium difficile associated diarrhea | |
| Clotting disorders | |
| COAD/COPD | |
| Cocaine addiction | |
| COL4A5-related disorders | |
| Cold contact urticaria | |
| Contraception, female | |
| Coronary artery diseases | |
| Corpus uteri cancer | |
| Corticobasal degeneration | |
| Crigler-Najjar syndrome | UDP-glucuronosyltransferase |
| Critical limb ischemia | |
| CTNS-related cystinosis | |
| Cutaneous lupus erythematosus | |
| Cutaneous neuroendocrine carcinoma (Merkel Cell) | |
| Cystic fibrosis | CFTR |

TABLE 4-continued

Exemplary Indications and Related Proteins

| Indication | Therapeutic Protein |
|---|---|
| Cystic fibrosis | Deoxyribonuclease I |
| Cystinosis | Cystinosin |
| Cystinuria | SLC7A9 |
| Dementia (Lewy body) | |
| Depression | |
| Diabetic foot infections | |
| Diabetic foot ulcer | |
| Diabetic peripheral neuropathy | |
| Diabetic ulcers | |
| Diarrhoeal diseases | |
| Diffuse large B-cell lymphoma | |
| DiGeorge syndrome | |
| Diverticulitis | |
| Drug use disorders | |
| Duchenne muscular dystrophy | Dystrophin |
| Dysarthria | |
| Dyskinesia (levodopa-induced) | |
| Early-onset autosomal dominant Alzheimer's disease | |
| Eczema | |
| Ehlers-Danlos syndrome, type 1 | |
| EIF2B1 | |
| EIF2B2 | |
| EIF2B3 | |
| EIF2B4 | |
| EIF2B5-related childhood ataxia with central nervous system hypomyelination/vanishing white matter | |
| Eosinophilic esophagitis | |
| Epilepsy | |
| Erectile dysfunction | |
| Erythropoietic protoporphyria | Ferrochelatase |
| Esophageal carcinoma | |
| Essential tremor | |
| Fabry disease | Alpha galactosidase |
| Familial adenomatous polyposis | APC |
| Familial chylomicronemia | Lipoprotein lipase |
| Familial dysbetalipoproteinemia | Apolipoprotein E |
| Familial isolated dilated cardiomyopathy | |
| Familial mediterranean fever | Pyrin (MEFV) |
| Familial melanoma | |
| Female infertility | Follicle stimulating hormone |
| Female sexual dysfunction | |
| Fibromyalgia | |
| FMR1-related disorders | |
| Fracture healing | |
| Fragile X Premature Ovarian Failure Syndrome | |
| Fragile X syndrome | FMRP |
| Fragile X-Associated Tremor/Ataxia Syndrome | |
| Friedreich's ataxia | |
| Frontotemporal dementia | |
| Fryns syndrome | |
| Galactocerebrosidase deficiencies | |
| GALE deficiency | Galactose epimerase |
| GALK deficiency | Galactokinase |
| GALT-related galactosemia | |
| Gastric cancer | |
| Gastroesophageal reflux disease | |
| Gaucher disease | Glucocerebrosidase |
| Gilbert syndrome | UDP-glucuronosyltransferase |
| Glioblastoma multiforme | |
| Glomerulonephritis | |
| Glutaric acidemia, type I | Glutaryl-CoA dehydrogenase |
| GM2 gangliosidosis | HEXA, HEXB |
| Gout | Urate oxidase |
| Graft versus host disease | |
| Growth hormone deficiency | Growth hormone 1/Growth hormone 2 |
| Head and neck cancer, Metastatic colorectal cancer | Anti-EGFr mAb |
| Hearing loss, adult onset | |
| Heart failure | |
| Hemachromatosis | HFE protein |
| Hemifacial spasm | |
| Hemolytic uremic syndrome | Anti-complement factor C5 mAb |
| Hemophilia A | Factor VIII |
| Hemophilia A, Hemophilia B | Factor VII |
| Hemophilia B | Factor IX |
| Hepatitis B, Hepatitis C | Interferon alpha |
| HER2+ breast cancer, gastric cancer | Anti-HER2 mAb |

TABLE 4-continued

Exemplary Indications and Related Proteins

| Indication | Therapeutic Protein |
|---|---|
| Hereditary angioedema | C1 esterase inhibitor |
| Hereditary hemorrhagic telangiectasia | |
| Hereditary hemorrhagic telangiectasia (AT) | |
| Hereditary spherocytosis | |
| Hidradenitis suppurativa | |
| Homocystinuria | Cystathionine beta-synthase |
| Homozygous familial hypercholesterolemia | LDL receptor |
| Hunter syndrome (MPS II) | Iduronate-2-sulfatase |
| Huntington disease | Huntingtin |
| Hurler syndrome (MPS I) | Alpha-L iduronidase |
| Hydrolethalus | |
| Hyperalgesia | |
| Hyperbilirubinemia | |
| Hyperhidrosis | |
| Hyperlipidemia | |
| Hypermethioninemia | Methionine adenosyltransferase |
| Hyperoxaluria, type I | Serine-pyruvate aminotransferase |
| Hypertension | |
| Hyperuricemia | |
| Hyponatremia | |
| Hypoparathyroidism | Parathyroid hormone |
| Hypophosphatasia | TNSALP |
| Idiopathic pulmonary fibrosis | |
| Iminoglycinuria | |
| Immunoglobulin deficiency | Immunoglobulin |
| Infection (adenovirus) | |
| Infection (anthrax prophylaxis) | |
| Infection (BK virus) | |
| Infection (Clostridium difficile prophylaxis) | |
| Infection (Dengue fever prophylaxis) | |
| Infection (Epstein-Barr virus) | |
| Infection (Hepatitis-D) | |
| Infection (Lyme disease prophylaxis) | |
| Infection (Smallpox virus) | |
| Infectious diseases vaccines | Infectious antigen |
| Inflammatory heart diseases | |
| Insomnia | |
| Interstitial cystitis | |
| Iron-deficiency anaemia | |
| Irritable bowel disease | |
| Ischaemic heart disease | |
| Isovaleric aciduria | Isovaleric acid CoA dehydrogenase deficiency |
| Jansky-Bielschowsky disease | |
| Juvenile Batten disease | |
| Juvenile Neuronal Ceroid Lipofuscinosis (JNCL) | |
| Juvenile rheumatoid arthritis | TNF-alpha inhibitors |
| Kennedy's disease (SBMA) | |
| Keratoconus | |
| Krabbe disease | Galactocerebrosidase |
| Leber's hereditary optic neuropathy | NADH dehydrogenase |
| Leiomyosarcoma | |
| Lennox-Gastaut syndrome | |
| Lesch-Nyhan syndrome | Hypoxanthine phosphoribosyltransferase 1 |
| Leukaemia | |
| Li-Fraumeni syndrome | TP53 |
| Lipoma | |
| Liposarcoma | |
| Liver cancer | |
| Long-chain 3-OH acyl-CoA dehydrogenase deficiency | Long-chain-3-hydroxyacyl-CoA dehydrogenase |
| Lower respiratory infections | |
| Lysosomal acid lipase deficiency | Lysosomal acid lipase |
| Macular degeneration | |
| Major depressive disorder | |
| Malignant fibrous histiocytoma | |
| Mantle cell lymphoma | |
| Maple syrup urine disease | 3-methyl-2-oxobutanoate dehydrogenase |
| Marfan syndrome | FBN1 |
| Maroteaux-Lamy syndrome (MPS VI) | N-acetylgalactosamine 4-sulfatase |
| Mastocytosis | |
| McArdle disease | Muscle glycogen phosphorylase |
| MECP2-related disorders | |
| MECP2-related Severe Neonatal Encephalopathy | |
| Medium-chain acyl-CoA dehydrogenase deficiency | Acyl-CoA dehydrogenase |
| Melanoma | Anti-CTLA4 mAb |
| Metachromatic leukodystrophy | Arylsulfatase A |
| Metastatic colorectal cancer, NSCLC, others | Anti-VEGF mAb |

TABLE 4-continued

Exemplary Indications and Related Proteins

| Indication | Therapeutic Protein |
|---|---|
| Methylmalonyl-CoA mutase deficiency | Methylmalonyl-CoA mutase |
| Migraine | |
| Mitochondrial oxidative phosphorylation disorders | |
| Morquio syndrome, type A (MPS IVA) | Galactose 6-sulfate sulfatase |
| Morquio syndrome, type B (MPS IVB) | Beta-galactosidase |
| Mouth and oropharynx cancers | |
| Multiple carboxylase deficiency | Biotin-methylcrotonoyl-CoA-carboxylase ligase |
| Multiple myeloma | |
| Multiple sclerosis | Anti-VLA-4 mAb |
| Multiple sclerosis | Interferon beta |
| Multiple system atrophy | |
| Myasthenia gravis | |
| Myelofibrosis | |
| Narcolepsy | |
| Neonatal bronchopulmonary dysplasia | |
| Neonatal infections | |
| Nephritis and nephrosis | |
| Neurofibromatosis, type 1 | NF-1 |
| Neuronal ceroid lipofuscinoses-related diseases | |
| Neutropenia | G-CSF |
| Niemann Pick disease, type A/B | SMPD1 |
| Niemann Pick disease, type C | NPC1 |
| Niemann-Pick disease Type C1 | |
| Nocturia | |
| Non-alcoholic fatty liver disease | |
| Non-Hodgkin lymphoma | Anti-CD20 mAb |
| Non-small cell lung cancer | |
| Notch-3 related cerebral autosomal dominant arteriopathy with subcortical infarcts and leukoencephalopathy (CADASIL) | |
| Obesity | |
| Ophthalmoparesis | |
| Opioid induced constipation | |
| Ornithine transcarbamylase deficiency | Ornithine transcarbamylase |
| Osteoarthritis | |
| Osteopetrosis | |
| Osteoporosis | Anti-RANKL mAb |
| Ovarian cancer | |
| Paget disease of bone | Sequestosome 1 |
| Pain | |
| Pancreatic carcinoma | |
| Panic disorder | |
| Parkinson disease | |
| Paroxysmal nocturnal hemoglobinuria | Anti-complement factor C5 Mab |
| *Pediculosis capitis* (head lice) | |
| Pelizaeus-Merzbacher disease | |
| Pemphigus vulgaris | |
| Peptic ulcer disease | |
| Peripheral neuropathy | |
| Peyronie's disease | |
| Phenylketonuria | Phenylalanine hydroxylase |
| Pneumococcal infection prophylaxis | |
| POLG-related sensory ataxic neuropathy | |
| Polycystic kidney disease | |
| Polycystic ovary syndrome | |
| Polycythaemia vera | |
| Polymerase G-related disorders | |
| Polymorphous light eruption | |
| Pompe disease | Alpha glucosidase |
| Porphyria cutanea tarda | Uroporphyrinogen decarboxylase |
| Post herpetic neuralgia | |
| Post-organ transplant | |
| Pouchitis | |
| PPM-X Syndrome | |
| Prader-Willi syndrome | |
| Preeclampsia | |
| Premature ejaculation | |
| Prematurity and low birth weight | |
| Primary ciliary dyskinesia | |
| Primary glomerular diseases | |
| Primary humoral immune deficiencies (e.g., CVID) | Immunoglobulin |
| Proctitis | |
| Progressive multifocal leukoencephalopathy | |
| Progressive supranuclear palsy | |
| Propionic acidemia | Propionyl-CoA carboxylase |
| Prostate cancer | |

TABLE 4-continued

Exemplary Indications and Related Proteins

| Indication | Therapeutic Protein |
|---|---|
| Psoriasis | Anti-IL-12 & IL-23 mAb |
| Psoriatic arthritis | TNF-alpha inhibitors |
| PTT-1 | |
| Pulmonary arterial hypertension | |
| Pulmonary arterial hypertension | |
| Raynaud's phenomenon | |
| Refractive errors | |
| Renal cell carcinoma | |
| Restless leg syndrome | |
| Retinitis pigmentosa | |
| Rheumatic heart disease | |
| Rheumatoid arthritis | Anti-interleukin-6 (IL-6) mAb |
| Rheumatoid arthritis | T-cell costimulation blocker |
| Rheumatoid arthritis | TNF-alpha inhibitor |
| Romano-Ward syndrome | |
| Rosacea | |
| Sanfilippo syndrome, type A (MPS IIIA) | Heparan N-sulfatase |
| Sanfilippo syndrome, type B (MPS IIIB) | N-acetyl-alpha-D-glucosaminidase |
| Santavuori-Haltia disease | |
| Schizophrenia | |
| Schnitzler syndrome | |
| Scleroderma | |
| SCN1A | |
| SCN1B-related seizure disorders | |
| Short-chain acyl-CoA dehydrogenase deficiency | Butyryl-CoA dehydrogenase |
| Sickle cell disease | Hemoglobin |
| SLC3A1-related disorders | |
| Small cell lung cancer | |
| SMN-1-related spinal muscular atrophy (SMA) | |
| Spinal muscular atrophy | Survival motor neuron protein |
| Squamous cell carcinoma of head and neck | |
| Stickler syndrome | |
| Stomach cancer | |
| Stroke prophylaxis | |
| Synovial sarcoma | |
| Systemic lupus erythematosus | Anti-BAFF |
| Systemic sclerosis | |
| Tetrahydrobiopterin-deficient hyperphenylalaninemia | Tetrahydrobiopterin |
| Thromboangiitis obliterans | |
| Thrombotic disorders | |
| Thyroid cancer | |
| TPP1 deficiencies | |
| Trachea, bronchus, lung cancers | |
| Tricuspid atresia | |
| TSC1 | |
| TSC2-related tuberous sclerosis | |
| Type 2 diabetes mellitus | Glucagon-like peptide 1 (GLP-1) agonist |
| Type 2 diabetes mellitus | Insulin |
| Tyrosinemia, type I | Fumarylacetoacetase |
| Ulcerative colitis | |
| Uterine fibroids | |
| Varicose veins | |
| Venous thromboembolism | |
| Very long-chain acyl-CoA dehydrogenase deficiency | Long-chain-acyl-CoA dehydrogenase |
| von Gierke's disease | Glucose-6-phosphatase |
| Von Hippel-Lindau disease | pVHL |
| Wegener granulomatosis | |
| Wilson disease | Wilson disease protein |
| X-Linked adrenal hypoplasia | |
| X-linked adrenoleukodystrophy | |
| X-linked agammaglobulinemia | Bruton's tyrosine kinase |

In some embodiments, the present invention is used to prevent, treat and/or cure a subject affected with a disease or disorder listed or associated with the proteins listed in Tables 1, 2, 3, or 4. In some embodiments, an mRNA encodes one or more of Cystic Fibrosis Transmembrane Conductance Regulator (CFTR), argininosuccinate synthetase (ASS1), Factor IX, survival motor neuron 1 (SMN1), or phenylalanine hydroxylase (PAH).

While certain compounds, compositions and methods of the present invention have been described with specificity in accordance with certain embodiments, the following examples serve only to illustrate the compounds of the invention and are not intended to limit the same.

EXAMPLES

Example 1: General Synthesis of Cationic Lipids

A cationic lipid (e.g., cationic lipids (1a)-(21a), (1b)-(21b), and (22)-(462)) can be prepared according to Scheme 1 or Scheme 2 as described herein.

Example 2: Exemplary Synthesis of a Common Synthetic Intermediate

Scheme 3 provides an exemplary synthesis of a common synthetic intermediate.

Scheme 3.
Synthesis of ((2R,3R,4R,5s)-3,4-5-Tris((tert-butyldimethylsilyl)oxy) tetrahydrofuran-2-yl)methyl 3-(dimethylamino)propanoate

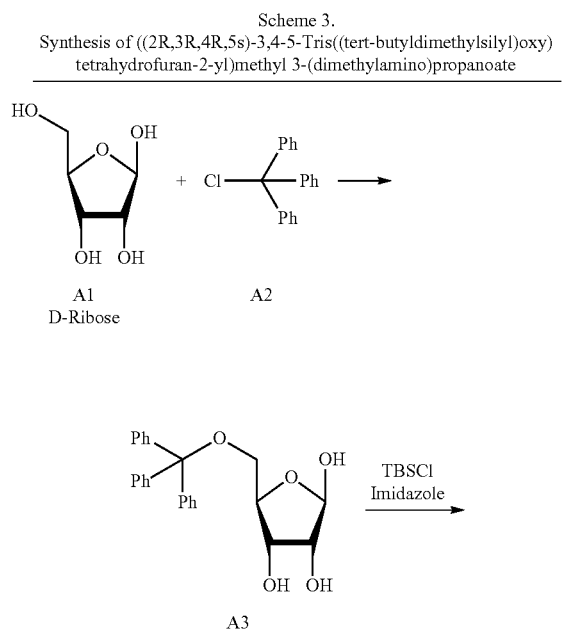

Synthesis of (2R,3R,4S,5R)-5-((trityloxy)methyl) tetrahydrofuran-2,3,4-triol (A3)

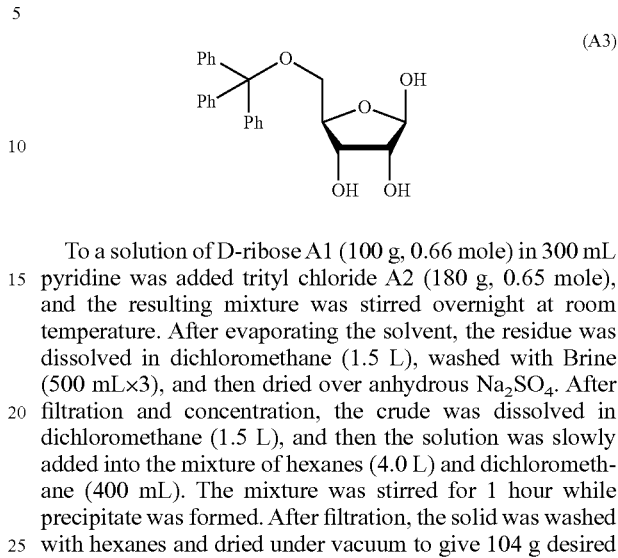

To a solution of D-ribose A1 (100 g, 0.66 mole) in 300 mL pyridine was added trityl chloride A2 (180 g, 0.65 mole), and the resulting mixture was stirred overnight at room temperature. After evaporating the solvent, the residue was dissolved in dichloromethane (1.5 L), washed with Brine (500 mL×3), and then dried over anhydrous $Na_2SO_4$. After filtration and concentration, the crude was dissolved in dichloromethane (1.5 L), and then the solution was slowly added into the mixture of hexanes (4.0 L) and dichloromethane (400 mL). The mixture was stirred for 1 hour while precipitate was formed. After filtration, the solid was washed with hexanes and dried under vacuum to give 104 g desired product A3 as white solid (Yield: 40%).

Synthesis of (((2S,3R,4R,5R)-5-((trityloxy)methyl) tetrahydrofuran-2,3,4-triyl)tris(oxy))tris(tert-butyldimethylsilane) (A4)

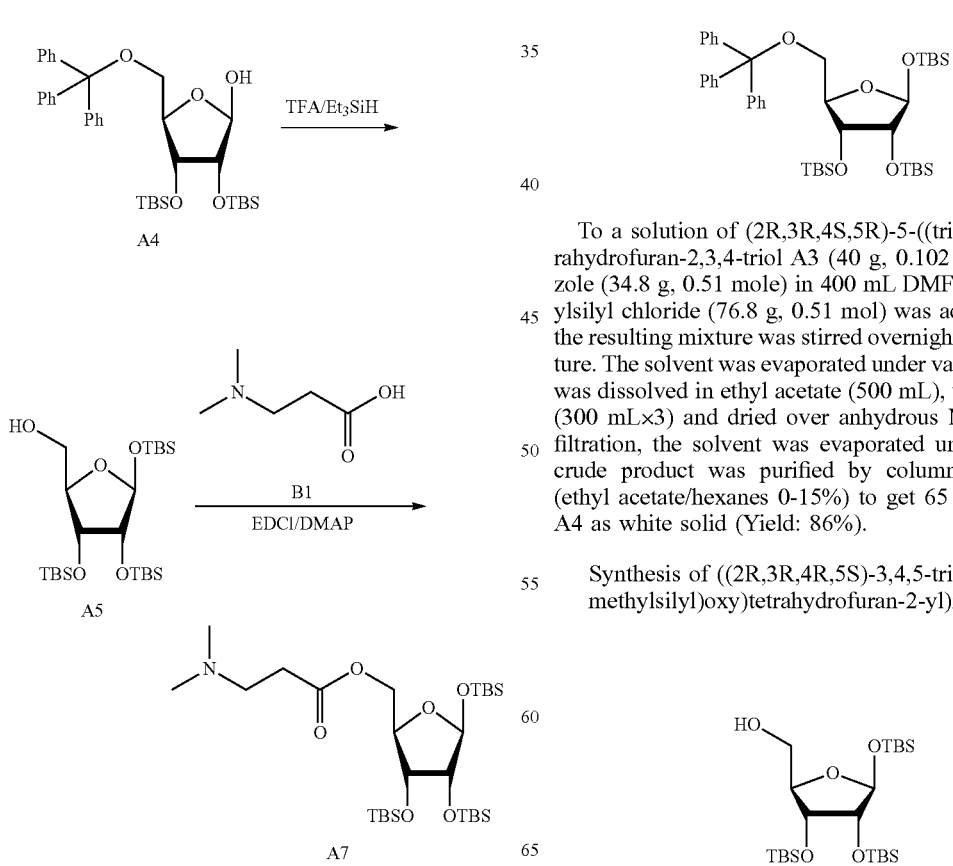

To a solution of (2R,3R,4S,5R)-5-((trityloxy)methyl)tetrahydrofuran-2,3,4-triol A3 (40 g, 0.102 mole) and imidazole (34.8 g, 0.51 mole) in 400 mL DMF, tert-butyldimethylsilyl chloride (76.8 g, 0.51 mol) was added at 0° C., and the resulting mixture was stirred overnight at room temperature. The solvent was evaporated under vacuum. The residue was dissolved in ethyl acetate (500 mL), washed with brine (300 mL×3) and dried over anhydrous $Na_2SO_4$. After the filtration, the solvent was evaporated under vacuum. The crude product was purified by column chromatography (ethyl acetate/hexanes 0-15%) to get 65 g desired product A4 as white solid (Yield: 86%).

Synthesis of ((2R,3R,4R,5S)-3,4,5-tris((tert-butyldimethylsilyl)oxy)tetrahydrofuran-2-yl)methanol (A5)

To a solution of (((2S,3R,4R,5R)-5-((trityloxy)methyl)tetrahydrofuran-2,3,4-triyl)tris(oxy))tris(tert-butyldimethylsilane) A4 (65 g, 88 mmol) in 600 mL dichloromethane, triethylsilane (60 mL, 0.352 mole) was added, and followed by the addition of trifluoroacetic acid (13.8 mL, 0.176 mole) at 0° C. The resulting mixture was stirred for 4 hours at this temperature. The reaction mixture was quenched with saturated $NaHCO_3$ solution to pH 7. The organic phase was separated and washed with saturated $NaHCO_3$ solution (200 mL×3) and brine (200 mL), and then dried over anhydrous $MgSO_4$. After the filtration, the solvent was evaporated under vacuum to afford 71 g of crude product A5, which was used for the next step without further purification.

Synthesis of ((2R,3R,4R,5S)-3,4,5-tris((tert-butyldimethylsilyl)oxy)tetrahydrofuran-2-yl)methyl 3-(dimethylamino)propanoate (A7)

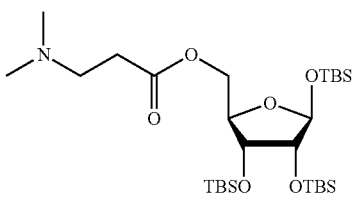

(A7)

To a solution of ((2R,3R,4R,5S)-3,4,5-tris((tert-butyldimethylsilyl)oxy)tetrahydrofuran-2-yl)methanol A5 (71 g, 88 mmol) and 3-(dimethylamino)propanoic acid B1 (13.6 g, 88 mmol) in 500 mL dichloromethane, DMAP (10.7 g, 88 mmol) and EDCI (16.8 g, 88 mmol) were added, and the resulting mixture was stirred overnight at room temperature. The reaction mixture was washed with Brine (200 mL×3) and dried over anhydrous $Na_2SO_4$. After the filtration, the solvent was evaporated under vacuum. The crude product was purified by column chromatography (330 g silica gel, 0-100% ethyl acetate in hexanes gradient) to get 19 g desired product A7 as colorless oil (Yield: 36%).

Example 3: Exemplary Synthesis of Lipids Comprising Biodegradable Lipid Arms

Synthesis of (2S,3R,4R,5R)-5-(((3-(Dimethylamino)propanoyl)oxy)methyl) tetrahydrofuran-2,3,4-triyl tris(decanoate) (2b)

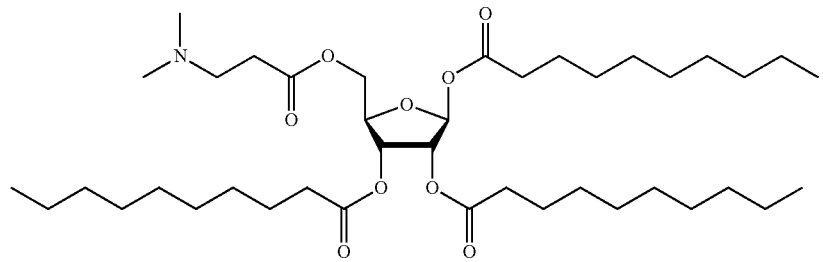

(2b)

To a solution of ((2R,3R,4R,5S)-3,4,5-tris((tert-butyldimethylsilyl)oxy)tetrahydrofuran-2-yl)methyl 3-(dimethylamino)propanoate A7 (0.8 g, 1.35 mmol) in 1 mL THF, HF-pyridine (0.72 mL, 40.5 mmol) was added, and the mixture was stirred at room temperature. After 3 hours, 2 mL dichloromethane, 4 mL pyridine and decanoyl chloride (2.3 g, 12.15 mmol) were added subsequently, and the resulting mixture was stirred for four days at room temperature. The volatiles were evaporated under vacuum, and then the residue was dissolved in dichloromethane (50 mL), washed with Brine (50 mL×3), and dried over anhydrous $Na_2SO_4$. After filtration and concentration, the crude product was purified with column chromatography (80 g silica gel gold column, 0-10% methanol in dichloromethane gradient) to obtain 375 mg of the desired product (2b) as clear oil (Yield: 39%).

This procedure is suitable for the preparation of other lipids described herein, which can be obtained by this representative procedure in similar yields.

Example 4: Exemplary Synthesis of Lipids Comprising Biodegradable Lipid Arms

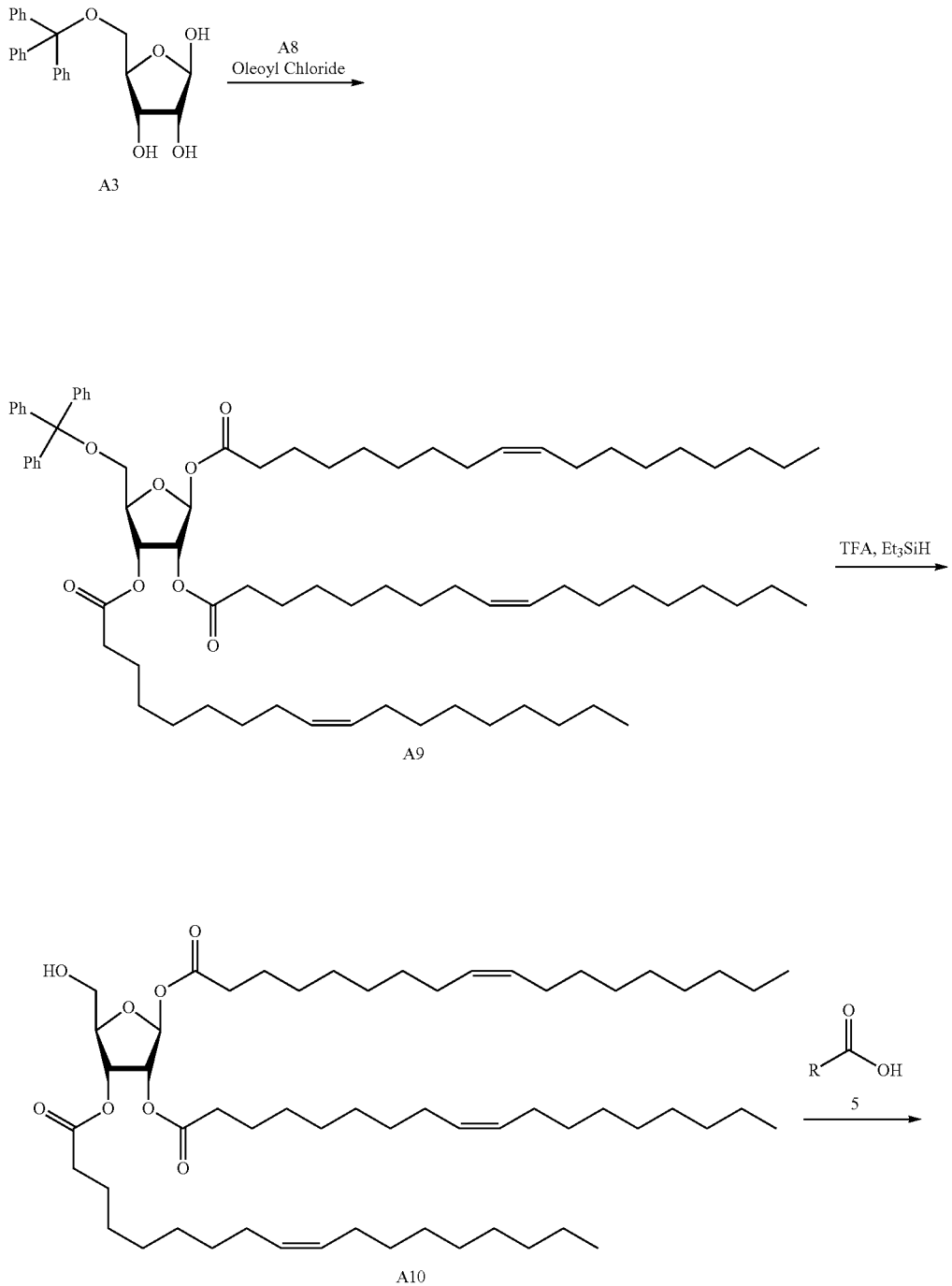

Scheme 4. Syntheses of Lipids with Biodegradable Lipid Groups

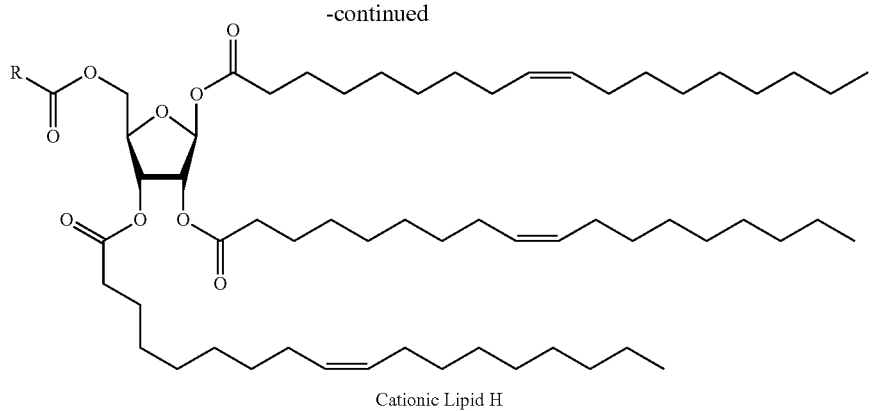
Cationic Lipid H
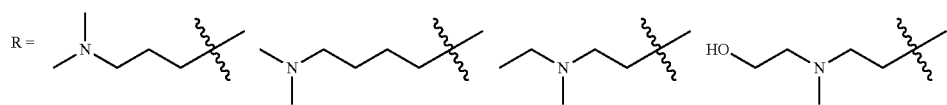
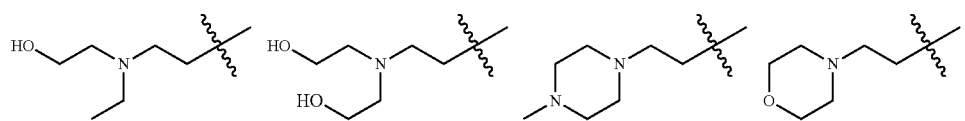
Synthesis of (2S,3R,4R,5R)-5-((Trityloxy)methyl)
tetrahydrofuran-2,3,4-triyl trioleate (A9)
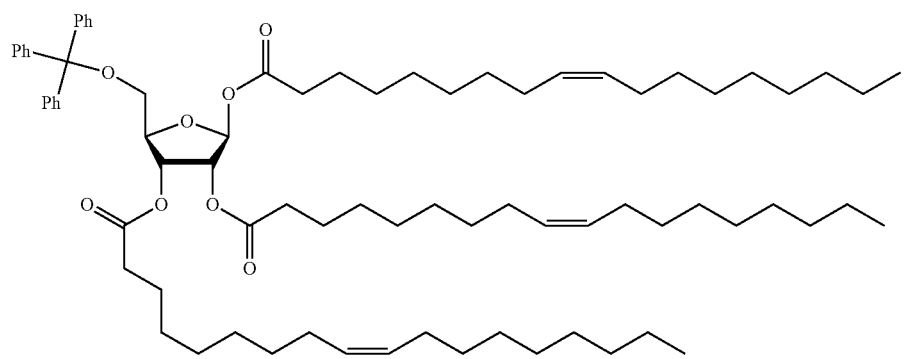

To a solution of (2R,3R,4S,5R)-5-((trityloxy)methyl)tetrahydrofuran-2,3,4-triol A3 (5.0 g, 1.67 mmol) in dichloromethane/pyridine (1/1 v/v, 100 mL) was added oleoyl chloride A8 (23 g, 9.4 mmol) at 0° C., and the mixture was warmed to room temperature and stirred at room temperature for 5 days. After concentrated, the residue was dissolved in dichloromethane and washed with water and brine. After dried over sodium sulfate and concentration, the crude was purified by flash chromatography (SiO$_2$: 0-40% dichloromethane/hexanes) to get 4 g desired product A9.

Synthesis of (2S,3R,4R,5R)-5-(Hydroxymethyl) tetrahydrofuran-2,3,4-triyl Trioleate (A10)

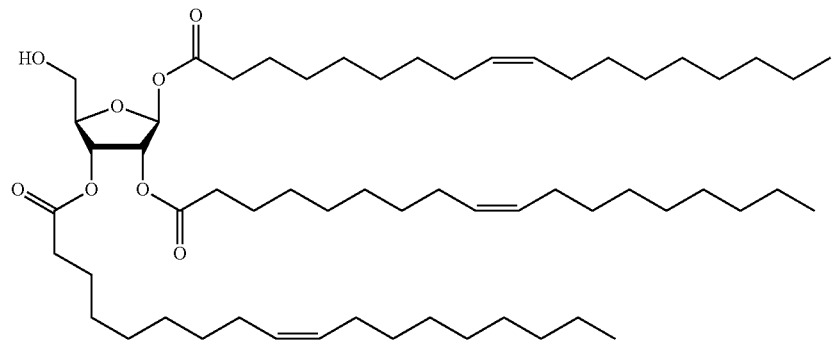

To a solution of (2S,3R,4R,5R)-5-((trityloxy)methyl)tetrahydrofuran-2,3,4-triyl trioleate A9 (0.8 g, 0.67 mmol) and triethylsilane (0.62 mL, 3.9 mmol) in 50 mL dichloromethane was added trifluoroacetic acid (0.12 mL, 1.06 mmol) at 0° C. After stirred at this temperature for 90 min, the reaction mixture was quenched with saturated sodium bicarbonate, and then washed with saturated sodium bicarbonate and brine, dried over MgSO$_4$. After concentration, 0.81 g crude A10 was obtained, which was used for next step without purification.

Synthesis of (2S,3R,4R,5R)-5-(((4-(Dimethylamino) butanoyl)oxy)methyl)tetrahydrofuran-2,3,4-triyl Trioleate (211)

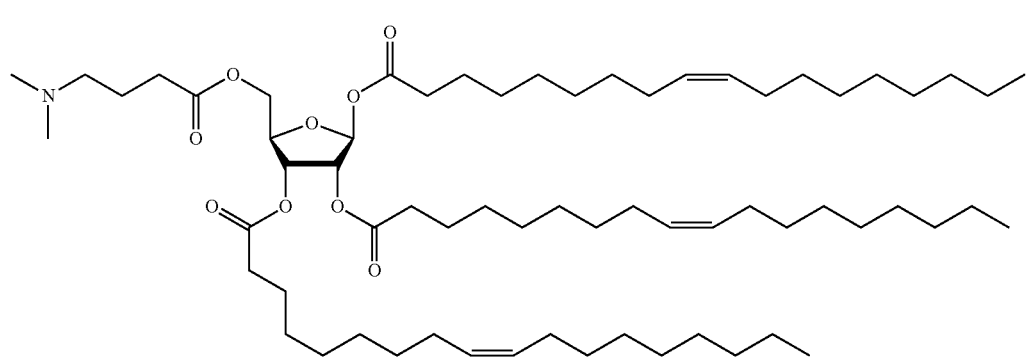

(211)

A mixture of (2S,3R,4R,5R)-5-(hydroxymethyl)tetrahydrofuran-2,3,4-triyl trioleate A9 (0.8 g, 0.67 mmol), EDCI (130 g, 0.67 mmol), 3-(dimethylamino)propanoic acid hydrochloride (108 mg, 0.7 mmol) and DMAP (82 mg, 0.67 mmol) in 50 mL dichloromethane was stirred at room temperature overnight. The reaction mixture was diluted with dichloromethane and then washed with water and brine. After concentration, the crude was purified by flash chromatography (SiO$_2$: 0-10% MeOH/dichloromethane) to get 250 mg desired product (211) (Yield: 36%, two steps).

As shown in Scheme 4, different acylating agents can be used in place of 3-(dimethylamino)propanoic acid hydrochloride to afford still other cationic lipids as described herein. Other lipids were prepared according the representative procedure and obtained in similar yields.

Example 5: Exemplary Synthesis of Lipids Comprising Aliphatic Lipid Arms—NaH Method Scheme 5. Sodium Hydride Route to Lipids with Aliphatic Lipid Groups

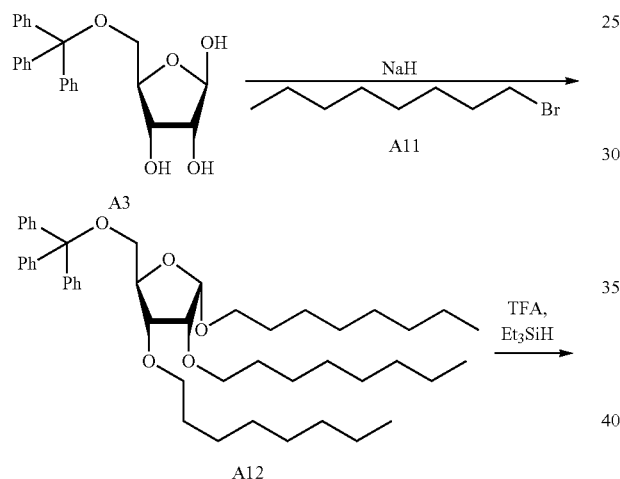

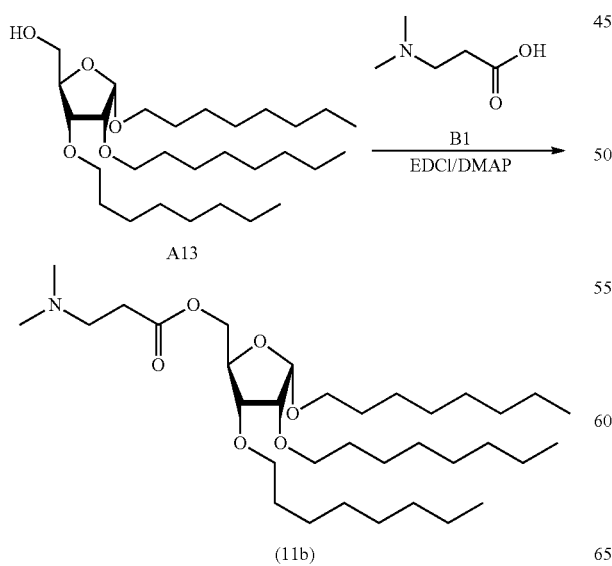

Synthesis of (2S,3R,4R,5R)-2,3,4-Tris(octyloxy)-5-((trityloxy)methyl)tetrahydrofuran (A12)

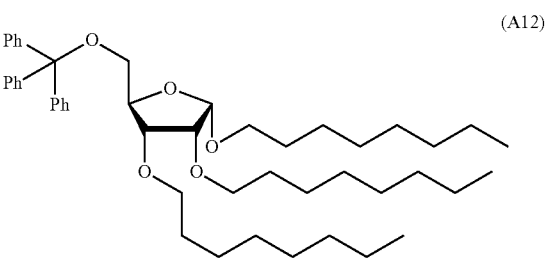

To a solution (2R,3R,4S,5R)-5-((trityloxy)methyl)tetrahydrofuran-2,3,4-triol A3 (3.0 g, 7.6 mmol) in 90 mL DMF was added sodium hydride (60% dispersion in oil, 2.7 g, 67.5 mmol) at 0° C. After 30 min, 1-bromooctane A11 (8.1 mL, 47 mmol) and tetrabutylammonium iodide (600 mg, 1.6 mmol) were added, and the resulting solution was stirred at room temperature overnight. The reaction mixture was quenched by ice/water, and then extracted by ethyl acetate. The combined organic layers were washed with water and brine. After concentration, the crude was purified by flash column chromatography (SiO$_2$: 0-40% ethyl acetate/hexanes) to get 290 mg desired product A12 as colorless oil (Yield: 5%).

Synthesis of ((2R,3R,4R,5S)-3,4,5-Tris(octyloxy)tetrahydrofuran-2-yl)methanol (A13)

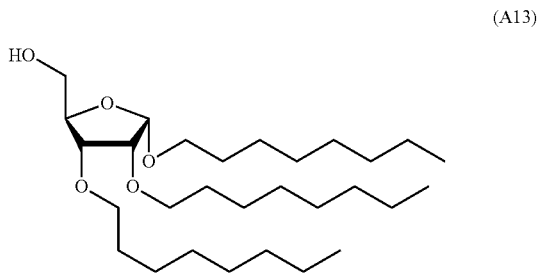

To a solution of (2S,3R,4R,5R)-2,3,4-tris(octyloxy)-5-((trityloxy)methyl)tetrahydrofuran A12 (290 mg, 0.4 mmol) and triethylsilane (0.25 mL, 1.6 mmol) in 2 mL dichloromethane was added trifluoroacetic acid (0.06 mL, 0.8 mmol) at 0° C. After stirred at this temperature for 1 h, the reaction mixture was quenched with saturated NaHCO$_3$, and then washed with saturated NaHCO$_3$ and brine, dried over MgSO$_4$. After concentration, 325 mg crude A13 was obtained, which was used for next step without purification.

Synthesis of ((2R,3R,4R,5S)-3,4,5-Tris(octyloxy) tetrahydrofuran-2-yl)methyl 3-(dimethylamino)propanoate (11b)

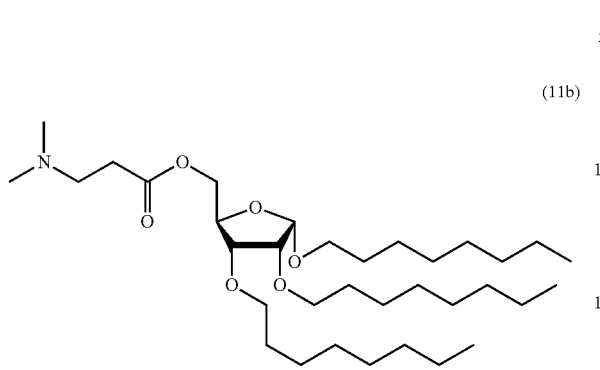

(11b)

A mixture of ((2R,3R,4R,5S)-3,4,5-tris(octyloxy)tetrahydrofuran-2-yl)methanol A13 (325 mg, 0.4 mmol), EDCI (76 mg, 0.4 mmol), 3-(dimethylamino)propanoic acid hydrochloride B1 (61 mg, 0.4 mmol) and DMAP (48 mg, 0.4 mmol) in 6 mL dichloromethane was stirred at room temperature overnight. The reaction mixture was diluted with dichloromethane, and then washed with water and brine. After concentration, the crude was purified by flash column chromatography (SiO$_2$: 0-10% MeOH/dichloromethane) to get 102 mg of the desired product as colorless oil (Yield: 43%, two steps).

Example 6: Exemplary Synthesis of Lipids Comprising Aliphatic Lipid Arms—Ti(O$^t$Bu)$_4$ Method Scheme 6. Ti-mediated Synthesis of Lipids with Aliphatic Arms

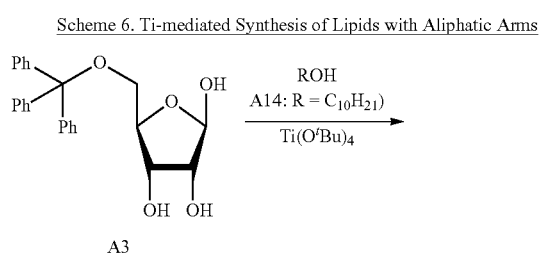

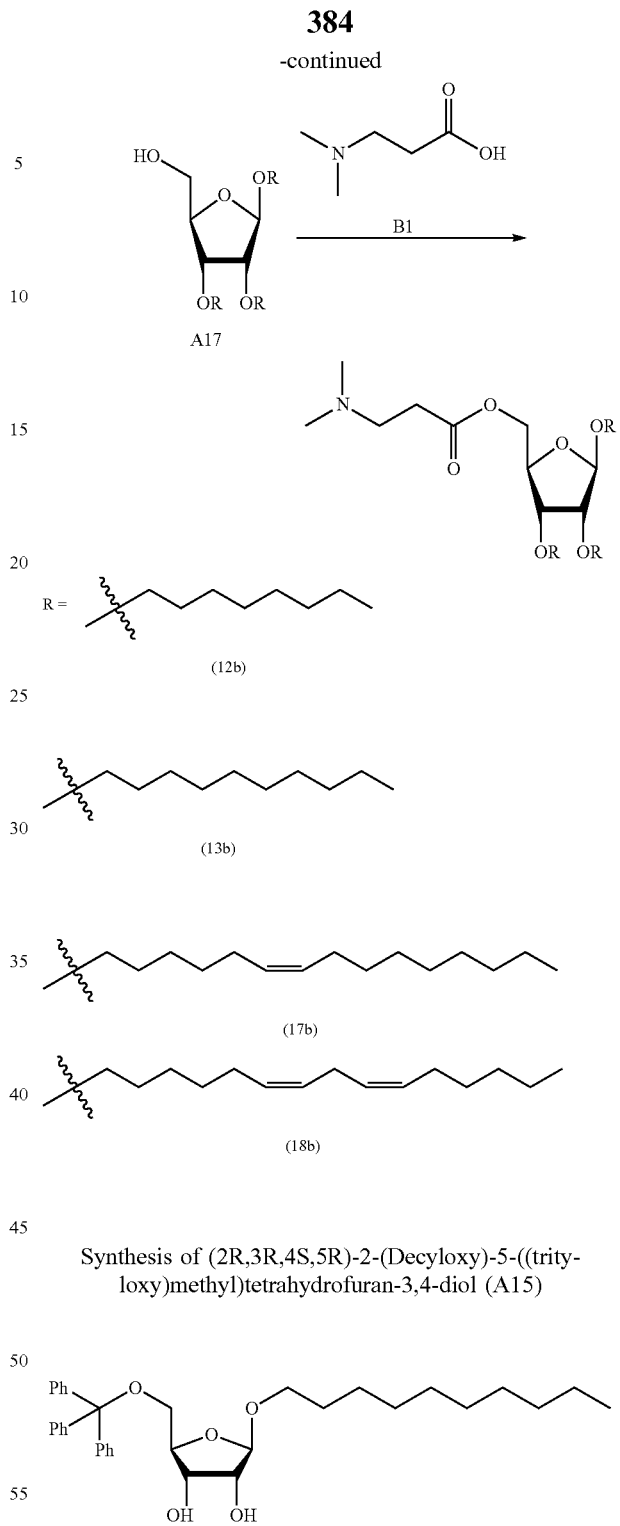

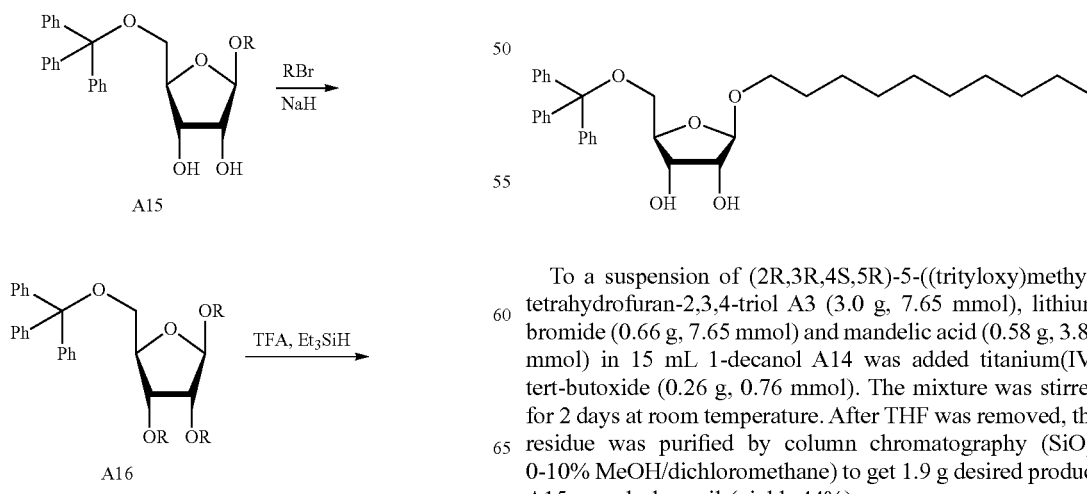

Synthesis of (2R,3R,4S,5R)-2-(Decyloxy)-5-((trityloxy)methyl)tetrahydrofuran-3,4-diol (A15)

To a suspension of (2R,3R,4S,5R)-5-((trityloxy)methyl) tetrahydrofuran-2,3,4-triol A3 (3.0 g, 7.65 mmol), lithium bromide (0.66 g, 7.65 mmol) and mandelic acid (0.58 g, 3.82 mmol) in 15 mL 1-decanol A14 was added titanium(IV) tert-butoxide (0.26 g, 0.76 mmol). The mixture was stirred for 2 days at room temperature. After THF was removed, the residue was purified by column chromatography (SiO$_2$, 0-10% MeOH/dichloromethane) to get 1.9 g desired product A15 as colorless oil (yield: 44%).

Synthesis of (2R,3R,4R,5R)-2,3,4-Tris(decyloxy)-5-((trityloxy)methyl)tetrahydrofuran (A16)

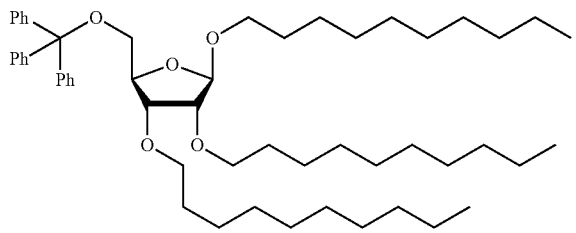

To a solution (2R,3R,4S,5R)-2-(decyloxy)-5-((trityloxy)methyl)tetrahydrofuran-3,4-diol A15 (1.7 g, 3 mmol) in DMF/THF (100 mL/100 mL) was added sodium hydride (60% dispersion in oil, 0.72 g, 18.2 mmol) at 0° C. After 5 min, 1-bromodecane (3.78 g, 15.2 mmol) was added, and the resulting solution was stirred at room temperature overnight. The reaction mixture was quenched by ice/water, and then extracted by ethyl acetate. The combined organic layers were washed with water and brine. After concentration, the crude was purified by flash column chromatography (SiO$_2$: 0-100% dichloromethane/hexanes) to get 1.5 g desired product A16 (Yield: 55%).

Synthesis of ((2R,3R,4R,5R)-3,4,5-Tris(decyloxy)tetrahydrofuran-2-yl)methanol (A17)

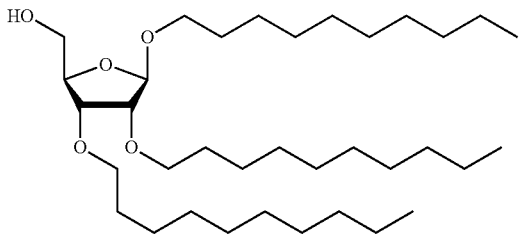

To a solution of (2R,3R,4R,5R)-2,3,4-tris(decyloxy)-5-((trityloxy)methyl)tetrahydrofuran A16 (1.5 g, 1.67 mmol) and triethylsilane (1.5 mL, 9.4 mmol) in 35 mL dichloromethane was added trifluoroacetic acid (0.3 mL, 3.89 mmol) at 0° C. After stirred at this temperature for 90 min, the reaction mixture was quenched with saturated NaHCO$_3$, and then washed with saturated NaHCO$_3$ and brine, dried over MgSO$_4$. After concentration, 1.7 g crude A17 was obtained, which was used for next step without purification.

Synthesis of ((2R,3R,4R,5R)-3,4,5-Tris(decyloxy)tetrahydrofuran-2-yl)methyl 3-(dimethylamino)propanoate (12b)

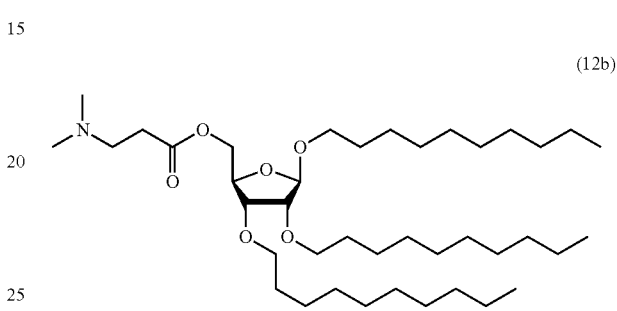

(12b)

A mixture of ((2R,3R,4R,5R)-3,4,5-tris(decyloxy)tetrahydrofuran-2-yl)methanol 17 (1.7 g, 1.67 mmol), EDCI (320 mg, 1.67 mmol), 3-(dimethylamino)propanoic acid hydrochloride 6 (260 mg, 1.9 mmol) and DMAP (200 mg, 1.67 mmol) in 100 mL dichloromethane was stirred at room temperature overnight. The reaction mixture was diluted with dichloromethane, and then washed with water and brine. After concentration, the crude was purified by flash column chromatography (SiO$_2$: 0-10% MeOH/dichloromethane) to get 460 mg desired product 12b (Yield: 36%, two steps).

Other lipids were prepared according the representative procedures in similar yields.

Example 7: Exemplary Synthesis of Lipids Comprising Aliphatic Lipid Arms—Tetraacetylribose Method

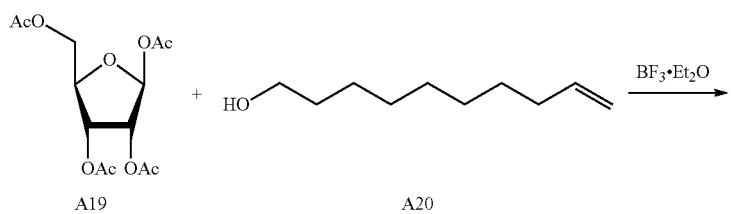

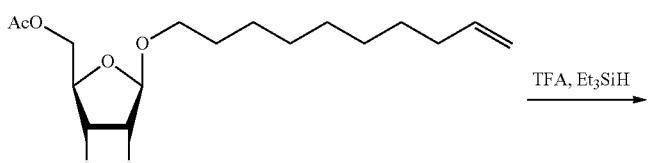

-continued
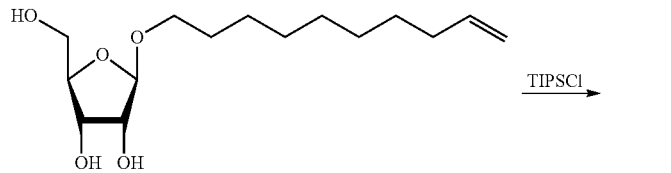
A22
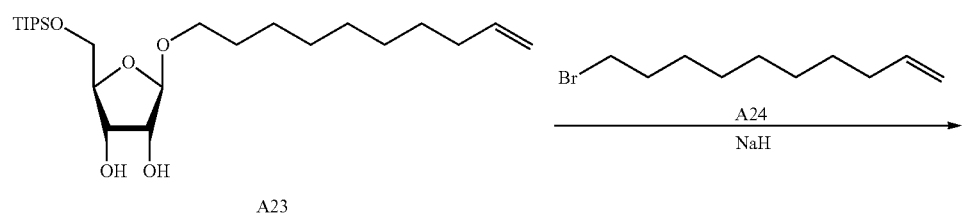
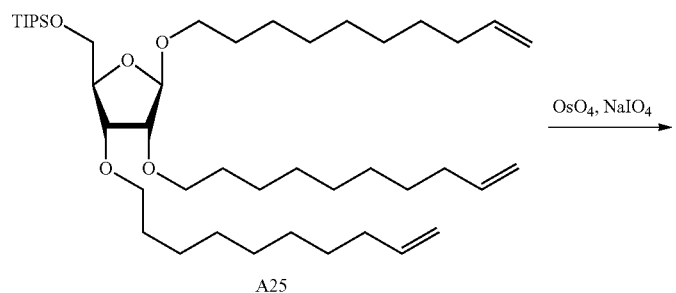
A25
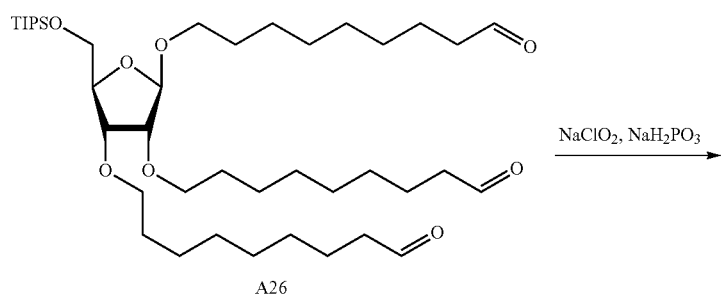
A26
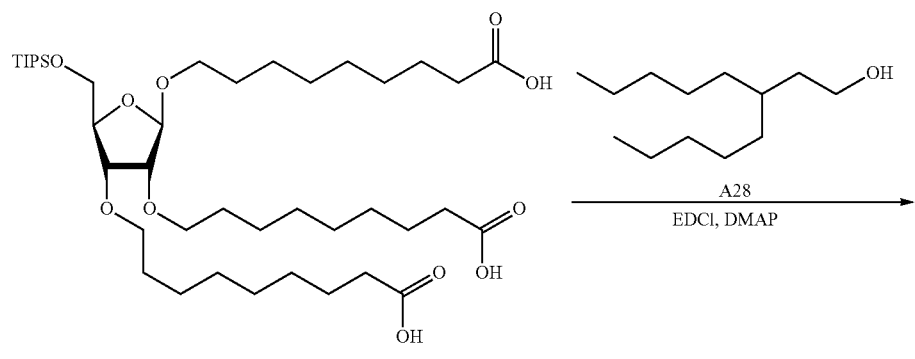
A27

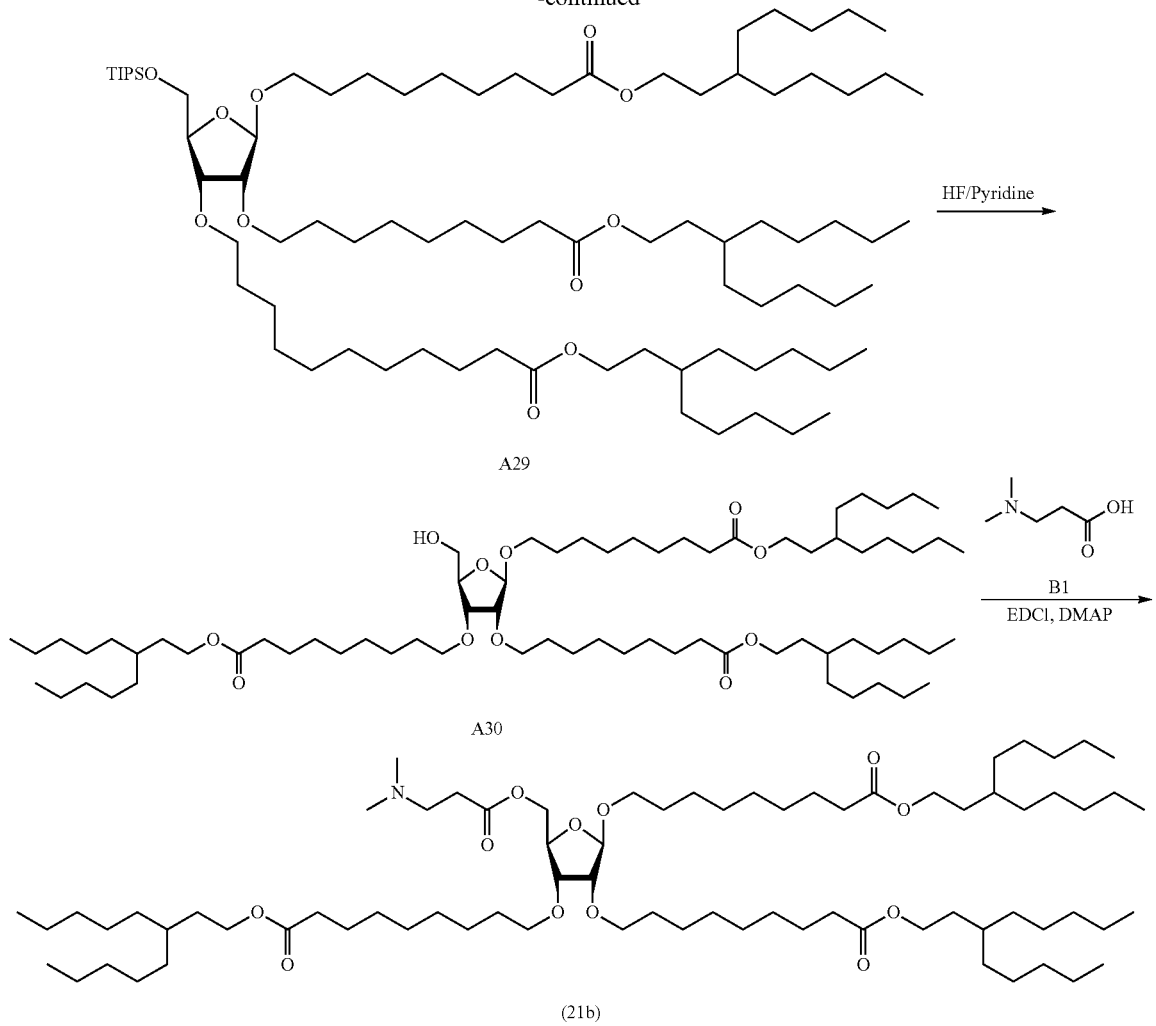

Synthesis of (2R,3R,4R,5R)-2-(Acetoxymethyl)-5-(dec-9-en-1-yloxy)tetrahydrofuran-3,4-diyl Diacetate (A21)

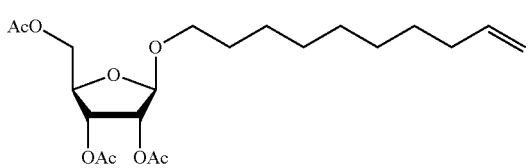

To a solution of 1,2,3,5-tetra-o-acetyl-beta-I-ribofuranose A19 (6.36 g, 20 mmol) and dec-9-en-1-ol A20 (4.3 mL, 24 mmol) in 100 mL dichloromethane at 0° C. was added $BF_3 \cdot OEt_2$ (3.2 mL, 26 mmol), and the reaction mixture was kept at this temperature for 3 h. The reaction mixture was poured into ice cold saturated $NaHCO_3$ and extracted by dichloromethane. The combined organic layers were dried over sodium sulfate. After concentration, the crude was purified by flash column chromatography ($SiO_2$: ethyl acetate/hexane 0-60%) to get a mixture of desired product A21 and dec-9-en-1-ol A20 (3.12 g) as yellowish oil, which was used for the next step without further purification.

Synthesis of (2R,3R,4S,5R)-2-(Dec-9-en-1-yloxy)-5-(hydroxymethyl)tetrahydrofuran-3,4-diol (A22)

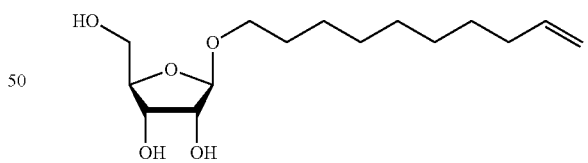

The mixture of (2R,3R,4R,5R)-2-(acetoxymethyl)-5-(dec-9-en-1-yloxy)tetrahydrofuran-3,4-diyl diacetate A21 and dec-9-en-1-ol A20 (3.12 g) was dissolved in THF/MeOH (40 mL/40 mL), and a solution of lithium hydroxide hydrate (3.16 g, 75 mmol) in 5 mL water was added. The resulting mixture was stirred at room temperature overnight. After concentrated to dryness, the residue was dissolved in dichloromethane and washed with brine. The organic layer was dried over sodium sulfate. After concentrated, the crude was purified by flash chromatography ($SiO_2$: methanol/dichloromethane 0-20%) to get 2.08 g pure product A22 as white solid (Yield: 36% in two steps).

Synthesis of (2R,3R,4S,5R)-2-(Dec-9-en-1-yloxy)-5-(((triisopropylsilyl)oxy)methyl)tetrahydrofuran-3,4-diol (A23)

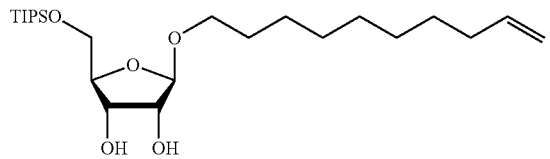

To a solution of (2R,3R,4S,5R)-2-(dec-9-en-1-yloxy)-5-(hydroxymethyl)tetrahydrofuran-3,4-diol A22 (1.63 g, 5.55 mmol) and imidazole (755 mg, 11.1 mmol) in DMF (60 mL) was added triisopropylsilyl chloride (1.3 mL, 6.1 mmol) and stirred at room temperature overnight. The reaction mixture was concentrated to dryness. The residue was partitioned with water and ether. After separation, the organic layer was dried and concentrated. The crude was purified by flash chromatography (SiO$_2$: methanol/dichloromethane 0-10%) to get 1.76 g desired product A23 as colorless oil (Yield: 71%).

Synthesis of Triisopropyl(((2R,3R,4R,5R)-3,4,5-tris(dec-9-en-1-yloxy)tetrahydrofuran-2-yl)methoxy)silane (A25)

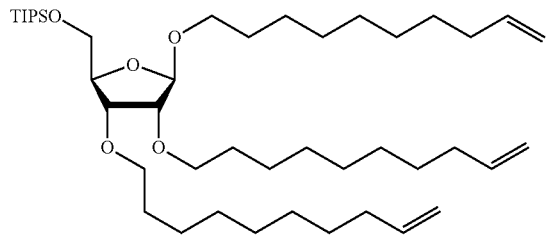

To a solution of (2R,3R,4S,5R)-2-(dec-9-en-1-yloxy)-5-(((triisopropylsilyl)oxy)methyl)tetrahydrofuran-3,4-diol A23 (1.76 g, 3.96 mmol) in DMF/THF (40 mL/40 mL) was added sodium hydride (0.95 g, 23.7 mmol) at 0° C. After 10 min, 10-bromodec-1-ene A24 (4.33 g, 19.8 mmol) was added, the resulting solution was stirred at room temperature overnight. The reaction mixture was quenched by ice/water, and then extracted by ether. The combined organic layers were washed with water and brine. After concentration, the crude was purified by flash chromatography (SiO$_2$: ethyl acetate/hexane 0-5%) to get 2.45 g product A25 as colorless oil (Yield: 85%).

Synthesis of 9,9',9''-(((2R,3R,4R,5R)-5-(((Triisopropylsilyl)oxy)methyl)tetrahydrofuran-2,3,4-triyl)tris(oxy))trinonanal (A26)

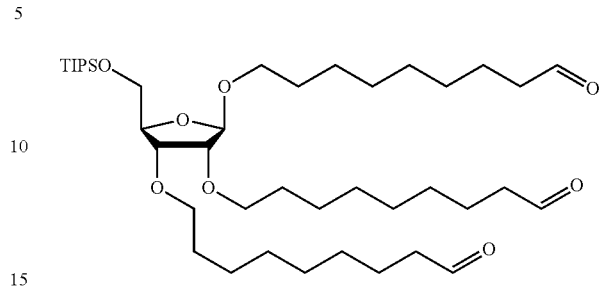

To a solution of triisopropyl(((2R,3R,4R,5R)-3,4,5-tris((9-(benzyloxy)nonyl)oxy)tetrahydrofuran-2-yl)methoxy)silane A25 (2.20 g, 3.05 mmol) and 2,6-Lutidine (4.3 mL, 36.6 mmol) in 80 mL dioxane, a solution of Osmium oxide in water (4 wt %, 0.84 mL, 0.137 mmol) was added, and followed by a solution of sodium periodate in water (7.83 g in 10 mL). After the reaction mixture was stirred at room temperature for 4 h, saturated sodium sulfite was added. The resulting mixture was stirred for 10 min and extracted with dichloromethane. The organic layer was separated and washed with 2 N HCl. After dried over sodium sulfate, the solvent was removed under vacuum to get 2.30 g desired product A26 as yellow semi-solid, which was used for the next step without purification.

Synthesis of 9,9',9''-(((2R,3R,4R,5R)-5-(((Triisopropylsilyl)oxy)methyl)tetrahydrofuran-2,3,4-triyl)tris(oxy))trinonanoic Acid (A27)

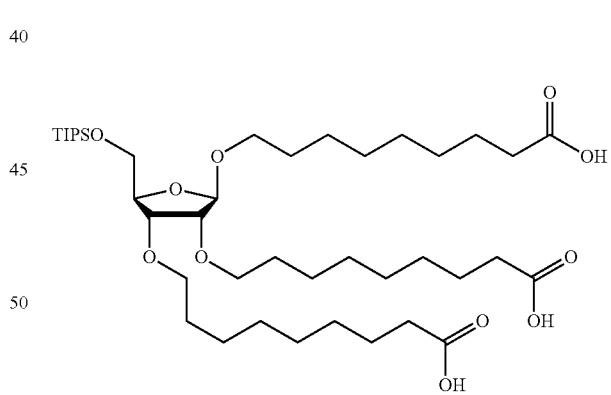

To a solution of 9,9',9''-(((2R,3R,4R,5R)-5-(((triisopropylsilyl)oxy)methyl)tetrahydrofuran-2,3,4-triyl)tris(oxy))trinonanal A26 (1.0 g, 1.3 mmol) in tBuOH/water (15 mL/1 mL), sodium chlorite (0.54 g, 5.9 mmol) and sodium dihydrogen phosphate (0.95 g, 7.9 mmol) were added, and the resulting mixture was stirred at room temperature for 30 min. TLC showed clean reaction. The reaction mixture was diluted with saturated sodium dihydrogen phosphate and extracted with ethyl acetate, and the combined organic layers were washed with brine. After concentration, 1.13 g desired product A27 was obtained as colorless oil, which was used for the next step without purification.

Synthesis of Tris(3-pentyloctyl) 9,9',9"-(((2R,3R,4R,5R)-5-((((triisopropylsilyl)oxy)methyl)tetrahydrofuran-2,3,4-triyl)tris(oxy))trinonanoate (A29)

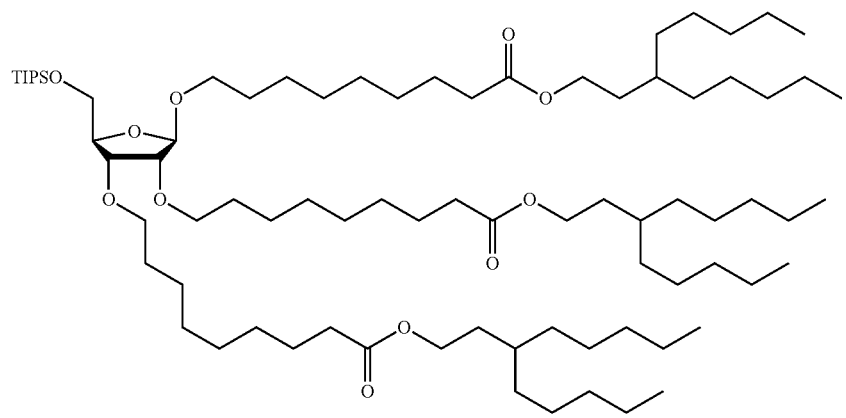

A mixture of 9,9',9"-(((2R,3R,4R,5R)-5-((((triisopropylsilyl)oxy)methyl)tetrahydrofuran-2,3,4-triyl)tris(oxy))trinonanoic acid A27 (1.13 g, 1.46 mmol), 3-pentyloctan-1-ol A28 (3.5 g, 17.5 mmol), EDCI (3.35 g, 17.5 mmol) and DMAP (215 mg, 1.75 mmol) in 100 mL dichloromethane was stirred at room temperature overnight. The reaction mixture was diluted with 1 N HCl and extracted with dichloromethane, and the combined organic layers were washed with brine. After concentration, the crude was purified by flash chromatography (SiO$_2$: ethyl acetate/hexane 0-10%) to get 0.64 g product A29 as colorless oil (Yield: 33%).

Synthesis of Tris(3-pentyloctyl) 9,9',9"-(((2R,3R,4R,5R)-5-(hydroxymethyl)tetrahydrofuran-2,3,4-triyl)tris(oxy))trinonanoate (A30)

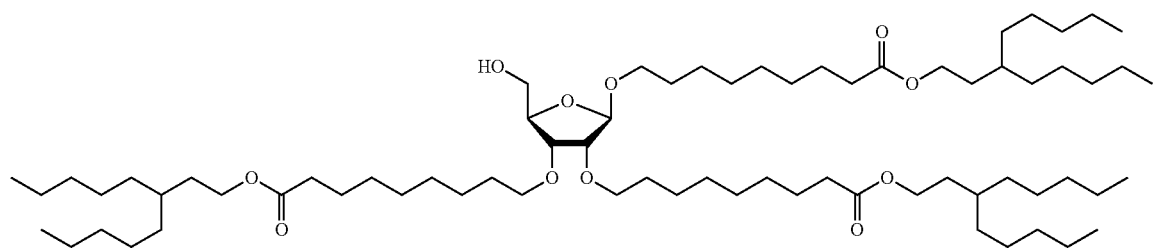

To a solution of tris(3-pentyloctyl) 9,9',9''-(((2R,3R,4R,5R)-5-((((triisopropylsilyl)oxy)methyl)tetrahydrofuran-2,3,4-triyl)tris(oxy))trinonanoate A29 (0.64 g, 0.48 mmol) in 8 mL THF, was added HF.Pyridine (70%, 1 mL), and the resulting solution was stirred for 3 h. The reaction mixture was diluted with dichloromethane, saturated sodium bicarbonate was added to adjust to pH7. The organic layer was separated and dried over sodium sulfate. After concentration, the crude was purified by flash chromatography ($SiO_2$: ethyl acetate/hexane 0-15%) to get 0.51 g pure product A30 as colorless oil (Yield: 91%).

Synthesis of Tris(3-pentyloctyl) 9,9',9''-(((2R,3R,4R,5R)-5-(((3-(dimethylamino)propanoyl)oxy)methyl)tetrahydrofuran-2,3,4-triyl)tris(oxy))trinonanoate (21b)

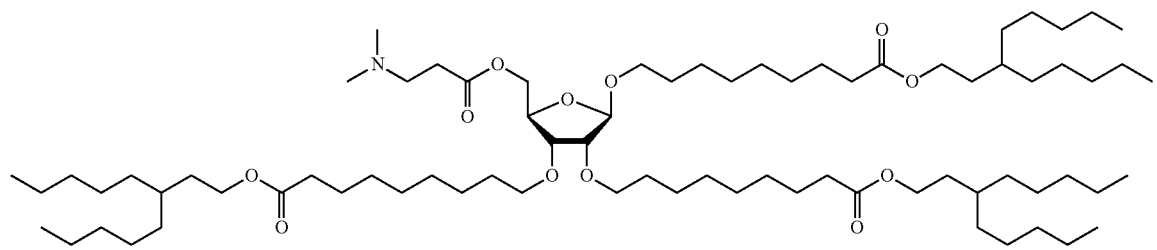

A mixture of tris(3-pentyloctyl) 9,9',9''-(((2R,3R,4R,5R)-5-(hydroxymethyl)tetrahydrofuran-2,3,4-triyl)tris(oxy))trinonanoate A30 (0.51 g, 0.437 mmol), 3-(dimethylamino)propanoic acid hydrochloride B1 (67 mg g, 0.437 mmol), EDCI (84 mg, 0.437 mmol) and DMAP (53 mg, 0.437 mmol) in 30 mL dichloromethane was stirred at room temperature overnight. The reaction mixture was diluted with water and extracted with dichloromethane, and the combined organic layers were washed with brine. After concentration, the crude was purified by flash chromatography ($SiO_2$: methanol/dichloromethane 0-5%) to get 322 mg desired product 21b as clear oil (Yield: 58%).

Compound 19b and 20b were prepared according the same procedures with similar yields.

19b

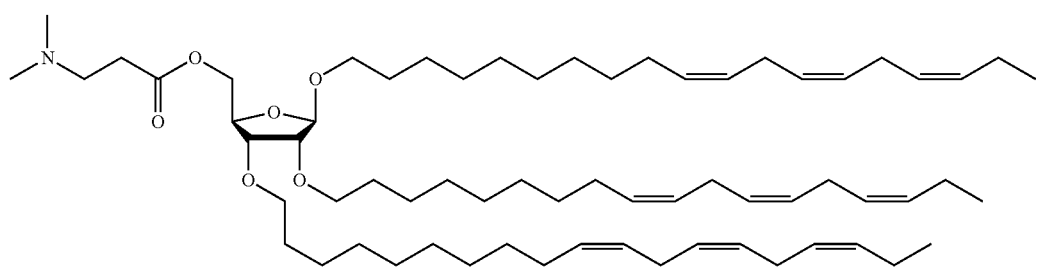

20b

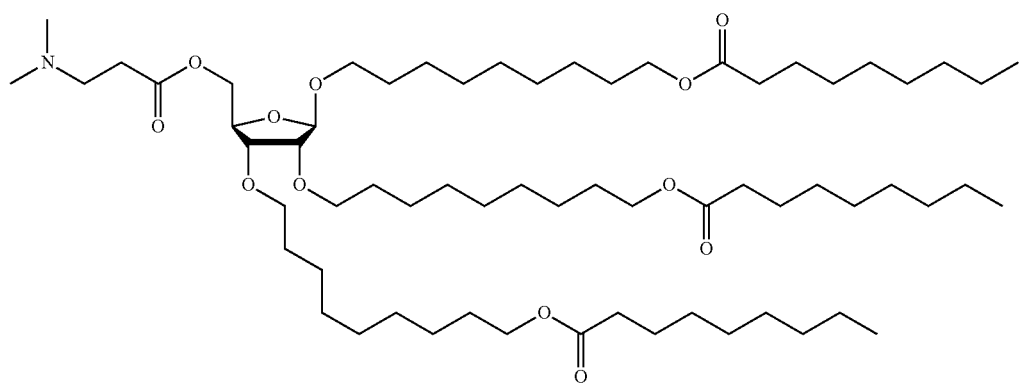

Example 8: Lipid Nanoparticle Formulation Using Ribose Cationic Lipids

Cationic lipids described herein can be used in the preparation of lipid nanoparticles according to methods known in the art. For example, suitable methods include methods described in International Publication No. WO 2018/089801, which is hereby incorporated by reference in its entirety.

One exemplary process for lipid nanoparticle formulation is Process A of WO 2018/089801 (see, e.g., Example 1 and FIG. 1 of WO 2018/089801). Process A ("A") relates to a conventional method of encapsulating mRNA by mixing mRNA with a mixture of lipids, without first pre-forming the lipids into lipid nanoparticles. In an exemplary process, an ethanol lipid solution and an aqueous buffered solution of mRNA were prepared separately. A solution of mixture of lipids (cationic lipid, helper lipids, zwitterionic lipids, PEG lipids etc.) was prepared by dissolving lipids in ethanol. The mRNA solution was prepared by dissolving the mRNA in citrate buffer, resulting in mRNA at a concentration of 0.0833 mg/ml in citrate buffer with a pH of 4.5. The mixtures were then both heated to 65° C. prior to mixing. Then, these two solutions were mixed using a pump system. In some instances, the two solutions were mixed using a gear pump system. In certain embodiments, the two solutions were mixing using a 'T' junction (or "Y" junction). The mixture was then purified by diafiltration with a TFF process. The resultant formulation concentrated and stored at 2-8° C. until further use.

A second exemplary process for lipid nanoparticle formulation is Process B of WO 2018/089801 (see, e.g., Example 2 and FIG. 2 of WO 2018/089801). Process B ("B") refers to a process of encapsulating messenger RNA (mRNA) by mixing pre-formed lipid nanoparticles with mRNA. A range of different conditions, such as varying temperatures (i.e., heating or not heating the mixture), buffers, and concentrations, may be employed in Process B. In an exemplary process, lipids dissolved in ethanol and citrate buffer were mixed using a pump system. The instantaneous mixing of the two streams resulted in the formation of empty lipid nanoparticles, which was a self-assembly process. The resultant formulation mixture was empty lipid nanoparticles in citrate buffer containing alcohol. The formulation was then subjected to a TFF purification process wherein buffer exchange occurred. The resulting suspension of pre-formed empty lipid nanoparticles was then mixed with mRNA using a pump system. For certain cationic lipids, heating the solution post-mixing resulted in a higher percentage of lipid nanoparticles containing mRNA and a higher total yield of mRNA.

Lipid nanoparticle formulations of Table 5 were prepared by using either Process A or Process B as described in WO 2018/089801. All of the lipid nanoparticle formulations comprised hEPO mRNA and the different lipids in following mol % ratios: Cationic Lipid:DMG-PEG2000; Cholesterol:DOPE=40:5:25:30.

TABLE 5

Exemplary lipid nanoparticle formulations

| mRNA | Formulation Composition | Process | N/P | Size | PDI | Encapsulation % |
|---|---|---|---|---|---|---|
| hEPO | (133): DMG-PEG2000:Cholesterol:DOPE | A | 4 | 76.08 | 0.376 | 80.47 |
| hEPO | (134): DMG-PEG2000:Cholesterol:DOPE | A | 4 | 57.76 | 0.354 | 93.03 |
| hEPO | (135): DMG-PEG2000:Cholesterol:DOPE | A | 4 | 54.21 | 0.183 | 90.28 |
| hEPO | (136): DMG-PEG2000:Cholesterol:DOPE | A | 4 | 80.23 | 0.156 | 89.58 |
| hEPO | (139): DMG-PEG2000:Cholesterol:DOPE | A | 4 | 76.92 | 0126 | 92.90 |
| hEPO | (140): DMG-PEG2000:Cholesterol:DOPE | A | 4 | 77.71 | 0.157 | 96.52 |
| hEPO | (141): DMG-PEG2000:Cholesterol:DOPE | A | 4 | 75.74 | 0.212 | 95.27 |
| hEPO | (143): DMG-PEG2000:Cholesterol:DOPE | A | 4 | 79.47 | 0.155 | 97.92 |
| hEPO | (457): DMG-PEG2000:Cholesterol:DOPE | A | 4 | 56.12 | 0.276 | 97.59 |
| hEPO | (94): DMG-PEG2000:Cholesterol:DOPE | A | 4 | 62.13 | 0293 | 84.42 |
| hEPO | (95): DMG-PEG2000:Cholesterol:DOPE | A | 4 | 52.93 | 0.209 | 97.99 |
| hEPO | (96): DMG-PEG2000:Cholesterol:DOPE | A | 4 | 67.39 | 0.152 | 95.25 |
| hEPO | (100): DMG-PEG2000:Cholesterol:DOPE | A | 4 | 78.04 | 0.161 | 96.80 |
| hEPO | (101): DMG-PEG2000:Cholesterol:DOPE | A | 4 | 79.22 | 0.156 | 94.65 |
| hEPO | (102): DMG-PEG2000:Cholesterol:DOPE | A | 4 | 74.05 | 0.173 | 95.89 |
| hEPO | (104): DMG-PEG2000:Cholesterol:DOPE | A | 4 | 76.99 | 0.155 | 96.77 |
| hEPO | (268): DMG-PEG2000:Cholesterol:DOPE | A | 4 | 91.37 | 0.138 | 97.38 |
| hEPO | (412): DMG-PEG2000:Cholesterol:DOPE | A | 4 | 74.71 | 0.147 | 86.76 |
| hEPO | (412): DMG-PEG2000:Cholesterol:DOPE | B | 4 | 111.6 | 0.189 | 95.73 |

TABLE 5-continued

Exemplary lipid nanoparticle formulations

| mRNA | Formulation Composition | Process | N/P | Size | PDI | Encapsulation % |
|---|---|---|---|---|---|---|
| hEPO | (211): DMG-PEG2000:Cholesterol:DOPE | A | 4 | 83.96 | 0.165 | 88.60 |
| hEPO | (244): DMG-PEG2000:Cholesterol:DOPE | A | 4 | 79.42 | 0184 | 86.91 |
| hEPO | (244): DMG-PEG2000:Cholesterol:DOPE | B | 4 | 129.7 | 0.221 | 94.86 |

Example 9: In Vivo Expression of hEPO in CD1 Mice Using Ribose Lipids

Intravenous (IV) administration of lipid nanoparticle formulations comprising a ribose cationic lipid and mRNA encoding hEPO (Table 5) was undertaken in order to study mRNA delivery and resultant hEPO expression. Male CD1 mice at 6-8 weeks old were given a single intravenous injection of the LNP formulations at a dosage level of 1 mg/kg. Blood samples were collected by tail snip at 6 and 24 hours post-dose. hEPO protein expression levels measured in the sera samples by ELISA (FIG. 1). These studies show that ribose cationic lipids described herein are highly effective at delivery mRNA in vivo, resulting in high expression of the protein or polypeptide encoded by the delivered mRNA.

What is claimed is:

1. A cationic lipid having a structure according to Formula (II),

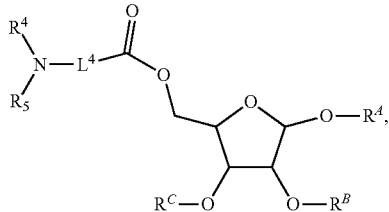

wherein $R^A$ is -$L^1$-$R^1$, $R^B$ is -$L^2$-$R^2$, and $R^C$ is -$L^3$-$R^3$; $R^A$ is hydrogen, $R^B$ is -$L^2$-$R^2$ and $R^C$ -$L^3$-$R^3$; $R^A$ is -$L^1$-$R^1$, $R^B$ is hydrogen, and $R^C$ is -$L^3$-$R^3$; or $R^A$ is -$L^1$-$R^1$, $R^B$ is -$L^2$-$R^2$, and $R^C$ is hydrogen;

each of $L^1$, $L^2$, and $L^3$ is independently a covalent bond, —C(O)—, —C(O)O—, —C(O)S—, or —C(O)$NR^L$—;

$L^4$ is independently $C_1$-$C_{10}$ alkylene;

each $R^1$, $R^2$, and $R^3$ is independently $C_6$-$C_{30}$ alkyl, $C_6$-$C_{30}$ alkenyl, or $C_6$-$C_{30}$ alkynyl;

each $R^4$ and $R^5$ is independently hydrogen, unsubstituted $C_1$-$C_{10}$ alkyl; unsubstituted $C_2$-$C_{10}$ alkenyl; or unsubstituted $C_2$-$C_{10}$ alkynyl; or $R^4$ and $R^5$ combine to form a 5- to 10-membered heterocyclyl or a 5- to 10-membered heteroaryl;

each $R^L$ is independently hydrogen, $C_1$-$C_{20}$ alkyl, $C_2$-$C_{20}$ alkenyl, or $C_2$-$C_{20}$ alkynyl.

2. The cationic lipid of claim 1, having a structure according to Formula (IId) or (IIe),

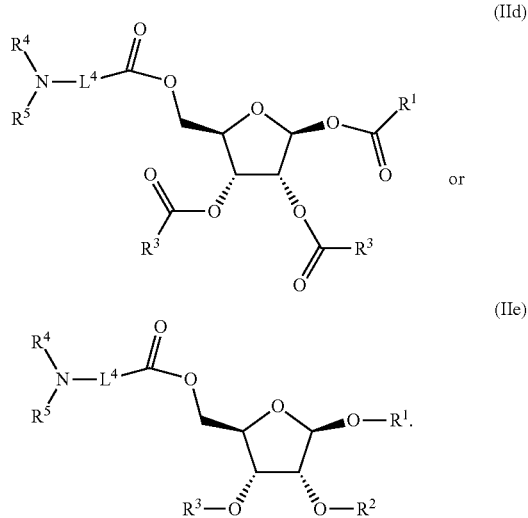

3. The cationic lipid of claim 1, wherein
$L^4$ is unsubstituted $C_1$-$C_6$ alkylene and/or
wherein each $R^4$ and $R^5$ is independently hydrogen or unsubstituted $C_1$-$C_6$ alkyl, or $R^4$ and $R^5$ combine to form a 5- to 6-membered heterocyclyl comprising one or two ring nitrogens.

4. The cationic lipid of claim 1, wherein each $R^1$, $R^2$, and $R^3$ is independently unsubstituted $C_6$-$C_{22}$ alkyl, unsubstituted $C_6$-$C_{22}$ alkenyl, or unsubstituted $C_6$-$C_{22}$ alkynyl.

5. The cationic lipid of claim 1, wherein each $R^1$, $R^2$, and $R^3$ is $C_6$-$C_{12}$ alkyl substituted by —O(CO)$R^6$ or —C(O)$OR^6$, wherein $R^6$ is unsubstituted $C_6$-$C_{14}$ alkyl.

6. The cationic lipid of claim 1, wherein $R^A$ is -$L^1$-$R^1$; $R^B$ is -$L^2$-$R^2$; and $R^C$ is -$L^3$-$R^3$.

7. The cationic lipid of claim 6, wherein each $R^4$ and $R^5$ is independently unsubstituted $C_1$-$C_{10}$ alkyl; unsubstituted $C_2$-$C_{10}$ alkenyl; or unsubstituted $C_2$-$C_{10}$ alkynyl; or $R^4$ and $R^5$ combine to form a 5- to 10-membered heterocyclyl or a 5- to 10-membered heteroaryl.

8. A composition comprising an mRNA encoding a protein, encapsulated within a liposome, wherein the liposome comprises one or more cationic lipids, one or more non-cationic lipids, one or more cholesterol-based lipids and one or more PEG-modified lipids, wherein at least one cationic lipid is according to claim 1.

9. The composition of claim 8, wherein the protein encoded by the mRNA is selected from the group consisting of an antigen from an infectious agent; cystic fibrosis transmembrane conductance regulator (CFTR) protein; and ornithine transcarbamylase (OTC) protein.

10. A cationic lipid having a structure according to Formula (I'),

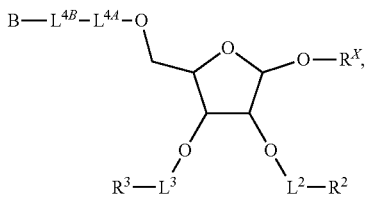

wherein
  $R^X$ is independently —H;
  each of $L^2$ and $L^3$ is independently a covalent bond, —C(O)—, or —C(O)O—;
  $L^{4A}$ is independently —C(O)—, —C(O)O—, or —C(O)NR$^L$;
  $L^{4B}$ is independently unsubstituted $C_2$-$C_{20}$ alkylene; unsubstituted $C_2$-$C_{20}$ alkenylene; or unsubstituted $C_2$-$C_{20}$ alkynylene;
  B is $NR_4R_5$, a 5- to 10-membered nitrogen-containing heterocyclyl, or a 5- to 10-membered nitrogen-containing heteroaryl;
  each $R_2$ and $R_3$ is independently $C_6$-$C_{30}$ alkyl, $C_6$-$C_{30}$ alkenyl, or $C_6$-$C_{30}$ alkynyl;
  each $R_4$ and $R_5$ is independently hydrogen, $C_1$-$C_{10}$ alkyl; $C_2$-$C_{10}$ alkenyl; or $C_2$-$C_{10}$ alkynyl; or $R_4$ and $R_5$ combine to form a 5- to 10-membered heterocyclyl or a 5- to 10-membered heteroaryl;
  each $R^L$ is independently hydrogen, $C_1$-$C_{20}$ alkyl, $C_2$-$C_{20}$ alkenyl, or $C_2$-$C_{20}$ alkynyl.

11. The cationic lipid of claim 10, wherein said cationic lipid has a structure selected from the group consisting of

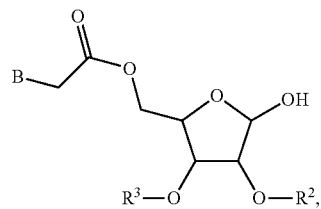

(IIIb)

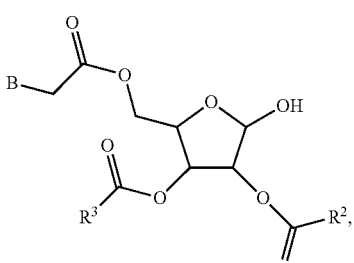

(IIIe)

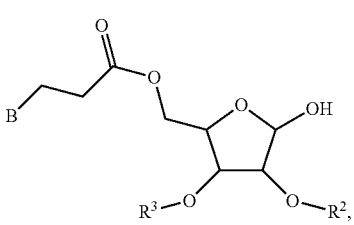

(IIIh)

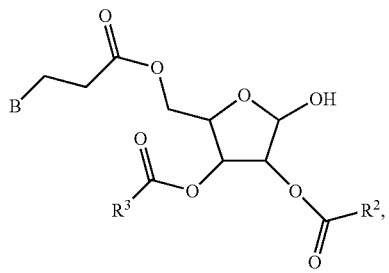

(IIIk)

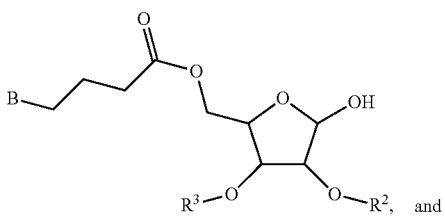

(IIIo)

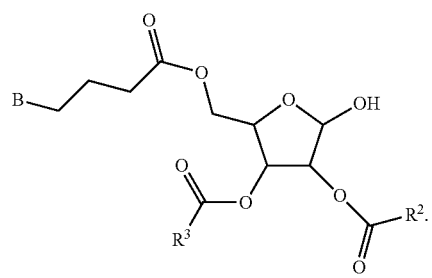

(IIIr)

12. A composition comprising an mRNA encoding a protein, encapsulated within a liposome, wherein the liposome comprises one or more cationic lipids, one or more non-cationic lipids, one or more cholesterol-based lipids and one or more PEG-modified lipids, wherein at least one cationic lipid is according to claim 10.

13. The composition of claim 12, wherein the protein encoded by the mRNA is selected from the group consisting of an antigen from an infectious agent; cystic fibrosis transmembrane conductance regulator (CFTR) protein; and ornithine transcarbamylase (OTC) protein.

14. The composition of claim 12, formulated for intravenous (IV) administration, intramuscular (IM) administration, or inhaled administration that is nebulization.

15. A cationic lipid selected from the group consisting of

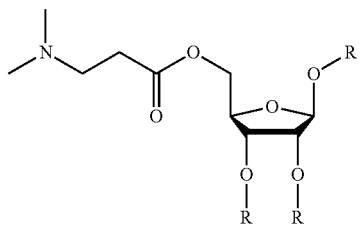

R =

R =
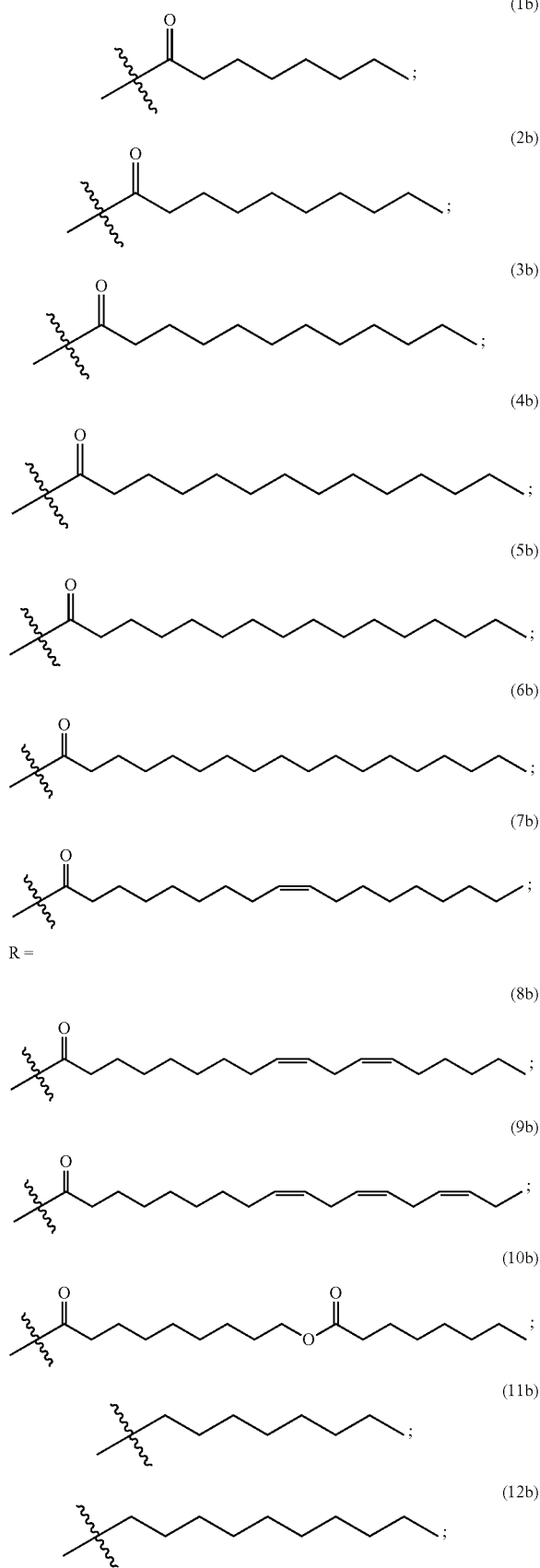
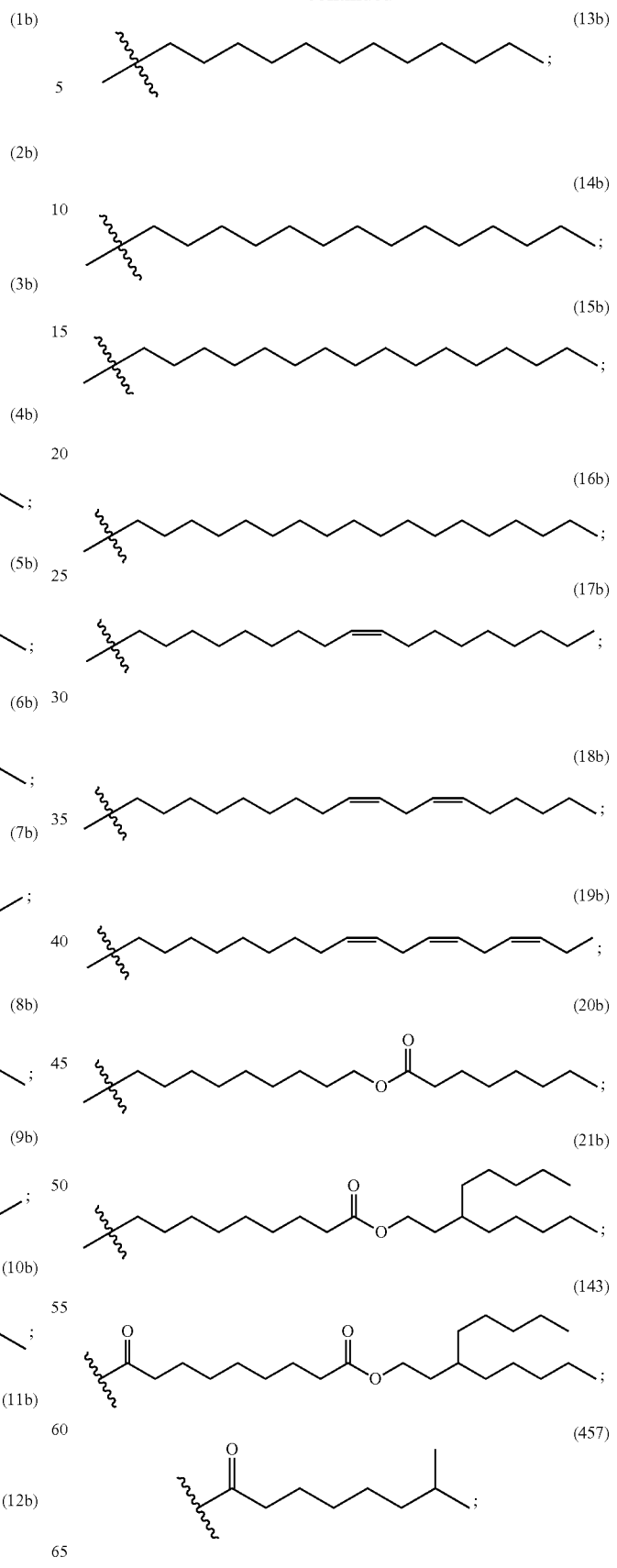

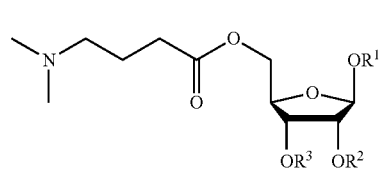
(IIIn-1)
$R^1 = R^2 = R^3 =$
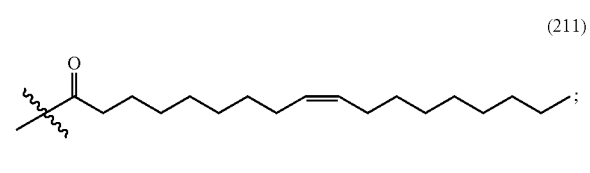
(211)
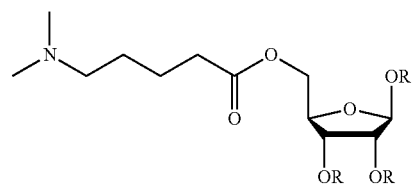
(IIIt)
R =
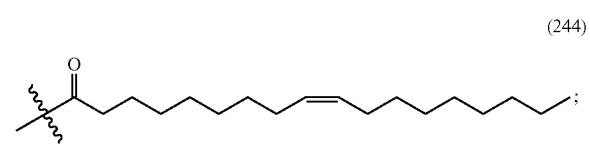
(244)
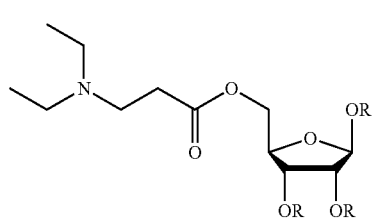
(IIIu)
R =
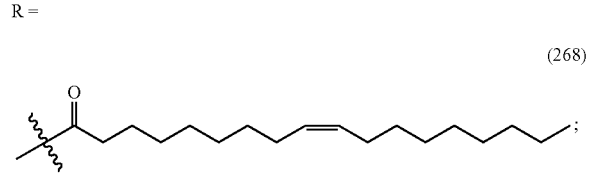
(268)
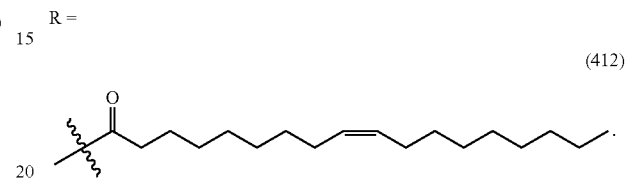
(IIIaa)
R =
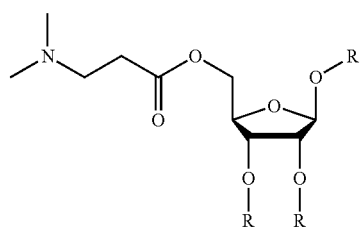
(412)
16. The cationic lipid of claim 15, selected from the group consisting of
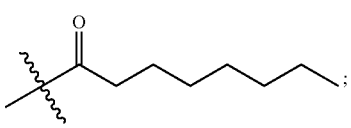
R =
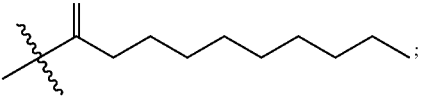
(1b)
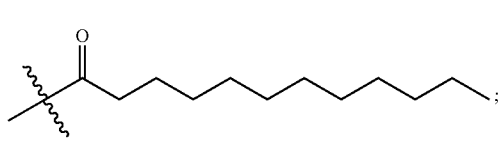
(2b)
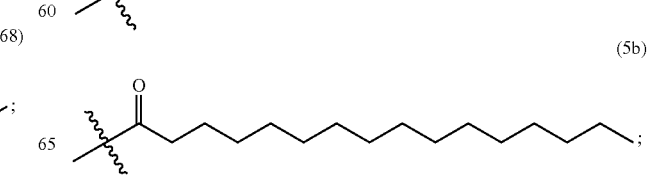
(3b)
(4b)
(5b)

(6b) 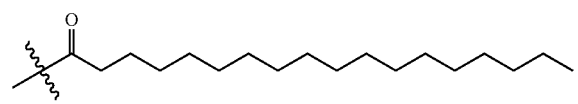
(7b) 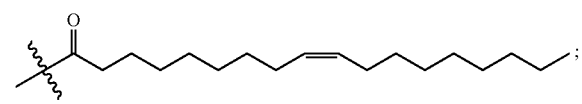
R =
(8b) 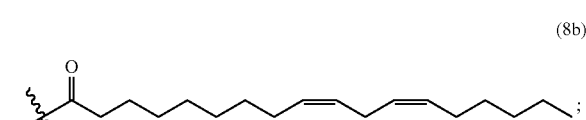
(9b) 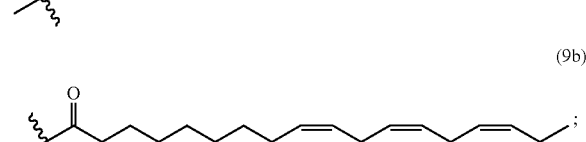
(10b) 
(11b) 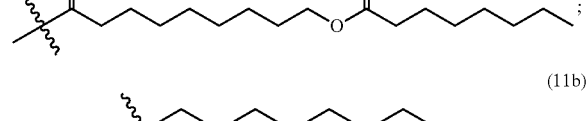
(12b) 
(13b) 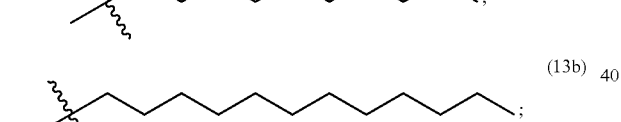
(14b) 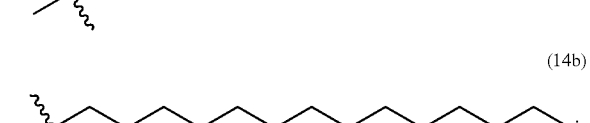
(15b) 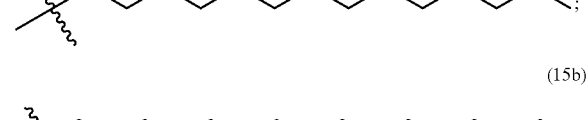
(16b) 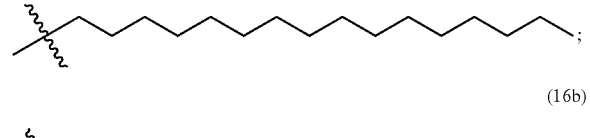
(17b) 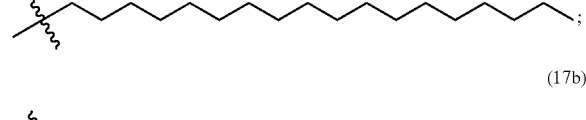
(18b) 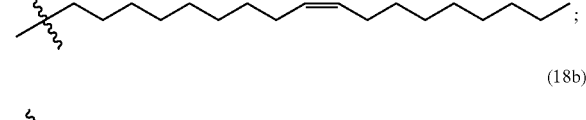
(19b) 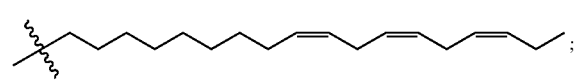
(20b) 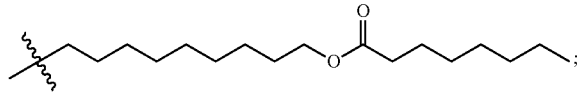
(21b) 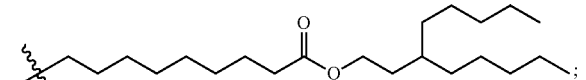
(143) 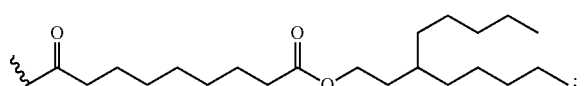
(457) 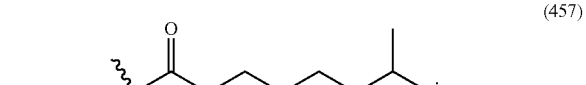
(IIIn-1) 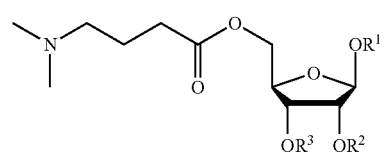
$R^1 = R^2 = R^3 =$
(211) 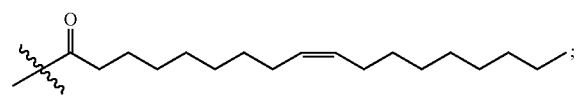
(IIIt) 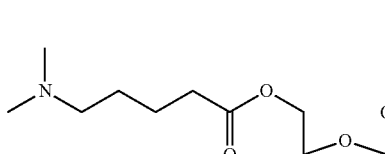
R =

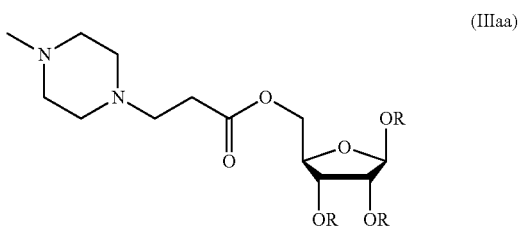
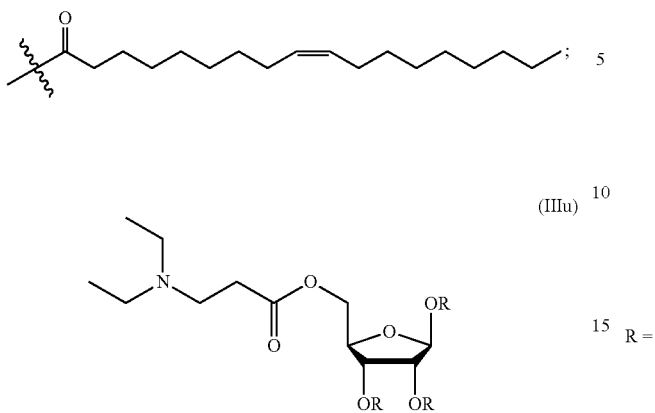
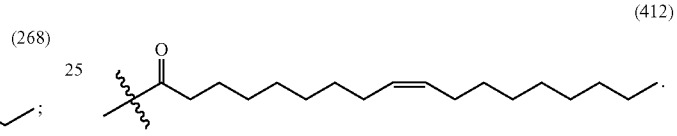
17. A cationic lipid selected from the group consisting of:
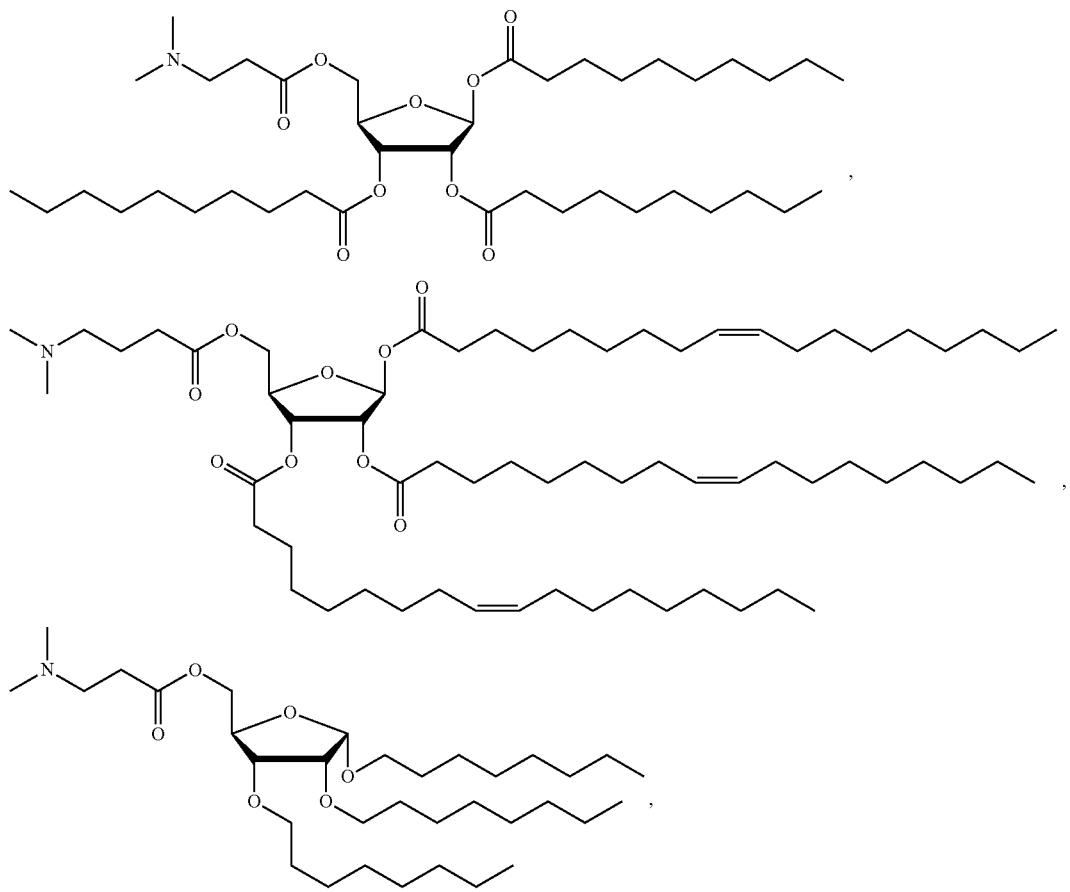

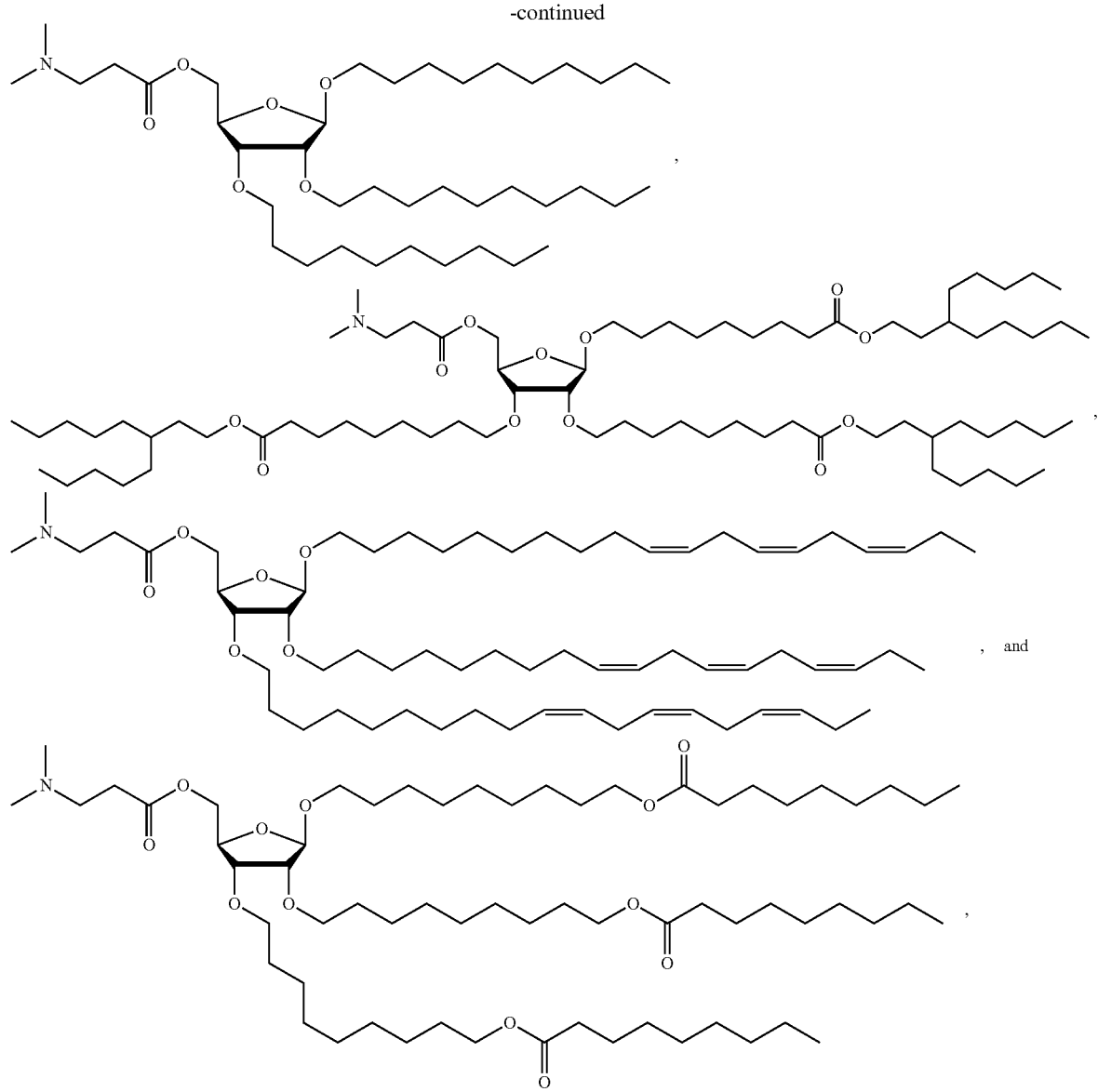
or a pharmaceutically acceptable salt thereof.
* * * * *